US012460008B2

(12) United States Patent
Zhu et al.

(10) Patent No.: US 12,460,008 B2
(45) Date of Patent: Nov. 4, 2025

(54) ANTIBODIES SPECIFICALLY RECOGNIZING GRANULOCYTE-MACROPHAGE COLONY STIMULATING FACTOR RECEPTOR ALPHA AND USES THEREOF

(71) Applicant: STAIDSON (BEIJING) BIOPHARMACEUTICALS CO., LTD., Beijing (CN)

(72) Inventors: Pingxia Zhu, Beijing (CN); Ran Wu, Beijing (CN); Qingshuang Zhang, Beijing (CN); Qun Huang, Beijing (CN)

(73) Assignee: STAIDSON (BEIJING) BIOPHARMACEUTICALS CO., LTD., Beijing (CN)

( * ) Notice: Subject to any disclaimer, the term of this patent is extended or adjusted under 35 U.S.C. 154(b) by 1126 days.

(21) Appl. No.: 17/297,421

(22) PCT Filed: Nov. 25, 2019

(86) PCT No.: PCT/CN2019/120545
§ 371 (c)(1),
(2) Date: May 26, 2021

(87) PCT Pub. No.: WO2020/108423
PCT Pub. Date: Jun. 4, 2020

(65) Prior Publication Data

US 2023/0002496 A1 Jan. 5, 2023

(30) Foreign Application Priority Data

Nov. 27, 2018 (WO) ................ PCT/CN2018/117581

(51) Int. Cl.
*C07K 16/28* (2006.01)
*C12N 15/79* (2006.01)

(52) U.S. Cl.
CPC .......... *C07K 16/2866* (2013.01); *C12N 15/79* (2013.01); *C07K 2317/24* (2013.01); *C07K 2317/52* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell |
| 4,816,567 | A | 3/1989 | Cabilly |
| 5,229,275 | A | 7/1993 | Goroff |
| 5,350,674 | A | 9/1994 | Boenisch |
| 5,399,346 | A | 3/1995 | Anderson |
| 5,500,362 | A | 3/1996 | Robinson |
| 5,545,806 | A | 8/1996 | Lonberg |
| 5,545,807 | A | 8/1996 | Surani |
| 5,567,610 | A | 10/1996 | Borrebaeck |
| 5,569,825 | A | 10/1996 | Lonberg |
| 5,580,859 | A | 12/1996 | Felgner |
| 5,585,362 | A | 12/1996 | Wilson |
| 5,589,466 | A | 12/1996 | Felgner |
| 5,591,669 | A | 1/1997 | Krimpenfort et al. |
| 5,591,828 | A | 1/1997 | Bosslet |
| 5,624,821 | A | 4/1997 | Winter |
| 5,625,126 | A | 4/1997 | Lonberg |
| 5,633,425 | A | 5/1997 | Lonberg |
| 5,648,260 | A | 7/1997 | Winter |
| 5,661,016 | A | 8/1997 | Lonberg |
| 5,750,373 | A | 5/1998 | Garrard |
| 5,821,337 | A | 10/1998 | Carter |
| 6,013,605 | A | 1/2000 | Rees |
| 6,194,551 | B1 | 2/2001 | Idusogie |
| 6,326,193 | B1 | 12/2001 | Liu |
| 6,602,684 | B1 | 8/2003 | Umana |
| 6,737,056 | B1 | 5/2004 | Presta |
| 7,332,581 | B2 | 2/2008 | Presta |
| 7,371,826 | B2 | 5/2008 | Presta |
| 7,521,541 | B2 | 4/2009 | Eigenbrot |
| 8,313,913 | B2 | 11/2012 | Nakamura |
| 8,679,491 | B2 | 3/2014 | Hanai |
| 8,945,867 | B2 | 2/2015 | Ogawa |
| 2002/0164328 | A1 | 11/2002 | Shinkawa |

(Continued)

FOREIGN PATENT DOCUMENTS

| | | | | |
|---|---|---|---|---|
| CN | 101443360 A | * | 5/2009 | ........... A61K 39/395 |
| CN | 103193882 A | | 7/2013 | |

(Continued)

OTHER PUBLICATIONS

English Translation of CN101443360B obtained from the internet at URL: https://patents.google.com/patent/CN101443360B/en?oq=CN+101443360 (Year: 2009).*

(Continued)

*Primary Examiner* — Anne M. Gussow
*Assistant Examiner* — Brianna K Swartwout
(74) *Attorney, Agent, or Firm* — Meunier Carlin & Curfman LLC

(57) ABSTRACT

The present application provides antibodies including antigen-binding fragment thereof that specifically recognizing Granulocyte-Macrophage Colony Stimulating Factor Receptor (GM-CSFRα). Also provided are methods of making and using these antibodies.

15 Claims, 21 Drawing Sheets

Specification includes a Sequence Listing.

(56) References Cited

U.S. PATENT DOCUMENTS

| | | | |
|---|---|---|---|
| 2003/0115614 A1 | 6/2003 | Kanda | |
| 2003/0157108 A1 | 8/2003 | Presta | |
| 2004/0093621 A1 | 5/2004 | Shitara | |
| 2004/0109865 A1 | 6/2004 | Niwa | |
| 2004/0110282 A1 | 6/2004 | Kanda | |
| 2004/0110704 A1 | 6/2004 | Yamane | |
| 2004/0132140 A1 | 7/2004 | Satoh | |
| 2005/0014934 A1 | 1/2005 | Hinton | |
| 2005/0031613 A1 | 2/2005 | Nakamura | |
| 2005/0079574 A1 | 4/2005 | Bond | |
| 2005/0119455 A1 | 6/2005 | Fuh | |
| 2005/0123546 A1 | 6/2005 | Umana | |
| 2005/0216958 A1 | 9/2005 | Yamane et al. | |
| 2005/0266000 A1 | 12/2005 | Bond | |
| 2007/0117126 A1 | 5/2007 | Sidhu | |
| 2007/0134759 A1 | 6/2007 | Nishiya | |
| 2007/0160598 A1 | 7/2007 | Dennis | |
| 2007/0237764 A1 | 10/2007 | Birtalan | |
| 2007/0292936 A1 | 12/2007 | Barthelemy | |
| 2008/0241884 A1 | 10/2008 | Shitara | |
| 2009/0002360 A1 | 1/2009 | Chen | |
| 2009/0130093 A1* | 5/2009 | Cohen | A61P 11/14<br>435/69.6 |

FOREIGN PATENT DOCUMENTS

| | | | |
|---|---|---|---|
| EP | 0404097 | A2 | 12/1990 |
| JP | 2009533020 | A | 9/2009 |
| WO | 199311161 | A1 | 6/1993 |
| WO | 199429351 | A2 | 12/1994 |
| WO | 199429351 | A3 | 2/1995 |
| WO | 199704801 | A1 | 2/1997 |
| WO | 199717852 | A1 | 5/1997 |
| WO | 199730087 | A1 | 8/1997 |
| WO | 199856418 | A1 | 12/1998 |
| WO | 199858964 | A1 | 12/1998 |
| WO | 1999022764 | A1 | 5/1999 |
| WO | 199951642 | A1 | 10/1999 |
| WO | 200042072 | A2 | 7/2000 |
| WO | 200061739 | A1 | 10/2000 |
| WO | 200042072 | A3 | 11/2000 |
| WO | 200129246 | A1 | 4/2001 |
| WO | 2001029058 | A1 | 4/2001 |
| WO | 200196584 | A2 | 12/2001 |
| WO | 2002031140 | A1 | 4/2002 |
| WO | 200196584 | A3 | 1/2003 |
| WO | 2003011878 | A2 | 2/2003 |
| WO | 2003048731 | A2 | 6/2003 |
| WO | 2003084570 | A1 | 10/2003 |
| WO | 2003085107 | A1 | 10/2003 |
| WO | 2003085119 | A1 | 10/2003 |
| WO | 2003011878 | A3 | 11/2003 |
| WO | 2003048731 | A3 | 1/2004 |
| WO | 2004056312 | A2 | 7/2004 |
| WO | 2005035586 | A1 | 4/2005 |
| WO | 2005035778 | A1 | 4/2005 |
| WO | 2004056312 | A3 | 5/2005 |
| WO | 2005053742 | A1 | 6/2005 |
| WO | 2005100402 | A1 | 10/2005 |
| WO | 2006029879 | A2 | 3/2006 |
| WO | 2006029879 | A3 | 9/2006 |
| WO | 2007110631 | A1 | 10/2007 |
| WO | 2008077546 | A1 | 7/2008 |

OTHER PUBLICATIONS

NASA. Star Basics. retrieved Jul. 25, 2024 from the Internet at <URL: https://universe.nasa.gov/stars/basics/>). (Year: 2024).*

Edwards et al. J Mol Biol. 2003. 334: 103â118 (Year: 2003).*

Protein Engineering, Design & Selection. 2009. 22(3): 159â168 (Year: 2009).*

British Journal of Haematology. 2018. 180: 808â820 (Year: 2018).*

Rudikoff et al. Proc Natl Acad Sci 1982. 79: 1979-1983 (Year: 1982).*

Bedouelle et al. FEES J. Jan. 2006;273(1):34-46 (Year: 2006).*

Vajdoes et al. J Mol Biol. Jul. 5, 2002;320(2):415-28 (Year: 2002).*

Extended European Search Report, dated Jul. 14, 2022, for European Patent Application No. 19891384.0, 10 pages.

Minter, R.R. et al. (Dec. 18, 2012). "Protein Engineering and Preclinical Development of a GM-CSF Receptor Antibody For the Treatment of Rheumatoid Arthritis," British Journal of Pharmacology 168(1):200-211.

Nicola, N.A. et al. (Sep. 15, 1993). "Neutralizing and Nonneutralizing Monoclonal Antibodies To The Human Granulocyte-Macrophage Colony-Stimulating Factor Receptor α-Chain," Blood 82(6):1724-1731.

Abhinandan, K.R. et al. (Aug. 2008, e-pub. Jul. 9, 2008). "Analysis and Improvements To Kabat and Structurally Correct Numbering Of Antibody Variable Domain," Molecular Immunology 45(14):3832-3839.

Adolf-Bryfogle, J. et al. (2015, e-pub. Nov. 11, 2014). "PylgClassify: A Database of Antibody CDR Structural Classifications," Nucleic Acids Res. 43:D432-D438.

Al-Lazikani, B. et al. (1997). "Standard Conformations for the Canonical Structures of Immunoglobulins," J. Mol. Biol. 273:927-948.

Boerner, P. et al. (Jul. 1, 1991). "Production of Antigen-Specific Human Monoclonal Antibodies From in Vitro-Primed Human Splenocytes," J. Immunol. 147(1):86-95.

Brown, M. et al. (Jun. 5, 1987). "Iac Repressor Can Regulate Expression From a Hybrid SV40 Early Promoter Containing a Iac Operator in Animal Cells," Cell 49:603-612.

Brüggemann, M. et al. (1993). "Designer Mice: The Production of Human Antibody Repertoires in Transgenic Animals," Year in Immuno. 7:33-40.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Burton, D.R. (1985). "Immunoglobulin G: Functional Sites," Molec. Immunol. 22(3):161-206.

Capel, P.J.A. et al. (1994). "Heterogeneity of Human IgG Fc Receptors," Immunomethods 4:25-34.

Chothia, C. et al. (Aug. 20, 1987). "Canonical Structures for the Hypervariable Regions of Immunoglobulins," J. Mol. Biol. 196(4):901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Clynes, R. et al. (Jan. 1998). "Fc Receptors are Required in Passive and Active Immunity to Melanoma," Proc. Natl. Acad. Sci. USA 95:652-656.

Cole, S.P.C. et al. (1985). "The EBV-Hybridoma Technique and Its Applicaton to Human Lung Cancer," in Monoclonal Antibodies and Cancer Therapy, Alan R. Liss, p. 77-96.

Cragg, M.S. et al. (Apr. 1, 2004). "Antibody Specificity Controls In Vivo Effector Mechanisms Of Anti-CD20 Reagents," Blood 103(7):2738-2743.

Cragg, M.S. et al. (Feb. 1, 2003). "Complement-Mediated Lysis By Anti-CD20 Mab Correlates With Segregation Into Lipid Rafts," Blood 101(3):1045-1052.

Cunningham, B.C. et al. (Jun. 2, 1989). "High-Resolution Epitope Mapping of hGH-Receptor Interactions by Alanine-Scanning Mutagenesis," Science 244:1081-1085.

Datta, R. et al. (Nov. 1992). "Ionizing Radiation Activates Transcription of the EGR1 Gene Via CArG Elements," Proc. Natl. Acad. Sci. USA 89(1):10149-10153.

Daeron, M. (1997). "Fc Receptor Biology," Ann. Rev. Immunol. 15:203-234.

De Haas, M. et al. (1995). Fcγ Receptors of Phagocytes, J. Lab. Clin. Med. 126(4):330-341.

Dranoff, G. et al. (Apr. 29, 1994). "Involvement of Granulocyte-Macrophage Colony-Stimulating Factor In Pulmonary Homeostasis," Science 264(5159):713-716.

(56) References Cited

OTHER PUBLICATIONS

Duncan, A.R. et al. (Apr. 21, 1988). "The Binding Site for C1q on IgG," Nature 322:738-740.
Edgar, R.C. (2004, e-pub. Mar. 19, 2004). "Muscle: Multiple Sequence Alignment With High Accuracy And High Throughput," Nucleic Acids Research 32(5):1792-1797.
Edgar, R.C. (Aug. 19, 2004). "Muscle: A Multiple Sequence Alignment Method With Reduced Time And Space Complexity," BMC Bioinformatics 5(113):1-19.
Ehrenmann, F. et al. (Jan. 2010, e-pub. Nov. 9, 2009). "IMGT/3Dstructure-DB and IMGT/DomainGapAlign: A Database and a Tool For Immunoglobulins or Antibodies, T Cell Receptors, MHC, IgSF and MhcSF," Nucleic Acids Res. 38:D301-D307.
Fellouse, F.A. et al. (Aug. 24, 2004). "Synthetic Antibodies From a Four-Amino-Acid Code: A Dominant Role for Tyrosine in Antigen Recognition," Proc. Natl. Acad. Sci. USA 101(34):12467-12472.
Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1, 4-N-Acetylglucosaminyltransferase III and Golgi α-Mannosidase," Biotechnology and Bioengineering 93(5):851-861.
Fishwild, D.M. et al. (Jul. 1996). "High-avidity human IgGK Monoclonal Antibodies from a Novel Strain of Minilocus Transgenic Mice," Nature Biotechnol. 14:845-851.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Ghetie, V. et al. (2000). "Multiple Roles For The Major Histocompatibility Complex Class I-Related Receptor FCRN," Annu. Rev. Immunol. 18:739-766.
Gingrich, J.R. et al. (1998). "Inducible Gene Expression in the Nervous System of Transgenic Mice," Annual Rev. Neurosci. 21:377-405.
Gossen, M. et al. (1993). "Anhydrotetracycline, A Novel Effector For Tetracycline Controlled Gene Expression Systems in Eukaryotic Cells," Nucleic Acids Research 21(18):4411-4412.
Green, M.R. et al. (2012). Molecular Cloning: A Laboratory Manual, Cold Spring Harbor Laboratory, New York, 34 pages.
Griffiths, A.D. et al. (1993). "Human Anti-Self Antibodies With High Specificity From Phage Display Libraries," EMBO J. 12(2):725-734.
Guyer, R.L. et al. (Aug. 1976). "Immunoglobulin Binding By Mouse Intestinal Epithelial Cell Receptors," J. Immunol. 117(2):587-593.
Haman, A. et al. (Nov. 26, 1999). "Molecular Determinants of the Granulocyte-Macrophage Colony-Stimulating Factor Receptor Complex Assembly," Journal of Biological Chemistry 274(48):34155-34163.
Harlow, E. et al. eds. (1988). "Using Antibodies: A Laboratory Manual," Cold Spring Harbor Laboratory Press, pp. iv-ix, (Table of Contents Only), 9 pages.
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hoet, R.M. et al. (2005), "Generation of high-affinity human antibodies by combining donor-derived and synthetic complementarity-determining-region diversity," Nat Biotechnol, 23(3):344-348.
Holliger, P. et al. (Jul. 1993). "Diabodies": Small Bivalent and Bispecific Antibody Fragments, Proc. Natl. Acad. Sci. USA 90:6444-6448.
Honegger, A. et al. (2001). "Yet Another Numbering Scheme for Immunoglobulin Variable Domains: An Automatic Modeling and Analysis Tool," J Mol Biol. 309(3):657-670.
Hoogenboom, H.R. et al. (2001). "Overview of Antibody Phage-Display Technology and Its Applications," Chapter 1 In Methods in Molecular Biology, O'Brien et al. ed., Humana Press, Totowa, NJ, 178:1-37.
Hoogenboom, H.R. et al. (Sep. 20, 1992). "By-Passing Immunisation Human Antibodies From Synthetic Repertoires Of Germline VH Gene Segments Rearranged In Vitro," J. Mol. Biol. 227(2):381-388.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability, issued May 25, 2021, for PCT Application No. PCT/CN2019/120545, filed Nov. 25, 2019, 6 pages.
International Search Report and Written Opinion, mailed Feb. 26, 2020, for PCT Application No. PCT/CN2019/120545, filed Nov. 25, 2019, 10 pages.
Jakobovits, A. et al. (Mar. 18, 1993). "Germ-Line Transmission and Expression of a Human-Derived Yeast Artificial Chromosome," Nature 362:255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, 5th ed., Public Health Service, National Institutes of Health, Bethesda, MD. TOC, 21 pages.
Kabat, E.A. et al. (Oct. 10, 1977). "Unusual Distributions Of Amino Acids In Complementarity-Determining (Hypervariable) Segments Of Heavy And Light Chains Of Immunoglobulins And Their Possible Roles In Specificity Of Antibody-Combining Sites," J. Biol. Chem. 252(19):6609-6616.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kim, J-K. et al. (1994). "Localization of the Site of the Murine IgGI Molecule That is Involved in Binding to the Murine Intestinal Fc Receptor," Eur. J. Immunol. 24:2429-2434.
Lawlor, K.E. et al. (Dec. 2005). "Acute CD4+ T Lymphocyte-Dependent Interleukin-1-Driven Arthritis Selectively Requires Interleukin-2 and Interleukin-4, Joint Macrophages, Granulocyte-Macrophage Colony-Stimulating Factor, Interleukin-6, and Leukemia Inhibitory Factor," Arthritis & Rheumatism 52(12):3749-3754.
Lee, C.V. et al. (2004). "Bivalent Antibody Phage Display Mimics Natural Immunoglobulin," Journal of Immunological Methods 284:119-132.
Lee, C.V. et al. (2004). "High-Affinity Human Antibodies From Phage-Displayed Synthetic Fab Libraries With A Single Framework Scaffold," J. Mol. Biol. 340:1073-1093.
Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.
Lonberg, N. et al. (1995, e-pub. Jul. 10, 2009). "Human Antibodies From Transgenic Mice," Int. Rev. Immunol. 13(1):65-93.
Lonberg, N. et al. (Apr. 28, 1994). "Antigen-Specific Human Antibodies From Mice Comprising Four Distinct Genetic Modifications," Nature 368(6474):856-859.
MacCallum, R.M. et al. (1996). "Antibody-Antigen Interactions: Contact Analysis and Binding Site Topography," J. Mol. Biol. 262:732-745.
Mader, S. et al. (Jun. 1993). "A Steroid-Inducible Promoter for the Controlled Overexpression of Cloned Genes in Eukaryotic Cells." Proc. Natl. Acad. Sci. USA 90:5603-5607.
Manome, Y. et al. (Oct. 1993). "Coinduction of c-jun Gene Expression and Internucleosomal DNA Fragmentation by Ionizing Radiation," Biochemistry 32(40):10607-10613.
Marks, J.D. et al. (1991). "By-Passing Immunization. Human Antibodies From V-Gene Libraries Displayed on Phage," J. Mol. Biol. 222:581-597.

(56) References Cited

OTHER PUBLICATIONS

Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
McCafferty, J. et al. (Dec. 6, 1990). "Phage Antibodies: Filamentous Phage Displaying Antibody Variable Domains," Nature 348:552-554.
McQualter, J.L. et al. (Oct. 1, 2001). "Granulocyte Macrophage Colony-stimulating Factor: A New Putative Therapeutic Target in Multiple Sclerosis," Journal of Experimental Medicine 194(7):873-881.
Morris, G.E. (1996). "Epitope Mapping Protocols," Methods in Molecular Biology 66:1-12.
Morrison, S.L. (Apr. 28, 1994). "Success in Specification," Nature 368:812-813.
Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.
Moschetta, M. et al. (2015, e-pub. Nov. 28, 2015). "Pancreatic Trauma: The Role of Computed Tomography For Guiding Therapeutic Approach," Nature Reviews Rheumatology 7(11):415-430.
Munson, P.J. et al. (1980). "Ligand: A Versatile Computerized Approach for Characterization of Ligand-Binding Systems," Anal. Biochem. 107:220-239.
Neuberger, M. (Jul. 1996). "Generating High-Avidity Human Mabs in Mice," Nature Biotechnology 14:826.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Ravetch, J.V. et al. (1991). "Fc Receptors," Annu. Rev. Immunol. 9:457-492.
Remington's Pharmaceutical Sciences. (1980). 16th edition, Osol, A. Ed, pp. 1-2, (Table of Contents Only).
Riechmann, L. et al. (Mar. 24, 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.
Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140(6):777-783.
Sidhu, S.S. et al. (2004). "Phage-Displayed Antibody Libraries Synthetic Heavy Chain Complementarity Determining Regions," J. Mol. Biol. 338(2):299-310.
Sonderegger, I. et al. (2008). "GM-CSF Mediates Autoimmunity By Enhancing IL-6-Dependent Th17 Cell Development and Survival," Journal of Experimental Medicine 205(10):2281-2294.
Spencer, D. M. et al. (Nov. 12, 1993). "Controlling Signal Transduction with Synthetic Ligands," Science 262 (5136):1019-1024.
Stanley, E. et al. (Jun. 1994). "Granulocyte/Macrophage Colony-Stimulating Factor-Deficient Mice Show No Major Perturbation Of Hematopoiesis But Develop A Characteristic Pulmonary Pathology," PNAS 91(12):5592-5596.
Trapnell, B.C. et al. (Dec. 25, 2003). "Pulmonary Alveolar Proteinosis," N. Engl. J. Med. 349(26):2527-2539.
Ui-Tel, K. et al. (2000). "Sensitive Assay of RNA Interference in *Drosophila* and Chinese Hamster Cultured Cells Using Firefly Luciferase Gene As Target," FEBS Letters 479:79-82.
Verhoeyen, M. et al. (Mar. 25, 1988). "Reshaping Human Antibodies: Grafting An Antilysozyme Activity," Science 239(4857):1534-1536.
Winter, G. et al. (1994). "Making Antibodies by Phage Display Technology," Ann. Rev. Immunol. 12:433-455.
Wright, A. et al. (Jan. 1997). "Effect of Glycosylation on Antibody Function: Implications for Genetics Engineering," Trends Biotechnol. 15:26-32.
Yamane-Ohnuki, N. et al. (Sep. 5, 2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87(5):614-622.

* cited by examiner

Blocking GMRah binding to GM-CSF 16 20 30 40 50 60 70 75
SLNVRFDSRTMQLSWDCQEQTTFSKCFLTDKKNRVVEPRLSNNECSCTFREICLHEGVTF 76 80 90 100 110 120 130 135
EVHVQTSQRGFQQKLLYPNSGREGTAAQNFSCFIYNADLMNCTWARGPTAPRDVQYFLYI 136 140 150 160 170 180 190 195
RNSKRRREIRCPYYIQDSGTHVGCHLDNLSGLTSRNYFLVNGTSREIGIQFFDSLLDTKK 196 200 210 220 230 240 250 255
TERFNPPSNVTVRCNTTHCLVRWKQPRTYQKLSYLDFQYQLDVHRKNTQPGTENLLINVS 256 260 270 280 290 296
GDLENRYNFPSSEPRAKHSVKIRAADVRILNWSSWSEAIEF (SEQ ID NO: 292)

SEQUENCE LISTING

<160> NUMBER OF SEQ ID NOS: 295

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Glu Leu Ser Ile His
1 5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Glu Leu Ser Met His
1 5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Glu Leu Pro Met His
1 5

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Glu Leu Cys Met His
1 5

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Gly Phe Asp Pro Glu Asp Gly Glu Thr Asn Tyr Ala Gln Lys Ser Gln
1 5 10 15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Gly Phe Asp Pro Glu Asp Gly Glu Thr Ile Tyr Ala Gln Lys Phe Gln
1 5 10 15

Gly

<210> SEQ ID NO 7

<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Gly Phe Asp Pro Glu Asp Gly Glu Thr Ile Tyr Ala Gln Lys Ser Gln
1 5 10 15

Gly

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Gly Phe Asp Pro Glu Asp Gly Glu Ala Ile Tyr Ala Gln Lys Ser Gln
1 5 10 15

Gly

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Gly Phe Asp Gly Asp Gly Glu Glu Thr Ile Tyr Ala Gln Lys Phe Gln
1 5 10 15

Gly

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Gly Phe Asp Gly Asp Ile Glu Glu Thr Ile Tyr Ala Gln Lys Phe Gln
1 5 10 15

Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Gly Phe Asp Thr Gly Asp Asp Glu Thr Ile Tyr Ala Gln Lys Phe Gln
1 5 10 15

Gly

<210> SEQ ID NO 12
<211> LENGTH: 17
<212> TYPE: PRT
<213> ORGANISM: Artificial Sequence
<220> FEATURE:

<223> OTHER INFORMATION: Synthetic Construct

<400> SEQUENCE: 12

Gly Phe Asp Ser Glu Trp Gly Glu Thr Ile Tyr Ala Gln Lys Phe Gln
1 5 10 15

Gly

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Gly Phe Asp Val Ala Ser Gly Glu Thr Ile Tyr Ala Gln Lys Phe Gln
1 5 10 15

Gly

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Gly Phe Asp Gly Asp Trp His Glu Thr Ile Tyr Ala Gln Lys Phe Gln
1 5 10 15

Gly

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Gly Phe Asp Pro Ala Trp Gly Glu Thr Ile Tyr Ala Gln Lys Phe Gln
1 5 10 15

Gly

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Gly Phe Asp Ser Glu Val Gly Glu Thr Ile Tyr Ala Gln Lys Phe Gln
1 5 10 15

Gly

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Gly Arg Tyr Cys Ser Thr Asp Thr Cys Tyr Gly Phe Asp Tyr
1 5 10

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Gly Arg Tyr Cys Gly His Ala Ser Cys Tyr Gly Phe Asp Tyr
1 5 10

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Gly Arg Tyr Thr Ser Leu Met Phe Thr Tyr Gly Phe Asp Tyr
1 5 10

<210> SEQ ID NO 20
<211> LENGTH: 14
<212> TYPE: PRT
<213> ORGANISM: Artificial Sequence
<220> FEATURE:
<223> OTHER INFORMATION: Synthetic Construct

<400> SEQUENCE: 20

Gly Arg Tyr Thr Glu Leu Tyr Gln Asn Tyr Gly Phe Asp Tyr
1 5 10

<210> SEQ ID NO 21
<211> LENGTH: 14
<212> TYPE: PRT
<213> ORGANISM: Artificial Sequence
<220> FEATURE:
<223> OTHER INFORMATION: Synthetic Construct

<400> SEQUENCE: 21

Gly Arg Tyr Thr Glu Leu Phe Ala Ser Tyr Gly Phe Asp Tyr
1 5 10

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Gly Arg Tyr Ser Glu His Ser Thr Ser Tyr Gly Phe Asp Tyr
1 5 10

<210> SEQ ID NO 23
<211> LENGTH: 14
<212> TYPE: PRT
<213> ORGANISM: Artificial Sequence
<220> FEATURE:
<223> OTHER INFORMATION: Synthetic Construct

<400> SEQUENCE: 23

Gly Arg Tyr Thr Gly Leu Met Asn Ser Tyr Gly Phe Asp Tyr 1 5 10

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Gly Arg Tyr Ile Ser Phe Met Phe Thr Tyr Gly Phe Asp Tyr
1 5 10

<210> SEQ ID NO 25
<211> LENGTH: 14
<212> TYPE: PRT
<213> ORGANISM: Artificial Sequence
<220> FEATURE:
<223> OTHER INFORMATION: Synthetic Construct

<400> SEQUENCE: 25

Gly Arg Tyr Cys Phe Pro Asp Thr Cys Tyr Gly Phe Asp Tyr
1 5 10

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Gly Arg Tyr Ser Phe Thr Asp Leu Ala Tyr Gly Phe Asp Tyr
1 5 10

<210> SEQ ID NO 27
<211> LENGTH: 14
<212> TYPE: PRT
<213> ORGANISM: Artificial Sequence
<220> FEATURE:
<223> OTHER INFORMATION: Synthetic Construct

<400> SEQUENCE: 27

Gly Arg Tyr Thr Ser Leu Ala Thr Thr Tyr Gly Phe Asp Tyr
1 5 10

<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Gly Arg Tyr Ala Phe Ile Asp Thr Ala Tyr Gly Phe Asp Tyr
1 5 10

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Gly Arg Tyr Cys Ser Ser Asp Leu Cys Tyr Gly Phe Asp Tyr
1 5 10

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Gly Arg Tyr Thr Ser Leu Asp Glu Ser Tyr Gly Phe Asp Tyr
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Gly Arg Tyr Ser Ser Tyr Asp Ile Ala Tyr Gly Phe Asp Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Construct

<400> SEQUENCE: 32

Gly Arg Tyr Ala Trp Thr Asp Ile Ala Tyr Gly Phe Asp Tyr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Gly Arg Tyr Cys Phe Tyr Asp Leu Cys Tyr Gly Phe Asp Tyr
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

Gly Arg Tyr Ser Ser Tyr Phe Thr Asn Tyr Gly Phe Asp Tyr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Gly Arg Tyr Val Ser Leu Phe Phe Asn Tyr Gly Phe Asp Tyr
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic Construct

<400> SEQUENCE: 36

Gly Arg Tyr Cys His Lys Asp Gly Cys Tyr Gly Phe Asp Tyr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Construct

<400> SEQUENCE: 37

Gly Arg Tyr Thr Gly Leu Tyr Ala Ser Tyr Gly Phe Asp Tyr
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

Gly Arg Tyr Cys Glu Thr Asp Ile Cys Tyr Gly Phe Asp Tyr
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Gly Arg Tyr Thr Ile Ile Thr Thr Asn Tyr Gly Phe Asp Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Gly Arg Tyr Thr Ser Leu Ala Ala Thr Tyr Gly Phe Asp Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Gly Arg Tyr Ala Val Thr Asp Met Ala Tyr Gly Phe Asp Tyr
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct

<400> SEQUENCE: 42

Gly Arg Tyr Ala Phe Ala Gly Leu Ala Tyr Gly Phe Asp Tyr
1 5 10

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Gly Arg Tyr Thr Asn Asp Phe Ala Asn Tyr Gly Phe Asp Tyr
1 5 10

<210> SEQ ID NO 44
<211> LENGTH: 14
<212> TYPE: PRT
<213> ORGANISM: Artificial Sequence
<220> FEATURE:
<223> OTHER INFORMATION: Synthetic Construct

<400> SEQUENCE: 44

Gly Arg Tyr Ser Ser Val Gly Ser Thr Tyr Gly Phe Asp Tyr
1 5 10

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Gly Arg Tyr Ala Asn Leu Tyr Asn Asn Tyr Gly Phe Asp Tyr
1 5 10

<210> SEQ ID NO 46
<211> LENGTH: 14
<212> TYPE: PRT
<213> ORGANISM: Artificial Sequence
<220> FEATURE:
<223> OTHER INFORMATION: Synthetic Construct

<400> SEQUENCE: 46

Gly Arg Tyr Val Tyr Leu Ala Ser Asn Tyr Gly Phe Asp Tyr
1 5 10

<210> SEQ ID NO 47
<211> LENGTH: 14
<212> TYPE: PRT
<213> ORGANISM: Artificial Sequence
<220> FEATURE:
<223> OTHER INFORMATION: Synthetic Construct

<400> SEQUENCE: 47

Gly Arg Tyr Ser Thr Asn Phe Ser Asn Tyr Gly Phe Asp Tyr
1 5 10

<210> SEQ ID NO 48

<211> LENGTH: 14
<212> TYPE: PRT
<213> ORGANISM: Artificial Sequence
<220> FEATURE:
<223> OTHER INFORMATION: Synthetic Construct

<400> SEQUENCE: 48

Gly Arg Tyr Thr Arg Gly Trp Phe Asn Tyr Gly Phe Asp Tyr
1 5 10

<210> SEQ ID NO 49
<211> LENGTH: 14
<212> TYPE: PRT
<213> ORGANISM: Artificial Sequence
<220> FEATURE:
<223> OTHER INFORMATION: Synthetic Construct

<400> SEQUENCE: 49

Gly Arg Tyr Thr Ser Leu Asp Ala Thr Tyr Gly Phe Asp Tyr
1 5 10

<210> SEQ ID NO 50
<211> LENGTH: 14
<212> TYPE: PRT
<213> ORGANISM: Artificial Sequence
<220> FEATURE:
<223> OTHER INFORMATION: Synthetic Construct

<400> SEQUENCE: 50

Gly Arg Tyr Ser Glu Ser Phe Ala Ser Tyr Gly Phe Asp Tyr
1 5 10

<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Arg Ala Ser Gln Ser Val Ser Ser Tyr Leu Ala
1 5 10

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Gly Ala Ser Ser Arg Ala Thr
1 5

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Gln Gln Tyr Asn Asn Trp Pro Pro Thr
1 5

<210> SEQ ID NO 54
<211> LENGTH: 9

<212> TYPE: PRT
<213> ORGANISM: Artificial Sequence
<220> FEATURE:
<223> OTHER INFORMATION: Synthetic Construct

<400> SEQUENCE: 54

Gln Gln Tyr Asp Asn Trp Pro Pro Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Tyr Asn Asn Trp Pro Tyr Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Construct

<400> SEQUENCE: 56

Gln Gln Tyr Asp Ser Trp Pro Tyr Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Gln Tyr Asp Asn Trp Pro Tyr Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Gln Gln Tyr Asp Asn Ser Pro His Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Gln Tyr Asp Ser Ser Pro Pro Thr
1               5

<210> SEQ ID NO 60
<211> LENGTH: 9
<212> TYPE: PRT

<213> ORGANISM: Artificial Sequence
<220> FEATURE:
<223> OTHER INFORMATION: Synthetic Construct

<400> SEQUENCE: 60

Gln Gln Tyr Ser Asn Ser Pro Pro Thr
1 5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Tyr Asp Asn Ser Pro Tyr Thr
1 5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Gln Gln Tyr Asn Ser Ser Pro Pro Thr
1 5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Gln Gln Tyr Asp Asn Ser Pro Ser Thr
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Gln Gln Tyr Asp Ser Ser Pro His Thr
1 5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Gln Gln Tyr Arg Asn Trp Pro Phe Thr
1 5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln Gln Tyr Ala Asn Pro Pro Asn Thr
1 5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Gln Gln Tyr Thr Asn Val Pro Asp Thr
1 5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Gln Gln Tyr Asn Asn Ser Pro Pro Thr
1 5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Gln Gln Tyr Asp Asn Ser Pro Pro Thr
1 5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Gln Gln Tyr Leu Asn Ser Pro Phe Thr
1 5

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

Gln Gln Tyr Ser Asn Val Pro Val Thr
1 5

<210> SEQ ID NO 72
<211> LENGTH: 9
<212> TYPE: PRT
<213> ORGANISM: Artificial Sequence
<220> FEATURE:

<223> OTHER INFORMATION: Synthetic Construct

<400> SEQUENCE: 72

Gln Gln Tyr Tyr Asn Gly Pro Gly Thr
1 5

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Gln Gln Tyr Gly Asn Arg Pro Asp Thr
1 5

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct

<400> SEQUENCE: 74

Gln Gln Tyr Asp Asn Gly Pro Glu Thr
1 5

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct

<400> SEQUENCE: 75

Gln Gln Tyr Arg Asn Gly Pro Pro Thr
1 5

<210> SEQ ID NO 76
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Glu, ASn, Gly, ASp, Met, Ser, Pro, Phe,
Tyr, Ala, Val, Lys, Trp, Arg, or Cys
<220> FEATURE:
<221> NAME/KEY: VARIANT
<222> LOCATION: 3
<223> OTHER INFORMATION: Xaa = Ser, Cys, or Pro
<220> FEATURE:
<221> NAME/KEY: VARIANT
<222> LOCATION: 4
<223> OTHER INFORMATION: Xaa = Ile or Met

<400> SEQUENCE: 76

Xaa Leu Xaa Xaa His
1 5

<210> SEQ ID NO 77
<211> LENGTH: 17
<212> TYPE: PRT
<213> ORGANISM: Artificial Sequence
<220> FEATURE:
<223> OTHER INFORMATION: Synthetic Construct

```
<220> FEATURE:
<221> NAME/KEY: VARIANT
<222> LOCATION: 4
<223> OTHER INFORMATION: Xaa = Pro, Gly, Thr, Ser, or Val
<220> FEATURE:
<221> NAME/KEY: VARIANT
<222> LOCATION: 5
<223> OTHER INFORMATION: Xaa = Glu, Asp, Gly, or Ala
<220> FEATURE:
<221> NAME/KEY: VARIANT
<222> LOCATION: 6
<223> OTHER INFORMATION: Xaa = Asp, Gly, Ile, Trp, Ser, or Val
<220> FEATURE:
<221> NAME/KEY: VARIANT
<222> LOCATION: 7
<223> OTHER INFORMATION: Xaa = Gly, Glu, Asp, or His
<220> FEATURE:
<221> NAME/KEY: VARIANT
<222> LOCATION: 9
<223> OTHER INFORMATION: Xaa = Thr or Ala
<220> FEATURE:
<221> NAME/KEY: VARIANT
<222> LOCATION: 10
<223> OTHER INFORMATION: Xaa = Asn or Ile
<220> FEATURE:
<221> NAME/KEY: VARIANT
<222> LOCATION: 15
<223> OTHER INFORMATION: Xaa = Ser or Phe

<400> SEQUENCE: 77

Gly Phe Asp Xaa Xaa Xaa Xaa Glu Xaa Xaa Tyr Ala Gln Lys Xaa Gln
1               5                   10                  15

Gly


<210> SEQ ID NO 78
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Cys, Thr, Ser, Ile, Ala, or Val
<220> FEATURE:
<221> NAME/KEY: VARIANT
<222> LOCATION: 5
<223> OTHER INFORMATION: Xaa = Ser, Gly, Glu, Phe, Trp, His, Ile, Val,
      Asn, Tyr, Thr, or Arg
<220> FEATURE:
<221> NAME/KEY: VARIANT
<222> LOCATION: 6
<223> OTHER INFORMATION: Xaa = Thr, His, Leu, Phe, Pro, Ile, Ser, Tyr,
      Lys, Ala, Asp, Val, Asn, or Gly
<220> FEATURE:
<221> NAME/KEY: VARIANT
<222> LOCATION: 7
<223> OTHER INFORMATION: Xaa = Asp, Ala, Met, Tyr, Phe, Ser, Thr, Gly,
      or Trp
<220> FEATURE:
<221> NAME/KEY: VARIANT
<222> LOCATION: 8
<223> OTHER INFORMATION: Xaa = Thr, Ser, Phe, Gln, Ala, Asn, Leu, Glu,
      Ile, Gly, or Met
<220> FEATURE:
<221> NAME/KEY: VARIANT
<222> LOCATION: 9
<223> OTHER INFORMATION: Xaa = Cys, Thr, Asn, Ser, or Ala

<400> SEQUENCE: 78

Gly Arg Tyr Xaa Xaa Xaa Xaa Xaa Xaa Tyr Gly Phe Asp Tyr
1               5                   10


<210> SEQ ID NO 79
```

```
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Asn, Asp, Ser, Arg, Ala, Thr, Leu, Tyr,
      Gln, Trp, or Gly
<220> FEATURE:
<221> NAME/KEY: VARIANT
<222> LOCATION: 5
<223> OTHER INFORMATION: Xaa = Asn, Asp, Glu, Thr, Tyr, Gly, Ala, Met,
      Phe, Ser, Ile, or Leu
<220> FEATURE:
<221> NAME/KEY: VARIANT
<222> LOCATION: 6
<223> OTHER INFORMATION: Xaa = Trp, Ser, Pro, Val, Gly, or Arg
<220> FEATURE:
<221> NAME/KEY: VARIANT
<222> LOCATION: 8
<223> OTHER INFORMATION: Xaa = Pro, Tyr, His, Ser, Phe, Asn, Asp, val,
      or Gly

<400> SEQUENCE: 79

Gln Gln Tyr Xaa Xaa Xaa Pro Xaa Thr
1               5


<210> SEQ ID NO 80
<211> LENGTH: 123
<212> TYPE: PRT
<213> ORGANISM: Artificial Sequence
<220> FEATURE:
<223> OTHER INFORMATION: Synthetic Construct

<400> SEQUENCE: 80

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Asn Tyr Ala Gln Lys Ser
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Cys Ser Thr Asp Thr Cys Tyr Gly Phe Asp Tyr
            100                 105                 110

Trp Gly Gln Gly Thr Leu Val Thr Val Ser Ser
        115                 120


<210> SEQ ID NO 81
<211> LENGTH: 123
<212> TYPE: PRT
<213> ORGANISM: Artificial Sequence
<220> FEATURE:
<223> OTHER INFORMATION: Synthetic Construct

<400> SEQUENCE: 81

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30
```

```
Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Cys Gly His Ala Ser Cys Tyr Gly Phe Asp Tyr
            100                 105                 110

Trp Gly Gln Gly Thr Leu Val Thr Val Ser Ser
        115                 120


<210> SEQ ID NO 82
<211> LENGTH: 123
<212> TYPE: PRT
<213> ORGANISM: Artificial Sequence
<220> FEATURE:
<223> OTHER INFORMATION: Synthetic Construct

<400> SEQUENCE: 82

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Met Phe Thr Tyr Gly Phe Asp Tyr
            100                 105                 110

Trp Gly Gln Gly Thr Leu Val Thr Val Ser Ser
        115                 120


<210> SEQ ID NO 83
<211> LENGTH: 123
<212> TYPE: PRT
<213> ORGANISM: Artificial Sequence
<220> FEATURE:
<223> OTHER INFORMATION: Synthetic Construct

<400> SEQUENCE: 83

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
```

85 90 95

Ala Thr Gly Arg Tyr Thr Glu Leu Tyr Gln Asn Tyr Gly Phe Asp Tyr
100 105 110

Trp Gly Gln Gly Thr Leu Val Thr Val Ser Ser
115 120

<210> SEQ ID NO 84
<211> LENGTH: 123
<212> TYPE: PRT
<213> ORGANISM: Artificial Sequence
<220> FEATURE:
<223> OTHER INFORMATION: Synthetic Construct

<400> SEQUENCE: 84

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Ser
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Glu Leu Phe Ala Ser Tyr Gly Phe Asp Tyr
100 105 110

Trp Gly Gln Gly Thr Leu Val Thr Val Ser Ser
115 120

<210> SEQ ID NO 85
<211> LENGTH: 123
<212> TYPE: PRT
<213> ORGANISM: Artificial Sequence
<220> FEATURE:
<223> OTHER INFORMATION: Synthetic Construct

<400> SEQUENCE: 85

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Ala Ile Tyr Ala Gln Lys Ser
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Ser Glu His Ser Thr Ser Tyr Gly Phe Asp Tyr
100 105 110

Trp Gly Gln Gly Thr Leu Val Thr Val Ser Ser
115 120

<210> SEQ ID NO 86
<211> LENGTH: 123

```
<212> TYPE: PRT
<213> ORGANISM: Artificial Sequence
<220> FEATURE:
<223> OTHER INFORMATION: Synthetic Construct

<400> SEQUENCE: 86

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Ser
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Gly Leu Met Asn Ser Tyr Gly Phe Asp Tyr
            100                 105                 110

Trp Gly Gln Gly Thr Leu Val Thr Val Ser Ser
        115                 120


<210> SEQ ID NO 87
<211> LENGTH: 123
<212> TYPE: PRT
<213> ORGANISM: Artificial Sequence
<220> FEATURE:
<223> OTHER INFORMATION: Synthetic Construct

<400> SEQUENCE: 87

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ile Ser Phe Met Phe Thr Tyr Gly Phe Asp Tyr
            100                 105                 110

Trp Gly Gln Gly Thr Leu Val Thr Val Ser Ser
        115                 120


<210> SEQ ID NO 88
<211> LENGTH: 123
<212> TYPE: PRT
<213> ORGANISM: Artificial Sequence
<220> FEATURE:
<223> OTHER INFORMATION: Synthetic Construct

<400> SEQUENCE: 88

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
```

```
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Cys Phe Pro Asp Thr Cys Tyr Gly Phe Asp Tyr
            100                 105                 110

Trp Gly Gln Gly Thr Leu Val Thr Val Ser Ser
        115                 120


<210> SEQ ID NO 89
<211> LENGTH: 123
<212> TYPE: PRT
<213> ORGANISM: Artificial Sequence
<220> FEATURE:
<223> OTHER INFORMATION: Synthetic Construct

<400> SEQUENCE: 89

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Cys Ser Thr Asp Thr Cys Tyr Gly Phe Asp Tyr
            100                 105                 110

Trp Gly Gln Gly Thr Leu Val Thr Val Ser Ser
        115                 120


<210> SEQ ID NO 90
<211> LENGTH: 123
<212> TYPE: PRT
<213> ORGANISM: Artificial Sequence
<220> FEATURE:
<223> OTHER INFORMATION: Synthetic Construct

<400> SEQUENCE: 90

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80
```

Leu Glu Leu Ser Ser Leu Arg Ser Glu Asp Thr Ala Leu Tyr Tyr Cys
85 90 95

Ala Thr Gly Arg Tyr Ser Phe Thr Asp Leu Ala Tyr Gly Phe Asp Tyr
100 105 110

Trp Gly Gln Gly Thr Leu Val Thr Val Ser Ser
115 120

<210> SEQ ID NO 91
<211> LENGTH: 123
<212> TYPE: PRT
<213> ORGANISM: Artificial Sequence
<220> FEATURE:
<223> OTHER INFORMATION: Synthetic Construct

<400> SEQUENCE: 91

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 92
<211> LENGTH: 123
<212> TYPE: PRT
<213> ORGANISM: Artificial Sequence
<220> FEATURE:
<223> OTHER INFORMATION: Synthetic Construct

<400> SEQUENCE: 92

Gln Met Gln Leu Val Gln Ser Gly Ala Glu Val Lys Lys Pro Gly Ala
1 5 10 15

Ser Val Lys Val Ser Cys Lys Val Ser Gly His Thr Leu Thr Glu Leu
20 25 30

Ser Met His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Ala Phe Ile Asp Thr Ala Tyr Gly Phe Asp Tyr
100 105 110

Trp Gly Gln Gly Thr Leu Val Thr Val Ser Ser
115 120

<210> SEQ ID NO 93

<211> LENGTH: 123
<212> TYPE: PRT
<213> ORGANISM: Artificial Sequence
<220> FEATURE:
<223> OTHER INFORMATION: Synthetic Construct

<400> SEQUENCE: 93

Gln Met Gln Leu Val Gln Ser Gly Ala Glu Val Lys Lys Pro Gly Ala
1 5 10 15

Ser Val Lys Val Ser Cys Lys Val Ser Gly His Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Cys Ser Ser Asp Leu Cys Tyr Gly Phe Asp Tyr
100 105 110

Trp Gly Gln Gly Thr Leu Val Thr Val Ser Ser
115 120

<210> SEQ ID NO 94
<211> LENGTH: 123
<212> TYPE: PRT
<213> ORGANISM: Artificial Sequence
<220> FEATURE:
<223> OTHER INFORMATION: Synthetic Construct

<400> SEQUENCE: 94

Gln Met Gln Leu Val Gln Ser Gly Ala Glu Val Lys Lys Pro Gly Ala
1 5 10 15

Ser Val Lys Val Ser Cys Lys Val Ser Gly His Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Asp Glu Ser Tyr Gly Phe Asp Tyr
100 105 110

Trp Gly Gln Gly Thr Leu Val Thr Val Ser Ser
115 120

<210> SEQ ID NO 95
<211> LENGTH: 123
<212> TYPE: PRT
<213> ORGANISM: Artificial Sequence
<220> FEATURE:
<223> OTHER INFORMATION: Synthetic Construct

<400> SEQUENCE: 95

Gln Met Gln Leu Val Gln Ser Gly Ala Glu Val Lys Lys Pro Gly Ala
1 5 10 15

```
Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ser Ser Tyr Asp Ile Ala Tyr Gly Phe Asp Tyr
            100                 105                 110

Trp Gly Gln Gly Thr Leu Val Thr Val Ser Ser
        115                 120


<210> SEQ ID NO 96
<211> LENGTH: 123
<212> TYPE: PRT
<213> ORGANISM: Artificial Sequence
<220> FEATURE:
<223> OTHER INFORMATION: Synthetic Construct

<400> SEQUENCE: 96

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ala Trp Thr Asp Ile Ala Tyr Gly Phe Asp Tyr
            100                 105                 110

Trp Gly Gln Gly Thr Leu Val Thr Val Ser Ser
        115                 120


<210> SEQ ID NO 97
<211> LENGTH: 123
<212> TYPE: PRT
<213> ORGANISM: Artificial Sequence
<220> FEATURE:
<223> OTHER INFORMATION: Synthetic Construct

<400> SEQUENCE: 97

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Ser
    50                  55                  60

Gln Gly Arg Val Thr Met Thr Gly Asp Thr Ser Thr Asp Thr Ala Tyr
65                  70                  75                  80
```

```
Leu Glu Leu Ser Ser Leu Arg Ser Glu Asp Thr Ala Leu Tyr Tyr Cys
                85                  90                  95

Ala Thr Gly Arg Tyr Cys Phe Tyr Asp Leu Cys Tyr Gly Phe Asp Tyr
            100                 105                 110

Trp Gly Gln Gly Thr Leu Val Thr Val Ser Ser
        115                 120
```

<210> SEQ ID NO 98
<211> LENGTH: 123
<212> TYPE: PRT
<213> ORGANISM: Artificial Sequence
<220> FEATURE:
<223> OTHER INFORMATION: Synthetic Construct

<400> SEQUENCE: 98

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Ser
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ser Ser Tyr Phe Thr Asn Tyr Gly Phe Asp Tyr
            100                 105                 110

Trp Gly Gln Gly Thr Leu Val Thr Val Ser Ser
        115                 120
```

<210> SEQ ID NO 99
<211> LENGTH: 123
<212> TYPE: PRT
<213> ORGANISM: Artificial Sequence
<220> FEATURE:
<223> OTHER INFORMATION: Synthetic Construct

<400> SEQUENCE: 99

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Ser
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Val Ser Leu Phe Phe Asn Tyr Gly Phe Asp Tyr
            100                 105                 110

Trp Gly Gln Gly Thr Leu Val Thr Val Ser Ser
        115                 120
```

<210> SEQ ID NO 100
<211> LENGTH: 123
<212> TYPE: PRT
<213> ORGANISM: Artificial Sequence
<220> FEATURE:
<223> OTHER INFORMATION: Synthetic Construct

<400> SEQUENCE: 100

Gln Met Gln Leu Val Gln Ser Gly Ala Glu Val Lys Lys Pro Gly Ala
1 5 10 15

Ser Val Lys Val Ser Cys Lys Val Ser Gly His Thr Leu Thr Glu Leu
20 25 30

Ser Met His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Cys His Lys Asp Gly Cys Tyr Gly Phe Asp Tyr
100 105 110

Trp Gly Gln Gly Thr Leu Val Thr Val Ser Ser
115 120

<210> SEQ ID NO 101
<211> LENGTH: 123
<212> TYPE: PRT
<213> ORGANISM: Artificial Sequence
<220> FEATURE:
<223> OTHER INFORMATION: Synthetic Construct

<400> SEQUENCE: 101

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Ser
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Gly Leu Tyr Ala Ser Tyr Gly Phe Asp Tyr
100 105 110

Trp Gly Gln Gly Thr Leu Val Thr Val Ser Ser
115 120

<210> SEQ ID NO 102
<211> LENGTH: 123
<212> TYPE: PRT
<213> ORGANISM: Artificial Sequence
<220> FEATURE:
<223> OTHER INFORMATION: Synthetic Construct

<400> SEQUENCE: 102

Gln Met Gln Leu Val Gln Ser Gly Ala Glu Val Lys Lys Pro Gly Ala
1 5 10 15

```
Ser Val Lys Val Ser Cys Lys Val Ser Gly His Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Cys Glu Thr Asp Ile Cys Tyr Gly Phe Asp Tyr
            100                 105                 110

Trp Gly Gln Gly Thr Leu Val Thr Val Ser Ser
        115                 120


<210> SEQ ID NO 103
<211> LENGTH: 123
<212> TYPE: PRT
<213> ORGANISM: Artificial Sequence
<220> FEATURE:
<223> OTHER INFORMATION: Synthetic Construct

<400> SEQUENCE: 103

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Pro Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ile Ile Thr Thr Asn Tyr Gly Phe Asp Tyr
            100                 105                 110

Trp Gly Gln Gly Thr Leu Val Thr Val Ser Ser
        115                 120


<210> SEQ ID NO 104
<211> LENGTH: 123
<212> TYPE: PRT
<213> ORGANISM: Artificial Sequence
<220> FEATURE:
<223> OTHER INFORMATION: Synthetic Construct

<400> SEQUENCE: 104

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Gly Asp Gly Glu Glu Thr Ile Tyr Ala Gln Lys Phe
    50                  55                  60

Gln Gly Arg Val Thr Met Thr Gly Asp Thr Ser Thr Asp Thr Ala Tyr
```

```
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Ala Thr Tyr Gly Phe Asp Tyr
            100                 105                 110

Trp Gly Gln Gly Thr Leu Val Thr Val Ser Ser
        115                 120


<210> SEQ ID NO 105
<211> LENGTH: 123
<212> TYPE: PRT
<213> ORGANISM: Artificial Sequence
<220> FEATURE:
<223> OTHER INFORMATION: Synthetic Construct

<400> SEQUENCE: 105

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Gly Asp Ile Glu Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 106
<211> LENGTH: 123
<212> TYPE: PRT
<213> ORGANISM: Artificial Sequence
<220> FEATURE:
<223> OTHER INFORMATION: Synthetic Construct

<400> SEQUENCE: 106

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Ala Thr Tyr Gly Phe Asp Tyr
            100                 105                 110

Trp Gly Gln Gly Thr Leu Val Thr Val Ser Ser
        115                 120
```

<210> SEQ ID NO 107
<211> LENGTH: 123
<212> TYPE: PRT
<213> ORGANISM: Artificial Sequence
<220> FEATURE:
<223> OTHER INFORMATION: Synthetic Construct

<400> SEQUENCE: 107

```
Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Cys Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Trp
                85                  90                  95

Ala Thr Gly Arg Tyr Ala Val Thr Asp Met Ala Tyr Gly Phe Asp Tyr
            100                 105                 110

Trp Gly Gln Glu Thr Leu Val Ser Val Ser Ser
        115                 120
```

<210> SEQ ID NO 108
<211> LENGTH: 123
<212> TYPE: PRT
<213> ORGANISM: Artificial Sequence
<220> FEATURE:
<223> OTHER INFORMATION: Synthetic Construct

<400> SEQUENCE: 108

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ala Phe Ala Gly Leu Ala Tyr Gly Phe Asp Tyr
            100                 105                 110

Trp Gly Gln Gly Thr Leu Val Thr Val Ser Ser
        115                 120
```

<210> SEQ ID NO 109
<211> LENGTH: 123
<212> TYPE: PRT
<213> ORGANISM: Artificial Sequence
<220> FEATURE:
<223> OTHER INFORMATION: Synthetic Construct

<400> SEQUENCE: 109

```
Gln Met Gln Leu Val Gln Ser Gly Ala Glu Val Lys Lys Pro Gly Ala
```

```
1               5                   10                  15

Ser Val Lys Val Ser Cys Lys Val Ser Gly His Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Ser
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Asn Asp Phe Ala Asn Tyr Gly Phe Asp Tyr
            100                 105                 110

Trp Gly Gln Gly Thr Leu Val Thr Val Ser Ser
        115                 120


<210> SEQ ID NO 110
<211> LENGTH: 123
<212> TYPE: PRT
<213> ORGANISM: Artificial Sequence
<220> FEATURE:
<223> OTHER INFORMATION: Synthetic Construct

<400> SEQUENCE: 110

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ser Ser Val Gly Ser Thr Tyr Gly Phe Asp Tyr
            100                 105                 110

Trp Gly Gln Gly Thr Leu Val Thr Val Ser Ser
        115                 120


<210> SEQ ID NO 111
<211> LENGTH: 123
<212> TYPE: PRT
<213> ORGANISM: Artificial Sequence
<220> FEATURE:
<223> OTHER INFORMATION: Synthetic Construct

<400> SEQUENCE: 111

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60
```

```
Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ala Asn Leu Tyr Asn Asn Tyr Gly Phe Asp Tyr
            100                 105                 110

Trp Gly Gln Gly Thr Leu Val Thr Val Ser Ser
        115                 120


<210> SEQ ID NO 112
<211> LENGTH: 123
<212> TYPE: PRT
<213> ORGANISM: Artificial Sequence
<220> FEATURE:
<223> OTHER INFORMATION: Synthetic Construct

<400> SEQUENCE: 112

Gln Met Gln Leu Val Gln Ser Gly Ala Glu Val Lys Lys Pro Gly Ala
1               5                   10                  15

Ser Val Lys Val Ser Cys Lys Val Ser Gly His Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Val Tyr Leu Ala Ser Asn Tyr Gly Phe Asp Tyr
            100                 105                 110

Trp Gly Gln Gly Thr Leu Val Thr Val Ser Ser
        115                 120


<210> SEQ ID NO 113
<211> LENGTH: 123
<212> TYPE: PRT
<213> ORGANISM: Artificial Sequence
<220> FEATURE:
<223> OTHER INFORMATION: Synthetic Construct

<400> SEQUENCE: 113

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ser Thr Asn Phe Ser Asn Tyr Gly Phe Asp Tyr
            100                 105                 110

Trp Gly Gln Gly Thr Leu Val Thr Val Ser Ser
        115                 120
```

<210> SEQ ID NO 114
<211> LENGTH: 123
<212> TYPE: PRT
<213> ORGANISM: Artificial Sequence
<220> FEATURE:
<223> OTHER INFORMATION: Synthetic Construct

<400> SEQUENCE: 114

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Met His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Ser
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Arg Gly Trp Phe Asn Tyr Gly Phe Asp Tyr
100 105 110

Trp Gly Gln Gly Thr Leu Val Thr Val Ser Ser
115 120

<210> SEQ ID NO 115
<211> LENGTH: 123
<212> TYPE: PRT
<213> ORGANISM: Artificial Sequence
<220> FEATURE:
<223> OTHER INFORMATION: Synthetic Construct

<400> SEQUENCE: 115

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Thr Gly Asp Asp Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Asp Ala Thr Tyr Gly Phe Asp Tyr
100 105 110

Trp Gly Gln Gly Thr Leu Val Thr Val Ser Ser
115 120

<210> SEQ ID NO 116
<211> LENGTH: 123
<212> TYPE: PRT
<213> ORGANISM: Artificial Sequence
<220> FEATURE:
<223> OTHER INFORMATION: Synthetic Construct

<400> SEQUENCE: 116

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Ser Glu Trp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 117
<211> LENGTH: 123
<212> TYPE: PRT
<213> ORGANISM: Artificial Sequence
<220> FEATURE:
<223> OTHER INFORMATION: Synthetic Construct

<400> SEQUENCE: 117

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Val Ala Ser Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Asp Ala Thr Tyr Gly Phe Asp Tyr
            100                 105                 110

Trp Gly Gln Gly Thr Leu Val Thr Val Ser Ser
        115                 120


<210> SEQ ID NO 118
<211> LENGTH: 123
<212> TYPE: PRT
<213> ORGANISM: Artificial Sequence
<220> FEATURE:
<223> OTHER INFORMATION: Synthetic Construct

<400> SEQUENCE: 118

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Gly Asp Trp His Glu Thr Ile Tyr Ala Gln Lys Phe
    50                  55                  60
```

```
Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Asp Ala Thr Tyr Gly Phe Asp Tyr
            100                 105                 110

Trp Gly Gln Gly Thr Leu Val Thr Val Ser Ser
        115                 120


<210> SEQ ID NO 119
<211> LENGTH: 123
<212> TYPE: PRT
<213> ORGANISM: Artificial Sequence
<220> FEATURE:
<223> OTHER INFORMATION: Synthetic Construct

<400> SEQUENCE: 119

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Ala Trp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 120
<211> LENGTH: 123
<212> TYPE: PRT
<213> ORGANISM: Artificial Sequence
<220> FEATURE:
<223> OTHER INFORMATION: Synthetic Construct

<400> SEQUENCE: 120

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Ser Glu Val Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Ala Thr Tyr Gly Phe Asp Tyr
            100                 105                 110

Trp Gly Gln Gly Thr Leu Val Thr Val Ser Ser
```

```
        115                 120


<210> SEQ ID NO 121
<211> LENGTH: 123
<212> TYPE: PRT
<213> ORGANISM: Artificial Sequence
<220> FEATURE:
<223> OTHER INFORMATION: Synthetic Construct

<400> SEQUENCE: 121

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Ser
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Ser Glu Ser Phe Ala Ser Tyr Gly Phe Asp Tyr
            100                 105                 110

Trp Gly Gln Gly Thr Leu Val Thr Val Ser Ser
        115                 120


<210> SEQ ID NO 122
<211> LENGTH: 107
<212> TYPE: PRT
<213> ORGANISM: Artificial Sequence
<220> FEATURE:
<223> OTHER INFORMATION: Synthetic Construct

<400> SEQUENCE: 122

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Asn Trp Pro Pro
                85                  90                  95

Thr Phe Gly Gln Gly Thr Lys Leu Glu Ile Lys
            100                 105


<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Glu Ile Val Met Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Pro
                85                  90                  95

Thr Phe Gly Gln Gly Thr Lys Leu Glu Ile Lys
            100                 105


<210> SEQ ID NO 124
<211> LENGTH: 107
<212> TYPE: PRT
<213> ORGANISM: Artificial Sequence
<220> FEATURE:
<223> OTHER INFORMATION: Synthetic Construct

<400> SEQUENCE: 124

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105


<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Trp Pro Tyr
                85                  90                  95

Thr Phe Gly Gln Gly Thr Lys Leu Glu Ile Lys
```

100 105

<210> SEQ ID NO 126
<211> LENGTH: 107
<212> TYPE: PRT
<213> ORGANISM: Artificial Sequence
<220> FEATURE:
<223> OTHER INFORMATION: Synthetic Construct

<400> SEQUENCE: 126

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Ser Pro His
85 90 95

Thr Phe Gly Gln Gly Thr Lys Leu Glu Ile Lys
100 105

<210> SEQ ID NO 128
<211> LENGTH: 107
<212> TYPE: PRT
<213> ORGANISM: Artificial Sequence
<220> FEATURE:
<223> OTHER INFORMATION: Synthetic Construct

<400> SEQUENCE: 128

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

```
Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Ser Pro Pro
                85                  90                  95

Thr Phe Gly Gln Gly Thr Lys Leu Glu Ile Lys
            100                 105


<210> SEQ ID NO 129
<211> LENGTH: 107
<212> TYPE: PRT
<213> ORGANISM: Artificial Sequence
<220> FEATURE:
<223> OTHER INFORMATION: Synthetic Construct

<400> SEQUENCE: 129

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ser Asn Ser Pro Pro
                85                  90                  95

Thr Phe Gly Gln Gly Thr Lys Leu Glu Ile Lys
            100                 105


<210> SEQ ID NO 130
<211> LENGTH: 107
<212> TYPE: PRT
<213> ORGANISM: Artificial Sequence
<220> FEATURE:
<223> OTHER INFORMATION: Synthetic Construct

<400> SEQUENCE: 130

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Ser Pro Tyr
                85                  90                  95

Thr Phe Gly Gln Gly Thr Lys Leu Glu Ile Lys
            100                 105
```

<210> SEQ ID NO 131
<211> LENGTH: 107
<212> TYPE: PRT
<213> ORGANISM: Artificial Sequence
<220> FEATURE:
<223> OTHER INFORMATION: Synthetic Construct

<400> SEQUENCE: 131

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asn Ser Ser Pro Pro
                85                  90                  95

Thr Phe Gly Gln Gly Thr Lys Leu Glu Ile Lys
            100                 105
```

<210> SEQ ID NO 132
<211> LENGTH: 107
<212> TYPE: PRT
<213> ORGANISM: Artificial Sequence
<220> FEATURE:
<223> OTHER INFORMATION: Synthetic Construct

<400> SEQUENCE: 132

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Ser Pro Ser
                85                  90                  95

Thr Phe Gly Gln Gly Thr Lys Leu Glu Ile Lys
            100                 105
```

<210> SEQ ID NO 133
<211> LENGTH: 107
<212> TYPE: PRT
<213> ORGANISM: Artificial Sequence
<220> FEATURE:
<223> OTHER INFORMATION: Synthetic Construct

<400> SEQUENCE: 133

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Ser Pro His
                85                  90                  95

Thr Phe Gly Gln Gly Thr Lys Leu Glu Ile Lys
            100                 105


<210> SEQ ID NO 134
<211> LENGTH: 107
<212> TYPE: PRT
<213> ORGANISM: Artificial Sequence
<220> FEATURE:
<223> OTHER INFORMATION: Synthetic Construct

<400> SEQUENCE: 134

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Arg Asn Trp Pro Phe
                85                  90                  95

Thr Phe Gly Gln Gly Thr Lys Leu Glu Ile Lys
            100                 105


<210> SEQ ID NO 135
<211> LENGTH: 107
<212> TYPE: PRT
<213> ORGANISM: Artificial Sequence
<220> FEATURE:
<223> OTHER INFORMATION: Synthetic Construct

<400> SEQUENCE: 135

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Asn Pro Pro Asn
                85                  90                  95

Thr Phe Gly Gln Gly Thr Lys Leu Glu Ile Lys
            100                 105


<210> SEQ ID NO 136
<211> LENGTH: 107
<212> TYPE: PRT
```

<213> ORGANISM: Artificial Sequence
<220> FEATURE:
<223> OTHER INFORMATION: Synthetic Construct

<400> SEQUENCE: 136

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Thr Asn Val Pro Asp
85 90 95

Thr Phe Gly Gln Gly Thr Lys Leu Glu Ile Lys
100 105

<210> SEQ ID NO 137
<211> LENGTH: 107
<212> TYPE: PRT
<213> ORGANISM: Artificial Sequence
<220> FEATURE:
<223> OTHER INFORMATION: Synthetic Construct

<400> SEQUENCE: 137

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asn Asn Ser Pro Pro
85 90 95

Thr Phe Gly Gln Gly Thr Lys Leu Glu Ile Lys
100 105

<210> SEQ ID NO 138
<211> LENGTH: 107
<212> TYPE: PRT
<213> ORGANISM: Artificial Sequence
<220> FEATURE:
<223> OTHER INFORMATION: Synthetic Construct

<400> SEQUENCE: 138

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

```
Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Ser Pro Pro
                85                  90                  95

Thr Phe Gly Gln Gly Thr Lys Leu Glu Ile Lys
            100                 105


<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Leu Asn Ser Pro Phe
                85                  90                  95

Thr Phe Gly Gln Gly Thr Lys Leu Glu Ile Lys
            100                 105


<210> SEQ ID NO 140
<211> LENGTH: 107
<212> TYPE: PRT
<213> ORGANISM: Artificial Sequence
<220> FEATURE:
<223> OTHER INFORMATION: Synthetic Construct

<400> SEQUENCE: 140

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ser Asn Val Pro Val
                85                  90                  95

Thr Phe Gly Gln Gly Thr Lys Leu Glu Ile Lys
            100                 105


<210> SEQ ID NO 141
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 141

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Tyr Asn Gly Pro Gly
85 90 95

Thr Phe Gly Gln Gly Thr Lys Leu Glu Ile Lys
100 105

<210> SEQ ID NO 142
<211> LENGTH: 107
<212> TYPE: PRT
<213> ORGANISM: Artificial Sequence
<220> FEATURE:
<223> OTHER INFORMATION: Synthetic Construct

<400> SEQUENCE: 142

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Gly Asn Arg Pro Asp
85 90 95

Thr Phe Gly Gln Gly Thr Lys Leu Glu Ile Lys
100 105

<210> SEQ ID NO 143
<211> LENGTH: 107
<212> TYPE: PRT
<213> ORGANISM: Artificial Sequence
<220> FEATURE:
<223> OTHER INFORMATION: Synthetic Construct

<400> SEQUENCE: 143

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

```
Glu Asp Phe Ala Val Tyr Tyr Cys Gln Gln Tyr Asp Asn Gly Pro Glu
                85                  90                  95

Thr Phe Gly Gln Gly Thr Lys Leu Glu Ile Lys
            100                 105


<210> SEQ ID NO 144
<211> LENGTH: 107
<212> TYPE: PRT
<213> ORGANISM: Artificial Sequence
<220> FEATURE:
<223> OTHER INFORMATION: Synthetic Construct

<400> SEQUENCE: 144

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Arg Asn Gly Pro Pro
                85                  90                  95

Thr Phe Gly Gln Gly Thr Lys Leu Glu Ile Lys
            100                 105


<210> SEQ ID NO 145
<211> LENGTH: 330
<212> TYPE: PRT
<213> ORGANISM: Artificial Sequence
<220> FEATURE:
<223> OTHER INFORMATION: Synthetic Construct

<400> SEQUENCE: 145

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 146
<211> LENGTH: 327
<212> TYPE: PRT
<213> ORGANISM: Artificial Sequence
<220> FEATURE:
<223> OTHER INFORMATION: Synthetic Construct

<400> SEQUENCE: 146

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 147
<211> LENGTH: 107
<212> TYPE: PRT
<213> ORGANISM: Artificial Sequence
<220> FEATURE:
<223> OTHER INFORMATION: Synthetic Construct

<400> SEQUENCE: 147

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 148
<211> LENGTH: 400
<212> TYPE: PRT
<213> ORGANISM: Artificial Sequence
<220> FEATURE:
<223> OTHER INFORMATION: Synthetic Construct

<400> SEQUENCE: 148

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60
```

```
Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
    210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
    290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
                325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
        355                 360                 365

Asn His Glu Val Glu Asp Glu Ile Ile Trp Glu Glu Phe Thr Pro Glu
    370                 375                 380

Glu Gly Lys Gly Tyr Arg Glu Glu Val Leu Thr Val Lys Glu Ile Thr
385                 390                 395                 400
```

<210> SEQ ID NO 149
<211> LENGTH: 320
<212> TYPE: PRT
<213> ORGANISM: Artificial Sequence
<220> FEATURE:
<223> OTHER INFORMATION: Synthetic Construct

<400> SEQUENCE: 149

```
Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30
```

```
Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
    210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
    290                 295                 300

Asn Trp Ser Ser Trp Ser Glu Ala Ile Glu Phe Gly Ser Asp Asp Gly
305                 310                 315                 320


<210> SEQ ID NO 150
<211> LENGTH: 107
<212> TYPE: PRT
<213> ORGANISM: Artificial Sequence
<220> FEATURE:
<223> OTHER INFORMATION: Synthetic Construct

<400> SEQUENCE: 150

Glu Ile Val Met Thr Gln Ser Pro Ala Thr Leu Ser Leu Ser Pro Gly
1               5                   10                  15

Glu Arg Ala Thr Leu Ser Cys Arg Ala Ala Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80
```

```
Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Glu Ile Val Met Thr Gln Ser Pro Ala Thr Leu Ser Leu Ser Pro Gly
1               5                   10                  15

Glu Arg Ala Thr Leu Ser Cys Arg Ala Cys Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 152
<211> LENGTH: 107
<212> TYPE: PRT
<213> ORGANISM: Artificial Sequence
<220> FEATURE:
<223> OTHER INFORMATION: Synthetic Construct

<400> SEQUENCE: 152

Glu Ile Val Met Thr Gln Ser Pro Ala Thr Leu Ser Leu Ser Pro Gly
1               5                   10                  15

Glu Arg Ala Thr Leu Ser Cys Arg Ala Gly Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 153
<211> LENGTH: 107
<212> TYPE: PRT
<213> ORGANISM: Artificial Sequence
<220> FEATURE:
<223> OTHER INFORMATION: Synthetic Construct

<400> SEQUENCE: 153

Glu Ile Val Met Thr Gln Ser Pro Ala Thr Leu Ser Leu Ser Pro Gly
```

1 5 10 15

Glu Arg Ala Thr Leu Ser Cys Arg Ala His Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 154
<211> LENGTH: 107
<212> TYPE: PRT
<213> ORGANISM: Artificial Sequence
<220> FEATURE:
<223> OTHER INFORMATION: Synthetic Construct

<400> SEQUENCE: 154

Glu Ile Val Met Thr Gln Ser Pro Ala Thr Leu Ser Leu Ser Pro Gly
1 5 10 15

Glu Arg Ala Thr Leu Ser Cys Arg Ala Ile Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 155
<211> LENGTH: 107
<212> TYPE: PRT
<213> ORGANISM: Artificial Sequence
<220> FEATURE:
<223> OTHER INFORMATION: Synthetic Construct

<400> SEQUENCE: 155

Glu Ile Val Met Thr Gln Ser Pro Ala Thr Leu Ser Leu Ser Pro Gly
1 5 10 15

Glu Arg Ala Thr Leu Ser Cys Arg Ala Lys Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 156
<211> LENGTH: 107
<212> TYPE: PRT
<213> ORGANISM: Artificial Sequence
<220> FEATURE:
<223> OTHER INFORMATION: Synthetic Construct

<400> SEQUENCE: 156

Glu Ile Val Met Thr Gln Ser Pro Ala Thr Leu Ser Leu Ser Pro Gly
1 5 10 15

Glu Arg Ala Thr Leu Ser Cys Arg Ala Leu Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 157
<211> LENGTH: 107
<212> TYPE: PRT
<213> ORGANISM: Artificial Sequence
<220> FEATURE:
<223> OTHER INFORMATION: Synthetic Construct

<400> SEQUENCE: 157

Glu Ile Val Met Thr Gln Ser Pro Ala Thr Leu Ser Leu Ser Pro Gly
1 5 10 15

Glu Arg Ala Thr Leu Ser Cys Arg Ala Met Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 158
<211> LENGTH: 107
<212> TYPE: PRT
<213> ORGANISM: Artificial Sequence
<220> FEATURE:
<223> OTHER INFORMATION: Synthetic Construct

<400> SEQUENCE: 158

Glu Ile Val Met Thr Gln Ser Pro Ala Thr Leu Ser Leu Ser Pro Gly
1 5 10 15

Glu Arg Ala Thr Leu Ser Cys Arg Ala Asn Gln Ser Val Ser Ser Tyr 20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 159
<211> LENGTH: 107
<212> TYPE: PRT
<213> ORGANISM: Artificial Sequence
<220> FEATURE:
<223> OTHER INFORMATION: Synthetic Construct

<400> SEQUENCE: 159

Glu Ile Val Met Thr Gln Ser Pro Ala Thr Leu Ser Leu Ser Pro Gly
1 5 10 15

Glu Arg Ala Thr Leu Ser Cys Arg Ala Gln Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 160
<211> LENGTH: 107
<212> TYPE: PRT
<213> ORGANISM: Artificial Sequence
<220> FEATURE:
<223> OTHER INFORMATION: Synthetic Construct

<400> SEQUENCE: 160

Glu Ile Val Met Thr Gln Ser Pro Ala Thr Leu Ser Leu Ser Pro Gly
1 5 10 15

Glu Arg Ala Thr Leu Ser Cys Arg Ala Arg Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

```
Glu Ile Val Met Thr Gln Ser Pro Ala Thr Leu Ser Leu Ser Pro Gly
1               5                   10                  15

Glu Arg Ala Thr Leu Ser Cys Arg Ala Thr Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 162
<211> LENGTH: 107
<212> TYPE: PRT
<213> ORGANISM: Artificial Sequence
<220> FEATURE:
<223> OTHER INFORMATION: Synthetic Construct

<400> SEQUENCE: 162

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Ala Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 163
<211> LENGTH: 107
<212> TYPE: PRT
<213> ORGANISM: Artificial Sequence
<220> FEATURE:
<223> OTHER INFORMATION: Synthetic Construct

<400> SEQUENCE: 163

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Cys Ser Val Ser Ser Tyr
            20                  25                  30

Leu Ala Trp Tyr Gln Gln Lys Pro Gly Gln Ala Pro Arg Leu Leu Ile
```

```
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 164
<211> LENGTH: 107
<212> TYPE: PRT
<213> ORGANISM: Artificial Sequence
<220> FEATURE:
<223> OTHER INFORMATION: Synthetic Construct

<400> SEQUENCE: 164

Glu Ile Val Met Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 165
<211> LENGTH: 107
<212> TYPE: PRT
<213> ORGANISM: Artificial Sequence
<220> FEATURE:
<223> OTHER INFORMATION: Synthetic Construct

<400> SEQUENCE: 165

Glu Ile Val Met Thr Gln Ser Pro Ala Thr Leu Ser Leu Ser Pro Gly
1               5                   10                  15

Glu Arg Ala Thr Leu Ser Cys Arg Ala Ser Phe Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 166
<211> LENGTH: 107
```

<212> TYPE: PRT
<213> ORGANISM: Artificial Sequence
<220> FEATURE:
<223> OTHER INFORMATION: Synthetic Construct

<400> SEQUENCE: 166

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Ile Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Leu Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 168
<211> LENGTH: 107
<212> TYPE: PRT
<213> ORGANISM: Artificial Sequence
<220> FEATURE:
<223> OTHER INFORMATION: Synthetic Construct

<400> SEQUENCE: 168

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Pro Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
```

```
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

Glu Ile Val Met Thr Gln Ser Pro Ala Thr Leu Ser Leu Ser Pro Gly
1               5                   10                  15

Glu Arg Ala Thr Leu Ser Cys Arg Ala Ser Arg Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 170
<211> LENGTH: 107
<212> TYPE: PRT
<213> ORGANISM: Artificial Sequence
<220> FEATURE:
<223> OTHER INFORMATION: Synthetic Construct

<400> SEQUENCE: 170

Glu Ile Val Met Thr Gln Ser Pro Ala Thr Leu Ser Leu Ser Pro Gly
1               5                   10                  15

Glu Arg Ala Thr Leu Ser Cys Arg Ala Ser Ser Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 171
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 171

Glu Ile Val Met Thr Gln Ser Pro Ala Thr Leu Ser Leu Ser Pro Gly
1 5 10 15

Glu Arg Ala Thr Leu Ser Cys Arg Ala Ser Thr Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 172
<211> LENGTH: 107
<212> TYPE: PRT
<213> ORGANISM: Artificial Sequence
<220> FEATURE:
<223> OTHER INFORMATION: Synthetic Construct

<400> SEQUENCE: 172

Glu Ile Val Met Thr Gln Ser Pro Ala Thr Leu Ser Leu Ser Pro Gly
1 5 10 15

Glu Arg Ala Thr Leu Ser Cys Arg Ala Ser Val Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 173
<211> LENGTH: 107
<212> TYPE: PRT
<213> ORGANISM: Artificial Sequence
<220> FEATURE:
<223> OTHER INFORMATION: Synthetic Construct

<400> SEQUENCE: 173

Glu Ile Val Met Thr Gln Ser Pro Ala Thr Leu Ser Leu Ser Pro Gly
1 5 10 15

Glu Arg Ala Thr Leu Ser Cys Arg Ala Ser Tyr Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro

```
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 174
<211> LENGTH: 107
<212> TYPE: PRT
<213> ORGANISM: Artificial Sequence
<220> FEATURE:
<223> OTHER INFORMATION: Synthetic Construct

<400> SEQUENCE: 174

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ala Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 175
<211> LENGTH: 107
<212> TYPE: PRT
<213> ORGANISM: Artificial Sequence
<220> FEATURE:
<223> OTHER INFORMATION: Synthetic Construct

<400> SEQUENCE: 175

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Glu Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 176
<211> LENGTH: 107
<212> TYPE: PRT
<213> ORGANISM: Artificial Sequence
<220> FEATURE:
<223> OTHER INFORMATION: Synthetic Construct

<400> SEQUENCE: 176
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Phe Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 177
<211> LENGTH: 107
<212> TYPE: PRT
<213> ORGANISM: Artificial Sequence
<220> FEATURE:
<223> OTHER INFORMATION: Synthetic Construct

<400> SEQUENCE: 177

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln His Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 178
<211> LENGTH: 107
<212> TYPE: PRT
<213> ORGANISM: Artificial Sequence
<220> FEATURE:
<223> OTHER INFORMATION: Synthetic Construct

<400> SEQUENCE: 178

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ile Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
```

```
                85                  90                  95

Thr Phe Gly Gln Gly Thr Lys Leu Glu Ile Lys
            100                 105


<210> SEQ ID NO 179
<211> LENGTH: 107
<212> TYPE: PRT
<213> ORGANISM: Artificial Sequence
<220> FEATURE:
<223> OTHER INFORMATION: Synthetic Construct

<400> SEQUENCE: 179

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Lys Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 180
<211> LENGTH: 107
<212> TYPE: PRT
<213> ORGANISM: Artificial Sequence
<220> FEATURE:
<223> OTHER INFORMATION: Synthetic Construct

<400> SEQUENCE: 180

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Leu Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 181
<211> LENGTH: 107
<212> TYPE: PRT
<213> ORGANISM: Artificial Sequence
<220> FEATURE:
<223> OTHER INFORMATION: Synthetic Construct

<400> SEQUENCE: 181

Glu Ile Val Met Thr Gln Ser Pro Ala Thr Leu Ser Leu Ser Pro Gly
1               5                   10                  15
```

Glu Arg Ala Thr Leu Ser Cys Arg Ala Ser Gln Pro Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 182
<211> LENGTH: 107
<212> TYPE: PRT
<213> ORGANISM: Artificial Sequence
<220> FEATURE:
<223> OTHER INFORMATION: Synthetic Construct

<400> SEQUENCE: 182

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Gln Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 183
<211> LENGTH: 107
<212> TYPE: PRT
<213> ORGANISM: Artificial Sequence
<220> FEATURE:
<223> OTHER INFORMATION: Synthetic Construct

<400> SEQUENCE: 183

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Arg Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys 100 105

<210> SEQ ID NO 184
<211> LENGTH: 107
<212> TYPE: PRT
<213> ORGANISM: Artificial Sequence
<220> FEATURE:
<223> OTHER INFORMATION: Synthetic Construct

<400> SEQUENCE: 184

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Thr Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 185
<211> LENGTH: 107
<212> TYPE: PRT
<213> ORGANISM: Artificial Sequence
<220> FEATURE:
<223> OTHER INFORMATION: Synthetic Construct

<400> SEQUENCE: 185

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Val Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 186
<211> LENGTH: 107
<212> TYPE: PRT
<213> ORGANISM: Artificial Sequence
<220> FEATURE:
<223> OTHER INFORMATION: Synthetic Construct

<400> SEQUENCE: 186

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Trp Val Ser Ser Tyr
20 25 30

```
Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 187
<211> LENGTH: 107
<212> TYPE: PRT
<213> ORGANISM: Artificial Sequence
<220> FEATURE:
<223> OTHER INFORMATION: Synthetic Construct

<400> SEQUENCE: 187

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ala Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 188
<211> LENGTH: 107
<212> TYPE: PRT
<213> ORGANISM: Artificial Sequence
<220> FEATURE:
<223> OTHER INFORMATION: Synthetic Construct

<400> SEQUENCE: 188

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Cys Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 189
<211> LENGTH: 107
<212> TYPE: PRT
<213> ORGANISM: Artificial Sequence
<220> FEATURE:
<223> OTHER INFORMATION: Synthetic Construct

<400> SEQUENCE: 189

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Glu Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 190
<211> LENGTH: 107
<212> TYPE: PRT
<213> ORGANISM: Artificial Sequence
<220> FEATURE:
<223> OTHER INFORMATION: Synthetic Construct

<400> SEQUENCE: 190

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Phe Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 191
<211> LENGTH: 107
<212> TYPE: PRT
<213> ORGANISM: Artificial Sequence
<220> FEATURE:
<223> OTHER INFORMATION: Synthetic Construct

<400> SEQUENCE: 191

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Gly Ser Tyr
20 25 30

Leu Ala Trp Tyr Gln Gln Lys Pro Gly Gln Ala Pro Arg Leu Leu Ile
35 40 45

```
Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 192
<211> LENGTH: 107
<212> TYPE: PRT
<213> ORGANISM: Artificial Sequence
<220> FEATURE:
<223> OTHER INFORMATION: Synthetic Construct

<400> SEQUENCE: 192

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Lys Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 193
<211> LENGTH: 107
<212> TYPE: PRT
<213> ORGANISM: Artificial Sequence
<220> FEATURE:
<223> OTHER INFORMATION: Synthetic Construct

<400> SEQUENCE: 193

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Leu Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 194
<211> LENGTH: 107
<212> TYPE: PRT
```

```
<213> ORGANISM: Artificial Sequence
<220> FEATURE:
<223> OTHER INFORMATION: Synthetic Construct

<400> SEQUENCE: 194

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Met Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 195
<211> LENGTH: 107
<212> TYPE: PRT
<213> ORGANISM: Artificial Sequence
<220> FEATURE:
<223> OTHER INFORMATION: Synthetic Construct

<400> SEQUENCE: 195

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Asn Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 196
<211> LENGTH: 107
<212> TYPE: PRT
<213> ORGANISM: Artificial Sequence
<220> FEATURE:
<223> OTHER INFORMATION: Synthetic Construct

<400> SEQUENCE: 196

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60
```

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 197
<211> LENGTH: 107
<212> TYPE: PRT
<213> ORGANISM: Artificial Sequence
<220> FEATURE:
<223> OTHER INFORMATION: Synthetic Construct

<400> SEQUENCE: 197

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Thr Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 198
<211> LENGTH: 107
<212> TYPE: PRT
<213> ORGANISM: Artificial Sequence
<220> FEATURE:
<223> OTHER INFORMATION: Synthetic Construct

<400> SEQUENCE: 198

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Val Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 199
<211> LENGTH: 107
<212> TYPE: PRT
<213> ORGANISM: Artificial Sequence
<220> FEATURE:
<223> OTHER INFORMATION: Synthetic Construct

<400> SEQUENCE: 199

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Trp Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105

<210> SEQ ID NO 200
<211> LENGTH: 107
<212> TYPE: PRT
<213> ORGANISM: Artificial Sequence
<220> FEATURE:
<223> OTHER INFORMATION: Synthetic Construct

<400> SEQUENCE: 200

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105

<210> SEQ ID NO 201
<211> LENGTH: 107
<212> TYPE: PRT
<213> ORGANISM: Artificial Sequence
<220> FEATURE:
<223> OTHER INFORMATION: Synthetic Construct

<400> SEQUENCE: 201

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ala Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 202
<211> LENGTH: 107
<212> TYPE: PRT
<213> ORGANISM: Artificial Sequence
<220> FEATURE:
<223> OTHER INFORMATION: Synthetic Construct

<400> SEQUENCE: 202

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Gly Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 203
<211> LENGTH: 107
<212> TYPE: PRT
<213> ORGANISM: Artificial Sequence
<220> FEATURE:
<223> OTHER INFORMATION: Synthetic Construct

<400> SEQUENCE: 203

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser His Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 204
<211> LENGTH: 107
<212> TYPE: PRT
<213> ORGANISM: Artificial Sequence
<220> FEATURE:
<223> OTHER INFORMATION: Synthetic Construct

<400> SEQUENCE: 204

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Leu Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 205
<211> LENGTH: 107
<212> TYPE: PRT
<213> ORGANISM: Artificial Sequence
<220> FEATURE:
<223> OTHER INFORMATION: Synthetic Construct

<400> SEQUENCE: 205

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Met Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 206
<211> LENGTH: 107
<212> TYPE: PRT
<213> ORGANISM: Artificial Sequence
<220> FEATURE:
<223> OTHER INFORMATION: Synthetic Construct

<400> SEQUENCE: 206

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Pro Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95
```

```
Thr Phe Gly Gln Gly Thr Lys Leu Glu Ile Lys
            100                 105


<210> SEQ ID NO 207
<211> LENGTH: 107
<212> TYPE: PRT
<213> ORGANISM: Artificial Sequence
<220> FEATURE:
<223> OTHER INFORMATION: Synthetic Construct

<400> SEQUENCE: 207

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gln Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 208
<211> LENGTH: 107
<212> TYPE: PRT
<213> ORGANISM: Artificial Sequence
<220> FEATURE:
<223> OTHER INFORMATION: Synthetic Construct

<400> SEQUENCE: 208

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 209
<211> LENGTH: 107
<212> TYPE: PRT
<213> ORGANISM: Artificial Sequence
<220> FEATURE:
<223> OTHER INFORMATION: Synthetic Construct

<400> SEQUENCE: 209

Glu Ile Val Met Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 210
<211> LENGTH: 107
<212> TYPE: PRT
<213> ORGANISM: Artificial Sequence
<220> FEATURE:
<223> OTHER INFORMATION: Synthetic Construct

<400> SEQUENCE: 210

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 211
<211> LENGTH: 107
<212> TYPE: PRT
<213> ORGANISM: Artificial Sequence
<220> FEATURE:
<223> OTHER INFORMATION: Synthetic Construct

<400> SEQUENCE: 211

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Leu
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 212
<211> LENGTH: 107
<212> TYPE: PRT
<213> ORGANISM: Artificial Sequence
<220> FEATURE:
<223> OTHER INFORMATION: Synthetic Construct

<400> SEQUENCE: 212

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Thr Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 213
<211> LENGTH: 107
<212> TYPE: PRT
<213> ORGANISM: Artificial Sequence
<220> FEATURE:
<223> OTHER INFORMATION: Synthetic Construct

<400> SEQUENCE: 213

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Gly Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 214
<211> LENGTH: 107
<212> TYPE: PRT
<213> ORGANISM: Artificial Sequence
<220> FEATURE:
<223> OTHER INFORMATION: Synthetic Construct

<400> SEQUENCE: 214

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
        35                  40                  45

Tyr Gly His Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 215
<211> LENGTH: 107
<212> TYPE: PRT
<213> ORGANISM: Artificial Sequence
<220> FEATURE:
<223> OTHER INFORMATION: Synthetic Construct

<400> SEQUENCE: 215

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Lys Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 216
<211> LENGTH: 107
<212> TYPE: PRT
<213> ORGANISM: Artificial Sequence
<220> FEATURE:
<223> OTHER INFORMATION: Synthetic Construct

<400> SEQUENCE: 216

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Met Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 217
```

<211> LENGTH: 107
<212> TYPE: PRT
<213> ORGANISM: Artificial Sequence
<220> FEATURE:
<223> OTHER INFORMATION: Synthetic Construct

<400> SEQUENCE: 217

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Arg Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 218
<211> LENGTH: 107
<212> TYPE: PRT
<213> ORGANISM: Artificial Sequence
<220> FEATURE:
<223> OTHER INFORMATION: Synthetic Construct

<400> SEQUENCE: 218

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ser Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 219
<211> LENGTH: 107
<212> TYPE: PRT
<213> ORGANISM: Artificial Sequence
<220> FEATURE:
<223> OTHER INFORMATION: Synthetic Construct

<400> SEQUENCE: 219

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Thr Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 220
<211> LENGTH: 107
<212> TYPE: PRT
<213> ORGANISM: Artificial Sequence
<220> FEATURE:
<223> OTHER INFORMATION: Synthetic Construct

<400> SEQUENCE: 220

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ala Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 221
<211> LENGTH: 107
<212> TYPE: PRT
<213> ORGANISM: Artificial Sequence
<220> FEATURE:
<223> OTHER INFORMATION: Synthetic Construct

<400> SEQUENCE: 221

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Phe Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 222
<211> LENGTH: 107
<212> TYPE: PRT
<213> ORGANISM: Artificial Sequence
<220> FEATURE:
<223> OTHER INFORMATION: Synthetic Construct

<400> SEQUENCE: 222

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala His Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 223
<211> LENGTH: 107
<212> TYPE: PRT
<213> ORGANISM: Artificial Sequence
<220> FEATURE:
<223> OTHER INFORMATION: Synthetic Construct

<400> SEQUENCE: 223

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Leu Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 224
<211> LENGTH: 107
<212> TYPE: PRT
<213> ORGANISM: Artificial Sequence
<220> FEATURE:
<223> OTHER INFORMATION: Synthetic Construct

<400> SEQUENCE: 224

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Asn Ser Arg Ala Thr Gly Ile Pro Asp Arg Phe Ser Gly
50 55 60

```
Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 225
<211> LENGTH: 107
<212> TYPE: PRT
<213> ORGANISM: Artificial Sequence
<220> FEATURE:
<223> OTHER INFORMATION: Synthetic Construct

<400> SEQUENCE: 225

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Gln Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 226
<211> LENGTH: 107
<212> TYPE: PRT
<213> ORGANISM: Artificial Sequence
<220> FEATURE:
<223> OTHER INFORMATION: Synthetic Construct

<400> SEQUENCE: 226

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Arg Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 227
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 227

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Thr Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 228
<211> LENGTH: 107
<212> TYPE: PRT
<213> ORGANISM: Artificial Sequence
<220> FEATURE:
<223> OTHER INFORMATION: Synthetic Construct

<400> SEQUENCE: 228

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Thr Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Asp Asn Trp Pro Tyr
85 90 95

Thr Phe Gly Gln Gly Thr Lys Leu Glu Ile Lys
100 105

<210> SEQ ID NO 229
<211> LENGTH: 107
<212> TYPE: PRT
<213> ORGANISM: Artificial Sequence
<220> FEATURE:
<223> OTHER INFORMATION: Synthetic Construct

<400> SEQUENCE: 229

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Trp Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

```
Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 230
<211> LENGTH: 107
<212> TYPE: PRT
<213> ORGANISM: Artificial Sequence
<220> FEATURE:
<223> OTHER INFORMATION: Synthetic Construct

<400> SEQUENCE: 230

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Trp Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 231
<211> LENGTH: 107
<212> TYPE: PRT
<213> ORGANISM: Artificial Sequence
<220> FEATURE:
<223> OTHER INFORMATION: Synthetic Construct

<400> SEQUENCE: 231

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Tyr Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105
```

<210> SEQ ID NO 232
<211> LENGTH: 107
<212> TYPE: PRT
<213> ORGANISM: Artificial Sequence
<220> FEATURE:
<223> OTHER INFORMATION: Synthetic Construct

<400> SEQUENCE: 232

```
Glu Ile Val Met Thr Gln Ser Pro Ala Thr Leu Ser Leu Ser Pro Gly
```

```
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Asn Trp Pro Tyr
                85                  90                  95

Thr Phe Gly Gln Gly Thr Lys Leu Glu Ile Lys
            100                 105


<210> SEQ ID NO 233
<211> LENGTH: 107
<212> TYPE: PRT
<213> ORGANISM: Artificial Sequence
<220> FEATURE:
<223> OTHER INFORMATION: Synthetic Construct

<400> SEQUENCE: 233

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gln Asn Trp Pro Tyr
                85                  90                  95

Thr Phe Gly Gln Gly Thr Lys Leu Glu Ile Lys
            100                 105


<210> SEQ ID NO 234
<211> LENGTH: 107
<212> TYPE: PRT
<213> ORGANISM: Artificial Sequence
<220> FEATURE:
<223> OTHER INFORMATION: Synthetic Construct

<400> SEQUENCE: 234

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Trp Asn Trp Pro Tyr
                85                  90                  95
```

```
Thr Phe Gly Gln Gly Thr Lys Leu Glu Ile Lys
            100                 105


<210> SEQ ID NO 235
<211> LENGTH: 107
<212> TYPE: PRT
<213> ORGANISM: Artificial Sequence
<220> FEATURE:
<223> OTHER INFORMATION: Synthetic Construct

<400> SEQUENCE: 235

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ala Trp Pro Tyr
                85                  90                  95

Thr Phe Gly Gln Gly Thr Lys Leu Glu Ile Lys
            100                 105


<210> SEQ ID NO 236
<211> LENGTH: 107
<212> TYPE: PRT
<213> ORGANISM: Artificial Sequence
<220> FEATURE:
<223> OTHER INFORMATION: Synthetic Construct

<400> SEQUENCE: 236

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asp Trp Pro Tyr
                85                  90                  95

Thr Phe Gly Gln Gly Thr Lys Leu Glu Ile Lys
            100                 105


<210> SEQ ID NO 237
<211> LENGTH: 107
<212> TYPE: PRT
<213> ORGANISM: Artificial Sequence
<220> FEATURE:
<223> OTHER INFORMATION: Synthetic Construct

<400> SEQUENCE: 237

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Glu Trp Pro Tyr
                85                  90                  95

Thr Phe Gly Gln Gly Thr Lys Leu Glu Ile Lys
            100                 105


<210> SEQ ID NO 238
<211> LENGTH: 107
<212> TYPE: PRT
<213> ORGANISM: Artificial Sequence
<220> FEATURE:
<223> OTHER INFORMATION: Synthetic Construct

<400> SEQUENCE: 238

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Phe Trp Pro Tyr
                85                  90                  95

Thr Phe Gly Gln Gly Thr Lys Leu Glu Ile Lys
            100                 105


<210> SEQ ID NO 239
<211> LENGTH: 107
<212> TYPE: PRT
<213> ORGANISM: Artificial Sequence
<220> FEATURE:
<223> OTHER INFORMATION: Synthetic Construct

<400> SEQUENCE: 239

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Gly Trp Pro Tyr
                85                  90                  95

Thr Phe Gly Gln Gly Thr Lys Leu Glu Ile Lys
            100                 105
```

<210> SEQ ID NO 240
<211> LENGTH: 107
<212> TYPE: PRT
<213> ORGANISM: Artificial Sequence
<220> FEATURE:
<223> OTHER INFORMATION: Synthetic Construct

<400> SEQUENCE: 240

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ile Trp Pro Tyr
                85                  90                  95

Thr Phe Gly Gln Gly Thr Lys Leu Glu Ile Lys
            100                 105
```

<210> SEQ ID NO 241
<211> LENGTH: 107
<212> TYPE: PRT
<213> ORGANISM: Artificial Sequence
<220> FEATURE:
<223> OTHER INFORMATION: Synthetic Construct

<400> SEQUENCE: 241

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Leu Trp Pro Tyr
                85                  90                  95

Thr Phe Gly Gln Gly Thr Lys Leu Glu Ile Lys
            100                 105
```

<210> SEQ ID NO 242
<211> LENGTH: 107
<212> TYPE: PRT
<213> ORGANISM: Artificial Sequence
<220> FEATURE:
<223> OTHER INFORMATION: Synthetic Construct

<400> SEQUENCE: 242

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Met Trp Pro Tyr
                85                  90                  95

Thr Phe Gly Gln Gly Thr Lys Leu Glu Ile Lys
            100                 105


<210> SEQ ID NO 243
<211> LENGTH: 107
<212> TYPE: PRT
<213> ORGANISM: Artificial Sequence
<220> FEATURE:
<223> OTHER INFORMATION: Synthetic Construct

<400> SEQUENCE: 243

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Trp Pro Tyr
                85                  90                  95

Thr Phe Gly Gln Gly Thr Lys Leu Glu Ile Lys
            100                 105


<210> SEQ ID NO 244
<211> LENGTH: 107
<212> TYPE: PRT
<213> ORGANISM: Artificial Sequence
<220> FEATURE:
<223> OTHER INFORMATION: Synthetic Construct

<400> SEQUENCE: 244

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Thr Trp Pro Tyr
                85                  90                  95

Thr Phe Gly Gln Gly Thr Lys Leu Glu Ile Lys
            100                 105


<210> SEQ ID NO 245
<211> LENGTH: 107
```

<212> TYPE: PRT
<213> ORGANISM: Artificial Sequence
<220> FEATURE:
<223> OTHER INFORMATION: Synthetic Construct

<400> SEQUENCE: 245

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Tyr Trp Pro Tyr
                85                  90                  95

Thr Phe Gly Gln Gly Thr Lys Leu Glu Ile Lys
            100                 105
```

<210> SEQ ID NO 246
<211> LENGTH: 123
<212> TYPE: PRT
<213> ORGANISM: Artificial Sequence
<220> FEATURE:
<223> OTHER INFORMATION: Synthetic Construct

<400> SEQUENCE: 246

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Ala Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 247
<211> LENGTH: 123
<212> TYPE: PRT
<213> ORGANISM: Artificial Sequence
<220> FEATURE:
<223> OTHER INFORMATION: Synthetic Construct

<400> SEQUENCE: 247

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Cys Leu Thr Glu Leu
            20                  25                  30

Ser Ile His Trp Val Arg Gln Ala Pro Gly Lys Gly Leu Glu Trp Met
```

35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 248
<211> LENGTH: 123
<212> TYPE: PRT
<213> ORGANISM: Artificial Sequence
<220> FEATURE:
<223> OTHER INFORMATION: Synthetic Construct

<400> SEQUENCE: 248

Gln Met Gln Leu Val Gln Ser Gly Ala Glu Val Lys Lys Pro Gly Ala
1 5 10 15

Ser Val Lys Val Ser Cys Lys Val Ser Gly Tyr Glu Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 249
<211> LENGTH: 123
<212> TYPE: PRT
<213> ORGANISM: Artificial Sequence
<220> FEATURE:
<223> OTHER INFORMATION: Synthetic Construct

<400> SEQUENCE: 249

Gln Met Gln Leu Val Gln Ser Gly Ala Glu Val Lys Lys Pro Gly Ala
1 5 10 15

Ser Val Lys Val Ser Cys Lys Val Ser Gly Tyr Gly Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

```
Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 250
<211> LENGTH: 123
<212> TYPE: PRT
<213> ORGANISM: Artificial Sequence
<220> FEATURE:
<223> OTHER INFORMATION: Synthetic Construct

<400> SEQUENCE: 250

Gln Met Gln Leu Val Gln Ser Gly Ala Glu Val Lys Lys Pro Gly Ala
1               5                   10                  15

Ser Val Lys Val Ser Cys Lys Val Ser Gly Tyr His Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 251
<211> LENGTH: 123
<212> TYPE: PRT
<213> ORGANISM: Artificial Sequence
<220> FEATURE:
<223> OTHER INFORMATION: Synthetic Construct

<400> SEQUENCE: 251

Gln Met Gln Leu Val Gln Ser Gly Ala Glu Val Lys Lys Pro Gly Ala
1               5                   10                  15

Ser Val Lys Val Ser Cys Lys Val Ser Gly Tyr Lys Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 252
<211> LENGTH: 123
<212> TYPE: PRT
<213> ORGANISM: Artificial Sequence
```

<220> FEATURE:
<223> OTHER INFORMATION: Synthetic Construct

<400> SEQUENCE: 252

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Leu Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 253
<211> LENGTH: 123
<212> TYPE: PRT
<213> ORGANISM: Artificial Sequence
<220> FEATURE:
<223> OTHER INFORMATION: Synthetic Construct

<400> SEQUENCE: 253

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Met Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 254
<211> LENGTH: 123
<212> TYPE: PRT
<213> ORGANISM: Artificial Sequence
<220> FEATURE:
<223> OTHER INFORMATION: Synthetic Construct

<400> SEQUENCE: 254

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Asn Leu Thr Glu Leu
            20                  25                  30
```

```
Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 255
<211> LENGTH: 123
<212> TYPE: PRT
<213> ORGANISM: Artificial Sequence
<220> FEATURE:
<223> OTHER INFORMATION: Synthetic Construct

<400> SEQUENCE: 255

Gln Met Gln Leu Val Gln Ser Gly Ala Glu Val Lys Lys Pro Gly Ala
1               5                   10                  15

Ser Val Lys Val Ser Cys Lys Val Ser Gly Tyr Pro Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 256
<211> LENGTH: 123
<212> TYPE: PRT
<213> ORGANISM: Artificial Sequence
<220> FEATURE:
<223> OTHER INFORMATION: Synthetic Construct

<400> SEQUENCE: 256

Gln Met Gln Leu Val Gln Ser Gly Ala Glu Val Lys Lys Pro Gly Ala
1               5                   10                  15

Ser Val Lys Val Ser Cys Lys Val Ser Gly Tyr Ser Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95
```

```
Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 257
<211> LENGTH: 123
<212> TYPE: PRT
<213> ORGANISM: Artificial Sequence
<220> FEATURE:
<223> OTHER INFORMATION: Synthetic Construct

<400> SEQUENCE: 257

Gln Met Gln Leu Val Gln Ser Gly Ala Glu Val Lys Lys Pro Gly Ala
1               5                   10                  15

Ser Val Lys Val Ser Cys Lys Val Ser Gly Tyr Val Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 258
<211> LENGTH: 123
<212> TYPE: PRT
<213> ORGANISM: Artificial Sequence
<220> FEATURE:
<223> OTHER INFORMATION: Synthetic Construct

<400> SEQUENCE: 258

Gln Met Gln Leu Val Gln Ser Gly Ala Glu Val Lys Lys Pro Gly Ala
1               5                   10                  15

Ser Val Lys Val Ser Cys Lys Val Ser Gly Tyr Trp Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 259
<211> LENGTH: 123
<212> TYPE: PRT
```

<213> ORGANISM: Artificial Sequence
<220> FEATURE:
<223> OTHER INFORMATION: Synthetic Construct

<400> SEQUENCE: 259

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Ala Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 260
<211> LENGTH: 123
<212> TYPE: PRT
<213> ORGANISM: Artificial Sequence
<220> FEATURE:
<223> OTHER INFORMATION: Synthetic Construct

<400> SEQUENCE: 260

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Asp Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 261
<211> LENGTH: 123
<212> TYPE: PRT
<213> ORGANISM: Artificial Sequence
<220> FEATURE:
<223> OTHER INFORMATION: Synthetic Construct

<400> SEQUENCE: 261

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Glu Glu Leu
20 25 30

```
Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 262
<211> LENGTH: 123
<212> TYPE: PRT
<213> ORGANISM: Artificial Sequence
<220> FEATURE:
<223> OTHER INFORMATION: Synthetic Construct

<400> SEQUENCE: 262

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Gly Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 263
<211> LENGTH: 123
<212> TYPE: PRT
<213> ORGANISM: Artificial Sequence
<220> FEATURE:
<223> OTHER INFORMATION: Synthetic Construct

<400> SEQUENCE: 263

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Lys Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
```

```
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 264
<211> LENGTH: 123
<212> TYPE: PRT
<213> ORGANISM: Artificial Sequence
<220> FEATURE:
<223> OTHER INFORMATION: Synthetic Construct

<400> SEQUENCE: 264

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Leu Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 265
<211> LENGTH: 123
<212> TYPE: PRT
<213> ORGANISM: Artificial Sequence
<220> FEATURE:
<223> OTHER INFORMATION: Synthetic Construct

<400> SEQUENCE: 265

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Met Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 266
<211> LENGTH: 123
```

<212> TYPE: PRT
<213> ORGANISM: Artificial Sequence
<220> FEATURE:
<223> OTHER INFORMATION: Synthetic Construct

<400> SEQUENCE: 266

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Asn Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 267
<211> LENGTH: 123
<212> TYPE: PRT
<213> ORGANISM: Artificial Sequence
<220> FEATURE:
<223> OTHER INFORMATION: Synthetic Construct

<400> SEQUENCE: 267

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Pro Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 268
<211> LENGTH: 123
<212> TYPE: PRT
<213> ORGANISM: Artificial Sequence
<220> FEATURE:
<223> OTHER INFORMATION: Synthetic Construct

<400> SEQUENCE: 268

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Gln Glu Leu
```

```
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 269
<211> LENGTH: 123
<212> TYPE: PRT
<213> ORGANISM: Artificial Sequence
<220> FEATURE:
<223> OTHER INFORMATION: Synthetic Construct

<400> SEQUENCE: 269

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Arg Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 270
<211> LENGTH: 123
<212> TYPE: PRT
<213> ORGANISM: Artificial Sequence
<220> FEATURE:
<223> OTHER INFORMATION: Synthetic Construct

<400> SEQUENCE: 270

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80
```

```
Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 271
<211> LENGTH: 123
<212> TYPE: PRT
<213> ORGANISM: Artificial Sequence
<220> FEATURE:
<223> OTHER INFORMATION: Synthetic Construct

<400> SEQUENCE: 271

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Val Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 272
<211> LENGTH: 123
<212> TYPE: PRT
<213> ORGANISM: Artificial Sequence
<220> FEATURE:
<223> OTHER INFORMATION: Synthetic Construct

<400> SEQUENCE: 272

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Trp Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 273

```
<211> LENGTH: 123
<212> TYPE: PRT
<213> ORGANISM: Artificial Sequence
<220> FEATURE:
<223> OTHER INFORMATION: Synthetic Construct

<400> SEQUENCE: 273

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Tyr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 274
<211> LENGTH: 123
<212> TYPE: PRT
<213> ORGANISM: Artificial Sequence
<220> FEATURE:
<223> OTHER INFORMATION: Synthetic Construct

<400> SEQUENCE: 274

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Ala Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 275
<211> LENGTH: 123
<212> TYPE: PRT
<213> ORGANISM: Artificial Sequence
<220> FEATURE:
<223> OTHER INFORMATION: Synthetic Construct

<400> SEQUENCE: 275

Gln Met Gln Leu Val Gln Ser Gly Ala Glu Val Lys Lys Pro Gly Ala
1               5                   10                  15
```

```
Ser Val Lys Val Ser Cys Lys Val Ser Gly Tyr Thr Leu Thr Cys Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 276
<211> LENGTH: 123
<212> TYPE: PRT
<213> ORGANISM: Artificial Sequence
<220> FEATURE:
<223> OTHER INFORMATION: Synthetic Construct

<400> SEQUENCE: 276

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asp Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 277
<211> LENGTH: 123
<212> TYPE: PRT
<213> ORGANISM: Artificial Sequence
<220> FEATURE:
<223> OTHER INFORMATION: Synthetic Construct

<400> SEQUENCE: 277

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Phe Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80
```

```
Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 278
<211> LENGTH: 123
<212> TYPE: PRT
<213> ORGANISM: Artificial Sequence
<220> FEATURE:
<223> OTHER INFORMATION: Synthetic Construct

<400> SEQUENCE: 278

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Gly Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 279
<211> LENGTH: 123
<212> TYPE: PRT
<213> ORGANISM: Artificial Sequence
<220> FEATURE:
<223> OTHER INFORMATION: Synthetic Construct

<400> SEQUENCE: 279

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Lys Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 280
<211> LENGTH: 123
<212> TYPE: PRT
<213> ORGANISM: Artificial Sequence
<220> FEATURE:
<223> OTHER INFORMATION: Synthetic Construct

<400> SEQUENCE: 280

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Met Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120

<210> SEQ ID NO 281
<211> LENGTH: 123
<212> TYPE: PRT
<213> ORGANISM: Artificial Sequence
<220> FEATURE:
<223> OTHER INFORMATION: Synthetic Construct

<400> SEQUENCE: 281

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asn Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120

<210> SEQ ID NO 282
<211> LENGTH: 123
<212> TYPE: PRT
<213> ORGANISM: Artificial Sequence
<220> FEATURE:
<223> OTHER INFORMATION: Synthetic Construct

<400> SEQUENCE: 282

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Pro Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 283
<211> LENGTH: 123
<212> TYPE: PRT
<213> ORGANISM: Artificial Sequence
<220> FEATURE:
<223> OTHER INFORMATION: Synthetic Construct

<400> SEQUENCE: 283

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Arg Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr
65 70 75 80

Leu Glu Leu Ser Ser Leu Arg Ser Glu Asp Thr Ala Leu Tyr Tyr Cys
85 90 95

Ala Thr Gly Arg Tyr Thr Ser Leu Ala Thr Thr Tyr Gly Phe Asp Tyr
100 105 110

Trp Gly Gln Gly Thr Leu Val Thr Val Ser Ser
115 120

<210> SEQ ID NO 284
<211> LENGTH: 123
<212> TYPE: PRT
<213> ORGANISM: Artificial Sequence
<220> FEATURE:
<223> OTHER INFORMATION: Synthetic Construct

<400> SEQUENCE: 284

Gln Met Gln Leu Val Gln Ser Gly Ala Glu Val Lys Lys Pro Gly Ala
1 5 10 15

Ser Val Lys Val Ser Cys Lys Val Ser Gly Tyr Thr Leu Thr Ser Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Gln Gly Arg Val Thr Met Thr Gly Asp Thr Ser Thr Asp Thr Ala Tyr

```
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 285
<211> LENGTH: 123
<212> TYPE: PRT
<213> ORGANISM: Artificial Sequence
<220> FEATURE:
<223> OTHER INFORMATION: Synthetic Construct

<400> SEQUENCE: 285

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Val Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120


<210> SEQ ID NO 286
<211> LENGTH: 123
<212> TYPE: PRT
<213> ORGANISM: Artificial Sequence
<220> FEATURE:
<223> OTHER INFORMATION: Synthetic Construct

<400> SEQUENCE: 286

Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Trp Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 287
<211> LENGTH: 123
<212> TYPE: PRT
<213> ORGANISM: Artificial Sequence
<220> FEATURE:
<223> OTHER INFORMATION: Synthetic Construct

<400> SEQUENCE: 287

```
Gln Met Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Tyr Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Cys
                85                  90                  95

Ala Thr Gly Arg Tyr Thr Ser Leu Ala Thr Thr Tyr Gly Phe Asp Tyr
            100                 105                 110

Trp Gly Gln Gly Thr Leu Val Thr Val Ser Ser
        115                 120
```

<210> SEQ ID NO 288
<211> LENGTH: 107
<212> TYPE: PRT
<213> ORGANISM: Artificial Sequence
<220> FEATURE:
<223> OTHER INFORMATION: Synthetic Construct

<400> SEQUENCE: 288

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Leu Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asp Trp Pro Tyr
                85                  90                  95

Thr Phe Gly Gln Gly Thr Lys Leu Glu Ile Lys
            100                 105
```

<210> SEQ ID NO 289
<211> LENGTH: 107
<212> TYPE: PRT
<213> ORGANISM: Artificial Sequence
<220> FEATURE:
<223> OTHER INFORMATION: Synthetic Construct

<400> SEQUENCE: 289

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
            20                  25                  30

Leu Ala Trp Tyr Gln Gln Lys Pro Gly Gln Ala Pro Arg Leu Leu Ile
        35                  40                  45

Tyr Gly Phe Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Asn Trp Pro Tyr
                85                  90                  95

Thr Phe Gly Gln Gly Thr Lys Leu Glu Ile Lys
            100                 105


<210> SEQ ID NO 290
<211> LENGTH: 123
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 27
<223> OTHER INFORMATION: Xaa = His or Tyr
<220> FEATURE:
<221> NAME/KEY: VARIANT
<222> LOCATION: 33
<223> OTHER INFORMATION: Xaa = Ser, Cys or Pro
<220> FEATURE:
<221> NAME/KEY: VARIANT
<222> LOCATION: 34
<223> OTHER INFORMATION: Xaa = Ile or Met
<220> FEATURE:
<221> NAME/KEY: VARIANT
<222> LOCATION: 53
<223> OTHER INFORMATION: Xaa = Pro, Gly, Thr, Ser, or Val
<220> FEATURE:
<221> NAME/KEY: VARIANT
<222> LOCATION: 54
<223> OTHER INFORMATION: Xaa = Glu, Asp, Gly, or Ala
<220> FEATURE:
<221> NAME/KEY: VARIANT
<222> LOCATION: 55
<223> OTHER INFORMATION: Xaa = Asp, Gly, Ile, Trp, Ser, or Val
<220> FEATURE:
<221> NAME/KEY: VARIANT
<222> LOCATION: 56
<223> OTHER INFORMATION: Xaa = Gly, Glu, Asp, or His
<220> FEATURE:
<221> NAME/KEY: VARIANT
<222> LOCATION: 58
<223> OTHER INFORMATION: Xaa = Thr or Ala
<220> FEATURE:
<221> NAME/KEY: VARIANT
<222> LOCATION: 59
<223> OTHER INFORMATION: Xaa = Asn or Ile
<220> FEATURE:
<221> NAME/KEY: VARIANT
<222> LOCATION: 64
<223> OTHER INFORMATION: Xaa = Ser or Phe
<220> FEATURE:
<221> NAME/KEY: VARIANT
<222> LOCATION: 96
<223> OTHER INFORMATION: Xaa = Cys or Trp
<220> FEATURE:
<221> NAME/KEY: VARIANT
<222> LOCATION: 102
<223> OTHER INFORMATION: Xaa = Cys, thr, Ser, Ile, Ala, or Val
<220> FEATURE:
<221> NAME/KEY: VARIANT
<222> LOCATION: 103
<223> OTHER INFORMATION: Xaa = Ser, Gly, Glu, Phe, Trp, His, Ile, Val,
      Asn, Tyr, Thr, or Arg
<220> FEATURE:
<221> NAME/KEY: VARIANT
```

```
<222> LOCATION: 104
<223> OTHER INFORMATION: Xaa = Thr, His, Leu, Phe, Pro, Ile, Ser, Tyr,
      Lys, Ala, Asp, Val, Asn, or Gly
<220> FEATURE:
<221> NAME/KEY: VARIANT
<222> LOCATION: 105
<223> OTHER INFORMATION: Xaa = Asp, Ala, Met, Tyr, Phe, Ser, Thr, Gly,
      or Trp
<220> FEATURE:
<221> NAME/KEY: VARIANT
<222> LOCATION: 106
<223> OTHER INFORMATION: Xaa = Thr, Ser, Phe, Gln, Ala, Asn, Leu, Glu,
      Ile, Gly, or Met
<220> FEATURE:
<221> NAME/KEY: VARIANT
<222> LOCATION: 107
<223> OTHER INFORMATION: Xaa = Cys, Thr, Asn, Ser, or Ala
<220> FEATURE:
<221> NAME/KEY: VARIANT
<222> LOCATION: 116
<223> OTHER INFORMATION: Xaa = Gly or Glu
<220> FEATURE:
<221> NAME/KEY: VARIANT
<222> LOCATION: 120
<223> OTHER INFORMATION: Xaa = Thr or Ser

<400> SEQUENCE: 290

Gln Met Gln Leu Val Gln Ser Gly Ala Glu Val Lys Lys Pro Gly Ala
1               5                   10                  15

Ser Val Lys Val Ser Cys Lys Val Ser Gly Xaa Thr Leu Thr Glu Leu
            20                  25                  30

Xaa Xaa His Trp Val Arg Gly Ala Pro Gly Lys Gly Leu Glu Trp Met
        35                  40                  45

Gly Gly Phe Asp Xaa Xaa Xaa Xaa Glu Xaa Xaa Tyr Ala Gln Lys Xaa
    50                  55                  60

Gln Gly Arg Val Thr Met Thr Gly Asp Thr Ser Thr Asp Thr Ala Tyr
65                  70                  75                  80

Leu Glu Leu Ser Ser Leu Arg Ser Glu Asp Thr Ala Leu Tyr Tyr Xaa
                85                  90                  95

Ala Thr Gly Arg Tyr Xaa Xaa Xaa Xaa Xaa Xaa Tyr Gly Phe Asp Tyr
            100                 105                 110

Trp Gly Gln Xaa Thr Leu Val Xaa Val Ser Ser
        115                 120


<210> SEQ ID NO 291
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 92
<223> OTHER INFORMATION: Xaa = Asn, Asp, Ser, ARg, Ala, Thr, Leu, Tyr,
      or Gly
<220> FEATURE:
<221> NAME/KEY: VARIANT
<222> LOCATION: 93
<223> OTHER INFORMATION: Xaa = Asn or Ser
<220> FEATURE:
<221> NAME/KEY: VARIANT
<222> LOCATION: 94
<223> OTHER INFORMATION: Xaa = Trp, Ser, Pro, Val, Gly, or Arg
<220> FEATURE:
<221> NAME/KEY: VARIANT
<222> LOCATION: 96
<223> OTHER INFORMATION: Xaa = Pro, Tyr, His, Wer, Phe, Asn, Asp, Val,
      or Gly

<400> SEQUENCE: 291
```

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Xaa Xaa Xaa Pro Xaa
85 90 95

Thr Phe Gly Gln Gly Thr Lys Leu Glu Ile Lys
100 105

<210> SEQ ID NO 292
<211> LENGTH: 281
<212> TYPE: PRT
<213> ORGANISM: Artificial Sequence
<220> FEATURE:
<223> OTHER INFORMATION: Synthetic Construct

<400> SEQUENCE: 292

Ser Leu Asn Val Arg Phe Asp Ser Arg Thr Met Gln Leu Ser Trp Asp
1 5 10 15

Cys Gln Glu Gln Thr Thr Phe Ser Lys Cys Phe Leu Thr Asp Lys Lys
20 25 30

Asn Arg Val Val Glu Pro Arg Leu Ser Asn Asn Glu Cys Ser Cys Thr
35 40 45

Phe Arg Glu Ile Cys Leu His Glu Gly Val Thr Phe Glu Val His Val
50 55 60

Gln Thr Ser Gln Arg Gly Phe Gln Gln Lys Leu Leu Tyr Pro Asn Ser
65 70 75 80

Gly Arg Glu Gly Thr Ala Ala Gln Asn Phe Ser Cys Phe Ile Tyr Asn
85 90 95

Ala Asp Leu Met Asn Cys Thr Trp Ala Arg Gly Pro Thr Ala Pro Arg
100 105 110

Asp Val Gln Tyr Phe Leu Tyr Ile Arg Asn Ser Lys Arg Arg Arg Glu
115 120 125

Ile Arg Cys Pro Tyr Tyr Ile Gln Asp Ser Gly Thr His Val Gly Cys
130 135 140

His Leu Asp Asn Leu Ser Gly Leu Thr Ser Arg Asn Tyr Phe Leu Val
145 150 155 160

Asn Gly Thr Ser Arg Glu Ile Gly Ile Gln Phe Phe Asp Ser Leu Leu
165 170 175

Asp Thr Lys Lys Ile Glu Arg Phe Asn Pro Pro Ser Asn Val Thr Val
180 185 190

Arg Cys Asn Thr Thr His Cys Leu Val Arg Trp Lys Gln Pro Arg Thr
195 200 205

Tyr Gln Lys Leu Ser Tyr Leu Asp Phe Gln Tyr Gln Leu Asp Val His
210 215 220

Arg Lys Asn Thr Gln Pro Gly Thr Glu Asn Leu Leu Ile Asn Val Ser
225 230 235 240

Gly Asp Leu Glu Asn Arg Tyr Asn Phe Pro Ser Ser Glu Pro Arg Ala
245 250 255

```
Lys His Ser Val Lys Ile Arg Ala Ala Asp Val Arg Ile Leu Asn Trp
            260                 265                 270

Ser Ser Trp Ser Glu Ala Ile Glu Phe
        275                 280


<210> SEQ ID NO 293
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ser, Leu, ASn, Ala, Lys, Arg, Ile, Gln,
      Gly, Thr, His, Met, or Cys
<220> FEATURE:
<221> NAME/KEY: VARIANT
<222> LOCATION: 4
<223> OTHER INFORMATION: Xaa = Gln, Tyr, Pro, Ala, Ile, Phe, Thr, Arg,
      Val, Leu, Glu, Ser, or Cys
<220> FEATURE:
<221> NAME/KEY: VARIANT
<222> LOCATION: 5
<223> OTHER INFORMATION: Xaa = Ser, His, Trp, Leu, Arg, Lys, Thr, Pro,
      Ile, Phe, Val, Glu, Ala, or Gln
<220> FEATURE:
<221> NAME/KEY: VARIANT
<222> LOCATION: 7
<223> OTHER INFORMATION: Xaa = Ser, Leu, Trp, Met, Ala, Tyr, Lys, Arg,
      Gly, Thr, Glu, Val, Asn, Phe, or Cys
<220> FEATURE:
<221> NAME/KEY: VARIANT
<222> LOCATION: 8
<223> OTHER INFORMATION: Xaa = Ser, Thr, Arg, Ala, His, Gln, Pro, Met,
      Leu, or Gly
<220> FEATURE:
<221> NAME/KEY: VARIANT
<222> LOCATION: 9
<223> OTHER INFORMATION: Xaa = Tyr, Leu, or Phe

<400> SEQUENCE: 293

Arg Ala Xaa Xaa Xaa Val Xaa Xaa Xaa Leu Ala
1               5                   10


<210> SEQ ID NO 294
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Thr
<220> FEATURE:
<221> NAME/KEY: VARIANT
<222> LOCATION: 2
<223> OTHER INFORMATION: Xaa = Ala, Gly, Arg, His, Lys, Ser, Thr, Met,
      or Phe
<220> FEATURE:
<221> NAME/KEY: VARIANT
<222> LOCATION: 3
<223> OTHER INFORMATION: Xaa = Ser, Ala, Trp, Arg, Leu, Thr, Gln, Phe,
      Tyr, His or Asn

<400> SEQUENCE: 294

Xaa Xaa Xaa Ser Arg Ala Thr
1               5


<210> SEQ ID NO 295
<211> LENGTH: 5
```

-continued

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ser, Cys, or Pro
<220> FEATURE:
<221> NAME/KEY: VARIANT
<222> LOCATION: 4
<223> OTHER INFORMATION: Xaa = Ile or Met

<400> SEQUENCE: 295

Glu Leu Xaa Xaa His
1               5
```

ANTIBODIES SPECIFICALLY RECOGNIZING GRANULOCYTE-MACROPHAGE COLONY STIMULATING FACTOR RECEPTOR ALPHA AND USES THEREOF

CROSS REFERENCE TO RELATED APPLICATIONS

This application is a national stage application under 35 U.S.C. § 371 of International Application No. PCT/CN2019/120545, filed internationally on Nov. 25, 2019, which claims the benefit of priority to international application PCT/CN2018/117581, filed Nov. 27, 2018, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 710262000100SUB2SEQLIST.TXT, date recorded: Apr. 3, 2025, size: 254,015 bytes).

FIELD OF THE APPLICATION

This application pertains to antibodies that specifically recognize granulocyte-macrophage colony stimulating factor receptor alpha (GM-CSFRα), and methods of manufacture and uses thereof, including methods of treating autoimmune and inflammatory conditions, and cancer.

BACKGROUND OF THE APPLICATION

Granulocyte-macrophage colony stimulating factor (GM-CSF) is also known as colony-stimulating factor 2 (CSF2). GM-CSF is a type I proinflammatory cytokine which plays a role in exacerbating inflammatory, respiratory and autoimmune diseases. The GM-CSF receptor is a member of the hematopoietic receptor superfamily. It is heterodimeric, consisting of an alpha and a beta subunit. GM-CSF is able to bind with relatively low affinity to the α subunit alone ($K_d$ 1-5 nM) but not at all to the β subunit alone. However, the presence of both α and β subunits results in a high affinity ligand-receptor complex (Kd≈100 pM). Neutralization of GM-CSF binding to GM-CSFRα is therefore a therapeutic approach to treating diseases and conditions mediated through GM-CSFR. An antibody against human GM-CSFRα, designated Mavrilimumab (Mab, used as a control in the Examples), is described in WO2007110631.

The disclosures of all publications, patents, patent applications and published patent applications referred to herein are hereby incorporated herein by reference in their entirety.

BRIEF SUMMARY OF THE APPLICATION

In one aspect, the present application provides an isolated anti-GM-CSFRα antibody that specifically binds to an epitope on human GM-CSFRα, wherein the epitope comprises one, two, three, four, five, or six amino acid residues selected from the group consisting of Val50, Glu59, Lys194, Lys195, Arg283, and Ile284 of human GM-CSFRα. In some embodiments, the epitope further comprises amino acid residues: (i) Val51, Thr63, and Ile196; (ii) Leu191 and Ile196; or (iii) Arg49, Val51, Asn57, and Ser61. In some embodiments, the isolated anti-GM-CSFRα antibody binds to the human GM-CSFRα with a $K_d$ from about 0.1 pM to about 1 nM.

In some embodiments according to any one of the isolated anti-GM-CSFRα antibodies described above, the isolated anti-GM-CSFRα antibody comprises: a heavy chain variable domain ($V_H$) comprising a heavy chain complementarity determining region (HC-CDR) 1 comprising $X_1LX_2X_3H$ (SEQ ID NO: 76), wherein $X_1$ is E, N, G, D, M, S, P, F, Y, A, V, K, W, R or C, $X_2$ is S, C or P, and $X_3$ is I or M; an HC-CDR2 comprising $GFDX_1X_2X_3X_4EX_5X_6YAQKX_7QG$ (SEQ ID NO: 77), wherein $X_1$ is P, G, T, S, or V, $X_2$ is E, D, G, or A, $X_3$ is D, G, I, W, S, or V, $X_4$ is G, E, D, or H, $X_5$ is T or A, $X_6$ is N or I, and $X_7$ is S or F; and an HC-CDR3 comprising $GRYX_1X_2X_3X_4X_5X_6YGFDY$ (SEQ ID NO: 78), wherein $X_1$ is C, T, S, I, A, or V, $X_2$ is S, G, E, F, W, H, I, V, N, Y, T, or R, $X_3$ is T, H, L, F, P, I, S, Y, K, A, D, V, N, or G, $X_4$ is D, A, M, Y, F, S, T, G, or W, $X_5$ is T, S, F, Q, A, N, L, E, I, G, or M, and $X_6$ is C, T, N, S, or A; and a light chain variable domain ($V_L$) comprising a light chain complementarity determining region (LC-CDR) 1 comprising $RAX_1X_2X_3VX_4X_5X_6LA$(SEQ ID NO: 293), wherein $X_1$ is S, L, N, A, K, R, I, Q, G, T, H, M, or C, $X_2$ is Q, Y, P, A, I, F, T, R, V, L, E, S, or C, $X_3$ is S, H, W, L, R, K, T, P, I, F, V, E, A, or Q, $X_4$ is S, L, W, M, A, Y, K, R, G, T, E, V, N, F, or C, $X_5$ is S, T, R, A, H, Q, P, M, L, or G, and $X_6$ is Y, L, or F; a LC-CDR2 comprising $X_1X_2X_3SRAT$(SEQ ID NO: 294), wherein $X_1$ is G or T, $X_2$ is A, G, R, H, K, S, T, M, or F, and $X_3$ is S, A, W, R, L, T, Q, F, Y, H, or N; and a LC-CDR3 comprising $QQYX_1X_2X_3PX_4T$(SEQ ID NO: 79), wherein $X_1$ is N, D, S, R, A, T, L, Y, Q, W or G, $X_2$ is N, D, E, T, Y, G, A, M, F, S, I or L, $X_3$ is W, S, P, V, G, or R, and $X_4$ is P, Y, H, S, F, N, D, V, or G. In some embodiments, the anti-GM-CSFRα antibody comprises: a $V_H$ comprising a HC-CDR1 comprising $ELX_1X_2H$(SEQ ID NO: 295), wherein $X_1$ is S, C or P, and $X_2$ is I or M; an HC-CDR2 comprising $GFDX_1X_2X_3X_4EX_5X_6YAQKX_7QG$ (SEQ ID NO: 77), wherein $X_1$ is P, G, T, S, or V, $X_2$ is E, D, G, or A, $X_3$ is D, G, I, W, S, or V, $X_4$ is G, E, D, or H, $X_5$ is T or A, $X_6$ is N or I, and $X_7$ is S or F; and an HC-CDR3 comprising $GRYX_1X_2X_3X_4X_5X_6YGFDY$ (SEQ ID NO: 78), wherein $X_1$ is C, T, S, I, A, or V, $X_2$ is S, G, E, F, W, H, I, V, N, Y, T, or R, $X_3$ is T, H, L, F, P, I, S, Y, K, A, D, V, N, or G, $X_4$ is D, A, M, Y, F, S, T, G, or W, $X_5$ is T, S, F, Q, A, N, L, E, I, G, or M, and $X_6$ is C, T, N, S, or A; and a $V_L$ comprising a LC-CDR1 comprising RASQSVSSYLA (SEQ ID NO: 51); a LC-CDR2 comprising GASSRAT (SEQ ID NO: 52); and a LC-CDR3 comprising $QQYX_1X_2X_3PX_4T$ (SEQ ID NO: 79), wherein $X_1$ is N, D, S, R, A, T, L, Y, Q, W or G, $X_2$ is N, D, E, T, Y, G, A, M, F, S, I or L, $X_3$ is W, S, P, V, G, or R, and $X_4$ is P, Y, H, S, F, N, D, V, or G.

In some embodiments, there is provided an isolated anti-GM-CSFRα antibody comprises: a $V_H$ comprising an HC-CDR1 comprising the amino acid sequence of any one of SEQ ID NOs: 1-4, or a variant thereof comprising up to about 3 amino acid substitutions; an HC-CDR2 comprising the amino acid sequence of any one of SEQ ID NOs: 5-16, or a variant thereof comprising up to about 3 amino acid substitutions; and an HC-CDR3 comprising the amino acid sequence of any one of SEQ ID NOs: 17-50, or a variant thereof comprising up to about 3 amino acid substitutions; and a $V_L$ comprising a LC-CDR1 comprising the amino acid sequence of SEQ ID NO: 51, or a variant thereof comprising up to about 3 amino acid substitutions; a LC-CDR2 comprising the amino acid sequence of SEQ ID NO: 52, or a variant thereof comprising up to about 3 amino acid substitutions; and a LC-CDR3 comprising the amino acid sequence of any one of SEQ ID NOs: 53-75, or a variant thereof comprising up to about 3 amino acid substitutions.

In some embodiments, there is provided an isolated anti-GM-CSFRα antibody comprising a $V_H$ comprising an HC-CDR1, an HC-CDR2, and an HC-CDR3 of a $V_H$ comprising the amino acid sequence of any one of SEQ ID NOs: 80-121; and a $V_L$ comprising a LC-CDR1, a LC-CDR2, and a LC-CDR3 of a $V_L$ comprising the amino acid sequence of any one of SEQ ID NOs: 122-144.

In some embodiments, there is provided an isolated anti-GM-CSFRα antibody comprises: (i) a $V_H$ comprising an HC-CDR1 comprising the amino acid sequence of SEQ ID NO: 1, an HC-CDR2 comprising the amino acid sequence of SEQ ID NO: 5, and an HC-CDR3 comprising the amino acid sequence of SEQ ID NO: 17, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 54, or a variant thereof comprising up to about 5 amino acid substitutions in the LC-CDRs; (ii) a $V_H$ comprising an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 56, or a variant thereof comprising up to about 5 amino acid substitutions in the LC-CDRs; (iii) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, or a variant thereof comprising up to about 5 amino acid substitutions in the LC-CDRs; (iv) a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, or a variant thereof comprising up to about 5 amino acid substitutions in the LC-CDRs; (v) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 53, or a variant thereof comprising up to about 5 amino acid substitutions in the LC-CDRs; (vi) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, or a variant thereof comprising up to about 5 amino acid substitutions in the LC-CDRs; (vii) a $V_H$ comprising an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 54, or a variant thereof comprising up to about 5 amino acid substitutions in the LC-CDRs; (viii) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, or a variant thereof comprising up to about 5 amino acid substitutions in the LC-CDRs; (ix) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 50, or a variant thereof comprising up to about 5 amino acid substitutions in the HC-CDRs; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, or a variant thereof comprising up to about 5 amino acid substitutions in the LC-CDRs.

In some embodiments according to any one of the isolated anti-GM-CSFRα antibodies described above, the isolated anti-GM-CSFRα antibody comprises amino acid residues: (i) E, H, N, G, D, M, S, P, F, Y, A, V, K, W, R, or C at position 31 of the $V_H$; and/or (ii) S, L, N, A, K, R, I, Q, G, T, H, M, or C at position 26 of the $V_L$; and/or (iii) Q, Y, P, A, I, F, T, R, V, L, E, S, or C at position 27 of the $V_L$; and/or (iv) S, H, W, L, R, K, T, P, I, F, V, E, A, or Q at position 28 of the $V_L$; and/or (v) S, L, W, M, A, Y, K, R, G, T, E, V, N, F, or C at position 30 of the $V_L$; and/or (vi) S, T, R, A, H, Q, P, M, L, or G at position 31 of the $V_L$; and/or (vii) Y, L or F at position 32 of the $V_L$; and/or (viii) G, or T at position 50 of the $V_L$; and/or (ix) A, G, R, H, K, S, T, M, F, N, or V at position 51 of the $V_L$; and/or (x) S, A, W, R, L, T, Q, F, Y, H, or N at position 52 of the $V_L$; and/or (xi) D, A, Q, or W at position 92 of the $V_L$; and/or (xii) N, D, E, T, Y, G, A, M, F, S, I, or L at position 93 of the $V_L$; and/or (xiii) amino acid residues selected from T, H, V, E, P, L, M, S, W, C, A, G, N, or K at position 28 of the $V_H$; and/or (xiv) amino acid residues selected from T, P, D, E, Y, W, V, M, N, L, Q, G, S, A, K, or R at position 30 of the $V_H$, wherein the numbering is according to the EU index of Kabat.

In some embodiments, according to any one of the isolated anti-GM-CSFRα antibodies described above, the isolated anti-GM-CSFRα antibody comprises: a $V_H$ comprising the amino acid sequence of any one of SEQ ID NOs: 80-121, and 246-287, or a variant thereof having at least about 90% sequence identity to the amino acid sequence of any one of SEQ ID NOs: 80-121, and 246-287; and a $V_L$ comprising the amino acid sequence of any one of SEQ ID NOs: 122-144, 150-245, and 288-289, or a variant thereof having at least about 90% sequence identity to the amino acid sequence of any one of SEQ ID NOs: 122-144, 150-245, and 288-289. In some embodiments, the isolated anti-GM-CSFRα antibody comprises: (i) a $V_H$ comprising the amino acid sequence of SEQ ID NO: 80; and a $V_L$ comprising the amino acid sequence of SEQ ID NO: 123; (ii) a $V_H$ comprising the amino acid sequence of SEQ ID NO: 85; and a $V_L$ comprising the amino acid sequence of SEQ ID NO: 125; (iii) a $V_H$ comprising the amino acid sequence of SEQ ID NO: 86; and a $V_L$ comprising the amino acid sequence of SEQ ID NO: 126; (iv) a $V_H$ comprising the amino acid sequence of SEQ ID NO: 91; and a $V_L$ comprising the amino acid sequence of SEQ ID NO: 126; (v) a $V_H$ comprising the amino acid sequence of SEQ ID NO: 99; and a $V_L$ comprising the amino acid sequence of SEQ ID NO: 122; (vi) a $V_H$ comprising the amino acid sequence of SEQ ID NO: 101; and a $V_L$ comprising the amino acid sequence of SEQ ID NO: 126; (vii) a $V_H$ comprising the amino acid sequence of SEQ ID NO: 103; and a $V_L$ comprising the amino acid sequence of SEQ ID NO: 123; (viii) a $V_H$ comprising the amino acid sequence of SEQ ID NO: 99; and a $V_L$ comprising the amino acid sequence of SEQ ID NO: 126; (ix) a $V_H$ comprising the amino acid sequence of SEQ ID NO: 121; and a $V_L$ comprising the amino acid sequence of SEQ ID NO: 126; (x) a $V_H$ comprising the amino acid sequence of SEQ ID NO: 250; and a $V_L$ comprising the amino acid sequence of SEQ ID NO: 241; (xi) a $V_H$ comprising the amino acid sequence of SEQ ID NO: 250; and a $V_L$ comprising the amino acid sequence of SEQ ID NO: 193; (xii) a $V_H$ comprising the amino acid sequence of SEQ ID NO: 248; and a $V_L$ comprising the amino acid sequence of SEQ ID NO: 188; (xiii) a $V_H$ comprising the amino acid sequence of SEQ ID NO: 248; and a $V_L$ comprising the amino acid sequence of SEQ ID NO: 193; (xiv) a $V_H$ comprising the amino acid sequence of SEQ ID NO: 250; and a $V_L$ comprising the amino acid sequence of SEQ ID NO: 288; (xv) a $V_H$ comprising the amino acid sequence of SEQ ID NO: 250; and a $V_L$ comprising the amino acid sequence of SEQ ID NO: 188; (xvi) a $V_H$ comprising the amino acid sequence of SEQ ID NO: 250; and a $V_L$ comprising the amino acid sequence of SEQ ID NO: 236; or (xvii) a $V_H$ comprising the amino acid sequence of SEQ ID NO: 91; and a $V_L$ comprising the amino acid sequence of SEQ ID NO: 288.

In some embodiments, there is provided an isolated anti-GM-CSFRα antibody that specifically binds to GM-CSFRα competitively with any one of the isolated anti-GM-CSFRα antibodies as described above. In some embodiments, there is provided an isolated anti-GM-CSFRα antibody that specifically binds to the same epitope as any one of isolated anti-GM-CSFRα antibodies as described above.

In some embodiments according to any of the isolated anti-GM-CSFRα antibodies described above, the isolated anti-GM-CSFRα antibody comprises an Fc fragment. In some embodiments, the isolated anti-GM-CSFRα antibody is a full-length IgG antibody. In some embodiments, the isolated anti-GM-CSFRα antibody is a full-length IgG1 or IgG4 antibody. In some embodiments, the anti-GM-CSFRα antibody is chimeric, human, or humanized. In some embodiments, the anti-GM-CSFRα antibody is an antigen binding fragment selected from the group consisting of a Fab, a Fab', a F(ab)'2, a Fab'-SH, a single-chain Fv (scFv), an Fv fragment, a dAb, a Fd, a Nanobody™, a diabody, and a linear antibody.

In some embodiments, there is provided isolated nucleic acid molecule(s) that encodes any one of the anti-GM-CSFRα antibodies described above. In some embodiments, there is provided a vector comprising a nucleic acid molecule according to any one of the nucleic acid molecules described above. In some embodiments, there is provided a host cell comprising any one of the anti-GM-CSFRα antibodies described above, any one of the nucleic acid molecules described above, or any one of the vectors described above. In some embodiments, there is provided a method of producing an anti-GM-CSFRα antibody, comprising: a) culturing any one of the host cells described above under conditions effective to express the anti-GM-CSFRα antibody; and b) obtaining the expressed anti-GM-CSFRα antibody from the host cell.

In some embodiments, there is provided a method of treating a disease or condition in an individual in need thereof, comprising administering to the individual an effective amount of an anti-GM-CSFRα antibody according to any one of the anti-GM-CSFRα antibodies described above. In some embodiments, the disease or condition is an inflammatory, respiratory or autoimmune disease or condition. In some embodiments, the disease or condition is selected from the group consisting of rheumatoid arthritis, asthma, chronic obstructive pulmonary disease, allergic response, multiple sclerosis, myeloid leukemia, atherosclerosis.

Also provided are pharmaceutical compositions, kits and articles of manufacture comprising any one of the anti-GM-CSFRα antibodies described above.

BRIEF DESCRIPTION OF THE DRAWINGS

FIG. 1A shows the binding curves of T119, E9, E16, E27, E29, E30, E35, E36, E54 and E34 to human GM-CSFRα. FIG. 1B shows the binding curves of T119, E108, E105, E113, E87, E85, E39, E40, EII55, E200a, and EII81 to human GM-CSFRα. FIG. 1C shows the binding curves of T119, E61, E83, E88, E90, E84, E172, E164, E1 and E31 to human GM-CSFRα.

FIG. 5A shows results of the competitive binding assay for T119, E01, E09, E194, E27, E29, E34, E35, E40, and E30. FIG. 5B shows results of the competitive binding assay for T119, E83, E87, EII81, E85, E54, EII55, E31, E105, and E84. FIG. 5C shows results of the competitive binding assay for T119, E164, E172, E108, E16, E36, E61, E88, and E39. FIG. 5D shows results of the competitive binding assay for T119, E90, EII33, E200a, E94, E113, and EII52.

FIG. 6A shows the thermal melting profiles of the antibodies. FIG. 6B shows the thermal aggregation profiles of the antibodies.

FIG. 12A shows results of the TNFα release assay for E35 and E87b as compared to Mab, as measured by the Human Macrophage/Microglia Panel. FIG. 12B shows results of the TNFα release assay for E35 and E87b as compared to Mab, as measured by ELISA.

FIG. 14A shows antibody serum concentrations of Mab and E35 upon intravenous injection of 2 mg/kg of the respective antibodies. FIG. 14B shows pharmacokinetics of Mab and E35 upon intravenous injection of 20 mg/kg of the respective antibodies.

FIG. 16A shows FACS plots of granulocytes prior to antibody administration. FIG. 16B shows FACS plots of granulocytes 14 days after antibody administration. FIG. 16C shows FACS plots of granulocytes 21 days after antibody administration. FIG. 16D shows results of the in vivo granulocyte shape change analysis from prior to antibody administration up to 21 days following antibody administration.

FIG. 17A shows results of the inhibitory effect of E35-IgG4 on GM-CSF-induced increase in white blood cells. FIG. 17B shows results of the inhibitory effect of E35-IgG4 on GM-CSF-induced increase in neutrophils. FIG. 17C shows results of the inhibitory effect of E35-IgG4 on GM-CSF-induced increase in lymphocytes. FIG. 17D shows results of the inhibitory effect of E35-IgG4 on GM-CSF-induced increase in basophils. FIG. 17E shows results of the inhibitory effect of E35-IgG4 on GM-CSF-induced increase in eosinophils. FIG. 17F shows results of the inhibitory effect of E35-IgG4 on GM-CSF-induced increase in monocytes. FIG. 17G shows results of the inhibitory effect of E35-IgG4 on GM-CSF-induced increase in red blood cells.

FIG. 18A shows the binding affinity of E35-IgG4 for wild type GMRah and mutated GMRah. FIG. 18B shows the binding affinity of E87b-IgG4 for wild type GMRah and mutated GMRah. FIG. 18C shows the binding affinity of T119-IgG4 for wild type GMRah and mutated GMRah.

FIG. 19A shows the sequence alignments of the heavy chain variable domain sequences. FIG. 19B shows the sequence alignments of the light chain variable domain sequences.

DETAILED DESCRIPTION OF THE APPLICATION

Figure 1A:
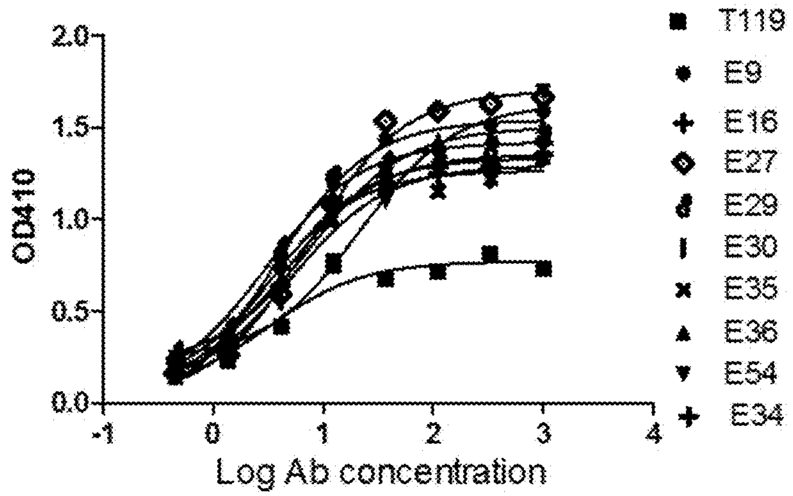
FIGS. 1A-1C show the binding affinity of exemplary anti-GM-CSFRα antibodies to human GM-CSFRα as analyzed by ELISA.

The present application in one aspect provides anti-GM-CSFRα antibodies. By using a combination of selections on naïve scFv phage libraries, affinity maturation and appropriately designed biochemical and biological assays, we have identified highly potent antibody molecules that bind to human GM-CSFRα and inhibit the action of human GM-CSF at its receptor. The results presented herein indicate that our antibodies bind a different region or epitope of GM-CSFRα compared with the known anti-GM-CSFRα antibody Mavrilimumab, and surprisingly are even more potent than Mavrilimumab as demonstrated in a variety of biological assays.

The anti-GM-CSFRα antibodies provided by the present application include, for example, full-length anti-GM-CSFRα antibodies, anti-GM-CSFRα scFvs, anti-GM-CSFRα Fc fusion proteins, multi-specific (such as bispecific) anti-GM-CSFRα antibodies, anti-GM-CSFRα immunoconjugates, and the like.

In one aspect, there are provided anti-GM-CSFRα antibodies that specifically bind to an epitope on human GM-CSFRα, wherein the epitope comprises amino acid residues Val50, Glu59, Lys194, Lys195, Arg283, and Ile284 of human GM-CSFRα.

In another aspect, there is provided an anti-GM-CSFRα antibody, wherein the anti-GM-CSFRα antibody comprises a heavy chain variable domain ($V_H$) comprising a heavy chain variable domain ($V_H$) comprising an HC-CDR1 comprising $X_1LX_2X_3H$ (SEQ ID NO: 76), wherein $X_1$ is E, N, G, D, M, S, P, F, Y, A, V, K, W, R or C, $X_2$ is S, C or P, and $X_3$ is I or M; an HC-CDR2 comprising $GFDX_1X_2X_3X_4EX_5X_6YAQKX_7QG$ (SEQ ID NO: 77), wherein $X_1$ is P, G, T, S, or V, $X_2$ is E, D, G, or A, $X_3$ is D, G, I, W, S, or V, $X_4$ is G, E, D, or H, $X_5$ is T or A, $X_6$ is N or I, and $X_7$ is S or F; and an HC-CDR3 comprising $GRYX_1X_2X_3X_4X_5X_6YGFDY$ (SEQ ID NO: 78), wherein $X_1$ is C, T, S, I, A, or V, $X_2$ is S, G, E, F, W, H, I, V, N, Y, T, or R, $X_3$ is T, H, L, F, P, I, S, Y, K, A, D, V, N, or G, $X_4$ is D, A, M, Y, F, S, T, G, or W, $X_5$ is T, S, F, Q, A, N, L, E, I, G, or M, and $X_6$ is C, T, N, S, or A; and a light chain variable domain ($V_L$) comprising a LC-CDR1 comprising $RAX_1X_2X_3VX_4X_5X_6LA$(SEQ ID NO: 293), wherein $X_1$ is S, L, N, A, K, R, I, Q, G, T, H, M, or C, $X_2$ is Q, Y, P, A, I, F, T, R, V, L, E, S, or C, $X_3$ is S, H, W, L, R, K, T, P, I, F, V, E, A, or Q, $X_4$ is S, L, W, M, A, Y, K, R, G, T, E, V, N, F, or C, $X_5$ is S, T, R, A, H, Q, P, M, L, or G, and $X_6$ is Y, L, or F; a LC-CDR2 comprising$X_1X_2X_3SRAT$ (SEQ ID NO: 294), wherein $X_1$ is G or T, $X_2$ is A, G, R, H, K, S, T, M, or F, and $X_3$ is S, A, W, R, L, T, Q, F, Y, H, or N; and a LC-CDR3 comprising $QQYX_1X_2X_3PX_4T$ (SEQ ID NO:

79), wherein $X_1$ is N, D, S, R, A, T, L, Y, Q, W or G, $X_2$ is N, D, E, T, Y, G, A, M, F, S, I or L, $X_3$ is W, S, P, V, G, or R, and $X_4$ is P, Y, H, S, F, N, D, V, or G.

Also provided are nucleic acids encoding the anti-GM-CSFRα antibodies, compositions comprising the anti-GM-CSFRα antibodies, and methods of making and using the anti-GM-CSFRα antibodies.

Definitions

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of the disease (such as, for example, tumor volume for cancer). The methods of the application contemplate any one or more of these aspects of treatment.

The term "antibody" includes full-length antibodies and antigen-binding fragments thereof. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (14 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab') 2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a single domain antibody, a Nanobody™, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody "competes" for binding to a target GM-CSFRα with a second antibody when the first antibody inhibits target GM-CSFRα binding of the second antibody by at least about 50% (such as at least about any of 55%, 60%, 65%, 70%, 75%, 80%, 85%, 90%, 95%, 98% or 99%) in the presence of an equimolar concentration of the first antibody, or vice versa. A high throughput process for "binning" antibodies based upon their cross-competition is described in PCT Publication No. WO 03/48731.

As use herein, the term "specifically binds," "specifically recognizing," or "is specific for" refers to measurable and reproducible interactions, such as binding between a target and an antibody that is determinative of the presence of the target in the presence of a heterogeneous population of molecules, including biological molecules. For example, an antibody that specifically recognizes a target (which can be an epitope) is an antibody that binds this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

An "isolated" anti-GM-CSFRα antibody as used herein refers to an anti-GM-CSFRα antibody that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.,* 273: 927-948 (1997); MacCallum et al., J. Mol. Biol. 262:732-745 (1996); Abhinandan and Martin, *Mol. Immunol.,* 45:3832-3839 (2008); Lefranc M. P. et al., *Dev. Comp. Immunol.,* 27:55-77 (2003); and Honegger and Plückthun, *J. Mol. Biol.,* 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.,* 45:3832-3839 (2008); Ehrenmann F. et al., *Nucleic Acids Res.,* 38: D301-D307 (2010); and Adolf-Bryfogle J. et al., *Nucleic Acids Res.,* 43: D432-D438 (2015). The contents of the references cited in this paragraph are incorporated herein by reference in their entireties for use in the present application and for possible inclusion in one or more claims herein.

TABLE 1

CDR DEFINITIONS

| | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this application (see U.S. Pat. No. 4,816,567; and Morrison et al., Proc. Natl. Acad. Sci. USA, 81:6851-6855 (1984)).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32 (5): 1792-1797, 2004; Edgar, R. C., *BMC Bioinformatics* 5 (1): 113, 2004).

The terms "Fc receptor" or "FcR" are used to describe a receptor that binds to the Fc region of an antibody. In some embodiments, an FcR of this application is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM)

in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.*22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent $K_d$ or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent $K_d$ or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See also, Idusogie et al. *J. Immunol.* 164:4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-GM-CSFRα antibody or composition as disclosed herein, is an amount sufficient to carry out a specifically stated purpose. An "effective amount" can be determined empirically and by known methods relating to the stated purpose.

The term "therapeutically effective amount" refers to an amount of an anti-GM-CSFRα antibody or composition as disclosed herein, effective to "treat" a disease or disorder in an individual. In the case of cancer, the therapeutically effective amount of the anti-GM-CSFRα antibody or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-GM-CSFRα antibody or composition as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that extends the survival of a patient. In some embodiments, the therapeutically effective amount is an amount that improves progression free survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "an," and "the" include plural referents unless the context clearly dictates otherwise.

Anti-GM-CSFRα Antibodies

In one aspect, the present application provides anti-GM-CSFRα antibodies that specifically bind to GM-CSFRα. Anti-GM-CSFRα antibodies include, but are not limited to, humanized antibodies, chimeric antibodies, mouse antibodies, human antibodies, and antibodies comprising the heavy chain and/or light chain CDRs discussed herein. In one aspect, the present application provides isolated antibodies that bind to GM-CSFRα. Contemplated anti-GM-CSFRα antibodies include, for example, full-length anti-GM-CSFRα antibodies (e.g., full-length IgG1 or IgG4), anti-GM-CSFRα scFvs, anti-GM-CSFRα Fc fusion proteins, multi-specific (such as bispecific) anti-GM-CSFRα antibodies, anti-GM-CSFRα immunoconjugates, and the like. In some embodiments, the anti-GM-CSFRα antibody is a full-length antibody (e.g., full-length IgG1 or IgG4) or antigen-binding fragment thereof, which specifically binds to GM-CSFRα. In some embodiments, the anti-GM-CSFRα antibody is a Fab, a Fab', a F(ab)'2, a Fab'-SH, a single-chain Fv (scFv), an Fv fragment, a dAb, a Fd, a Nanobody™, a diabody, or a linear antibody. In some embodiments, reference to an antibody that specifically binds to GM-CSFRα means that the antibody binds to GM-CSFRα with an affinity that is at least about 10 times (including for example at least about any one of 10, $10^2$, $10^3$, $10^4$, $10^5$, $10^6$, or $10^7$ times) more tightly than its binding affinity for a non-target. In some embodiments, the non-target is an antigen that is not GM-CSFRα. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay or biolayer interferometry (BLI).

Although anti-GM-CSFRα antibodies containing human sequences (e.g., human heavy and light chain variable domain sequences comprising human CDR sequences) are extensively discussed herein, non-human anti-GM-CSFRα antibodies are also contemplated. In some embodiments, non-human anti-GM-CSFRα antibodies comprise human CDR sequences from an anti-GM-CSFRα antibody as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-GM-CSFRα antibody includes an anti-GM-CSFRα antibody generated by grafting one or more human CDR sequences as described herein onto a non-human framework sequence (e.g., a mouse or chicken framework sequence).

The complete amino acid sequence of an exemplary human GM-CSFRα comprises or consists of the amino acid sequence of SEQ ID NO: 148.

```
  1 MLLLVTSLLL CELPHPAFLL IPEKSDLRTV APASSLNVRF
    DSRTMNLSWD CQENTTFSKC
 61 FLTDKKNRVV EPRLSNNECS CTFREICLHE GVTFEVHVNT
    SQRGFQQKLL YPNSGREGTA
121 AQNFSCFIYN ADLMNCTWAR GPTAPRDVQY FLYIRNSKRR
    REIRCPYYIQ DSGTHVGCHL
181 DNLSGLTSRN YFLVNGTSRE IGIQFFDSLL DTKKIERFNP
    PSNVTVRCNT THCLVRWKQP
241 RTYQKLSYLD FQYQLDVHRK NTQPGTENLL INVSGDLENR
    YNFPSSEPRA KHSVKIRAAD
301 VRILNWSSWS EAIEFGSDDG NLGSVYIYVL LIVGTLVCGI
    VLGFLFKRFL RIQRLFPPVP
361 QIKDKLNDNH EVEDEIIWEE FTPEEGKGYR EEVLTVKEIT
```

The amino acid sequence of the extracellular domain of an exemplary human GM-CSFRα comprises or consists of the amino acid sequence of SEQ ID NO: 149.

```
  1 MLLLVTSLLL CELPHPAFLL IPEKSDLRTV APASSLNVRF
    DSRTMNLSWD CQENTTFSKC
 61 FLTDKKNRVV EPRLSNNECS CTFREICLHE GVTFEVHVNT
    SQRGFQQKLL YPNSGREGTA
121 AQNFSCFIYN ADLMNCTWAR GPTAPRDVQY FLYIRNSKRR
    REIRCPYYIQ DSGTHVGCHL
181 DNLSGLTSRN YFLVNGTSRE IGIQFFDSLL DTKKIERFNP
    PSNVTVRCNT THCLVRWKQP
241 RTYQKLSYLD FQYQLDVHRK NTQPGTENLL INVSGDLENR
    YNFPSSEPRA KHSVKIRAAD
301 VRILNWSSWS EAIEFGSDDG
```

In some embodiments, the anti-GM-CSFRα antibody described herein specifically recognizes an epitope within human GM-CSFRα. In some embodiments, the anti-GM-CSFRα antibody cross-reacts with GM-CSFRα from species other than human. In some embodiments, the anti-GM-CSFRα antibody is completely specific for human GM-CSFRα and does not exhibit species or other types of non-human cross-reactivity.

In some embodiments, the anti-GM-CSFRα antibody described herein specifically binds to a linear epitope within human GM-CSFRα. In some embodiments, the anti-GM-CSFRα antibody described herein specifically binds to a nonlinear epitope within human GM-CSFRα. In some embodiments, the anti-GM-CSFRα antibody described herein specifically binds to an epitope on human GM-CSFRα, wherein the epitope comprises one, two, three, four, five, or six amino acid residues selected from the group consisting of Val50, Glu59, Lys194, Lys195, Arg283, and Ile284 of human GM-CSFRα. In some embodiments, the anti-GM-CSFRα antibody described herein specifically binds to an epitope on human GM-CSFRα, wherein the epitope comprises Val50, Glu59, Lys194, Lys195, Arg283, and Ile284 of human GM-CSFRα. In some embodiments, the anti-GM-CSFRα antibody described herein specifically binds to an epitope on human GM-CSFRα, wherein the epitope comprises one, two, three, four, five, six, seven, eight, or nine amino acid residues selected from the group consisting of Val50, Glu59, Lys194, Lys195, Arg283, Ile284, Val51, Thr63, and Ile196. In some embodiments, the anti-GM-CSFRα antibody described herein specifically binds to an epitope on human GM-CSFRα, wherein the epitope comprises amino acid residues Val50, Glu59, Lys194, Lys195, Arg283, Ile284, Val51, Thr63, and Ile196. In some embodiments, the anti-GM-CSFRα antibody described herein specifically binds to an epitope on human GM-CSFRα, wherein the epitope comprises one, two, three, four, five, six, seven, or eight amino acid residues selected from the group consisting of Val50, Glu59, Lys194, Lys195, Arg283, Ile284, Leu191 and Ile196. In some embodiments, the anti-GM-CSFRα antibody described herein specifically binds to an epitope on human GM-CSFRα, wherein the epitope comprises amino acid residues Val50, Glu59, Lys194, Lys195, Arg283, Ile284, Leu191 and Ile196. In some embodiments, the anti-GM-CSFRα antibody described herein specifically binds to an epitope on human GM-CSFRα, wherein the epitope comprises one, two, three, four, five, six, seven, eight, nine, or ten amino acid residues selected from the group consisting of Val50, Glu59, Lys194, Lys195, Arg283, Ile284, Arg49, Val51, Asn57, and Ser61. In some embodiments, the anti-GM-CSFRα antibody described herein specifically binds to an epitope on human GM-CSFRα, wherein the epitope comprises amino acid residues Val50, Glu59, Lys194, Lys195, Arg283, Ile284, Arg49, Val51, Asn57, and Ser61.

In some embodiments, the anti-GM-CSFRα antibody cross-reacts with at least one allelic variant of the GM-CSFRα protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring GM-CSFRα (or fragments thereof). In some embodiments, the anti-GM-CSFRα antibody does not cross-react with any allelic variant of the GM-CSFRα protein (or fragments thereof).

In some embodiments, the anti-GM-CSFRα antibody cross-reacts with at least one interspecies variant of the GM-CSFRα protein. In some embodiments, for example, the GM-CSFRα protein (or fragments thereof) is human GM-CSFRα and the interspecies variant of the GM-CSFRα protein (or fragments thereof) is a cynomolgus monkey variant thereof. In some embodiments, the anti-GM-CSFRα antibody does not cross-react with any interspecies variant of the GM-CSFRα protein.

In some embodiments, according to any of the anti-GM-CSFRα antibodies described herein, the anti-GM-CSFRα antibody comprises an antibody heavy chain constant region and an antibody light chain constant region. In some embodiments, the anti-GM-CSFRα antibody comprises an IgG1 heavy chain constant region. In some embodiments, the anti-GM-CSFRα antibody comprises an IgG2 heavy chain constant region. In some embodiments, the anti-GM-CSFRα antibody comprises an IgG3 heavy chain constant region. In some embodiments, the anti-GM-CSFRα antibody comprises an IgG4 heavy chain constant region. In some embodiments, the heavy chain constant region comprises (including consisting of or consisting essentially of) the amino acid sequence of SEQ ID NO: 145. In some embodiments, the heavy chain constant region comprises (including consisting of or consisting essentially of) the amino acid sequence of SEQ ID NO: 146. In some embodiments, the anti-GM-CSFRα comprises a lambda light chain constant region. In some embodiments, the anti-GM-CSFRα antibody comprises a kappa light chain constant region. In some embodiments, the light chain constant region comprises (including consisting of or consisting essentially of) the amino acid sequence of SEQ ID NO: 147. In some embodiments, the anti-GM-CSFRα antibody comprises an antibody heavy chain variable domain and an antibody light chain variable domain.

In some embodiments, the anti-GM-CSFRα antibody comprises a $V_H$ comprising an HC-CDR1 comprising $X_1LX_2X_3H$ (SEQ ID NO: 76), wherein $X_1$ is E, N, G, D, M, S, P, F, Y, A, V, K, W, R or C, $X_2$ is S, C or P, and $X_3$ is I or M; an HC-CDR2 comprising $GFDX_1X_2X_3X_4EX_5X_6YAQKX_7QG$ (SEQ ID NO: 77), wherein $X_1$ is P, G, T, S, or V, $X_2$ is E, D, G, or A, $X_3$ is D, G, I, W, S, or V, $X_4$ is G, E, D, or H, $X_5$ is T or A, $X_6$ is N or I, and $X_7$ is S or F; and an HC-CDR3 comprising $GRYX_1X_2X_3X_4X_5X_6YGFDY$ (SEQ ID NO: 78), wherein $X_1$ is C, T, S, I, A, or V, $X_2$ is S, G, E, F, W, H, I, V, N, Y, T, or R, $X_3$ is T, H, L, F, P, I, S, Y, K, A, D, V, N, or G, $X_4$ is D, A, M, Y, F, S, T, G, or W, $X_5$ is T, S, F, Q, A, N, L, E, I, G, or M, and $X_6$ is C, T, N, S, or A; and a $V_L$ comprising a LC-CDR1 comprising $RAX_1X_2X_3$ $VX_4X_5X_6LA$(SEQ ID NO: 293), wherein $X_1$ is S, L, N, A, K, R, I, Q, G, T, H, M, or C, $X_2$ is Q, Y, P, A, I, F, T, R, V, L, E, S, or C, $X_3$ is S, H, W, L, R, K, T, P, I, F, V, E, A, or Q, $X_4$ is S, L, W, M, A, Y, K, R, G, T, E, V, N, F, or C, $X_5$ is S, T, R, A, H, Q, P, M, L, or G, and $X_6$ is Y, L, or F; a LC-CDR2 comprising$X_1X_2X_3SRAT$(SEQ ID NO: 294), wherein $X_1$ is G or T, $X_2$ is A, G, R, H, K, S, T, M, or F, and $X_3$ is S, A, W, R, L, T, Q, F, Y, H, or N; and a LC-CDR3 comprising $QQYX_1X_2X_3PX_4T$ (SEQ ID NO: 79), wherein $X_1$ is N, D, S, R, A, T, L, Y, Q, W or G, $X_2$ is N, D, E, T, Y, G, A, M, F, S, I or L, $X_3$ is W, S, P, V, G, or R, and $X_4$ is P, Y, H, S, F, N, D, V, or G.

In some embodiments, the anti-GM-CSFRα antibody comprises a $V_H$ comprising a HC-CDR1 comprising $ELX_1X_2H$ (SEQ ID NO: 295), wherein $X_1$ is S, C or P, and $X_2$ is I or M; an HC-CDR2 comprising $GFDX_1X_2X_3X_4EX_5X_6YAQKX_7QG$ (SEQ ID NO: 77), wherein $X_1$ is P, G, T, S, or V, $X_2$ is E, D, G, or A, $X_3$ is D, G, I, W, S, or V, $X_4$ is G, E, D, or H, $X_5$ is T or A, $X_6$ is N or I, and $X_7$ is S or F; and an HC-CDR3 comprising $GRYX_1X_2X_3X_4X_5X_6YGFDY$ (SEQ ID NO: 78), wherein $X_1$ is C, T, S, I, A, or V, $X_2$ is S, G, E, F, W, H, I, V, N, Y, T, or R, $X_3$ is T, H, L, F, P, I, S, Y, K, A, D, V, N, or G, $X_4$ is D, A, M, Y, F, S, T, G, or W, $X_5$ is T, S, F, Q, A, N, L, E, I, G, or M, and $X_6$ is C, T, N, S, or A; and a $V_L$ comprising: a LC-CDR1 comprising RASQSVSSYLA (SEQ ID NO: 51); a LC-CDR2 comprising GASSRAT (SEQ ID NO: 52); and a LC-CDR3 comprising $QQYX_1X_2X_3PX_4T$ (SEQ ID NO: 79), wherein $X_1$ is N, D, S, R, A, T, L, Y, Q, W or G, $X_2$ is N, D, E, T, Y, G, A, M, F, S, I or L, $X_3$ is W, S, P, V, G, or R, and $X_4$ is P, Y, H, S, F, N, D, V, or G.

In some embodiments, the anti-GM-CSFRα antibody comprises a $V_H$ comprising: an HC-CDR1 comprising the amino acid sequence of any one of SEQ ID NOs: 1-4, or a variant thereof comprising up to about 3 (such as about any of 1, 2, or 3) amino acid substitutions, an HC-CDR2 comprising the amino acid sequence of any one of SEQ ID NOs: 5-16, or a variant thereof comprising up to about 3 (such as about any of 1, 2, or 3) amino acid substitutions, and an HC-CDR3 comprising the amino acid sequence of any one of SEQ ID NOs: 17-50, or a variant thereof comprising up to about 3 (such as about any of 1, 2, or 3) amino acid substitutions.

In some embodiments, the anti-GM-CSFRα antibody comprises a $V_H$ comprising: an HC-CDR1 comprising the amino acid sequence of any one of SEQ ID NOs: 1-4, an HC-CDR2 comprising the amino acid sequence of any one of SEQ ID NOs: 5-16, and an HC-CDR3 comprising the amino acid sequence of any one of SEQ ID NOs: 17-50.

In some embodiments, the anti-GM-CSFRα antibody comprises a $V_L$ comprising: an LC-CDR1 comprising the amino acid sequence of SEQ ID NO: 51, or a variant thereof comprising up to about 3 (such as about any of 1, 2, or 3) amino acid substitutions, an LC-CDR2 comprising the amino acid sequence of SEQ ID NO: 52, or a variant thereof comprising up to about 3 (such as about any of 1, 2, or 3) amino acid substitutions, and an LC-CDR3 comprising the amino acid sequence of any one of SEQ ID NOs: 53-75, or a variant thereof comprising up to about 3 (such as about any of 1, 2, or 3) amino acid substitutions.

In some embodiments, the anti-GM-CSFRα antibody comprises a $V_L$ comprising: an LC-CDR1 comprising the amino acid sequence of SEQ ID NOs: 51, an LC-CDR2 comprising the amino acid sequence of SEQ ID NO: 52, and an LC-CDR3 comprising the amino acid sequence of any one of SEQ ID NOs: 53-75.

In some embodiments, the anti-GM-CSFRα antibody comprises a $V_H$ comprising: an HC-CDR1 comprising the amino acid sequence of any one of SEQ ID NOs: 1-4, or a variant thereof comprising up to about 3 (such as about any of 1, 2, or 3) amino acid substitutions, an HC-CDR2 comprising the amino acid sequence of any one of SEQ ID NOs: 5-16, or a variant thereof comprising up to about 3 (such as about any of 1, 2, or 3) amino acid substitutions, and an HC-CDR3 comprising the amino acid sequence of any one of SEQ ID NOs: 17-50, or a variant thereof comprising up to about 3 (such as about any of 1, 2, or 3) amino acid substitutions; and a $V_L$ comprising: an LC-CDR1 comprising the amino acid sequence of SEQ ID NO: 51, or a variant thereof comprising up to about 3 (such as about any of 1, 2, or 3) amino acid substitutions, an LC-CDR2 comprising the amino acid sequence of SEQ ID NO: 52, or a variant thereof comprising up to about 3 (such as about any of 1, 2, or 3) amino acid substitutions, and an LC-CDR3 comprising the amino acid sequence of any one of SEQ ID NOs: 53-75, or a variant thereof comprising up to about 3 (such as about any of 1, 2, or 3) amino acid substitutions.

In some embodiments, the anti-GM-CSFRα antibody comprises a $V_H$ comprising: an HC-CDR1 comprising the amino acid sequence of any one of SEQ ID NOs: 1-4, an HC-CDR2 comprising the amino acid sequence of any one of SEQ ID NOs: 5-16, and an HC-CDR3 comprising the amino acid sequence of any one of SEQ ID NOs: 17-50; and a $V_L$ comprising: an LC-CDR1 comprising the amino acid sequence of SEQ ID NOs: 51, an LC-CDR2 comprising the amino acid sequence of SEQ ID NO: 52, and an LC-CDR3 comprising the amino acid sequence of any one of SEQ ID NOs: 53-75.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 5, and an HC-CDR3 comprising the amino acid sequence of SEQ ID NO: 17, or a variant thereof comprising up to about 5 amino acid substitutions in the HC-CDRs; and a $V_L$ comprising: an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 5, and an HC-CDR3 comprising the amino acid sequence of SEQ ID NO: 17; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 56, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 56.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to about 5 amino acid substitutions in the LC-CDRs.

In some embodiments, the anti-GM-CSFRα antibody comprises a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57.

In some embodiments, the anti-GM-CSFRα antibody comprises a $V_H$ comprising: an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 50, or a variant thereof comprising up to about 5 amino acid substitutions in the HC-CDRs; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to about 5 amino acid substitutions in the LC-CDRs.

In some embodiments, the anti-GM-CSFRα antibody comprises a $V_H$ comprising: an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 50; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57.

In some embodiments, the anti-GM-CSFRα antibody comprises a $V_H$ comprising the amino acid sequences of SEQ ID NOs: 1-50, or a variant thereof comprising up to about 5 amino acid substitutions; and a $V_L$ comprising the amino acid sequences of SEQ ID NOs: 51-75, or a variant thereof comprising up to about 5 amino acid substitutions. In some embodiments, the anti-GM-CSFRα antibody comprises a $V_H$ comprising the amino acid sequences of SEQ ID NOs: 1-50; and a $V_L$ comprising the amino acid sequences of SEQ ID NOs: 51-75.

In some embodiments, the anti-GM-CSFRα antibody comprises a $V_H$ comprising the amino acid sequences of SEQ ID NOs: 1, 5 and 17, or a variant thereof comprising up to about 5 amino acid substitutions; and a $V_L$ comprising the amino acid sequences of SEQ ID NOs: 51, 52 and 54, or a variant thereof comprising up to about 5 amino acid substitutions. In some embodiments, the anti-GM-CSFRα antibody comprises a $V_H$ comprising the amino acid sequences of SEQ ID NOs: 1, 5 and 17; and a $V_L$ comprising the amino acid sequences of SEQ ID NOs: 51, 52 and 54.

In some embodiments, the anti-GM-CSFRα antibody comprises a $V_H$ comprising the amino acid sequences of SEQ ID NOs: 1, 8 and 22, or a variant thereof comprising up to about 5 amino acid substitutions; and a $V_L$ comprising the amino acid sequences of SEQ ID NOs: 51, 52 and 56, or a variant thereof comprising up to about 5 amino acid substitutions. In some embodiments, the anti-GM-CSFRα antibody comprises a $V_H$ comprising the amino acid sequences of SEQ ID NOs: 1, 8 and 22; and a $V_L$ comprising the amino acid sequences of SEQ ID NOs: 51, 52 and 56.

In some embodiments, the anti-GM-CSFRα antibody comprises a $V_H$ comprising the amino acid sequences of SEQ ID NOs: 1, 7 and 23, or a variant thereof comprising up to about 5 amino acid substitutions; and a $V_L$ comprising the amino acid sequences of SEQ ID NOs: 51, 52 and 57, or a variant thereof comprising up to about 5 amino acid substitutions. In some embodiments, the anti-GM-CSFRα antibody comprises a $V_H$ comprising the amino acid sequences of SEQ ID NOs: 1, 7 and 23; and a $V_L$ comprising the amino acid sequences of SEQ ID NOs: 51, 52 and 57.

In some embodiments, the anti-GM-CSFRα antibody comprises a $V_H$ comprising the amino acid sequences of SEQ ID NOs: 1, 6 and 27, or a variant thereof comprising up to about 5 amino acid substitutions; and a $V_L$ comprising the amino acid sequences of SEQ ID NOs: 51, 52 and 57, or a variant thereof comprising up to about 5 amino acid substitutions. In some embodiments, the anti-GM-CSFRα antibody comprises a $V_H$ comprising the amino acid sequences of SEQ ID NOs: 1, 6 and 27; and a $V_L$ comprising the amino acid sequences of SEQ ID NOs: 51, 52 and 57.

In some embodiments, the anti-GM-CSFRα antibody comprises a $V_H$ comprising the amino acid sequences of SEQ ID NOs: 1, 7 and 35, or a variant thereof comprising up to about 5 amino acid substitutions; and a $V_L$ comprising the amino acid sequences of SEQ ID NOs: 51, 52 and 53, or a variant thereof comprising up to about 5 amino acid substitutions. In some embodiments, the anti-GM-CSFRα antibody comprises a $V_H$ comprising the amino acid sequences of SEQ ID NOs: 1, 7 and 35; and a $V_L$ comprising the amino acid sequences of SEQ ID NOs: 51, 52 and 53.

In some embodiments, the anti-GM-CSFRα antibody comprises a $V_H$ comprising the amino acid sequences of SEQ ID NOs: 1, 7 and 37, or a variant thereof comprising up to about 5 amino acid substitutions; and a $V_L$ comprising the amino acid sequences of SEQ ID NOs: 51, 52 and 57, or a variant thereof comprising up to about 5 amino acid substitutions. In some embodiments, the anti-GM-CSFRα antibody comprises a $V_H$ comprising the amino acid sequences of SEQ ID NOs: 1, 7 and 37; and a $V_L$ comprising the amino acid sequences of SEQ ID NOs: 51, 52 and 57.

In some embodiments, the anti-GM-CSFRα antibody comprises a $V_H$ comprising the amino acid sequences of SEQ ID NOs: 3, 6 and 39, or a variant thereof comprising up to about 5 amino acid substitutions; and a $V_L$ comprising the amino acid sequences of SEQ ID NOs: 51, 52 and 54, or a variant thereof comprising up to about 5 amino acid substitutions. In some embodiments, the anti-GM-CSFRα antibody comprises a $V_H$ comprising the amino acid sequences of SEQ ID NOs: 3, 6 and 39; and a $V_L$ comprising the amino acid sequences of SEQ ID NOs: 51, 52 and 54.

In some embodiments, the anti-GM-CSFRα antibody comprises a $V_H$ comprising the amino acid sequences of SEQ ID NOs: 1, 7 and 35, or a variant thereof comprising up to about 5 amino acid substitutions; and a $V_L$ comprising the amino acid sequences of SEQ ID NOs: 51, 52 and 57, or a variant thereof comprising up to about 5 amino acid substitutions. In some embodiments, the anti-GM-CSFRα antibody comprises a $V_H$ comprising the amino acid sequences of SEQ ID NOs: 1, 7 and 35; and a $V_L$ comprising the amino acid sequences of SEQ ID NOs: 51, 52 and 57.

In some embodiments, the anti-GM-CSFRα antibody comprises a $V_H$ comprising the amino acid sequences of SEQ ID NOs: 1, 7 and 50, or a variant thereof comprising up to about 5 amino acid substitutions; and a $V_L$ comprising the amino acid sequences of SEQ ID NOs: 51, 52 and 57, or a variant thereof comprising up to about 5 amino acid substitutions. In some embodiments, the anti-GM-CSFRα antibody comprises a $V_H$ comprising the amino acid sequences of SEQ ID NOs: 1, 7 and 50; and a $V_L$ comprising the amino acid sequences of SEQ ID NOs: 51, 52 and 57.

In some embodiments, the anti-GM-CSFRα antibody comprises a $V_H$ comprising an HC-CDR1, an HC-CDR2 and an HC-CDR3 of the $V_H$ comprising the amino acid sequence of any one of SEQ ID NOs: 80-121, and 246-287; and a $V_L$ comprising a LC-CDR1, a LC-CDR2, and a LC-CDR3 of the $V_L$ comprising the amino acid sequence of any one of SEQ ID NOs: 122-144, 150-245, and 288-289.

In some embodiments, the anti-GM-CSFRα antibody comprises a $V_H$ comprising one, two or three HC-CDRs of SEQ ID NO: 80. In some embodiments, the anti-GM-CSFRα antibody comprises a $V_H$ comprising one, two or three HC-CDRs of SEQ ID NO: 85. In some embodiments, the anti-GM-CSFRα antibody comprises a $V_H$ comprising one, two or three HC-CDRs of SEQ ID NO: 86. In some embodiments, the anti-GM-CSFRα antibody comprises a $V_H$ comprising one, two or three HC-CDRs of SEQ ID NO: 91. In some embodiments, the anti-GM-CSFRα antibody comprises a $V_H$ comprising one, two or three HC-CDRs of SEQ ID NO: 99. In some embodiments, the anti-GM-CSFRα antibody comprises a $V_H$ comprising one, two or three HC-CDRs of SEQ ID NO: 101. In some embodiments, the anti-GM-CSFRα antibody comprises a $V_H$ comprising one, two or three HC-CDRs of SEQ ID NO: 103. In some embodiments, the anti-GM-CSFRα antibody comprises a $V_H$ comprising one, two or three HC-CDRs of SEQ ID NO: 121.

In some embodiments, the anti-GM-CSFRα antibody comprises a $V_L$ comprising one, two or three LC-CDRs of SEQ ID NO: 123. In some embodiments, the anti-GM-CSFRα antibody comprises a $V_L$ comprising one, two or three LC-CDRs of SEQ ID NO: 125. In some embodiments, the anti-GM-CSFRα antibody comprises a $V_L$ comprising one, two or three LC-CDRs of SEQ ID NO: 126. In some embodiments, the anti-GM-CSFRα antibody comprises a $V_L$ comprising one, two or three LC-CDRs of SEQ ID NO: 122.

In some embodiments, the anti-GM-CSFRα antibody comprises a $V_H$ comprising HC-CDR1, HC-CDR2 and HC-CDR3 of the $V_H$ of SEQ ID NO: 80, and a $V_L$ comprising LC-CDR1, LC-CDR2 and LC-CDR3 of the $V_L$ of SEQ ID NO: 123. In some embodiments, the anti-GM-CSFRα antibody comprises a $V_H$ comprising HC-CDR1, HC-CDR2 and HC-CDR3 of the $V_H$ of SEQ ID NO: 85, and a $V_L$ comprising LC-CDR1, LC-CDR2 and LC-CDR3 of the $V_L$ of SEQ ID NO: 125. In some embodiments, the anti-GM-CSFRα antibody comprises a $V_H$ comprising HC-CDR1, HC-CDR2 and HC-CDR3 of the $V_H$ of SEQ ID NO: 86, and a $V_L$ comprising LC-CDR1, LC-CDR2 and LC-CDR3 of the $V_L$ of SEQ ID NO: 126. In some embodiments, the anti-GM-CSFRα antibody comprises a $V_H$ comprising HC-CDR1, HC-CDR2 and HC-CDR3 of the $V_H$ of SEQ ID NO: 91, and a $V_L$ comprising LC-CDR1, LC-CDR2 and LC-CDR3 of the $V_L$ of SEQ ID NO: 126. In some embodiments, the anti-GM-CSFRα antibody comprises a $V_H$ comprising HC-CDR1, HC-CDR2 and HC-CDR3 of the $V_H$ of SEQ ID NO: 99, and a $V_L$ comprising LC-CDR1, LC-CDR2 and LC-CDR3 of the $V_L$ of SEQ ID NO: 122. In some embodiments, the anti-GM-CSFRα antibody comprises a $V_H$ comprising HC-CDR1, HC-CDR2 and HC-CDR3 of the $V_H$ of SEQ ID NO: 101, and a $V_L$ comprising LC-CDR1, LC-CDR2 and LC-CDR3 of the $V_L$ of SEQ ID NO: 126. In some embodiments, the anti-GM-CSFRα antibody comprises a $V_H$ comprising HC-CDR1, HC-CDR2 and HC-CDR3 of the $V_H$ of SEQ ID NO: 103, and a $V_L$ comprising LC-CDR1, LC-CDR2 and LC-CDR3 of the $V_L$ of SEQ ID NO: 123. In some embodiments, the anti-GM-CSFRα antibody comprises a $V_H$ comprising HC-CDR1, HC-CDR2 and HC-CDR3 of the $V_H$ of SEQ ID NO: 99, and a $V_L$ comprising LC-CDR1, LC-CDR2 and LC-CDR3 of the $V_L$ of SEQ ID NO: 126. In some embodiments, the anti-GM-CSFRα antibody comprises a $V_H$ comprising HC-CDR1, HC-CDR2 and HC-CDR3 of the $V_H$ of SEQ ID NO: 121, and a $V_L$ comprising LC-CDR1, LC-CDR2 and LC-CDR3 of the $V_L$ of SEQ ID NO: 126.

In some embodiments, the anti-GM-CSFRα antibody comprises a $V_H$ comprising the amino acid sequence of any one of SEQ ID NOs: 80-121 and 246-287, or a variant thereof having at least about 90% (for example at least about any of 91%, 92%, 93%, 94%, 95%, 96%, 97%, 98%, or 99%) sequence identity, and a $V_L$ comprising the amino acid sequence of any one of SEQ ID NOs: 122-144, 150-245, and 288-289, or a variant thereof having at least about 90% sequence identity. In some embodiments, the anti-GM-CSFRα antibody comprises a $V_H$ comprising the amino acid sequence of any one of SEQ ID NOs: 80-121 and 246-287, and a $V_L$ comprising the amino acid sequence of any one of SEQ ID NOs: 122-144, 150-245, and 288-289.

In some embodiments, the anti-GM-CSFRα antibody comprises a $V_H$ comprising the amino acid sequence of SEQ ID NO: 80, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 123, or a variant thereof having at least about 90% sequence identity. In some embodiments, the anti-GM-CSFRα antibody comprises a $V_H$ comprising the amino acid sequence of SEQ ID NO: 80 and a $V_L$ comprising the amino acid sequence of SEQ ID NO: 123.

In some embodiments, the anti-GM-CSFRα antibody comprises a $V_H$ comprising the amino acid sequence of SEQ ID NO: 85, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 125, or a variant thereof having at least about 90% sequence identity. In some embodiments, the anti-GM-CSFRα antibody comprises a $V_H$ comprising the amino acid sequence of SEQ ID NO: 85 and a $V_L$ comprising the amino acid sequence of SEQ ID NO: 125.

In some embodiments, the anti-GM-CSFRα antibody comprises a $V_H$ comprising the amino acid sequence of SEQ ID NO: 86, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% sequence identity. In some embodiments, the anti-GM-CSFRα antibody comprises a $V_H$ comprising the amino acid sequence of SEQ ID NO: 86 and a $V_L$ comprising the amino acid sequence of SEQ ID NO: 126.

In some embodiments, the anti-GM-CSFRα antibody comprises a $V_H$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% sequence identity. In some embodiments, the anti-GM-CSFRα antibody comprises a $V_H$ comprising the amino acid sequence of SEQ ID NO: 91 and a $V_L$ comprising the amino acid sequence of SEQ ID NO: 126.

In some embodiments, the anti-GM-CSFRα antibody comprises a $V_H$ comprising the amino acid sequence of SEQ ID NO: 99, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 122, or a variant thereof having at least about 90% sequence identity. In some embodiments, the anti-GM-CSFRα antibody comprises a $V_H$ comprising the amino acid sequence of SEQ ID NO: 99 and a $V_L$ comprising the amino acid sequence of SEQ ID NO: 122.

In some embodiments, the anti-GM-CSFRα antibody comprises a $V_H$ comprising the amino acid sequence of SEQ ID NO: 101, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% sequence identity. In some embodiments, the anti-GM-CSFRα antibody comprises a $V_H$ comprising the amino acid sequence of SEQ ID NO: 101 and a $V_L$ comprising the amino acid sequence of SEQ ID NO: 126.

In some embodiments, the anti-GM-CSFRα antibody comprises a $V_H$ comprising the amino acid sequence of SEQ ID NO: 103, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 123, or a variant thereof having at least about 90% sequence identity. In some embodiments, the anti-GM-CSFRα antibody comprises a $V_H$ comprising the amino acid sequence of SEQ ID NO: 103 and a $V_L$ comprising the amino acid sequence of SEQ ID NO: 123.

In some embodiments, the anti-GM-CSFRα antibody comprises a $V_H$ comprising the amino acid sequence of SEQ ID NO: 99, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% sequence identity. In some embodiments, the anti-GM-CSFRα antibody comprises a $V_H$ comprising the amino acid sequence of SEQ ID NO: 99 and a $V_L$ comprising the amino acid sequence of SEQ ID NO: 126.

In some embodiments, the anti-GM-CSFRα antibody comprises a $V_H$ comprising the amino acid sequence of SEQ ID NO: 121, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 126, or a variant thereof having at least about 90% sequence identity. In some embodiments, the anti-GM-CSFRα antibody comprises a $V_H$ comprising the amino acid sequence of SEQ ID NO: 121 and a $V_L$ comprising the amino acid sequence of SEQ ID NO: 126.

In some embodiments, functional epitopes can be mapped by combinatorial alanine scanning. In this process, a combinatorial alanine-scanning strategy can be used to identify amino acids in the GM-CSFRα protein that are necessary for interaction with GM-CSFRα antibodies. In some embodiments, the epitope is conformational and crystal structure of anti-GM-CSFRα antibodies bound to GM-CSFRα may be employed to identify the epitopes.

In some embodiments, the present application provides antibodies which compete with any one of the GM-CSFRα antibodies described herein for binding to GM-CSFRα. In some embodiments, the present application provides antibodies which compete with any one of the anti-GM-CSFRα antibodies provided herein for binding to an epitope on the GM-CSFRα. In some embodiments, an anti-GM-CSFRα antibody is provided that binds to the same epitope as an anti-GM-CSFRα antibody comprising a $V_H$ comprising the amino acid sequence of any one of SEQ ID NOs: 80-121, and 246-287, and a $V_L$ comprising the amino acid sequence of any one of SEQ ID NOs: 122-144, 150-245, and 288-289. In some embodiments, an anti-GM-CSFRα antibody is provided that specifically binds to GM-CSFRα competitively with an anti-GM-CSFRα antibody comprising a $V_H$ comprising the amino acid sequence of any one of SEQ ID NOs: 80-121, and 246-287 and a $V_L$ comprising the amino acid sequence of any one of SEQ ID NOs: 122-144, 150-245, and 288-289.

In some embodiments, competition assays may be used to identify a monoclonal antibody that competes with an anti-GM-CSFRα antibody described herein for binding to GM-CSFRα. Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) “Epitope Mapping Protocols,” in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-GM-CSFRα antibody described herein is a chimeric, humanized or human antibody.

Figure 19A:
FIGS. 19A-19B show the sequence alignments of the variable domain sequences of the anti-GM-CSFRα antibodies. The complementarity determining regions are denoted.
Figures 19B, 20:
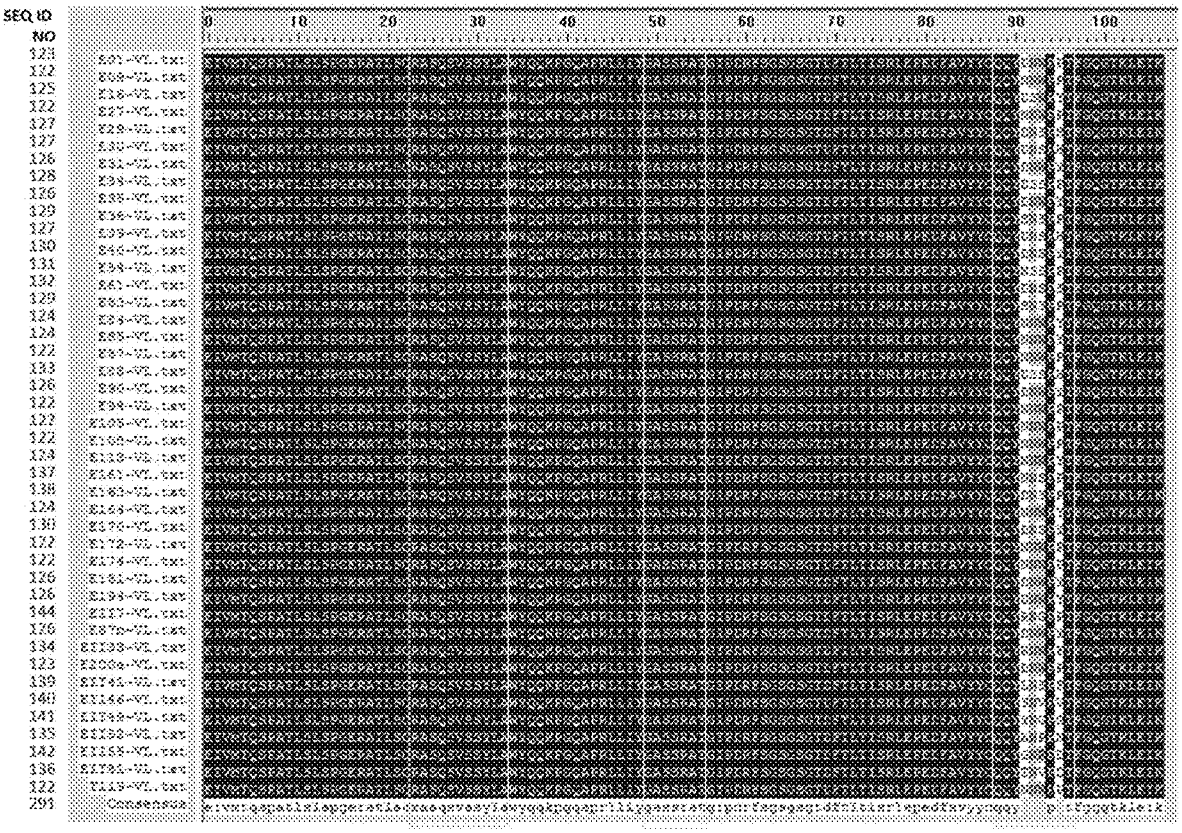
FIG. 20 shows the numbering of amino acid residues 16-296 in GM-CSFRα.

Exemplary anti-GM-CSFRα antibody sequences are shown in Tables 2, 3 and 18, and in FIGS. 19A, 19B. Those skilled in the art will recognize that many algorithms are known for prediction of CDR positions and for delimitation of antibody heavy chain and light chain variable regions. Anti-GM-CSFRα antibodies comprising CDRs, $V_H$ and/or $V_L$ sequences from antibodies described herein, but based on prediction algorithms other than those exemplified in the tables below, are within the scope of this invention.

TABLE 2

Exemplary anti-GM-CSFRα antibody CDR sequences.

| Antibody Name | HC-CDR1 | HC-CDR2 | HC-CDR3 |
|---|---|---|---|
| T119 | ELSIH (SEQ ID NO: 1) | GFDPEDGETNYAQKSQG (SEQ ID NO: 5) | GRYCSTDTCYGFDY(SEQ ID NO: 17) |
| E01 | ELSIH (SEQ ID NO: 1) | GFDPEDGETNYAQKSQG (SEQ ID NO: 5) | GRYCSTDTCYGFDY(SEQ ID NO: 17) |
| E09 | ELSMH (SEQ ID NO: 2) | GFDPEDGETIYAQKFQG (SEQ ID NO: 6) | GRYCGHASCYGFDY(SEQ ID NO: 18) |
| E105 | ELSIH (SEQ ID NO: 1) | GFDPEDGETIYAQKFQG (SEQ ID NO: 6) | GRYTSLMFTYGFDY(SEQ ID NO: 19) |
| E108 | ELSIH (SEQ ID NO: 1) | GFDPEDGETIYAQKFQG (SEQ ID NO: 6) | GRYTELYQNYGFDY(SEQ ID NO: 20) |
| E113 | ELSIH (SEQ ID NO: 1) | GFDPEDGETIYAQKSQG (SEQ ID NO: 7) | GRYTELFASYGFDY(SEQ ID NO: 21) |
| E16 | ELSIH (SEQ ID NO: 1) | GFDPEDGEAIYAQKSQG (SEQ ID NO: 8) | GRYSEHSTSYGFDY(SEQ ID NO: 22) |
| E194 | ELSIH (SEQ ID NO: 1) | GFDPEDGETIYAQKSQG (SEQ ID NO: 7) | GRYTGLMNSYGFDY(SEQ ID NO: 23) |
| E27 | ELSIH (SEQ ID NO: 1) | GFDPEDGETIYAQKFQG (SEQ ID NO: 6) | GRYISFMFTYGFDY(SEQ ID NO: 24) |
| E29 | ELSIH (SEQ ID NO: 1) | GFDPEDGETIYAQKFQG (SEQ ID NO: 6) | GRYCFPDTCYGFDY(SEQ ID NO: 25) |
| E30 | ELSIH (SEQ ID NO: 1) | GFDPEDGETIYAQKFQG (SEQ ID NO: 6) | GRYCSTDTCYGFDY(SEQ ID NO: 17) |
| E34 | ELSIH (SEQ ID NO: 1) | GFDPEDGETIYAQKFQG (SEQ ID NO: 6) | GRYSFTDLAYGFDY(SEQ ID NO: 26) |
| E35 | ELSIH (SEQ ID NO: 1) | GFDPEDGETIYAQKFQG (SEQ ID NO: 6) | GRYTSLATTYGFDY(SEQ ID NO: 27) |
| E36 | ELSMH (SEQ ID NO: 2) | GFDPEDGETIYAQKFQG (SEQ ID NO: 6) | GRYAFIDTAYGFDY(SEQ ID NO: 28) |
| E39 | ELSIH (SEQ ID NO: 1) | GFDPEDGETIYAQKFQG (SEQ ID NO: 6) | GRYCSSDLCYGFDY(SEQ ID NO: 29) |
| E40 | ELSIH (SEQ ID NO: 1) | GFDPEDGETIYAQKFQG (SEQ ID NO: 6) | GRYTSLDESYGFDY(SEQ ID NO: 30) |
| E54 | ELSMH (SEQ ID NO: 2) | GFDPEDGETIYAQKFQG (SEQ ID NO: 6) | GRYSSYDIAYGFDY(SEQ ID NO: 31) |
| E61 | ELSMH (SEQ ID NO: 2) | GFDPEDGETIYAQKFQG (SEQ ID NO: 6) | GRYAWTDIAYGFDY(SEQ ID NO: 32) |
| E83 | ELSIH (SEQ ID NO: 1) | GFDPEDGETIYAQKSQG (SEQ ID NO: 7) | GRYCFYDLCYGFDY(SEQ ID NO: 33) |
| E85 | ELSIH (SEQ ID NO: 1) | GFDPEDGETIYAQKSQG (SEQ ID NO: 7) | GRYSSYFTNYGFDY(SEQ ID NO: 34) |
| E87 | ELSIH (SEQ ID NO: 1) | GFDPEDGETIYAQKSQG (SEQ ID NO: 7) | GRYVSLFFNYGFDY(SEQ ID NO: 35) |
| E88 | ELSMH (SEQ ID NO: 2) | GFDPEDGETIYAQKFQG (SEQ ID NO: 6) | GRYCHKDGCYGFDY(SEQ ID NO: 36) |
| E90 | ELSIH (SEQ ID NO: 1) | GFDPEDGETIYAQKSQG (SEQ ID NO: 7) | GRYTGLYASYGFDY(SEQ ID NO: 37) |
| E94 | ELSMH (SEQ ID NO: 2) | GFDPEDGETIYAQKFQG (SEQ ID NO: 6) | GRYCETDICYGFDY(SEQ ID NO: 38) |
| E200a | ELPMH (SEQ ID NO: 3) | GFDPEDGETIYAQKFQG (SEQ ID NO: 6) | GRYTIITTNYGFDY(SEQ ID NO: 39) |

TABLE 2-continued

| Exemplary anti-GM-CSFRα antibody CDR sequences. | | | |
|---|---|---|---|
| EII33 | ELSIH (SEQ ID NO: 1) | GFDGDGEETIYAQKFQG (SEQ ID NO: 9) | GRYTSLAATYGFDY(SEQ ID NO: 40) |
| EII52 | ELSIH (SEQ ID NO: 1) | GFDGDIEETIYAQKFQG (SEQ ID NO: 10) | GRYTSLATTYGFDY(SEQ ID NO: 27) |
| EII81 | ELSIH (SEQ ID NO: 1) | GFDPEDGETIYAQKFQG (SEQ ID NO: 6) | GRYTSLAATYGFDY(SEQ ID NO: 40) |
| E161 | ELCMH (SEQ ID NO: 4) | GFDPEDGETIYAQKFQG (SEQ ID NO: 6) | GRYAVTDMAYGFDY(SEQ ID NO: 41) |
| E163 | ELSIH (SEQ ID NO: 1) | GFDPEDGETIYAQKFQG (SEQ ID NO: 6) | GRYAFAGLAYGFDY(SEQ ID NO: 42) |
| E164 | ELSMH (SEQ ID NO: 2) | GFDPEDGETIYAQKSQG (SEQ ID NO: 7) | GRYTNDFANYGFDY(SEQ ID NO: 43) |
| E170 | ELSMH (SEQ ID NO: 2) | GFDPEDGETIYAQKFQG (SEQ ID NO: 6) | GRYSSVGSTYGFDY(SEQ ID NO: 44) |
| E172 | ELSMH (SEQ ID NO: 2) | GFDPEDGETIYAQKFQG (SEQ ID NO: 6) | GRYANLYNNYGFDY(SEQ ID NO: 45) |
| E174 | ELSIH (SEQ ID NO: 1) | GFDPEDGETIYAQKFQG (SEQ ID NO: 6) | GRYVYLASNYGFDY(SEQ ID NO: 46) |
| E181 | ELSMH (SEQ ID NO: 2) | GFDPEDGETIYAQKFQG (SEQ ID NO: 6) | GRYSTNFSNYGFDY(SEQ ID NO: 47) |
| E84 | ELSMH (SEQ ID NO: 2) | GFDPEDGETIYAQKSQG (SEQ ID NO: 7) | GRYTRGWFNYGFDY(SEQ ID NO: 48) |
| EII55 | ELSIH (SEQ ID NO: 1) | GFDGDWHETIYAQKFQG (SEQ ID NO: 14) | GRYTSLDATYGFDY(SEQ ID NO: 49) |
| E87b | ELSIH (SEQ ID NO: 1) | GFDPEDGETIYAQKSQG (SEQ ID NO: 7) | GRYVSLFFNYGFDY(SEQ ID NO: 35) |
| E31 | ELSIH (SEQ ID NO: 1) | GFDPEDGETIYAQKSQG (SEQ ID NO: 7) | GRYSESFASYGFDY(SEQ ID NO: 50) |
| E41 | ELSIH (SEQ ID NO: 1) | GFDPAWGETIYAQKFQG (SEQ ID NO: 15) | GRYTSLATTYGFDY(SEQ ID NO: 27) |
| EII41 | ELSIH (SEQ ID NO: 1) | GFDTGDDETIYAQKFQG (SEQ ID NO: 11) | GRYTSLDATYGFDY(SEQ ID NO: 49) |
| EII46 | ELSIH (SEQ ID NO: 1) | GFDSEWGETIYAQKFQG (SEQ ID NO: 12) | GRYTSLATTYGFDY(SEQ ID NO: 27) |
| EII49 | ELSIH (SEQ ID NO: 1) | GFDVASGETIYAQKFQG (SEQ ID NO: 13) | GRYTSLDATYGFDY(SEQ ID NO: 49) |
| EII7 | ELSIH (SEQ ID NO: 1) | GFDSEVGETIYAQKFQG (SEQ ID NO: 16) | GRYTSLAATYGFDY(SEQ ID NO: 40) |
| E35a | ELSIH (SEQ ID NO: 1) | GFDPEDGETIYAQKFQG (SEQ ID NO: 6) | GRYTSLATTYGFDY(SEQ ID NO: 27) |
| E35b | ELSIH (SEQ ID NO: 1) | GFDPEDGETIYAQKFQG (SEQ ID NO: 6) | GRYTSLATTYGFDY(SEQ ID NO: 27) |
| E35c | ELSIH (SEQ ID NO: 1) | GFDPEDGETIYAQKFQG (SEQ ID NO: 6) | GRYTSLATTYGFDY(SEQ ID NO: 27) |
| E35d | ELSIH (SEQ ID NO: 1) | GFDPEDGETIYAQKFQG (SEQ ID NO: 6) | GRYTSLATTYGFDY(SEQ ID NO: 27) |
| E35e | ELSIH (SEQ ID NO: 1) | GFDPEDGETIYAQKFQG (SEQ ID NO: 6) | GRYTSLATTYGFDY(SEQ ID NO: 27) |

TABLE 2-continued

| Exemplary anti-GM-CSFRα antibody CDR sequences. | | | |
|---|---|---|---|
| Antibody Name | LC-CDR1 | LC-CDR2 | LC-CDR3 |
| T119 | RASQSVSSYLA (SEQ ID NO: 51) | GASSRAT (SEQ ID NO: 52) | QQYNNWPPT (SEQ ID NO: 53) |
| E01 | RASQSVSSYLA (SEQ ID NO: 51) | GASSRAT (SEQ ID NO: 52) | QQYDNWPPT (SEQ ID NO: 54) |
| E09 | RASQSVSSYLA (SEQ ID NO: 51) | GASSRAT (SEQ ID NO: 52) | QQYNNWPPT (SEQ ID NO: 53) |
| E105 | RASQSVSSYLA (SEQ ID NO: 51) | GASSRAT (SEQ ID NO: 52) | QQYNNWPPT (SEQ ID NO: 53) |
| E108 | RASQSVSSYLA (SEQ ID NO: 51) | GASSRAT (SEQ ID NO: 52) | QQYNNWPPT (SEQ ID NO: 53) |
| E113 | RASQSVSSYLA (SEQ ID NO: 51) | GASSRAT (SEQ ID NO: 52) | QQYNNWPYT (SEQ ID NO: 55) |
| E16 | RASQSVSSYLA (SEQ ID NO: 51) | GASSRAT (SEQ ID NO: 52) | QQYDSWPYT (SEQ ID NO: 56) |
| E194 | RASQSVSSYLA (SEQ ID NO: 51) | GASSRAT (SEQ ID NO: 52) | QQYDNWPYT (SEQ ID NO: 57) |
| E27 | RASQSVSSYLA (SEQ ID NO: 51) | GASSRAT (SEQ ID NO: 52) | QQYNNWPPT (SEQ ID NO: 53) |
| E29 | RASQSVSSYLA (SEQ ID NO: 51) | GASSRAT (SEQ ID NO: 52) | QQYDNSPHT (SEQ ID NO: 58) |
| E30 | RASQSVSSYLA (SEQ ID NO: 51) | GASSRAT (SEQ ID NO: 52) | QQYDNSPHT (SEQ ID NO: 58) |
| E34 | RASQSVSSYLA (SEQ ID NO: 51) | GASSRAT (SEQ ID NO: 52) | QQYDSSPPT (SEQ ID NO: 59) |
| E35 | RASQSVSSYLA (SEQ ID NO: 51) | GASSRAT (SEQ ID NO: 52) | QQYDNWPYT (SEQ ID NO: 57) |
| E36 | RASQSVSSYLA (SEQ ID NO: 51) | GASSRAT (SEQ ID NO: 52) | QQYSNSPPT (SEQ ID NO: 60) |
| E39 | RASQSVSSYLA (SEQ ID NO: 51) | GASSRAT (SEQ ID NO: 52) | QQYDNSPHT (SEQ ID NO: 58) |
| E40 | RASQSVSSYLA (SEQ ID NO: 51) | GASSRAT (SEQ ID NO: 52) | QQYDNSPYT (SEQ ID NO: 61) |
| E54 | RASQSVSSYLA (SEQ ID NO: 51) | GASSRAT (SEQ ID NO: 52) | QQYNSSPPT (SEQ ID NO: 62) |
| E61 | RASQSVSSYLA (SEQ ID NO: 51) | GASSRAT (SEQ ID NO: 52) | QQYDNSPST (SEQ ID NO: 63) |
| E83 | RASQSVSSYLA (SEQ ID NO: 51) | GASSRAT (SEQ ID NO: 52) | QQYSNSPPT (SEQ ID NO: 60) |
| E85 | RASQSVSSYLA (SEQ ID NO: 51) | GASSRAT (SEQ ID NO: 52) | QQYNNWPYT (SEQ ID NO: 55) |
| E87 | RASQSVSSYLA (SEQ ID NO: 51) | GASSRAT (SEQ ID NO: 52) | QQYNNWPPT (SEQ ID NO: 53) |
| E88 | RASQSVSSYLA (SEQ ID NO: 51) | GASSRAT (SEQ ID NO: 52) | QQYDSSPHT (SEQ ID NO: 64) |
| E90 | RASQSVSSYLA (SEQ ID NO: 51) | GASSRAT (SEQ ID NO: 52) | QQYDNWPYT (SEQ ID NO: 57) |
| E94 | RASQSVSSYLA (SEQ ID NO: 51) | GASSRAT (SEQ ID NO: 52) | QQYNNWPPT (SEQ ID NO: 53) |
| E200a | RASQSVSSYLA (SEQ ID NO: 51) | GASSRAT (SEQ ID NO: 52) | QQYDNWPPT (SEQ ID NO: 54) |

TABLE 2-continued

| Exemplary anti-GM-CSFRα antibody CDR sequences. | | | |
|---|---|---|---|
| EII33 | RASQSVSSYLA (SEQ ID NO: 51) | GASSRAT (SEQ ID NO: 52) | QQYRNWPFT (SEQ ID NO: 65) |
| EII52 | RASQSVSSYLA (SEQ ID NO: 51) | GASSRAT (SEQ ID NO: 52) | QQYANPPNT (SEQ ID NO: 66) |
| EII81 | RASQSVSSYLA (SEQ ID NO: 51) | GASSRAT (SEQ ID NO: 52) | QQYTNVPDT (SEQ ID NO: 67) |
| E161 | RASQSVSSYLA (SEQ ID NO: 51) | GASSRAT (SEQ ID NO: 52) | QQYNNSPPT (SEQ ID NO: 68) |
| E163 | RASQSVSSYLA (SEQ ID NO: 51) | GASSRAT (SEQ ID NO: 52) | QQYDNSPPT (SEQ ID NO: 69) |
| E164 | RASQSVSSYLA (SEQ ID NO: 51) | GASSRAT (SEQ ID NO: 52) | QQYNNWPYT (SEQ ID NO: 55) |
| E170 | RASQSVSSYLA (SEQ ID NO: 51) | GASSRAT (SEQ ID NO: 52) | QQYDNSPYT (SEQ ID NO: 61) |
| E172 | RASQSVSSYLA (SEQ ID NO: 51) | GASSRAT (SEQ ID NO: 52) | QQYNNWPPT (SEQ ID NO: 53) |
| E174 | RASQSVSSYLA (SEQ ID NO: 51) | GASSRAT (SEQ ID NO: 52) | QQYNNWPPT (SEQ ID NO: 53) |
| E181 | RASQSVSSYLA (SEQ ID NO: 51) | GASSRAT (SEQ ID NO: 52) | QQYDNWPYT (SEQ ID NO: 57) |
| E84 | RASQSVSSYLA (SEQ ID NO: 51) | GASSRAT (SEQ ID NO: 52) | QQYNNWPYT (SEQ ID NO: 55) |
| EII55 | RASQSVSSYLA (SEQ ID NO: 51) | GASSRAT (SEQ ID NO: 52) | QQYGNRPDT (SEQ ID NO: 73) |
| E87b | RASQSVSSYLA (SEQ ID NO: 51) | GASSRAT (SEQ ID NO: 52) | QQYDNWPYT (SEQ ID NO: 57) |
| E31 | RASQSVSSYLA (SEQ ID NO: 51) | GASSRAT (SEQ ID NO: 52) | QQYDNWPYT (SEQ ID NO: 57) |
| E41 | RASQSVSSYLA (SEQ ID NO: 51) | GASSRAT (SEQ ID NO: 52) | QQYDNGPET (SEQ ID NO: 74) |
| EII41 | RASQSVSSYLA (SEQ ID NO: 51) | GASSRAT (SEQ ID NO: 52) | QQYLNSPFT (SEQ ID NO: 70) |
| EII46 | RASQSVSSYLA (SEQ ID NO: 51) | GASSRAT (SEQ ID NO: 52) | QQYSNVPVT (SEQ ID NO: 71) |
| EII49 | RASQSVSSYLA (SEQ ID NO: 51) | GASSRAT (SEQ ID NO: 52) | QQYYNGPGT (SEQ ID NO: 72) |
| EII7 | RASQSVSSYLA (SEQ ID NO: 51) | GASSRAT (SEQ ID NO: 52) | QQYRNGPPT (SEQ ID NO: 75) |
| E35a | RASQSVSSYLA (SEQ ID NO: 51) | GASSRAT (SEQ ID NO: 52) | QQYDNSPHT (SEQ ID NO: 58) |
| E35b | RASQSVSSYLA (SEQ ID NO: 51) | GASSRAT (SEQ ID NO: 52) | QQYDNSPYT (SEQ ID NO: 61) |
| E35c | RASQSVSSYLA (SEQ ID NO: 51) | GASSRAT (SEQ ID NO: 52) | QQYDSSPHT (SEQ ID NO: 64) |
| E35d | RASQSVSSYLA (SEQ ID NO: 51) | GASSRAT (SEQ ID NO: 52) | QQYDNWPPT (SEQ ID NO: 54) |
| E35e | RASQSVSSYLA (SEQ ID NO: 51) | GASSRAT (SEQ ID NO: 52) | QQYSNSPPT (SEQ ID NO: 60) |

TABLE 3

| SEQ ID NO | Description | Sequence |
|---|---|---|
| Exemplary sequences. | | |
| 148 | hGM-CSFRα | MLLLVTSLLLCELPHPAFLLIPEKSDLRTVAPASSLNVRFDSRTMNLSWDCQENT TFSKCFLTDKKNRVVEPRLSNNECSCTFREICLHEGVTFEVHVNTSQRGFQQKLL YPNSGREGTAAQNFSCFIYNADLMNCTWARGPTAPRDVQYFLYIRNSKRRREIR CPYYIQDSGTHVGCHLDNLSGLTSRNYFLVNGTSREIGIQFFDSLLDTKKIERFNP PSNVTVRCNTTHCLVRWKQPRTYQKLSYLDFQYQLDVHRKNTQPGTENLLINV SGDLENRYNFPSSEPRAKHSVKIRAADVRILNWSSWSEAIEFGSDDGNLGSVYIY VLLIVGTLVCGIVLGFLFKRFLRIQRLFPPVPQIKDKLNDNHEVEDEIIWEEFTPEE GKGYREEVLTVKEIT |
| 80 | E01, T119 $V_H$ | QMQLVQSGAEVKKPGASVKVSCKVSGHTLTELSIHWVRQAPGKGLEWMGGFD PEDGETNYAQKSQGRVTMTGDTSTDTAYLELSSLRSEDTALYYCATGRYCSTDT CYGFDYWGQGTLVTVSS |
| 81 | E09 $V_H$ | QMQLVQSGAEVKKPGASVKVSCKVSGHTLTELSMHWVRQAPGKGLEWMGGF DPEDGETIYAQKFQGRVTMTGDTSTDTAYLELSSLRSEDTALYYCATGRYCGHA SCYGFDYWGQGTLVTVSS |
| 82 | E105 $V_H$ | QMQLVQSGAEVKKPGASVKVSCKVSGYTLTELSIHWVRQAPGKGLEWMGGFD PEDGETIYAQKFQGRVTMTGDTSTDTAYLELSSLRSEDTALYYCATGRYTSLMF TYGFDYWGQGTLVTVSS |
| 83 | E108 $V_H$ | QMQLVQSGAEVKKPGASVKVSCKVSGHTLTELSIHWVRQAPGKGLEWMGGFD PEDGETIYAQKFQGRVTMTGDTSTDTAYLELSSLRSEDTALYYCATGRYTELYQ NYGFDYWGQGTLVTVSS |
| 84 | E113 $V_H$ | QMQLVQSGAEVKKPGASVKVSCKVSGYTLTELSIHWVRQAPGKGLEWMGGFD PEDGETIYAQKSQGRVTMTGDTSTDTAYLELSSLRSEDTALYYCATGRYTELFA SYGFDYWGQGTLVTVSS |
| 85 | E16 $V_H$ | QMQLVQSGAEVKKPGASVKVSCKVSGYTLTELSIHWVRQAPGKGLEWMGGFD PEDGEAIYAQKSQGRVTMTGDTSTDTAYLELSSLRSEDTALYYCATGRYSEHST SYGFDYWGQGTLVTVSS |
| 86 | E194 $V_H$ | QMQLVQSGAEVKKPGASVKVSCKVSGYTLTELSIHWVRQAPGKGLEWMGGFD PEDGETIYAQKSQGRVTMTGDTSTDTAYLELSSLRSEDTALYYCATGRYTGLMN SYGFDYWGQGTLVTVSS |
| 87 | E27 $V_H$ | QMQLVQSGAEVKKPGASVKVSCKVSGYTLTELSIHWVRQAPGKGLEWMGGFD PEDGETIYAQKFQGRVTMTGDTSTDTAYLELSSLRSEDTALYYCATGRYISFMFT YGFDYWGQGTLVTVSS |
| 88 | E29 $V_H$ | QMQLVQSGAEVKKPGASVKVSCKVSGHTLTELSIHWVRQAPGKGLEWMGGFD PEDGETIYAQKFQGRVTMTGDTSTDTAYLELSSLRSEDTALYYCATGRYCFPDT CYGFDYWGQGTLVTVSS |
| 89 | E30 $V_H$ | QMQLVQSGAEVKKPGASVKVSCKVSGHTLTELSIHWVRQAPGKGLEWMGGFD PEDGETIYAQKFQGRVTMTGDTSTDTAYLELSSLRSEDTALYYCATGRYCSTDT CYGFDYWGQGTLVTVSS |
| 90 | E34 $V_H$ | QMQLVQSGAEVKKPGASVKVSCKVSGYTLTELSIHWVRQAPGKGLEWMGGFD PEDGETIYAQKFQGRVTMTGDTSTDTAYLELSSLRSEDTALYYCATGRYSFTDL AYGFDYWGQGTLVTVSS |
| 91 | E35, $E35_{a-e}$ $V_H$ | QMQLVQSGAEVKKPGASVKVSCKVSGYTLTELSIHWVRQAPGKGLEWMGGFD PEDGETIYAQKFQGRVTMTGDTSTDTAYLELSSLRSEDTALYYCATGRYTSLAT TYGFDYWGQGTLVTVSS |
| 92 | E36 $V_H$ | QMQLVQSGAEVKKPGASVKVSCKVSGHTLTELSMHWVRQAPGKGLEWMGGF DPEDGETIYAQKFQGRVTMTGDTSTDTAYLELSSLRSEDTAIYYCATGRYAFID TAYGFDYWGQGTLVTVSS |
| 93 | E39 $V_H$ | QMQLVQSGAEVKKPGASVKVSCKVSGHTLTELSIHWVRQAPGKGLEWMGGFD PEDGETIYAQKFQGRVTMTGDTSTDTAYLELSSLRSEDTALYYCATGRYCSSDL CYGFDYWGQGTLVTVSS |
| 94 | E40 $V_H$ | QMQLVQSGAEVKKPGASVKVSCKVSGHTLTELSIHWVRQAPGKGLEWMGGFD PEDGETIYAQKFQGRVTMTGDTSTDTAYLELSSLRSEDTALYYCATGRYTSLDE SYGFDYWGQGTLVTVSS |
| 95 | E54 $V_H$ | QMQLVQSGAEVKKPGASVKVSCKVSGYTLTELSMHWVRQAPGKGLEWMGGF DPEDGETIYAQKFQGRVTMTGDTSTDTAYLELSSLRSEDTALYYCATGRYSSYDI AYGFDYWGQGTLVTVSS |

TABLE 3-continued

Exemplary sequences.

| SEQ ID NO | Description | Sequence |
|---|---|---|
| 96 | E61 $V_H$ | QMQLVQSGAEVKKPGASVKVSCKVSGYTLTELSMHWVRQAPGKGLEWMGGFDPEDGITIYAQKFQGRVTMTGDTSTDTAYLELSSLRSEDTALYYCATGRYAWTDIAYGFDYWGQGTLVTVSS |
| 97 | E83 $V_H$ | QMQLVQSGAEVKKPGASVKVSCKVSGYTLTELSIHWVRQAPGKGLEWMGGFDPEDGETIYAQKSQGRVTMTGDTSTDTAYLELSSLRSEDTALYYCATGRYCFYDLCYGFDYWGQGTLVTVSS |
| 98 | E85 $V_H$ | QMQLVQSGAEVKKPGASVKVSCKVSGYTLTELSIHWVRQAPGKGLEWMGGFDPEDGETIYAQKSQGRVTMTGDTSTDTAYLELSSLRSEDTALYYCATGRYSSYFTNYGFDYWGQGTLVTVSS |
| 99 | E87, E87b $V_H$ | QMQLVQSGAEVKKPGASVKVSCKVSGYTLTELSIHWVRQAPGKGLEWMGGFDPEDGETIYAQKSQGRVTMTGDTSTDTAYLELSSLRSEDTALYYCATGRYVSLFFNYGFDYWGQGTLVTVSS |
| 100 | E88 $V_H$ | QMQLVQSGAEVKKPGASVKVSCKVSGHTLTELSMHWVRQAPGKGLEWMGGFDPEDGITIYAQKFQGRVTMTGDTSTDTAYLELSSLRSED1ALYYCATGRYCHKDGCYGFDYWGQGTLVTVSS |
| 101 | E90 $V_H$ | QMQLVQSGAEVKKPGASVKVSCKVSGYTLTELSIHWVRQAPGKGLEWMGGFDPEDGETIYAQKSQGRVTMTGDTSTDTAYLELSSLRSEDTALYYCATGRYTGLYASYGFDYWGQGTLVTVSS |
| 102 | E94 $V_H$ | QMQLVQSGAEVKKPGASVKVSCKVSGHTLTELSMHWVRQAPGKGLEWMGGFDPEDGETIYAQKFQGRVTMTGDTSTDTAYLELSSLRSEDTALYYCATGRYCETDICYGFDYWGQGTLVTVSS |
| 103 | E200a $V_H$ | QMQLVQSGAEVKKPGASVKVSCKVSGYTLTELPMHWVRQAPGKGLEWMGGFDPEDGETIYAQKFQGRVTMTGDTSTDTAYLELSSLRSEDTALYYCATGRYTIITTNYGFDYWGQGTLVTVSS |
| 104 | EII33 $V_H$ | QMQLVQSGAEVKKPGASVKVSCKVSGYTLTELSIHWVRQAPGKGLEWMGGFDGDGEETIYAQKFQGRVTMTGDTSTDTAYLELSSLRSED1ALYYCATGRYTSLAATYGFDYWGQGTLVTVSS |
| 105 | EII52 $V_H$ | QMQLVQSGAEVKKPGASVKVSCKVSGYTLTELSIHWVRQAPGKGLEWMGGFDGDIEETIYAQKFQGRVTMTGDTSTDTAYLELSSLRSEDTALYYCATGRYTSLATTYGFDYWGQGTLVTVSS |
| 106 | EII81 $V_H$ | QMQLVQSGAEVKKPGASVKVSCKVSGYTLTELSIHWVRQAPGKGLEWMGGFDPEDGETIYAQKFQGRVTMTGDTSTDTAYLELSSLRSEDTALYYCATGRYTSLAATYGFDYWGQGTLVTVSS |
| 107 | E161 $V_H$ | QMQLVQSGAEVKKPGASVKVSCKVSGHTLTELCMHWVRQAPGKGLEWMGGFDPEDGETIYAQKFQGRVTMTGDTSTDTAYLELSSLRSEDTALYYWATGRYAVTDMAYGFDYWGQETLVSVSS |
| 108 | E163 $V_H$ | QMQLVQSGAEVKKPGASVKVSCKVSGYTLTELSIHWVRQAPGKGLEWMGGFDPEDGETIYAQKFQGRWMTGDTSTDTAYLELSSLRSEDTALYYCATGRYAFAGLAYGFDYWGQGTLVTVSS |
| 109 | E164 $V_H$ | QMQLVQSGAEVKKPGASVKVSCKVSGHTLTELSMHWVRQAPGKGLEWMGGFDPEDGETIYAQKSQGRVTMTGDTSTDTAYLELSSLRSEDTALYYCATGRYTNDFANYGFDYWGQGTLVTVSS |
| 110 | E170 $V_H$ | QMQLVQSGAEVKKPGASVKVSCKVSGHTLTELSMHWVRQAPGKGLEWMGGFDPEDGETIYAQKFQGRVTMTGDTSTDTAYLELSSLRSEDTALYYCATGRYSSVGSTYGFDYWGQGTLVTVSS |
| 111 | E172 $V_H$ | QMQLVQSGAEVKKPGASVKVSCKVSGYTLTELSMHWVRQAPGKGLEWMGGFDPEDGETIYAQKFQGRVTMTGDTSTDTAYLELSSLRSEDTALYYCATGRYANLYNNYGFDYWGQGTLVTVSS |
| 112 | E174 $V_H$ | QMQLVQSGAEVKKPGASVKVSCKVSGHTLTELSIHWVRQAPGKGLEWMGGFDPEDGETIYAQKFQGRVTMTGDTSTDTAYLELSSLRSEDTALYYCATGRYVYLASNYGFDYWGQGTLVTVSS |
| 113 | E181 $V_H$ | QMQLVQSGAEVKKPGASVKVSCKVSGYTLTELSMHWVRQAPGKGLEWMGGFDPEDGETIYAQKFQGRVTMTGDTSTDTAYLELSSLRSEDTALYYCATGRYSTNFSNYGFDYWGQGTLVTVSS |

TABLE 3-continued

Exemplary sequences.

| SEQ ID NO | Description | Sequence |
|---|---|---|
| 114 | E84 $V_H$ | QMQLVQSGAEVKKPGASVKVSCKVSGYTLTELSMHWVRQAPGKGLEWMGGF DPEDGETIYAQKSQGRVTMTGDTSTDTAYLELSSLRSEDTALYYCATGRYTRG WFNYGFDYWGQGTLVTVSS |
| 115 | EII41 $V_H$ | QMQLVQSGAEVKKPGASVKVSCKVSGYTLTELSIHWVRQAPGKGLEWMGGFD TGDDETIYAQKFQGRVTMTGDTSTDTAYLELSSLRSEDTALYYCATGRYTSLDA TYGFDYWGQGTLVTVSS |
| 116 | EII46 $V_H$ | QMQLVQSGAEVKKPGASVKVSCKVSGYTLTELSIHWVRQAPGKGLEWMGGFD SEWGETIYAQKFQGRVTMTGDTSTDTAYLELSSLRSEDTALYYCATGRYTSLAT TYGFDYWGQGTLVTVSS |
| 117 | EII49 $V_H$ | QMQLVQSGAEVKKPGASVKVSCKVSGYTLTELSIHWVRQAPGKGLEWMGGFD VASGETIYAQKFQGRVTMTGDTSTDTAYLELSSLRSEDTALYYCATGRYTSLDA TYGFDYWGQGTLVTVSS |
| 118 | EII55 $V_H$ | QMQLVQSGAEVKKPGASVKVSCKVSGYTLTELSIHWVRQAPGKGLEWMGGFD GDWHETIYAQKFQGRVTMTGDTSTDTAYLELSSLRSEDTALYYCATGRYTSLD ATYGFDYWGQGTLVTVSS |
| 119 | E41 $V_H$ | QMQLVQSGAEVKKPGASVKVSCKVSGYTLTELSIHWVRQAPGKGLEWMGGFD PAWGETIYAQKFQGRVTMTGDTSTDTAYLELSSLRSEDTALYYCATGRYTSLAT TYGFDYWGQGTLVTVSS |
| 120 | EII7 $V_H$ | QMQLVQSGAEVKKPGASVKVSCKVSGYTLTELSIHWVRQAPGKGLEWMGGFD SEVGETIYAQKFQGRVTMTGDTSTDTAYLELSSLRSEDTALYYCATGRYTSLAA TYGFDYWGQGTLVTVSS |
| 121 | E31 $V_H$ | QMQLVQSGAEVKKPGASVKVSCKVSGYTLTELSIHWVRQAPGKGLEWMGGFD PEDGETIYAQKSQGRVTMTGDTSTDTAYLELSSLRSEDTALYYCATGRYSESFAS YGFDYWGQGTLVTVSS |
| 122 | T119,E87, E09, E105, E108, E27, E94, E172, E174, $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYNNWPPTFGQGTKLE1K |
| 123 | E01, E200a, E35d $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNWPPTFGQGTKLEIK |
| 124 | E113, E85, E164, E84, $V_L$ | EIVMTQSPATLSLSPGERATLSCRASQSVSSYLAWYQQKPGQAPRLLIYGASSRA TGIPDRFSGSGSGTDFTLT1SRLEPEDFAVYYCQQYNNWPYTFGQGTKLEIK |
| 125 | E16 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDSWPYTFGQGTKLEIK |
| 126 | E194, E35, E90, E181, E87b, E31 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNWPYTFGQGTKLEIK |
| 127 | E29, E30, E39, E35a$V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNSPHTFGQGTKLEIK |
| 128 | E34 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDSSPPTFGQGTKLEIK |
| 129 | E36, E83, E35e $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYSNSPPTFGQGTKLEIK |
| 130 | E40, E170, E35b $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNSPYTFGQGTKLEIK |
| 131 | E54 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYNSSPPTFGQGTKLEIK |
| 132 | E61 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNSPSTFGQGTKLEIK |
| 133 | E88, E35c $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDSSPHTFGQGTKLEIK |

TABLE 3-continued

Exemplary sequences.

| SEQ ID NO | Description | Sequence |
|---|---|---|
| 134 | EII33 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYRNWPFTFGQGTKLEIK |
| 135 | EII52 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYANPPNTFGQGTKLEIK |
| 136 | EII81 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYTNVPDTFGQGTKLEIK |
| 137 | E161 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYNNSPPTFGQGTKLEIK |
| 138 | E163 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNSPPTFGQGTKLEIK |
| 139 | EII41 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYLNSPFTFGQGTKLEIK |
| 140 | EII46 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYSNVPVTFGQGTKLEIK |
| 141 | EII49 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYYNGPGTFGQGTKLEIK |
| 142 | EII55 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYGNRPDTFGQGTKLEIK |
| 143 | E41 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYDNGPETFGQGTKLEIK |
| 144 | EII7 $V_L$ | EIVMTQSPATLSLSPGERATLSCRASQSVSSYLAWYQQKPGQAPRLLIYGASSRA TGIPDRFSGSGSGTDFTLTISRLEPEDFAVYYCQQYRNGPPTFGQGTKLEIK |
| 145 | IgG1 heavy chain, constant region. | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPEN NYKTTPPVLDSDGSFFLYSKLTVDKSRWQQGNVFSCSVMHEALHNHYTQKSLS LSPGK |
| 146 | IgG4 heavy chain constant region | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPSCP APEFLGGPSVFLFPPKPKDTLMISRTPEVTCVVVDVSQEDPEVQFNWYVDGVEV HNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYK TTPPVLDSDGSFFLYSRLTVDKSRWQEGNVFSCSVMHEALHNHYTQKSLSLSLG K |
| 147 | Light chain constant region | RTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |

GM-CSF

Granulocyte-macrophage colony stimulating factor (GM-CSF), also known as colony-stimulating factor 2 (CSF2), is produced by macrophages, T cells, mast cells, natural killer cells, endothelial cells, and fibroblasts. GM-CSF is a type I proinflammatory cytokine which enhances survival, proliferation, and/or differentiation of a broad range of hematopoietic cell types including neutrophils, eosinophils, monocytes, and macrophages, such as, myeloid differentiation, recruitment and differentiation of monocyte-derived dendritic cells, initiation and activation of neutrophils. It is also involved in promoting formation of blood vessels as well as tumor growth. Clinically, GM-CSF is often used to enhance the restoration of bone marrow following radiation procedures.

GM-CSF is one of the first proinflammatory cytokines that are present at the inflammation sites and is critical in the regulation of the inflammatory process, by for example, enhancing the differentiation of hematopoietic cell types into neutrophils, eosinophils, monocytes, and macrophages (Nature Reviews Rheumatology 2015; 7 (11): 415-430). By activating the vascular endothelial cells, GM-CSF promotes the recruitment of monocytes and macrophages. GM-CSF also enhances the proliferation of monocytes and macrophages, such as macrophages of the synovial joints in rheumatoid arthritis; as well as promoting cytokine production from macrophages, including GM-CSF and other inflammatory cytokines such as TNF-α, IL-6, IL-1 and chemokines. GM-CSF is further involved in modulating antigen-presenting cells in the inflammatory tissues, and promoting IL-23 production by macrophages and dendritic cells, which together with IL-6 and IL-1, modulates T cell differentiation. Endogenous GM-CSF modulates sensory neurons by relying pain signals and promoting sensitivity to pain. In GM-CSF knockout mice, myeloid cell development was not affected, suggesting a limited role for GM-CSF in promoting myeloid cell development (Stanley et al. PNAS 1994; 91 (12): 5592-5594). However, due to the lack of appropriate inflammatory reactions, GM-CSF knockout mice were more prone to infections (Trapnell et al. N Engl J Med 2003; 349:2527-2539; Dranoff et al. Science 1994; 264:713-716). Lack of GM-CSF reduced the occurrence of rheumatoid arthritis, encephalomyelitis, and autoimmune myocardioptis, suggesting that GM-CSF is primarily involved in the inflammatory process (Lawlor et al. Arthritis & Rheumatism 2005; (52) 3749-3754; McQualter et al. Journal of Experimental Medicine 2001; 194 (7): 873-882; Sonderegger et al. Journal of Experimental Medicine 2008; 205 (10): 2281-2294).

GM-CSFR

The GM-CSF receptor is a member of the hematopoietic receptor superfamily. It is heterodimeric, consisting of an alpha and a beta subunit. The alpha subunit is highly specific for GM-CSF whereas the beta subunit is shared with other cytokine receptors, including IL3 and IL5. This is reflected in a broader tissue distribution of the beta receptor subunit. The alpha subunit, GM-CSFRα, is primarily expressed on myeloid cells and non-hematopoietic cells, such as neutrophils, macrophages, eosinophils, dendritic cells, endothelial cells and respiratory epithelial cells. Full length GM-CSFRα is a 400 amino acid type I membrane glycoprotein that belongs to the type I cytokine receptor family, and consists of a 22 amino acid signal peptide (positions 1-22), a 298 amino acid extracellular domain (positions 23-320), a transmembrane domain from positions 321-345 and a short 55 amino acid intra-cellular domain. The signal peptide is cleaved to provide the mature form of GM-CSFRα as a 378 amino acid protein. cDNA clones of the human and murine GM-CSFRα are available and, at the protein level, the receptor subunits have 36% identity. GM-CSF is able to bind with relatively low affinity to the α subunit alone (Kd 1-5 nM) but not at all to the β subunit alone. However, the presence of both α and β subunits results in a high affinity ligand-receptor complex (Kd≈100 pM). GM-CSF signaling occurs through its initial binding to the GM-CSFR α chain and then cross-linking with a larger subunit the common β chain to generate the high affinity interaction, which phosphorylates the JAK-STAT pathway. GM-CSFR binding to GM-CSF is reviewed in Haman et al. *Journal of Biological Chemistry* 1999; 274 (48). This interaction is also capable of signaling through tyrosine phosphorylation and activation of the MAP kinase pathway. Pathologically, GM-CSF has been shown to play a role in exacerbating inflammatory, respiratory and autoimmune diseases. Neutralization of GM-CSF binding to GM-CSFRα is therefore a therapeutic approach to treating diseases and conditions mediated through GM-CSFR.

Full-Length Anti-GM-CSFRα Antibody

The anti-GM-CSFRα antibody in some embodiments is a full-length anti-GM-CSFRα antibody. In some embodiments, the full-length anti-GM-CSFRα antibody is an IgA, IgD, IgE, IgG, or IgM. In some embodiments, the full-length anti-GM-CSFRα antibody comprises IgG constant domains, such as constant domains of any of IgG1, IgG2, IgG3, and IgG4 including variants thereof. In some embodiments, the full-length anti-GM-CSFRα antibody comprises a lambda light chain constant region. In some embodiments, the full-length anti-GM-CSFRα antibody comprises a kappa light chain constant region. In some embodiments, the full-length anti-GM-CSFRα antibody is a full-length human anti-GM-CSFRα antibody. In some embodiments, the full-length anti-GM-CSFRα antibody comprises an Fc sequence of a mouse immunoglobulin. In some embodiments, the full-length anti-GM-CSFRα antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-GM-CSFRα antibody comprising IgG1 constant domains, wherein the anti-GM-CSFRα antibody specifically binds to GM-CSFRα. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG2 constant domains, wherein the anti-GM-CSFRα antibody specifically binds to GM-CSFRα. In some embodiments, the IgG2 is human IgG2. In some embodiments, the light chain constant region comprises or consists of the amino acid sequence of SEQ ID NO: 147.

In some embodiments, there is provided a full-length anti-GM-CSFRα antibody comprising IgG3 constant domains, wherein the anti-GM-CSFRα antibody specifically binds to GM-CSFRα. In some embodiments, the IgG3 is human IgG3. In some embodiments, the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody specifically binds to GM-CSFRα. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of any one of SEQ ID NOs: 1-4, or a variant thereof comprising up to about 3 (such as about any of 1, 2, or 3) amino acid substitutions, an HC-CDR2 comprising the amino acid sequence of any one of SEQ ID NOs: 5-16, or a variant thereof comprising up to about 3 (such as about any of 1, 2, or 3) amino acid substitutions, and an HC-CDR3 comprising the amino acid sequence of any one of SEQ ID NOs: 17-50, or a variant thereof comprising up to about 3 (such as about any of 1, 2, or 3) amino acid substitutions; and b) a light chain variable domain comprising an LC-CDR1 comprising the amino acid sequence of SEQ ID NO: 51, or a variant thereof comprising up to about 3 (such as about any of 1, 2, or 3) amino acid substitutions, an LC-CDR2 comprising the amino acid sequence of SEQ ID NO: 52, or a variant thereof comprising up to about 3 (such as about any of 1, 2, or 3) amino acid substitutions, and an LC-CDR3 comprising the amino acid sequence of any one of SEQ ID NOs: 53-75, or a variant thereof comprising up to about 3 (such as about any of 1, 2, or 3) amino acid substitutions. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG2 constant domains, wherein the anti-GM-CSFRα antibody comprises a) a heavy chain variable domain comprising an HC-CDR1 comprising the amino acid sequence of any one of SEQ ID NOs: 1-4, or a variant thereof comprising up to about 3 (such as about any of 1, 2, or 3) amino acid substitutions, an HC-CDR2 comprising the amino acid sequence of any one of SEQ ID NOs: 5-16, or a variant thereof comprising up to about 3 (such as about any of 1, 2, or 3) amino acid substitutions, and an HC-CDR3 comprising the amino acid sequence of any one of SEQ ID NOs: 17-50, or a variant thereof comprising up to about 3 (such as about any of 1, 2, or 3) amino acid substitutions; and b) a light chain variable domain comprising an LC-CDR1 comprising the amino acid sequence of SEQ ID NO: 51, or a variant thereof comprising up to about 3 (such as about any of 1, 2, or 3) amino acid substitutions, an LC-CDR2 comprising the amino acid sequence of SEQ ID NO: 52, or a variant thereof comprising up to about 3 (such as about any of 1, 2, or 3) amino acid substitutions, and an LC-CDR3 comprising the amino acid sequence of any one of SEQ ID NOs: 53-75, or a variant thereof comprising up to about 3 (such as about any of 1, 2, or 3) amino acid substitutions. In some embodiments, the IgG2 is human IgG2. In some embodiments, the light chain constant region comprises or consists of the amino acid sequence of SEQ ID NO: 147.

In some embodiments, there is provided a full-length anti-GM-CSFRα antibody comprising IgG3 constant domains, wherein the anti-GM-CSFRα antibody comprises a) a heavy chain variable domain comprising an HC-CDR1 comprising the amino acid sequence of any one of SEQ ID NOs: 1-4, or a variant thereof comprising up to about 3 (such as about any of 1, 2, or 3) amino acid substitutions, an HC-CDR2 comprising the amino acid sequence of any one of SEQ ID NOs: 5-16, or a variant thereof comprising up to about 3 (such as about any of 1, 2, or 3) amino acid substitutions, and an HC-CDR3 comprising the amino acid sequence of any one of SEQ ID NOs: 17-50, or a variant thereof comprising up to about 3 (such as about any of 1, 2, or 3) amino acid substitutions; and b) a light chain variable domain comprising an LC-CDR1 comprising the amino acid sequence of SEQ ID NO: 51, or a variant thereof comprising up to about 3 (such as about any of 1, 2, or 3) amino acid substitutions, an LC-CDR2 comprising the amino acid sequence of SEQ ID NO: 52, or a variant thereof comprising up to about 3 (such as about any of 1, 2, or 3) amino acid substitutions, and an LC-CDR3 comprising the amino acid sequence of any one of SEQ ID NOs: 53-75, or a variant thereof comprising up to about 3 (such as about any of 1, 2, or 3) amino acid substitutions. In some embodiments, the IgG3 is human IgG3. In some embodiments, the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of any one of SEQ ID NOs: 1-4, or a variant thereof comprising up to about 3 (such as about any of 1, 2, or 3) amino acid substitutions, an HC-CDR2 comprising the amino acid sequence of any one of SEQ ID NOs: 5-16, or a variant thereof comprising up to about 3 (such as about any of 1, 2, or 3) amino acid substitutions, and an HC-CDR3 comprising the amino acid sequence of any one of SEQ ID NOs: 17-50, or a variant thereof comprising up to about 3 (such as about any of 1, 2, or 3) amino acid substitutions; and b) a light chain variable domain comprising an LC-CDR1 comprising the amino acid sequence of SEQ ID NO: 51, or a variant thereof comprising up to about 3 (such as about any of 1, 2, or 3) amino acid substitutions, an LC-CDR2 comprising the amino acid sequence of SEQ ID NO: 52, or a variant thereof comprising up to about 3 (such as about any of 1, 2, or 3) amino acid substitutions, and an LC-CDR3 comprising the amino acid sequence of any one of SEQ ID NOs: 53-75, or a variant thereof comprising up to about 3 (such as about any of 1, 2, or 3) amino acid substitutions. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of any one of SEQ ID NOs: 1-4, an HC-CDR2 comprising the amino acid sequence of any one of SEQ ID NOs: 5-16, and an HC-CDR3 comprising the amino acid sequence of any one of SEQ ID NOs: 17-50, or a variant thereof comprising up to about 3 (such as about any of 1, 2, or 3) amino acid substitutions in the HC-CDR sequences; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of any one of SEQ ID NOs: 53-75, or a variant thereof comprising up to about 3 (such as about any of 1, 2, or 3) amino acid substitutions in the LC-CDR sequences. In some embodiments, the IgG1 is human IgG1. In some embodiments, the anti-GM-CSFRα heavy chain constant region comprises or consists of the amino acid sequence of SEQ ID NO: 145. In some embodiments, the anti-GM-CSFRα light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of any one of SEQ ID NOs: 1-4, an HC-CDR2 comprising the amino acid sequence of any one of SEQ ID NOs: 5-16, and an HC-CDR3 comprising the amino acid sequence of any one of SEQ ID NOs: 17-50, or a variant thereof comprising up to about 3 (such as about any of 1, 2, or 3) amino acid substitutions in the HC-CDR sequences; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of any one of SEQ ID NOs: 53-75, or a variant thereof comprising up to about 3 (such as about any of 1, 2, or 3) amino acid substitutions in the LC-CDR sequences. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of any one of SEQ ID NOs: 1-4, an HC-CDR2 comprising the amino acid sequence of any one of SEQ ID NOs: 5-16, and an HC-CDR3 comprising the amino acid sequence of any one of SEQ ID NOS: 17-50; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of any one of SEQ ID NOs: 53-75. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of any one of SEQ ID NOs: 1-4, an HC-CDR2 comprising the amino acid sequence of any one of SEQ ID NOs: 5-16, and an HC-CDR3 comprising the amino acid sequence of any one of SEQ ID NOs: 17-50; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of any one of SEQ ID NOs: 53-75. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 5, and an HC-CDR3 comprising the amino acid sequence of SEQ ID NO: 17; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 56. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 50; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 5, and an HC-CDR3 comprising the amino acid sequence of SEQ ID NO: 17; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 56. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a) a heavy chain variable domain comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 50; and b) a light chain variable domain comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of any one of SEQ ID NOs: 80-121, and 246-287, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 122-144, 150-245, and 288-289, or a variant thereof having at least about 90% (for example at least about any of 91%, 92%, 93%, 94%, 95%, 96%, 97%, 98%, or 99%) sequence identity. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG2 constant domains, wherein the anti-GM-CSFRα antibody comprises a heavy chain variable domain comprising the amino acid sequence of any one of SEQ ID NOs: 80-121, and 246-287, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 122-144, 150-245, and 288-289, or a variant thereof having at least about 90% (for example at least about any of 91%, 92%, 93%, 94%, 95%, 96%, 97%, 98%, or 99%) sequence identity. In some embodiments, the IgG2 is human IgG2. In some embodiments, the light chain constant region comprises or consists of the amino acid sequence of SEQ ID NO: 147.

In some embodiments, there is provided a full-length anti-GM-CSFRα antibody comprising IgG3 constant domains, wherein the anti-GM-CSFRα antibody comprises a heavy chain variable domain comprising the amino acid sequence of any one of SEQ ID NOs: 80-121, and 246-287, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 122-144, 150-245, and 288-289, or a variant thereof having at least about 90% (for example at least about any of 91%, 92%, 93%, 94%, 95%, 96%, 97%, 98%, or 99%) sequence identity. In some embodiments, the IgG3 is human IgG3. In some embodiments, the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of any one of SEQ ID NOs: 80-121, and 246-287, or a variant thereof having at least about 90% (for example at least about any of 91%, 92%, 93%, 94%, 95%, 96%, 97%, 98%, or 99%) sequence identity, and a light chain variable domain comprising the amino acid sequence of any one of SEQ ID NOs: 122-144, 150-245, and 288-289, or a variant thereof having at least about 90% (for example at least about any of 91%, 92%, 93%, 94%, 95%, 96%, 97%, 98%, or 99%) sequence identity. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO:146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of any one of SEQ ID NOs: 80-121, and 246-287, and a light chain variable domain comprising the amino acid sequence of any one of SEQ ID NOs: 122-144, 150-245, and 288-289. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of any one of SEQ ID NOs: 80-121, and 246-287, and a light chain variable domain comprising the amino acid sequence of any one of SEQ ID NOs: 122-144, 150-245, and 288-289. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 80 and a light chain variable domain comprising the amino acid sequence of SEQ ID NO: 123. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 85 and a light chain variable domain comprising the amino acid sequence of SEQ ID NO: 125. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 86 and a light chain variable domain comprising the amino acid sequence of SEQ ID NO: 126. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 91 and a light chain variable domain comprising the amino acid sequence of SEQ ID NO: 126. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 99 and a light chain variable domain comprising the amino acid sequence of SEQ ID NO: 122. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 101 and a light chain variable domain comprising the amino acid sequence of SEQ ID NO: 126. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 103 and a light chain variable domain comprising the amino acid sequence of SEQ ID NO: 123. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 99 and a light chain variable domain comprising the amino acid sequence of SEQ ID NO: 126. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG1 constant domains, wherein the anti-GM-CSFRα antibody comprises a heavy chain variable domain comprising the amino acid sequence of SEQ ID NO: 121 and a light chain variable domain comprising the amino acid sequence of SEQ ID NO: 126. In some embodiments, the IgG1 is human IgG1. In some embodiments, the heavy chain constant region comprises or consists of the amino acid sequence of SEQ ID NO: 145. In some embodiments, the light chain constant region comprises or consists of the amino acid sequence of SEQ ID NO: 147. In some embodiments, the heavy chain constant region comprises or consists of the amino acid sequence of SEQ ID NO: 145 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 80 and a light chain variable domain comprising the amino acid sequence of SEQ ID NO: 123. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 85 and a light chain variable domain comprising the amino acid sequence of SEQ ID NO: 125. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 86 and a light chain variable domain comprising the amino acid sequence of SEQ ID NO: 126. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO:146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 91 and a light chain variable domain comprising the amino acid sequence of SEQ ID NO: 126. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 99 and a light chain variable domain comprising the amino acid sequence of SEQ ID NO: 122. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO:146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 101 and a light chain variable domain comprising the amino acid sequence of SEQ ID NO: 126. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 103 and a light chain variable domain comprising the amino acid sequence of SEQ ID NO:

123. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 99 and a light chain variable domain comprising the amino acid sequence of SEQ ID NO: 126. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

In some embodiments, there is provided a full-length anti-GM-CSFRα antibody comprising IgG4 constant domains, wherein the anti-GM-CSFRα antibody comprises a heavy chain variable domain comprising the amino acid sequence of SEQ ID NO: 121 and a light chain variable domain comprising the amino acid sequence of SEQ ID NO: 126. In some embodiments, the IgG4 is human IgG4. In some embodiments, the heavy chain constant region comprises or consists of the amino acid sequence of SEQ ID NO: 146. In some embodiments, the light chain constant region comprises or consists of the amino acid sequence of SEQ ID NO: 147. In some embodiments, the heavy chain constant region comprises or consists of the amino acid sequence of SEQ ID NO: 146 and the light chain constant region comprises or consists of the amino acid sequence of SEQ ID NO: 147.

Binding Affinity

Binding affinity can be indicated by $K_d$, $K_{off}$, $K_{on}$, or $K_a$. The term "$K_{off}$", as used herein, is intended to refer to the off-rate constant for dissociation of an antibody from the antibody/antigen complex, as determined from a kinetic selection set up. The term "$K_{on}$", as used herein, is intended to refer to the on-rate constant for association of an antibody to the antigen to form the antibody/antigen complex. The term equilibrium dissociation constant "$K_d$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$. The measurement of $K_d$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$.

The dissociation constant ($K_d$) is used as an indicator showing affinity of antibody moieties to antigens. For example, easy analysis is possible by the Scatchard method using antibodies marked with a variety of marker agents, as well as by using Biacore (made by Amersham Biosciences), analysis of biomolecular interactions by surface plasmon resonance, according to the user's manual and attached kit. The $K_d$ value that can be derived using these methods is expressed in units of M (Mols). An antibody that specifically binds to a target may have a $K_d$ of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody can be determined experimentally by methods known in the art. Such methods comprise, but are not limited to, Western blots, ELISA-, RIA-, ECL-, IRMA-, EIA-, BIAcore-tests and peptide scans.

In some embodiments, the anti-GM-CSFRα antibody specifically binds to a target GM-CSFRα with a $K_d$ of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M). Thus in some embodiments, the $K_d$ of the binding between the anti-GM-CSFRα antibody and GM-CSFRα, is about $10^{-7}$ M to about $10^{-13}$ M, about $1\times10^{-7}$ M to about $5\times10^{-13}$ M, about $10^{-7}$ M to about $10^{-12}$ M, about $10^{-7}$ M to about $10^{-11}$ M, about $10^{-7}$ M to about $10^{-10}$M, about $10^{-7}$ M to about $10^{-9}$ M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about$10^{-13}$ M, about $1\times10^{-10}$ M to about $5\times10^{-13}$ M, about $1\times10^{-10}$ M to about $1\times10^{-12}$ M, about $1\times10^{-10}$ M to about $5\times10^{-12}$ M, about $1\times10^{-10}$ M to about $1\times10^{-11}$ M, about $10^{-11}$ M to about $10^{-13}$ M, about $1\times10^{-11}$ M to about $5\times10^{-13}$ M, about $10^{-11}$ M to about $10^{-12}$ M, or about $10^{-12}$ M to about $10^{-13}$ M. In some embodiments, the $K_d$ of the binding between the anti-GM-CSFRα antibody and a GM-CSFRα is about $10^{-7}$ M to about $10^{-13}$ M.

In some embodiments, the $K_d$ of the binding between the anti-GM-CSFRα antibody and a non-target is more than the $K_d$ of the binding between the anti-GM-CSFRα antibody and the target, and is herein referred to in some embodiments as the binding affinity of the anti-GM-CSFRα antibody to the target (e.g., GM-CSFRα) is higher than that to a non-target. In some embodiments, the non-target is an antigen that is not GM-CSFRα. In some embodiments, the $K_d$ of the binding between the anti-GM-CSFRα antibody (against GM-CSFRα) and a non-GM-CSFRα target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-GM-CSFRα antibody and a target GM-CSFRα.

In some embodiments, the anti-GM-CSFRα antibody binds to a non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the non-target is an antigen that is not GM-CSFRα. Thus in some embodiments, the $K_d$ of the binding between the anti-GM-CSFRα antibody and a non-GM-CSFRα target is about $10^{-1}$ M to about $10^{-6}$ M, about $1\times10^{-1}$ M to about $5\times10^{-6}$ M, about $10^{-1}$ M to about $10^{-5}$ M, about $1\times10^{-1}$ M to about $5\times10^{-5}$ M, about $10^{-1}$ M to about $10^{-4}$ M, about $1\times10^{-1}$ M to about $5\times10^{-4}$ M, about $10^{-1}$ M to about $10^{-3}$ M, about $1\times10^{-1}$ M to about $5\times10^{-3}$ M, about $10^{-1}$ M to about $10^{-2}$ M, about $10^{-2}$ M to about $10^{-6}$ M, about $1\times10^{-2}$ M to about $5\times10^{-6}$ M, about $10^{-2}$ M to about $10^{-5}$ M, about $1\times10^{-2}$ M to about $5\times10^{-5}$ M, about $10^{-2}$ M to about $10^{-4}$ M, about $1\times10^{-2}$ M to about $5\times10^{-4}$ M, about $10^{-2}$ M to about $10^{-3}$ M, about $10^{-3}$ M to about $10^{-6}$ M, about $1\times10^{-3}$ M to about $5\times10^{-6}$ M, about $10^{-3}$ M to about $10^{-5}$ M, about $1\times10^{-3}$ M to about $5\times10^{-5}$ M, about $10^{-3}$ M to about 104 M, about $10^{-4}$ M to about $10^{-6}$ M, about $1\times10^{-4}$ M to about $5\times10^{-6}$ M, about $10^{-4}$ M to about $10^{-5}$ M, or about $10^{-5}$ M to about $10^{-6}$ M.

In some embodiments, when referring to that the anti-GM-CSFRα antibody specifically recognizes a target GM-CSFRα at a high binding affinity, and binds to a non-target at a low binding affinity, the anti-GM-CSFRα antibody will bind to the target GM-CSFRα with a $K_d$ of about $10^{-7}$ M to about $10^{-13}$ M (such as about $10^{-7}$ M to about $10^{-13}$ M, about $10^{-8}$ M to about $10^{-13}$ M, about $10^{-9}$ M to about $10^{-13}$ M, or about $10^{-10}$ M to about $10^{-12}$ M), and will bind to the non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, when referring to that the anti-GM-CSFRα antibody specifically recognizes GM-CSFRα, the binding affinity of the anti-GM-CSFRα antibody is compared to a control anti-GM-CSFRα antibody (such as Mavrilimumab). In some embodiments, the $K_d$ of the binding between the control anti-GM-CSFRα antibody and GM-CSFRα can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times of the $K_d$ of the binding between the anti-GM-CSFRα antibody described herein and GM-CSFRα.

Nucleic Acids

Nucleic acid molecules encoding the anti-GM-CSFRα antibodies are also contemplated. In some embodiments, there is provided a nucleic acid (or a set of nucleic acids) encoding a full-length anti-GM-CSFRα antibody, including any of the full-length anti-GM-CSFRα antibodies described herein. In some embodiments, the nucleic acid (or a set of nucleic acids) encoding the anti-GM-CSFRα antibody described herein may further comprises a nucleic acid sequence encoding a peptide tag (such as protein purification tag, e.g., His-tag, HA tag).

Also contemplated here are isolated host cells comprising an anti-GM-CSFRα antibody, an isolated nucleic acid encoding the polypeptide components of the anti-GM-CSFRα antibody, or a vector comprising a nucleic acid encoding the polypeptide components of the anti-GM-CSFRα antibody described herein.

The present application also includes variants to these nucleic acid sequences. For example, the variants include nucleotide sequences that hybridize to the nucleic acid sequences encoding the anti-GM-CSFRα antibodies of the present application under at least moderately stringent hybridization conditions.

The present application also provides vectors in which a nucleic acid of the present application is inserted.

In brief summary, the expression of an anti-GM-CSFRα antibody (e.g., full-length anti-GM-CSFRα antibody) by a natural or synthetic nucleic acid encoding the anti-GM-CSFRα antibody can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present application may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the application provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, *Molecular Cloning: A Laboratory Manual*, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the application should not be limited to the use of constitutive promoters. Inducible promoters are also contemplated as part of the application. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-GM-CSFRα antibody is inducible. In some embodiments, a nucleic acid sequence encoding the anti-GM-CSFRα antibody is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262:1019-1024) and ionizing radiation-regulated elements (e.g., see Manome, Y. et al. (1993) Biochemistry 32:10607-10613; Datta, R. et al. (1992) Proc. Natl. Acad. Sci. USA 89:1014-10153). Further exemplary inducible promoter systems for use in in vitro or in vivo mammalian systems are reviewed in Gingrich et al. (1998) Annual Rev. Neurosci 21:377-405. In some embodiments, the inducible promoter system for use to express the anti-GM-CSFRα antibody is the Tet system. In some embodiments, the inducible promoter system for use to express the anti-GM-CSFRα antibody is the lac repressor system from *E. coli.*

An exemplary inducible promoter system for use in the present application is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli* (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a full-length anti-GM-CSFRα antibody according to any of the full-length anti-GM-CSFRα antibodies described herein. In some embodiments, the nucleic acid comprises one or more nucleic acid sequences encoding the heavy and light chains of the full-length anti-GM-CSFRα antibody. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present application, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the application.

Preparation of Anti-GM-CSFRα Antibodies

In some embodiments, the anti-GM-CSFRα antibody is a monoclonal antibody or derived from a monoclonal antibody. In some embodiments, the anti-GM-CSFRα antibody comprises $V_H$ and $V_L$ domains, or variants thereof, from the monoclonal antibody. In some embodiments, the anti-GM-CSFRα antibody further comprises CH1 and CL domains, or variants thereof, from the monoclonal antibody. Monoclonal antibodies can be prepared, e.g., using known methods in the art, including hybridoma methods, phage display methods, or using recombinant DNA methods. Additionally, exemplary phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the anti-GM-CSFRα antibodies described herein, the anti-GM-CSFRα antibody comprises sequences from a clone selected from an antibody library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352:624-628 (1991); Marks et al., *J. Mol. Biol.* 222:581-597 (1992); Marks and Bradbury, *Methods in Molecular Biology* 248: 161-175 (Lo, ed., Human Press, Totowa, N.J., 2003); Sidhu et al., *J. Mol. Biol.* 338 (2): 299-310 (2004); Lee et al., *J. Mol. Biol.* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12:433-455 (1994). Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12:725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227:381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-GM-CSFRα antibodies can be prepared using phage display to screen libraries for anti-GM-CSFRα antibody moieties specific to the target GM-CSFRα. The library can be a human scFv phage display library having a diversity of at least one×109 (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23 (3): 344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target GM-CSFRα with high affinity can be selected by iterative binding of phage to the target GM-CSFRα, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. The panning can be performed for multiple (such as about any of 2, 3, 4, 5, 6 or more) rounds with solution panning, cell panning, or a combination of both, to enrich for phage clones binding specifically to the target GM-CSFRα. Enriched phage clones can be tested for specific binding to the target GM-CSFRα by any methods known in the art, including for example ELISA and FACS.

Monoclonal antibodies can also be made by recombinant DNA methods, such as those described in U.S. Pat. No. 4,816,567. DNA encoding the monoclonal antibodies of the application can be readily isolated and sequenced using conventional procedures (e.g., by using oligonucleotide probes that are capable of binding specifically to genes encoding the heavy and light chains of murine antibodies).

Hybridoma cells as described above or GM-CSFRα-specific phage clones of the application can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the application, or can be substituted for the variable domains of one antigen-combining site of an antibody of the application to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism.

Human and Humanized Antibodies

The anti-GM-CSFRα antibodies (e.g., full-length anti-GM-CSFRα antibodies) can be humanized antibodies or human antibodies. Humanized forms of non-human (e.g., murine) antibody moieties are chimeric immunoglobulins, immunoglobulin chains, or fragments thereof (such as Fv, Fab, Fab', $F(ab')_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology,* 10:779-783 (1992); Lonberg et al., *Nature,* 368:856-859 (1994); Morrison, *Nature,* 368:812-813 (1994); Fishwild et al., *Nature Biotechnology,* 14:845-851 (1996); Neuberger, *Nature Biotechnology,* 14:826 (1996); *Lonberg and Huszar, Intern. Rev. Immunol.,* 13:65-93 (1995).

Human antibodies may also be generated by in vitro activated B cells (see U.S. Pat. Nos. 5,567,610 and 5,229,275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy, Alan R. Liss*, p. 77 (1985) and Boerner et al., *J. Immunol.,* 147 (1): 86-95 (1991).

Anti-GM-CSFRα Antibody Variants

In some embodiments, amino acid sequence variants of the anti-GM-CSFRα antibodies (e.g., full-length anti-GM- CSFRα antibody) provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, anti-GM-CSFRα antibody variants having one or more amino acid substitutions are provided. Sites of interest for substitutional mutagenesis include the HVRs and FRs. Amino acid substitutions may be introduced into an antibody of interest and the products screened for a desired activity, e.g., improved bioactivity, retained/improved antigen binding, decreased immunogenicity, or improved ADCC or CDC.

Conservative substitutions are shown in Table 4 below.

TABLE 4

CONSERVATIVE SUBSTITUTIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;

b. neutral hydrophilic: Cys, Ser, Thr, Asn, Gln;

c. acidic: Asp, Glu;

d. basic: His, Lys, Arg;

e. residues that influence chain orientation: Gly, Pro;

f. aromatic: Trp, Tyr, Phe.

Non-conservative substitutions will entail exchanging a member of one of these classes for another class.

An exemplary substitutional variant is an affinity matured antibody, which may be conveniently generated, e.g., using phage display-based affinity maturation techniques. Briefly, one or more CDR residues are mutated and the variant antibody moieties displayed on phage and screened for a particular biological activity (e.g., bioactivity based on TF-1 cell proliferation assay or binding affinity). Alterations (e.g., substitutions) may be made in HVRs, e.g., to improve bioactivity based on TF-1 cell proliferation assay or antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001)).

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In some embodiments, provided herein are anti-GM-CSFRα antibodies comprising a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27, or a variant thereof comprising up to about 5 amino acid substitutions in the $V_H$; and a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, or a variant thereof comprising up to about 5 amino acid substitutions in the $V_L$.

In some embodiments, provided herein are anti-GM-CSFRα antibodies comprising a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27, wherein the $V_H$ comprises amino acid substitutions comprising amino acid residues E, H, N, G, D, M, S, P, F, Y, A, V, K, W, R, or C at position 31.

In some embodiments, provided herein are anti-GM-CSFRα antibodies comprising a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27, wherein the $V_H$ comprises amino acid residues selected from T, H, V, E, P, L, M, S, W, C, A, G, N, or K at position 28, and/or amino acid residues selected from T, P, D, E, Y, W, V, M, N, L, Q, G, S, A, K, or R at position 30.

In some embodiments, provided herein are anti-GM-CSFRα antibodies comprising a $V_L$ comprising a LC-CDR1 comprising the amino acid sequence of SEQ ID NO: 51, a LC-CDR2 comprising the amino acid sequence of SEQ ID NO: 52, and a LC-CDR3 comprising the amino acid sequence of SEQ ID NO: 57, wherein the $V_L$ comprises amino acid substitutions comprising S, L, N, A, K, R, I, Q, G, T, H, M, or C at position 26; and/or Q, Y, P, A, I, F, T, R, V, L, E, S, or C at position 27; and/or S, H, W, L, R, K, T, P, I, F, V, E, A, or Q at position 28; and/or S, L, W, M, A, Y, K, R, G, T, E, V, N, F, or C at position 30; and/or S, T, R, A, H, Q, P, M, L, or G at position 31; and/or Y, L or F at position 32; and/or G or T at position 50; and/or A, G, R, H, K, S, T, M, F, N, or V at position 51; and/or S, A, W, R, L, T, Q, F, Y, H, or N at position 52; and/or D, A, Q, or W at position 92; and/or N, D, E, T, Y, G, A, M, F, S, I, or L at position 93.

In some embodiments, any one or combination of the amino acid substitutions as shown in Table 15 is contemplated.

In some embodiments, the anti-GM-CSFRα antibody comprises a $V_H$ comprising the amino acid sequence of SEQ ID NO: 250, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 241, or a variant thereof having at least about 90% sequence identity. In some embodiments, the anti-GM-CSFRα antibody comprises a $V_H$ comprising the amino acid sequence of SEQ ID NO: 250 and a $V_L$ comprising the amino acid sequence of SEQ ID NO: 241.

In some embodiments, the anti-GM-CSFRα antibody comprises a $V_H$ comprising the amino acid sequence of SEQ ID NO: 250, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 193, or a variant thereof having at least about 90% sequence identity. In some embodiments, the anti-GM-CSFRα antibody comprises a $V_H$ comprising the amino acid sequence of SEQ ID NO: 250 and a $V_L$ comprising the amino acid sequence of SEQ ID NO: 193.

In some embodiments, the anti-GM-CSFRα antibody comprises a $V_H$ comprising the amino acid sequence of SEQ ID NO: 248, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 188, or a variant thereof having at least about 90% sequence identity. In some embodiments, the anti-GM-CSFRα antibody comprises a $V_H$ comprising the amino acid sequence of SEQ ID NO: 248 and a $V_L$ comprising the amino acid sequence of SEQ ID NO: 188.

In some embodiments, the anti-GM-CSFRα antibody comprises a $V_H$ comprising the amino acid sequence of SEQ ID NO: 248, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 193, or a variant thereof having at least about 90% sequence identity. In some embodiments, the anti-GM-CSFRα antibody comprises a $V_H$ comprising the amino acid sequence of SEQ ID NO: 248 and a $V_L$ comprising the amino acid sequence of SEQ ID NO: 193.

In some embodiments, the anti-GM-CSFRα antibody comprises a $V_H$ comprising the amino acid sequence of SEQ ID NO: 250, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 288, or a variant thereof having at least about 90% sequence identity. In some embodiments, the anti-GM-CSFRα antibody comprises a $V_H$ comprising the amino acid sequence of SEQ ID NO: 250 and a $V_L$ comprising the amino acid sequence of SEQ ID NO: 288.

In some embodiments, the anti-GM-CSFRα antibody comprises a $V_H$ comprising the amino acid sequence of SEQ ID NO: 250, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 188, or a variant thereof having at least about 90% sequence identity. In some embodiments, the anti-GM-CSFRα antibody comprises a $V_H$ comprising the amino acid sequence of SEQ ID NO: 250 and a $V_L$ comprising the amino acid sequence of SEQ ID NO: 188.

In some embodiments, the anti-GM-CSFRα antibody comprises a $V_H$ comprising the amino acid sequence of SEQ ID NO: 250, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 236, or a variant thereof having at least about 90% sequence identity. In some embodiments, the anti-GM-CSFRα antibody comprises a $V_H$ comprising the amino acid sequence of SEQ ID NO: 250 and a $V_L$ comprising the amino acid sequence of SEQ ID NO: 236.

In some embodiments, the anti-GM-CSFRα antibody comprises a $V_H$ comprising the amino acid sequence of SEQ ID NO: 91, or a variant thereof having at least about 90% (for example at least about any of 91%, 92%, 93%, 94%, 95%, 96%, 97%, 98%, or 99%) sequence identity, and a $V_L$ comprising the amino acid sequence of SEQ ID NO: 288, or a variant thereof having at least about 90% sequence identity. In some embodiments, the anti-GM-CSFRα antibody comprises a $V_H$ comprising the amino acid sequence of SEQ ID NO: 91 and a $V_L$ comprising the amino acid sequence of SEQ ID NO: 288.

Fc Region Variants

In some embodiments, one or more amino acid modifications may be introduced into the Fc region of an antibody (e.g., a full-length anti-GM-CSFRα antibody or anti-GM-CSFRα Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9 (2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-GM-CSFRα antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the application contemplates an anti-GM-CSFRα antibody variant (such as a full-length anti-GM-CSFRα antibody variant) comprising an Fc region that possesses some but not all effector functions, which makes it a desirable candidate for applications in which the half-life of the anti-GM-CSFRα antibody in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CYTOTOX 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18 (12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9 (2): 6591-6604 (2001).)

In some embodiments, there is provided an anti-GM-CSFRα antibody (such as a full-length anti-GM-CSFRα antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-GM-CSFRα antibody (e.g., full-length anti-GM-CSFRα antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164:4178-4184 (2000).

In some embodiments, there is provided an anti-GM-CSFRα antibody (such as a full-length anti-GM-CSFRα antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-GM-CSFRα antibodies (such as full-length anti-GM-CSFRα antibodies) comprising any of the Fc variants described herein, or combinations thereof, are contemplated.

Glycosylation Variants

In some embodiments, an anti-GM-CSFRα antibody (such as a full-length anti-GM-CSFRα antibody) provided herein is altered to increase or decrease the extent to which the anti-GM-CSFRα antibody is glycosylated. Addition or deletion of glycosylation sites to an anti-GM-CSFRα antibody may be conveniently accomplished by altering the amino acid sequence of the anti-GM-CSFRα antibody or polypeptide portion thereof such that one or more glycosylation sites is created or removed.

Wherein the anti-GM-CSFRα antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-GM-CSFRα antibody of the application may be made in order to create anti-GM-CSFRα antibody variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., *J. Biochem.* 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-GM-CSFRα antibody (such as a full-length anti-GM-CSFRα antibody) variants are provided comprising an Fc region wherein a carbohydrate structure attached to the Fc region has reduced fucose or lacks fucose, which may improve ADCC function. Specifically, anti-GM-CSFRα antibodies are contemplated herein that have reduced fucose relative to the amount of fucose on the same anti-GM-CSFRα antibody produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-GM-CSFRα antibody is one wherein less than about 50%, 40%, 30%, 20%, 10%, or 5% of the N-linked glycans thereon comprise fucose. For example, the amount of fucose in such an anti-GM-CSFRα antibody may be from 1% to 80%, from 1% to 65%, from 5% to 65% or from 20% to 40%. In some embodiments, the anti-GM-CSFRα antibody is one wherein none of the N-linked glycans thereon comprise fucose, i.e., wherein the anti-GM-CSFRα antibody is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such asa-1,6-fucosyltransferase gene, FUT8, knockout CHO cells (see, e.g., Yamane-Ohnuki et al. *Biotech. Bioeng.* 87:614 (2004); Kanda, Y. et al., *Biotechnol. Bioeng.,* 94 (4): 680-688 (2006); and WO2003/085107).

Anti-GM-CSFRα antibody (such as a full-length anti-GM-CSFRα antibody) variants are further provided with bisected oligosaccharides, e.g., in which a biantennary oligosaccharide attached to the Fc region of the anti-GM-CSFRα antibody is bisected by GlcNAc. Such anti-GM-CSFRα antibody (such as a full-length anti-GM-CSFRα antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93 (5): 851-861 (2006). Anti-GM-CSFRα antibody (such as full-length anti-GM-CSFRα antibody) variants with at least one galactose residue in the oligosaccharide attached to the Fc region are also provided. Such anti-GM-CSFRα antibody variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-GM-CSFRα antibody (such as a full-length anti-GM-CSFRα antibody) variants comprising an Fc region are capable of binding to an FcγRIII. In some embodiments, the anti-GM-CSFRα antibody (such as a full-length anti-GM-CSFRα antibody) variants comprising an Fc region have ADCC activity in the presence of human effector cells (e.g., T cell) or have increased ADCC activity in the presence of human effector cells compared to the otherwise same anti-GM-CSFRα antibody (such as a full-length anti-GM-CSFRα antibody) comprising a human wild-type IgG1Fc region.

Cysteine Engineered Variants

In some embodiments, it may be desirable to create cysteine engineered anti-GM-CSFRα antibodies (such as a full-length anti-GM-CSFRα antibody) in which one or more amino acid residues are substituted with cysteine residues. In some embodiments, the substituted residues occur at accessible sites of the anti-GM-CSFRα antibody. By substituting those residues with cysteine, reactive thiol groups are thereby positioned at accessible sites of the anti-GM-CSFRα antibody and may be used to conjugate the anti-GM-CSFRα antibody to other moieties, such as drug moieties or linker-drug moieties, to create an anti-GM-CSFRα immunoconjugate, as described further herein. Cysteine engineered anti-GM-CSFRα antibodies (e.g., full-length anti-GM-CSFRα antibodies) may be generated as described, e.g., in U.S. Pat. No. 7,521,541.

Derivatives

In some embodiments, an anti-GM-CSFRα antibody (such as a full-length anti-GM-CSFRα antibody) provided herein may be further modified to contain additional non-proteinaceous moieties that are known in the art and readily available. The moieties suitable for derivatization of the anti-GM-CSFRα antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-GM-CSFRα antibody may vary, and if more than one polymer are attached, they can be the same or different molecules. In general, the number and/or type of polymers used for derivatization can be determined based on considerations including, but not limited to, the particular properties or functions of anti-GM-CSFRα antibody to be improved, whether the anti-GM-CSFRα antibody derivative will be used in a therapy under defined conditions, etc.

Pharmaceutical Compositions

Also provided herein are compositions (such as pharmaceutical compositions, also referred to herein as formulations) comprising any of the anti-GM-CSFRα antibodies (such as a full-length anti-GM-CSFRα antibody), nucleic acids encoding the antibodies, vectors comprising the nucleic acids encoding the antibodies, or host cells comprising the nucleic acids or vectors described herein. In some embodiments, there is provided a pharmaceutical composition comprising any one of the anti-GM-CSFRα antibodies described herein and a pharmaceutically acceptable carrier.

Suitable formulations of the anti-GM-CSFRα antibodies are obtained by mixing an anti-GM-CSFRα antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-GM-CSFRα antibodies of this application into cells.

The formulation herein may also contain one or more active compounds in addition to the anti-GM-CSFRα antibody (such as a full-length anti-GM-CSFRα antibody) as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-GM-CSFRα antibody. Such molecules are suitably present in combination in amounts that are effective for the purpose intended. The effective amount of such other agents depends on the amount of anti-GM-CSFRα antibody present in the formulation, the type of disease or disorder or treatment, and other factors discussed above. These are generally used in the same dosages and with administration routes as described herein or about from 1 to 99% of the heretofore employed dosages.

The anti-GM-CSFRα antibodies (e.g., full-length anti-GM-CSFRα antibodies) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Sustained-release preparations may be prepared.

Sustained-release preparations of the anti-GM-CSFRα antibodies (e.g., full-length anti-GM-CSFRα antibodies) can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D(−)-3-hydroxybutyric acid. While polymers such as ethylene-vinyl acetate and lactic acid-glycolic acid enable release of molecules for over 100 days, certain hydro gels release proteins for shorter time periods. When encapsulated antibody remain in the body for a long time, they can denature or aggregate as a result of exposure to moisture at 37° C., resulting in a loss of biological activity and possible changes in immunogenicity. Rational strategies can be devised for stabilization of anti-GM-CSFRα antibodies depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-GM-CSFRα antibody (such as a full-length anti-GM-CSFRα antibody) is formulated in a buffer comprising a citrate, NaCl, acetate, succinate, glycine, polysorbate 80 (Tween 80), or any combination of the foregoing.

The formulations to be used for in vivo administration must be sterile. This is readily accomplished by, e.g., filtration through sterile filtration membranes.

Methods of Treatment Using Anti-GM-CSFRα Antibodies

The anti-GM-CSFRα antibodies (e.g., full-length anti-GM-CSFRα antibodies) and/or compositions of the application can be administered to individuals (e.g., mammals such as humans) to treat a disease and/or disorder associated with high expression levels of GM-CSF and/or GM-CSFRα, and disease and/or disorder with deregulated GM-CSF and/or GM-CSFRα function, such as autoimmune and/or inflammatory conditions or cancer characterized by high GM-CSF and/or GM-CSFRα expression and/or abnormal GM-CSF/GM-CSFRα function, for example, rheumatoid arthritis, asthma, and myeloid leukemia pulmonary disease. The present application thus in some embodiments provides a method of treating an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) in an individual comprising administering to the individual an effective amount of a composition (such as a pharmaceutical composition) comprising an anti-GM-CSFRα antibody (e.g., a full-length anti-GM-CSFRα antibody), such as any one of the anti-GM-CSFRα antibodies (e.g., full-length anti-GM-CSFRα antibodies) described herein.

In some embodiments, the disease or condition is selected, for example, from the group consisting of rheumatoid arthritis, asthma, chronic obstructive pulmonary disease, allergic response, multiple sclerosis, myeloid leukemia, and atherosclerosis. In some embodiments, the individual is human.

For example, in some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a pharmaceutical composition comprising an anti-GM-CSFRα antibody (e.g., full-length anti-GM-CSFRα antibody) specifically binding to an epitope on human GM-CSFRα, wherein the epitope comprises amino acid residues Val50, Glu59, Lys194, Lys195, Arg283, and Ile284 of human GM-CSFRα. In some embodiments, the anti-GM-CSFRα antibody described herein specifically binds to an epitope on human GM-CSFRα, wherein the epitope comprises amino acid residues Val50, Glu59, Lys194, Lys195, Arg283, Ile284, Val51, Thr63, and Ile196. In some embodiments, the anti-GM-CSFRα antibody described herein specifically binds to an epitope on human GM-CSFRα, wherein the epitope comprises amino acid residues Val50, Glu59, Lys194, Lys195, Arg283, Ile284, Leu191 and Ile196. In some embodiments, the anti-GM-CSFRα antibody described herein specifically binds to an epitope on human GM-CSFRα, wherein the epitope comprises amino acid residues Val50, Glu59, Lys194, Lys195, Arg283, Ile284, Arg49, Val51, Asn57, and Ser61. In some embodiments, the anti-GM-CSFRα antibody is a full-length antibody. In some embodiments, the full-length anti-GM-CSFRα antibody is an IgG1 or IgG4 antibody. In some embodiments, the disease or condition is selected from the group consisting of rheumatoid arthritis, asthma, chronic obstructive pulmonary disease, allergic response, multiple sclerosis, myeloid leukemia, and atherosclerosis. In some embodiments, the individual is human.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a pharmaceutical composition comprising an anti-GM-CSFRα antibody (e.g., full-length anti-GM-CSFRα antibody) comprising a heavy chain variable domain ($V_H$) comprising an HC-CDR1 comprising $X_1LX_2X_3H$ (SEQ ID NO: 76), wherein $X_1$ is E, N, G, D, M, S, P, F, Y, A, V, K, W, R or C, $X_2$ is S, C or P, and $X_3$ is I or M; an HC-CDR2 comprising $GFDX_1X_2X_3X_4EX_5X_6YAQKX_7QG$ (SEQ ID NO: 77), wherein $X_1$ is P, G, T, S, or V, $X_2$ is E, D, G, or A, $X_3$ is D, G, I, W, S, or V, $X_4$ is G, E, D, or H, $X_5$ is T or A, $X_6$ is N or I, and $X_7$ is S or F; and an HC-CDR3 comprising $GRYX_1X_2X_3X_4X_5X_6YGFDY$ (SEQ ID NO: 78), wherein $X_1$ is C, T, S, I, A, or V, $X_2$ is S, G, E, F, W, H, I, V, N, Y, T, or R, $X_3$ is T, H, L, F, P, I, S, Y, K, A, D, V, N, or G, $X_4$ is D, A, M, Y, F, S, T, G, or W, $X_5$ is T, S, F, Q, A, N, L, E, I, G, or M, and $X_6$ is C, T, N, S, or A; and a $V_L$ comprising a LC-CDR1 comprising $RAX_1X_2X_3$ $VX_4X_5X_6LA$ (SEQ ID NO: 293), wherein $X_1$ is S, L, N, A, K, R, I, Q, G, T, H, M, or C, $X_2$ is Q, Y, P, A, I, F, T, R, V, L, E, S, or C, $X_3$ is S, H, W, L, R, K, T, P, I, F, V, E, A, or Q, $X_4$ is S, L, W, M, A, Y, K, R, G, T, E, V, N, F, or C, $X_5$ is S, T, R, A, H, Q, P, M, L, or G, and $X_6$ is Y, L, or F; a LC-CDR2 comprising$X_1X_2X_3SRAT$ (SEQ ID NO: 294), wherein $X_1$ is G or T, $X_2$ is A, G, R, H, K, S, T, M, or F, and $X_3$ is S, A, W, R, L, T, Q, F, Y, H, or N; and a LC-CDR3 comprising $QQYX_1X_2X_3PX_4T$ (SEQ ID NO: 79), wherein $X_1$ is N, D, S, R, A, T, L, Y, Q, W or G, $X_2$ is N, D, E, T, Y, G, A, M, F, S, I or L, $X_3$ is W, S, P, V, G, or R, and $X_4$ is P, Y, H, S, F, N, D, V, or G.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NOs: 1-4, an HC-CDR2 comprising the amino acid sequence of SEQ ID NOs: 5-16, and an HC-CDR3 comprising the amino acid sequence of SEQ ID NOs: 17-50, or a variant thereof comprising up to 5 amino acid substitutions; and a $V_L$ comprising an LC-CDR1 comprising the amino acid sequence of SEQ ID NOs: 51, an LC-CDR2 comprising the amino acid sequence of SEQ ID NOs: 52, and an LC-CDR3 comprising the amino acid sequence of SEQ ID NOs: 53-75, or a variant thereof comprising up to 5 amino acid substitutions.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising a $V_H$ comprising the amino acid sequence of SEQ ID NOs: 80-121, and 246-287 or a variant thereof having at least about 90% sequence identity to the amino acid sequence of any one of SEQ ID NOs: 80-121, and 246-287, and a $V_L$ comprising the amino acid sequence of SEQ ID NOs: 122-144, 150-245, and 288-289, or a variant thereof having at least about 90% sequence identity to the amino acid sequence of any one of SEQ ID NOs: 122-144, 150-245, and 288-289.

In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 5, and an HC-CDR3 comprising the amino acid sequence of SEQ ID NO: 17, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54, or a variant thereof comprising up to 5 amino acid substitutions.

In some embodiments, the anti-GM-CSFRα antibody provided herein comprises a $V_H$ comprising the amino acid sequence of SEQ ID NO: 80 and a $V_L$ comprising the amino acid sequence of SEQ ID NO: 123. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 56, or a variant thereof comprising up to 5 amino acid substitutions.

In some embodiments, the anti-GM-CSFRα antibody provided herein comprises a $V_H$ comprising the amino acid sequence of SEQ ID NO: 85 and a $V_L$ comprising the amino acid sequence of SEQ ID NO: 125. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to 5 amino acid substitutions.

In some embodiments, the anti-GM-CSFRα antibody provided herein comprises a $V_H$ comprising the amino acid sequence of SEQ ID NO: 86 and a $V_L$ comprising the amino acid sequence of SEQ ID NO: 126. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to 5 amino acid substitutions.

In some embodiments, the anti-GM-CSFRα antibody provided herein comprises a $V_H$ comprising the amino acid sequence of SEQ ID NO: 91 and a $V_L$ comprising the amino acid sequence of SEQ ID NO: 126. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53, or a variant thereof comprising up to 5 amino acid substitutions.

In some embodiments, the anti-GM-CSFRα antibody provided herein comprises a $V_H$ comprising the amino acid sequence of SEQ ID NO: 99 and a $V_L$ comprising the amino acid sequence of SEQ ID NO: 122. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to 5 amino acid substitutions.

In some embodiments, the anti-GM-CSFRα antibody provided herein comprises a $V_H$ comprising the amino acid sequence of SEQ ID NO: 101 and a $V_L$ comprising the amino acid sequence of SEQ ID NO: 126. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54, or a variant thereof comprising up to 5 amino acid substitutions.

In some embodiments, the anti-GM-CSFRα antibody provided herein comprises a $V_H$ comprising the amino acid sequence of SEQ ID NO: 103 and a $V_L$ comprising the amino acid sequence of SEQ ID NO: 123. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to 5 amino acid substitutions.

In some embodiments, the anti-GM-CSFRα antibody provided herein comprises a $V_H$ comprising the amino acid sequence of SEQ ID NO: 99 and a $V_L$ comprising the amino acid sequence of SEQ ID NO: 126. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, there is provided a method of treating an individual having an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia) comprising administering to the individual an effective amount of a composition comprising an anti-GM-CSFRα antibody comprising: a $V_H$ comprising an HC-CDR1 comprising the amino acid sequence of SEQ ID NO: 1, an HC-CDR2 comprising the amino acid sequence of SEQ ID NO:7, and an HC-CDR3 comprising the amino acid sequence of SEQ ID NO: 50, or a variant thereof comprising up to 5 amino acid substitutions; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, or a variant thereof comprising up to 5 amino acid substitutions.

In some embodiments, the anti-GM-CSFRα antibody provided herein comprises a $V_H$ comprising the amino acid sequence of SEQ ID NO: 121 and a $V_L$ comprising the amino acid sequence of SEQ ID NO: 126. In some embodiments, the anti-GM-CSFRα antibody provided herein is a full-length anti-GM-CSFRα antibody comprising IgG1 or IgG4 constant domains. In some embodiments, the IgG1 is human IgG1. In some embodiments, the IgG4 is human IgG4. In some embodiments, the heavy chain constant region comprises or consists of the amino acid sequence of SEQ ID NO: 145. In some embodiments, the heavy chain constant region comprises or consists of the amino acid sequence of SEQ ID NO: 146. In some embodiments, the light chain constant region comprises or consists of the amino acid sequence of SEQ ID NO: 147.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or genetically prone to one or more of the diseases or disorders described herein (such as rheumatoid arthritis, asthma, chronic obstructive pulmonary disease, allergic response, multiple sclerosis, myeloid leukemia, or atherosclerosis). In some embodiments, the individual has one or more risk factors associated with one or more diseases or disorders described herein.

The present application in some embodiments provides a method of delivering an anti-GM-CSFRα antibody (such as any one of the anti-GM-CSFRα antibodies described herein, e.g., an isolated anti-GM-CSFRα antibody) to a cell expressing GM-CSFRα on its surface in an individual, the method comprising administering to the individual a composition comprising the anti-GM-CSFRα antibody.

Many diagnostic methods for cancer or any other disease exhibiting abnormal GM-CSF and/or GM-CSFRα expression and the clinical delineation of those diseases are known in the art. Such methods include, but are not limited to, e.g., immunohistochemistry, PCR, and fluorescent in situ hybridization (FISH).

In some embodiments, the anti-GM-CSFRα antibodies (e.g., full-length anti-GM-CSFRα antibodies) and/or compositions of the application are administered in combination with a second, third, or fourth agent (including, e.g., an antineoplastic agent, a growth inhibitory agent, a cytotoxic agent, or a chemotherapeutic agent) to treat diseases or disorders involving abnormal GM-CSF/GM-CSFRα expression.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation $100-(T/C\times100)$, where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%. In some embodiments, the efficacy of treatment is measured using shape change of granulocytes and/or increase in the survival of granulocytes. In some embodiments, the efficacy of treatment is measured by the increase of cytokine secretion by monocytes.

Dosing and Method of Administering the Anti-GM-CSFRα Antibodies

The dose of the anti-GM-CSFRα antibody (such as isolated anti-GM-CSFRα antibody) compositions administered to an individual (such as a human) may vary with the particular composition, the mode of administration, and the type of disease being treated. In some embodiments, the amount of the composition (such as composition comprising isolated anti-GM-CSFRα antibody) is effective to result in an objective response (such as a partial response or a complete response) in the treatment of cancer. In some embodiments, the amount of the anti-GM-CSFRα antibody composition is sufficient to result in a complete response in the individual. In some embodiments, the amount of the anti-GM-CSFRα antibody composition is sufficient to result in a partial response in the individual. In some embodiments, the amount of the anti-GM-CSFRα antibody composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-GM-CSFRα antibody composition. Responses of an individual to the treatment of the methods described herein can be determined, for example, based on RECIST levels.

In some embodiments, the amount of the composition (such as composition comprising isolated anti-GM-CSFRα antibody) is sufficient to prolong progress-free survival of the individual. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-GM-CSFRα antibody composition.

In some embodiments, the amount of the composition (such as composition comprising isolated anti-GM-CSFRα antibody), alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-GM-CSFRα antibody (such as a full-length anti-GM-CSFRα antibody) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-GM-CSFRα antibody (such as a full-length anti-GM-CSFRα antibody) in the composition is included in a range of about 0.001 μg to about 1000 μg.

In some embodiments of any of the above aspects, the effective amount of anti-GM-CSFRα antibody (such as a full-length anti-GM-CSFRα antibody) in the composition is in the range of about 0.1 μg/kg to about 100 mg/kg of total body weight.

The anti-GM-CSFRα antibody compositions can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion. In some embodiments, the administration is to an injection site distal to a first disease site.

Articles of Manufacture and Kits

In some embodiments of the application, there is provided an article of manufacture containing materials useful for the treatment of autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia), or for delivering an anti-GM-CSFRα antibody (such as a full-length anti-GM-CSFRα antibody) to a cell expressing GM-CSFRα on its surface. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-GM-CSFRα antibody of the application. The label or package insert indicates that the composition is used for treating the particular condition. The label or package insert will further comprise instructions for administering the anti-GM-CSFRα antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating autoimmune and/or inflammatory conditions (such as rheumatoid arthritis, asthma, chronic obstructive pulmonary disease, allergic response, multiple sclerosis, myeloid leukemia, and atherosclerosis). In some embodiments, the package insert indicates that the composition is used for treating cancer (e.g. myeloid leukemia).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia), or for delivering an anti-GM-CSFRα antibody (such as a full-length anti-GM-CSFRα antibody) to a cell expressing GM-CSFRα on its surface, optionally in combination with the articles of manufacture. Kits of the application include one or more containers comprising anti-GM-CSFRα antibody composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the application are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-GM-CSFRα antibody (such as a full-length anti-GM-CSFRα antibody). In some embodiments, the kit comprises a) a composition comprising any one of the anti-GM-CSFRα antibodies described herein, and b) an effective amount of at least one other agent, wherein the other agent enhances the effect (e.g., treatment effect, detecting effect) of the anti-GM-CSFRα antibody. In some embodiments, the kit comprises a) a composition comprising any one of the anti-GM-CSFRα antibodies described herein, and b) instructions for administering the anti-GM-CSFRα antibody composition to an individual for treatment of an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia). In some embodiments, the kit comprises a) a composition comprising any one of the anti-GM-CSFRα antibodies described herein, b) an effective amount of at least one other agent, wherein the other agent enhances the effect (e.g., treatment effect, detecting effect) of the anti-GM-CSFRα antibody, and c) instructions for administering the anti-GM-CSFRα antibody composition and the other agent(s) to an individual for treatment of an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia). The anti-GM-CSFRα antibody and the other agent(s) can be present in separate containers or in a single container. For example, the kit may comprise one distinct composition or two or more compositions wherein one composition comprises an anti-GM-CSFRα antibody and another composition comprises another agent.

In some embodiments, the kit comprises a nucleic acid (or set of nucleic acids) encoding an anti-GM-CSFRα antibody (such as a full-length anti-GM-CSFRα antibody). In some embodiments, the kit comprises a) a nucleic acid (or set of nucleic acids) encoding an anti-GM-CSFRα antibody, and b) a host cell for expressing the nucleic acid (or set of nucleic acids). In some embodiments, the kit comprises a) a nucleic acid (or set of nucleic acids) encoding an anti-GM-CSFRα antibody, and b) instructions for i) expressing the anti-GM-CSFRα antibody in a host cell, ii) preparing a composition comprising the anti-GM-CSFRα antibody, and iii) administering the composition comprising the anti-GM-CSFRα antibody to an individual for the treatment of an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia). In some embodiments, the kit comprises a) a nucleic acid (or set of nucleic acids) encoding an anti-GM-CSFRα antibody, b) a host cell for expressing the nucleic acid (or set of nucleic acids), and c) instructions for i) expressing the anti-GM-CSFRα antibody in the host cell, ii) preparing a composition comprising the anti-GM-CSFRα antibody, and iii) administering the composition comprising the anti-GM-CSFRα antibody to an individual for the treatment of an autoimmune and/or inflammatory condition or cancer characterized by high GM-CSF and/or GM-CSFRα expression and/or abnormal GM-CSF/GM-CSFRα function (e.g., rheumatoid arthritis, asthma, or myeloid leukemia).

The kits of the application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-GM-CSFRα antibody compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-GM-CSFRα antibody (such as a full-length anti-GM-CSFRα antibody) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-GM-CSFRα antibody and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this application. The application will now be described in greater detail by reference to the following non-limiting examples. The following examples further illustrate the application but, of course, should not be construed as in any way limiting its scope.

EXAMPLES

In the experimental disclosure which follows, the following abbreviations apply: GMF (human GM-CSF); GMRa (human GM-CSFRα); GMRb (human GM-CSFRβ); Mab (Mavrilimumab); GMRah (human GM-CSFRα-6His); BGMRa (Biotin-Avi-GM-CSFRα); mGMRa(cynomolgus monkey GM-CSFRα); mGMRah (cynomolgus monkey GM-CSFRα-6His).

Example 1: Generation of Recombinant Human GM-CSFRα and Selection of Anti-GM-CSFRα scFv Antibodies

Generation of Recombinant GM-CSFRα

The full-length sequence of human GM-CSFRα (hereon referred to as GMRa) was subcloned from the vector pSC-GM-CSFRα (Generay, Shanghai) into the expression vector pTT5 using restriction enzyme recognition sites HindIII and XhoI. His-tag or other conventionally used tags were used to tag GMRa. Expression vectors pTT5-GMRa-6his (ECD), pTT5-Avi-10His-GMRa (ECD), and pTT5-GMRa (400a.a) were generated. "ECD" stands for extracellular domain, "his or His" stands for His-tag, and "Avi" stands for Avidin tag.

Additionally, recombinant cynomolgus monkey GM-CSFRα construct was cloned. Primers were designed based on the sequence of cynomolgus monkey GM-CSFRα in NCBI database (XM_024791666.1), and used to obtain GM-CSFRα cDNA by reverse transcription of RNA from peripheral blood mononuclear cells (PBMC) of cynomolgus monkeys. The ECD-encoding sequence was amplified from the GM-CSFRα cDNA and cloned into an eukaryotic expression vector pTT5 to generate pTT5-mGMRa-6his (ECD).

The expression and purification of recombinant human GM-CSFRα, including GMRa-6his (ECD), Avi-10His-GMRa (ECD), and mGMRa-6his (ECD) were carried out according to manufacturer's protocol. Briefly, 293F cells were transfected with the expression vectors, and the cells were cultured at 37° C., under 8% $CO_2$ and 120 rpm for 5 days. The culture media was collected and proteins expressing His-tag were purified using Ni Sepharose purification according to manufacturer's protocol. Specifically, the Qiagen Ni-NTA superflow cartridges were used for immobilized metal affinity chromatography (IMAC) analysis. The cartridges were first equilibrated with buffer A1 (50 mM $Na_3PO_4$, 0.15 M NaCl, pH 7.2) with a flow rate of 150 cm/h. The pH of the supernatant of the culture media was adjusted to 7.2 and flown through the cartridges at room temperature at 150 cm/h. Next, buffer A1 (6 times the volume of that of the cartridges) was used to equilibrate the cartridges at 150 cm/h. A 50 mM PB solution (0.15M NaCl and 0.2M Imidazole, pH 7.2) with a volume that is 10 times that of the cartridges was used to wash the cartridges and the elution was collected.

Generation of Biotinylated GM-CSFRα Antigen

Biotinylation of Avi-10His-GMRa using the biotin ligase B0101A (GeneCopoeia) was carried out according to the manufacturer's protocol. Briefly, buffer A/B and BirA ligase were added to Avi-10His-GMRa, followed by 2 hours of incubation at 30° C. The biotinylated GMRa is referred to as Bavih-GMRa. The efficiency of biotinylation was measured using ELISA. Briefly, Bavih-GMRa was serially diluted at a 1:2 ratio, from a starting concentration of 500 ng/mL, before being used to coat the ELISA plate. SA-HRP was used for detection and standard biotinylation products were used as control. The biotinylation efficiency was determined to be 70%. The bioactivity of Bavih-GMRa was confirmed using TF-1 cell proliferation assay.

Selection of Anti-GM-CSFRα scFv Antibodies

Generation of yeast scFv antibody display library: RNA collected from 2000 human blood samples was reverse-transcribed into cDNA, and the $V_H$ and $V_K$ fragments were amplified using $V_H$- and $V_K$-specific primers. Upon gel extraction and purification, scFvs were generated by linking $V_H$ and $V_K$, and were cloned into the yeast display plasmid PYD1, which were then electroporated into yeast to generate the yeast scFv antibody display library.

Selection of anti-GM-CSFRα scFv antibodies: scFvs which recognized GM-CSFRα were isolated from the yeast display library. Briefly, magnetic-activated cell sorting (MACS) was used to enrich for cells expressing anti-GM-CSFRα scFv antibodies. 1000 OD yeast cells were subjected to centrifugation for 5 minutes at 2500 g. Cell pellet was obtained and resuspended in 1 L of SGCAA culture media with OD600=1 as the starting concentration. Expression was induced for 40-48 hours at 20° C. and 250 rpm. After centrifugation and washing with PBSM, the pellet was resuspended in 5-10 times volume of 1 μM Bavih-GMRa (in PBSM), and incubated for an hour at 4° C. After centrifugation and washing with PBSM, unbound antigens were washed off with PBSM. Magnetic beads were added and mixed thoroughly before incubation for 30 minutes at 4° C. on a rotator. The supernatant was discarded after centrifugation at 2500 g for 5 minutes, and the pellet was resuspended in PBSM with 5-10 times the volume. 7 mL of cells was added to the column at a time until all cells were passed through the column. Bound cells were collected and upon further culturing and centrifugation were subjected to plasmid isolation.

Generation of phage display library and selection of scFv antibodies: scFv antibody fragments from the selected yeast cells were PCR amplified using scFv-F and scFv-R primers. To generate phage display libraries, the scFv fragments were then cloned into the phage display vector pDAN5 using SfiI. Upon ligation, the vector was used to transduce TG1 phage display electroporation-competent cells to obtain the phage scFv antibody display library. scFv antibodies specific to GM-CSFRα were isolated from the phage display library in a series of repeated selection cycles. Briefly, phage scFv library ($2\times10^{11}$ PFU) was added to biotinylated GM-CSFRα, and incubated for 2 hours at 37° C. GM-CSFRα with phage bound was captured on streptavidin coated magnetic beads. Unbound phage were washed away. After washing with TBST for 8-15 times (increasing number of washes for every round of selection), phage that specifically bound to GM-CSFRα were washed off with Glycine-HCl (pH2.2). These phages were used to transduce TG1 cells in log phase, with the addition of Ampicillin, and cultured for an hour. Upon the addition of helper phage, the cells were cultured on a rocking bed for overnight at 200 rpm at 28° C. Culture media was collected the next day, centrifuged to obtain the supernatant, and was subjected to the next round of selection. A panel of positive scFv antibodies was obtained at the end of the selection process.

Monoclonal scFv antibodies were selected and subjected to ligand binding assays. The first assay was designed to identify scFv antibodies that bound human GM-CSFRα and/or cynomolgus monkey GM-CSFRα. Briefly, a 96-well plate was coated with GMRah (human GM-CSFRα-6His) or mGMRah (cynomolgus monkey GM-CSFRα-6His) in PBS at 0.2 μg/well and left overnight at 4° C. Before loading the scFv antibodies, the plates were washed with TBST, blocked for 1-2 hours at 37° C. using 5% milk and washed again with TBST. Each scFv sample was first diluted to 40 μg/mL, and 150 μL was added to the first row of wells. The 40 μg/mL scFv samples were then serially diluted at a 1:3 ratio and added to the remaining wells. After incubating for an hour at 37° C., followed by washing with TBST for 6 times, 100 μl of the primary antibody and secondary antibody mixture (mouse anti-flag (1:2500) and anti-mouse FC-AP (1:2000)) was added to each well. After incubation for an hour under 37° C., the plate was washed for 3 times using TBST. pNPP was then added at 50 μL/well and incubated for $10^{-20}$ minutes at 37° C. 3M NaOH was used to stop the reaction. The ELISA results (OD410) were then analyzed and the binding curves were generated by PRISM.

The second assay was designed to identify scFv antibodies that were capable of inhibiting binding of GM-CSF to GM-CSFRα, as measured by competitive ELISA. Briefly, a 96-well plate was coated with 0.5 μg/well of GM-CSF and 5% milk, incubated for 1-2 hours at 37° C., and followed by washing with TBST. Each scFv antibody sample was first diluted to 40 μg/mL, and 100 μL was added to the first row of wells. The 40 μg/mL scFv antibody samples were then serially diluted at a 1:2 ratio and added to the remaining wells. 50 μL of 2.5 μg/mL Bavih-GMRa in PBS was added to each well. After incubating for an hour at 37° C., the wells were washed with TBST for 6 times. 100 μL of SA-HRP (1:20,000) was then added to each well and incubated for an hour at 37° C. The wells were washed with TBST for 6 times before adding 50 μL/well of TMB, and incubated for 5-10 minutes at 37° C. 2M $H_2SO_4$ was used to stop the reaction. The ELISA results (OD450) were analyzed, and the binding curves were generated by PRISM.

TF-1 proliferation assay: scFv antibodies able to inhibit binding between GM-CSF and GM-CSFRα were assessed for biological activity in a TF-1 proliferation assay, which analyzed the ability of the antibodies to inhibit the proliferation of TF-1 cells stimulated with GM-CSF. TF-1 is a human premyeloid cell line established from a patient with erythroleukemia. This cell line is factor-dependent for survival and proliferation, and is routinely maintained in human GM-CSF. Briefly, TF-1 cells were maintained in RPMI1640, 10% FBS, 10 ng/mL GM-CSF media, and were passaged twice every week. Cells were washed with media without GM-CSF (RPMI1640, 10% FBS) for three times, and resuspended in the same media. Approximately 10,000 cells were added to each well of a 96-well plate and cultured overnight. The following day, the scFv antibodies were serially diluted at a 1:10 ratio (from 10 μg/mL to 0.0001 μg/mL), and were added to the cells. After incubating at 37° C. for an hour, GM-CSF (Peprotech) was added at a final concentration of 200 pg/mL. The following day, cell survival was analyzed using the Celltiter-glo assay kit (Promega). $IC_{50}$ was calculated by PRISM.

Example 2: Generation and Characterization of Full-Length Human Anti-GM-CSFRα Antibodies Generation of Full-Length Anti-GM-CSFRα Antibodies The most potent scFv antibodies were reformatted as human IgG1 or IgG4 antibody molecules with a human IgG1 or IgG4 heavy chain constant domain, and a human kappa light chain constant domain. $V_L$ and $V_H$ were amplified from the prokaryotic expression vector and introduced into eukaryotic expression vectors pTT5-L (containing kappa constant domain) and pTT5-H1 (containing IgG1 heavy chain constant domain), or pTT5-H4 (containing IgG4 heavy chain constant domain). Plasmids expressing the light and heavy chains were extracted and used to transform 293F cells. After the cells were cultured at 37° C., 8% $CO_2$ and 120 rpm for five days, the culture media was purified using Protein A affinity chromatography. Briefly, Protein A column was first equilibrated with a PBS buffer containing 50 mM PBS and 0.15M NaCl (pH7.2), at a flow rate of 150 cm/h and with a volume that is six times the volume of the column. The supernatant of the culture media (pH was adjusted to 7.2) was passed through the column at 150 cm/h. Upon further equilibration, the column was washed off using 50 mM sodium citrate (pH3.5) and the elution was collected. Out of the full-length antibodies that were generated, T119 was selected as the lead parent antibody. Using the scFv of T119, a phage scFv display library containing mutations in the CDR regions was generated. Variants that were able to bind human GM-CSFRα with high affinity, and with low dissociation rate were assessed for biological activity in the TF-1 proliferation assay. scFv antibodies that showed improved biological activity as compared to the scFv of T119 were used to generate full-length antibodies. A further round of selection of the full-length antibodies using the TF-1 proliferation assay was carried out. The selected lead-optimized antibodies were then subjected to further biochemical and biological analysis.

Affinity of Anti-GM-CSFRα Antibodies

Figure 1B:
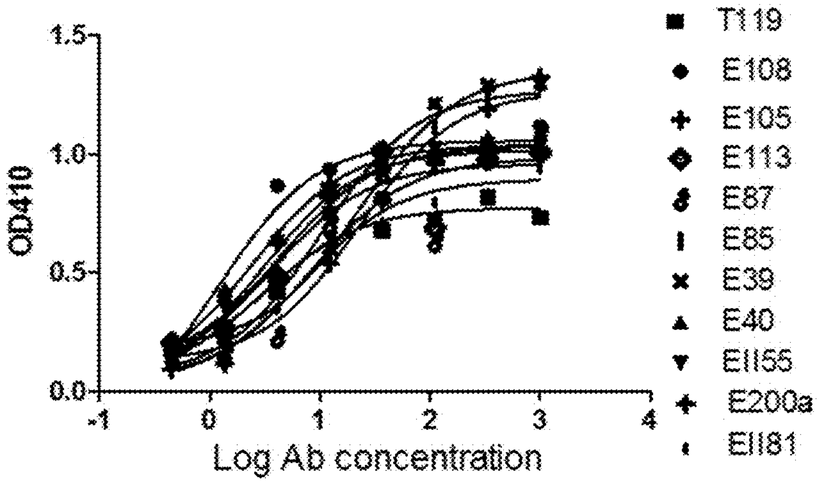
Figure 1C:
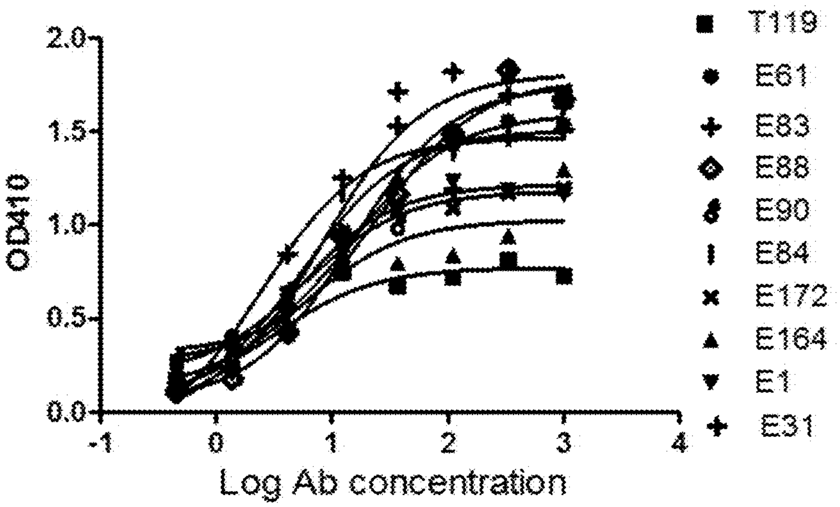
Figure 2:
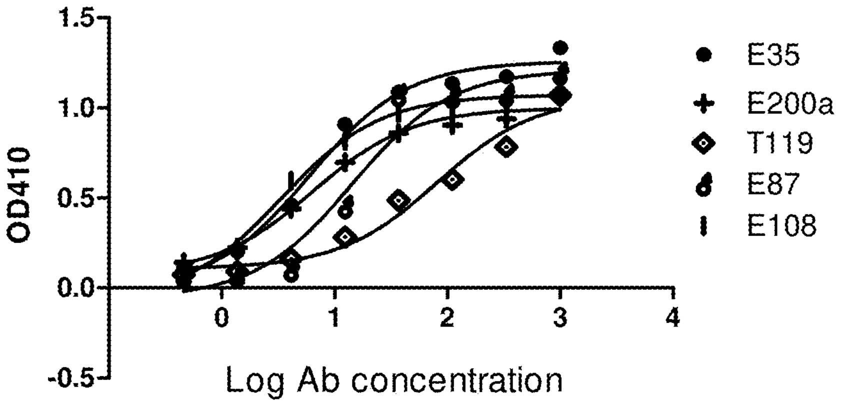
FIG. 2 shows the binding affinity of E35, E200a, T119, E87, and E108 for cynomolgus monkey GM-CSFRα as analyzed by ELISA.

The affinity of the parent antibody T119 and the lead-optimized antibodies (reformatted as human IgG1) for human GM-CSFRα was evaluated using ELISA. As shown in FIGS. 1A-1C, the lead-optimized antibodies exhibited improved binding affinity as compared to T119. Next, the affinity of the parent antibody T119 and lead-optimized antibodies E35, E200a, E87, and E108 (reformatted as human IgG4) for cynomolgus monkey GM-CSFRα (mGMRah) was evaluated using ELISA. As shown in FIG. 2, the anti-GM-CSFRα antibodies cross-reacted with cynomolgus monkey GM-CSFRα.

Specificity of Anti-GM-CSFRα Antibodies

Figure 3:
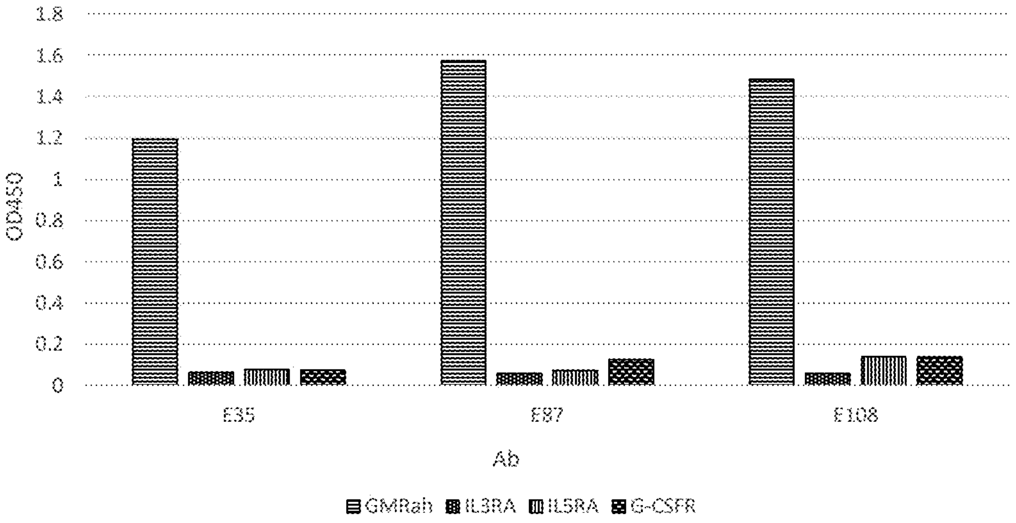
FIG. 3 shows the binding affinity of E35, E87, and E108 for IL3RA, IL5RA, and G-CSFR as compared to GM-CSFRα.

Cross-reactivity to homologous proteins: Using ELISA, antibodies E35, E87, and E108 (reformatted as human IgG4) were tested for cross-reactivity to homologous proteins of GM-CSFRα, including IL3RA, IL5RA, and G-CSFR. As shown in FIG. 3, the antibodies bound specifically to GMRah as compared to the other homologous proteins tested, suggesting that the anti-GM-CSFRα antibodies have specificity for GM-CSFRα.

Figure 4:
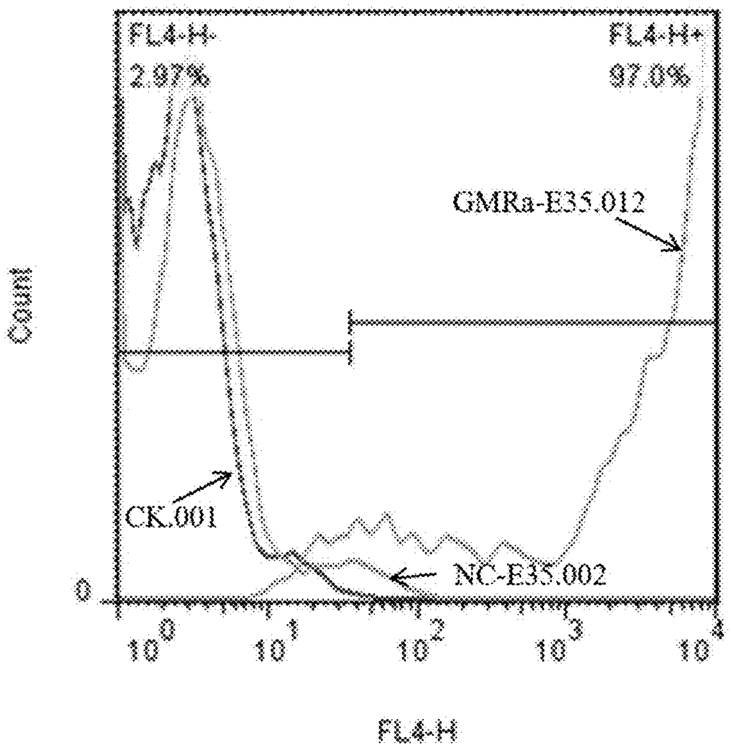
FIG. 4 shows the binding affinity of E35-IgG4 to WIL2S cells expressing GM-CSFRα as compared to control WIL2S cells that do not express GM-CSFRα, as analyzed by FACS.
Figure 5A:
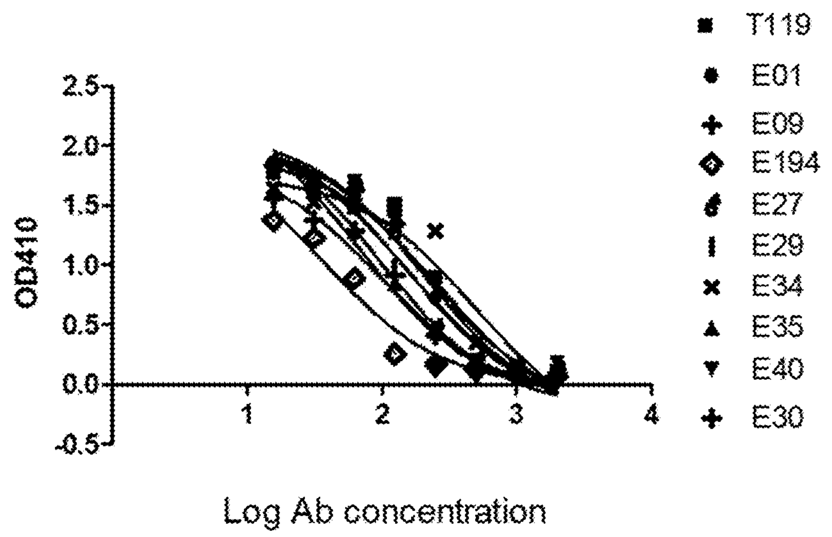
FIGS. 5A-5D show results of the competitive binding assay for the ability of the parental antibody T119 and lead-optimized antibodies to compete with GM-CSF for binding to GM-CSFRα, as measured using competitive ELISA.
Figure 5B:
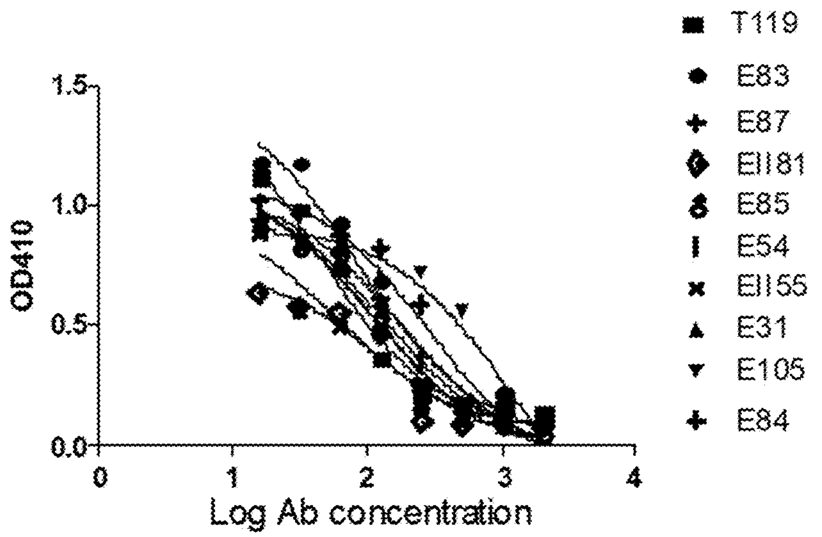
Figure 5C:
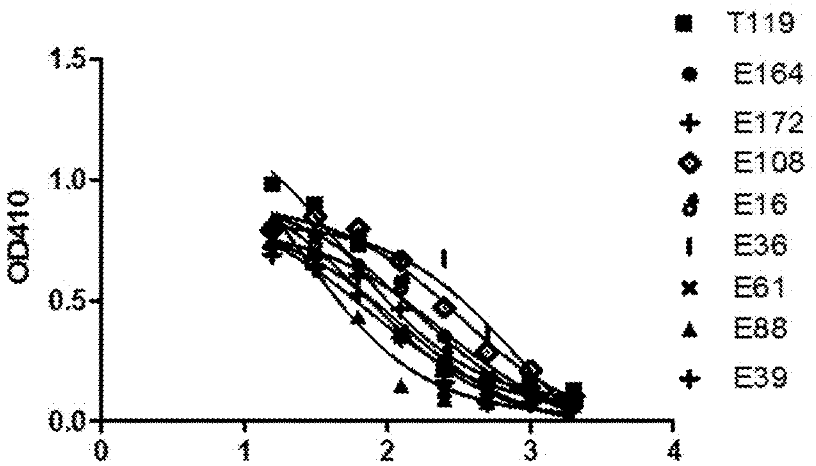
Figure 5D:
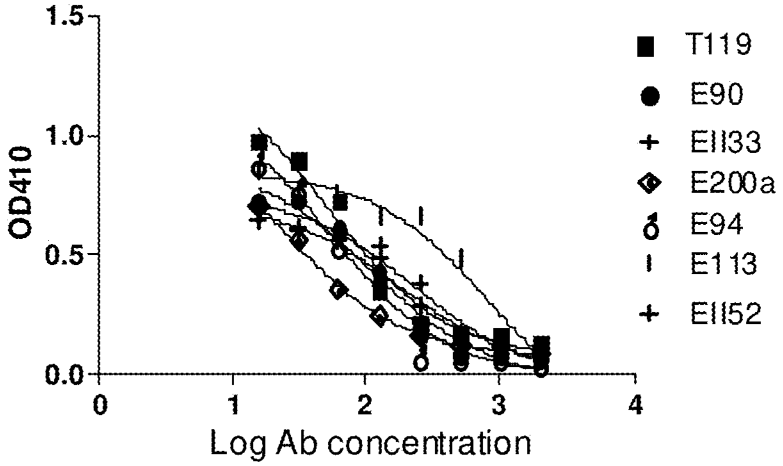

Binding specificity to GM-CSFRα-expressing WIL2S cells: The anti-GM-CSFRα antibody E35-IgG4 was further assessed for binding to WIL2S cells expressing GM-CSFRα. Anti-GM-CSFRα antibody E35-IgG4 was fluorescently labeled with GYL-650 (Dylight Amine-Reactive Dyes, Thermo Fisher) according to manufacturer's protocol. WIL2S cells expressing GM-CSFRα were generated via electroporation with an expression vector containing the full-length GM-CSFRα, and untreated WIL2S were used as controls. 48 hours after electroporation, both electroporated and untreated cells were transferred into 15 ml conical tubes, centrifuged for 5 minutes at 1000 rpm, and resuspended in DPBS. $1\times10^6$ cells were then added to each Eppendorf tube and centrifuged for 5 minutes at 1000 g. GM-CSFRα-expressing WIL2S cells were treated with 15 μg/mL of E35-IgG4 in 100 μL 1% BSA (GMRa-E35), and control WIL2S cells were treated with either 100 μL of 1% BSA (CK) or 5 μg/mL of E35-IgG4 in 100 μL 1% BSA (NC-E35). Cells from all three groups were incubated for 40 minutes at 37° C., washed with 1 mL PBS twice, resuspended in 0.2 mL PBS, and subjected to FACS analysis. As shown in FIG. 4, E35-IgG4 did not bind to control WIL2S cells but showed strong binding to WIL2S cells expressing GM-CSFRα.

Characterization of Binding Affinity and Dissociation Constant ($K_d$)

The binding affinity of anti-GM-CSFRα antibodies E35, and E87b (reformatted as human IgG4) were characterized using Biacore T200 (GE). Antibodies E35 and E87b were stabilized on sensor chip CM5. The affinities for GMRah at various concentrations were measured. The range of concentrations included 10, 5, 2.5, 1.25, 0.625, 0.3125, 0.15625, 0.078, 0.039, 0.0195, and 0 nm. The concentrations of 0.625 and 0 nM were repeated once. Using the SPR technology, the association and dissociation rates were measured, and binding affinity was determined. Table 5 shows the $K_{on}$, $K_{off}$, and $K_d$ of E35 and E87b.

TABLE 5

| Antibody | $K_{on}$ (l/Ms) | $K_{off}$(l/s) | $K_d$ (M) |
|---|---|---|---|
| E35 | 5.37E+06 | 4.78E−05 | 8.90E−12 |
| E87b | 3.58E+06 | 2.42E−05 | 6.75E−12 |

Anti-GM-CSFRα Antibodies Compete with GM-CSF for Binding to GM-CSFRα

Competitive ELISA experiments were carried out as described in Example 1 to assess the ability of the anti-GM-CSFRα antibodies to recognize the ligand-binding site on GM-CSFRα and compete with GM-CSF for binding to GM-CSFRα. As shown in FIGS. 5A-5D, the parent antibody T119 and lead-optimized antibodies (reformatted as human IgG4) were able to block GM-CSF from binding to human GM-CSFRα, suggesting competitive binding of the antibodies to the ligand-binding site on GM-CSFRα.

Anti-GM-CSFRα Antibody Stability Assays

Figure 6A:
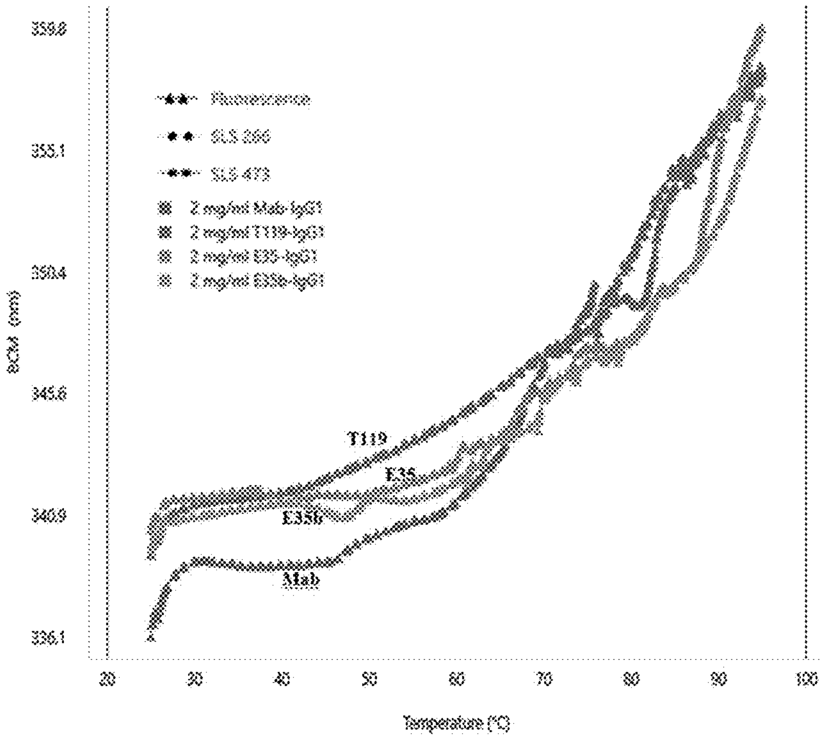
FIGS. 6A and 6B show the thermal melting profiles and the thermal aggregation profiles of the anti-GM-CSFRα antibodies Mab-IgG1, T119-IgG1, E35-IgG1 and E35b-IgG1 as analyzed by UNcle.
Figure 6B:
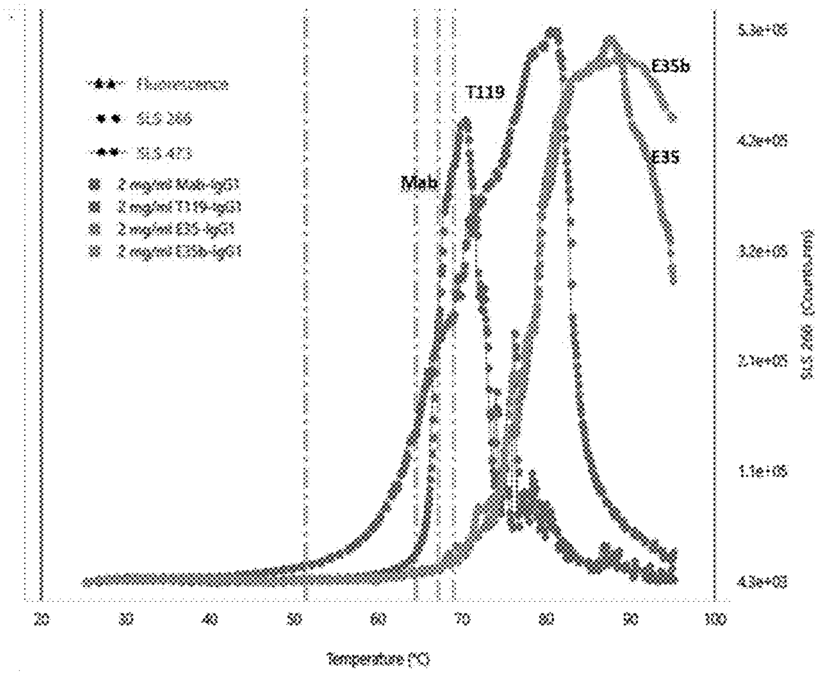

Thermal stability analysis: The thermal stability of T119-IgG1, E35-IgG1, E35b-IgG1, and Mab-IgG1 were analyzed using the UNcle platform. The thermal melting ($T_m$) and thermal aggregation ($T_{agg}$) values for each antibody were measured. $T_m$ indicates the unfolding temperature of the antibody during a thermal ramp, and $T_{agg}$ indicates the aggregation temperature of the antibody during a thermal ramp. As shown in Table 6 and FIGS. 6A-6B, T119-IgG1, E35-IgG1 and E35b-IgG1 showed increased thermal melting temperature as compared to Mab-IgG1, with E35-IgG1 and E35b-IgG1 exhibiting higher melting temperature than the parent T119-IgG1. T119-IgG1, E35-IgG1 and E35b-IgG1 also showed increased thermal aggregation temperature as compared to Mab-IgG1, with E35-IgG1 and E35b-IgG1 exhibiting higher aggregation temperature than the parent T119-IgG1. These results suggest that E35-IgG1 and E35b-IgG1 exhibited improved thermal stability as compared to the parental T119-IgG1 antibody, as well as the control Mab-IgG1 antibody.

TABLE 6

| Well | Sample | $T_m1$ (° C.) | $T_{agg}$ 266 (° C.) | $T_{agg}$ 473 (° C.) |
|---|---|---|---|---|
| H1 | 2 mg/ml Mab-IgG1 | 67.8 | 64.56 | 65.6 |
| I1 | 2 mg/ml T119-IgG1 | 69.53 | 56.65 | 70.01 |
| J1 | 2 mg/ml E35-IgG1 | 73.52 | 67.15 | 77.37 |
| K1 | 2 mg/ml E35b-IgG1 | 70.42 | 69.01 | 77.64 |

TF-1 Proliferation Assay

Figure 7:
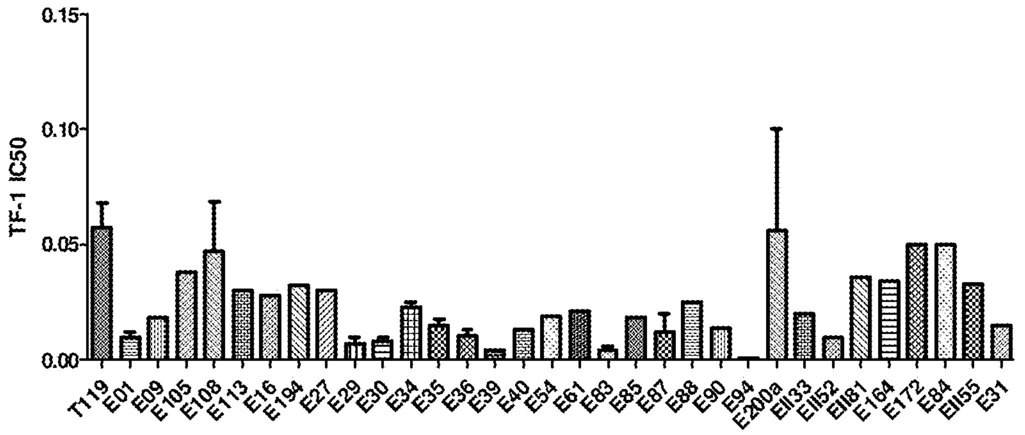
FIG. 7 shows results of the TF-1 proliferation assay for the parental antibody T119 and lead-optimized antibodies.

TF-1 proliferation assay was performed as described in Example 1. The parent antibody T119 and lead-optimized antibodies (reformatted as human IgG4) were tested for their abilities to inhibit TF-1 cell proliferation. As shown in FIG. 7, the lead-optimized antibodies showed comparable or improved ability to inhibit TF-1 cell proliferation as compared to the parental T119 antibody.

Granulocyte Shape Change Assay

Figure 8:
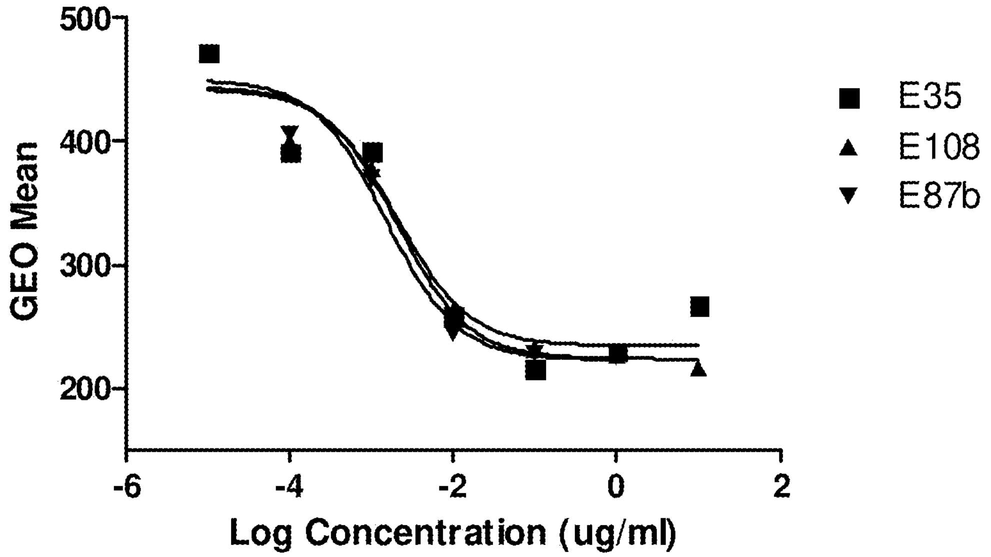
FIG. 8 shows results of the human granulocyte shape change assay for E35, E108 and E87b.

The anti-GM-CSFRα antibodies were further evaluated using human granulocyte shape change assays. Briefly, PBMCs were removed from 10 mL human peripheral blood using Ficoll gradient. Upon removal of PBMCs and the Ficoll buffer, red blood cells were lysed using cell lysis buffer. The remaining cells were washed with PBS and cell culture media. 100,000 cells were added to each well of a 96-well plate, and incubated for 30 minutes at 37° C. Cells were then treated with 100 pg/mL GM-CSF, as well as serially diluted antibodies (1:10 dilution; 10 μg/mL to 0.0001 μg/mL). After incubation for 3 hours at 37° C., the cells were subjected to FACS analysis, and the shape change of the granulocytes was evaluated based on the GEO mean of the forward scatter. As shown in FIGS. 8, E35, E108 and E87b (reformatted as human IgG4) prevented granulocyte shape change. The IC50 of each antibody is shown in Table 7 below.

TABLE 7

| Antibody | E35 | E108 | E87b |
|---|---|---|---|
| IC50 (μg/mL) | 0.002050 | 0.002066 | 0.001505 |

Figure 9:
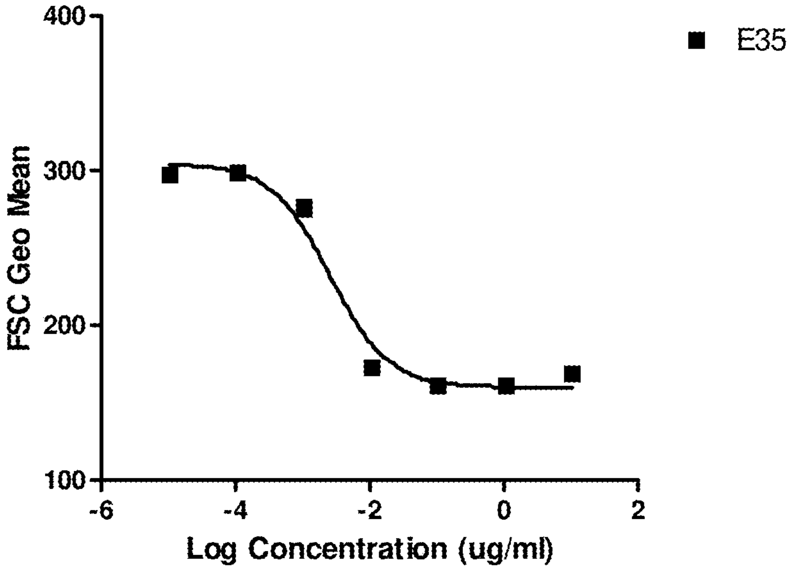
FIG. 9 shows results of the cynomolgus monkey granulocyte shape change assay for E35.

The anti-GM-CSFRα antibody E35 (reformatted as human IgG4) was further evaluated using cynomolgus monkey granulocyte shape change assays. Cynomolgus monkey granulocytes were purified from whole blood, and treated with 100 pg/mL GM-CSF, as well as serially diluted E35 (1:10 dilution; 10 μg/mL to 0.0001 μg/mL). The cells were subjected to FACS analysis, and the shape change of the granulocytes was evaluated based on the GEO mean of the forward scatter. The results showed that E35 prevented cynomolgus monkey granulocyte shape change (FIG. 9), with an IC50 of 0.002527 μg/mL.

Human Granulocyte Survival Assay

Figure 10:
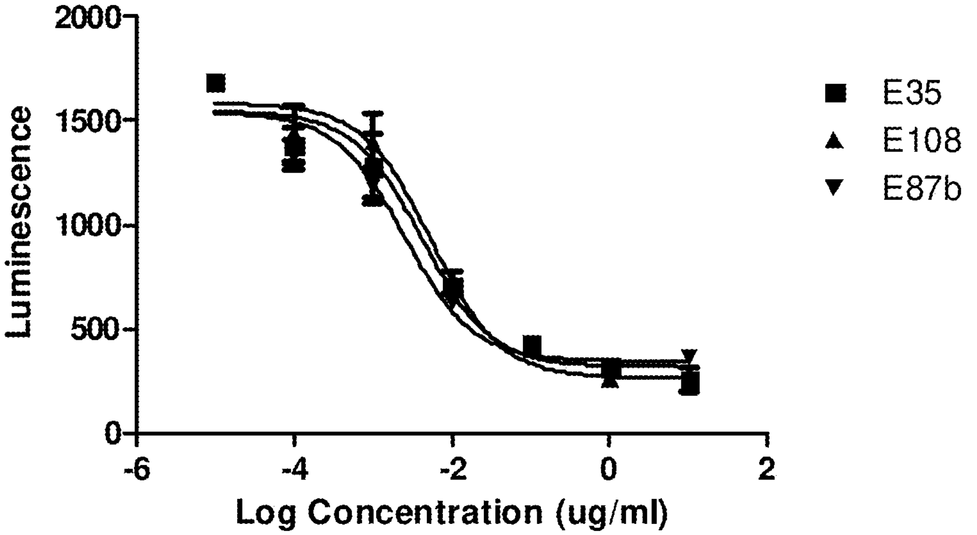
FIG. 10 shows results of the granulocyte survival assay for E35, E108, and E87b.

Granulocytes are able to survive for longer in the presence of GM-CSF. In the human granulocyte survival assay, the ability of the anti-GM-CSFRα antibodies to inhibit this response was assessed. Briefly, granulocytes were isolated from human peripheral blood and treated with 100 pg/mL GM-CSF. Antibodies were serially diluted at a 1:10 ratio (10 μg/mL to 0.0001 μg/mL) and were added to the cells. After incubation for 48 hours, cell survival was analyzed using the Celltiter-glo assay kit (Promega). As shown in FIGS. 10, E35, E108, and E87b effectively inhibited granulocyte survival. Table 8 shows the IC50 of each antibody for inhibiting human granulocyte survival.

TABLE 8

| Antibody | E35-IgG4 | E108-IgG4 | E87b-IgG4 |
|---|---|---|---|
| IC50 (μg/mL) | 0.004200 | 0.005521 | 0.002528 |

Inhibitory Effect on Cytokine Release

Figure 11:
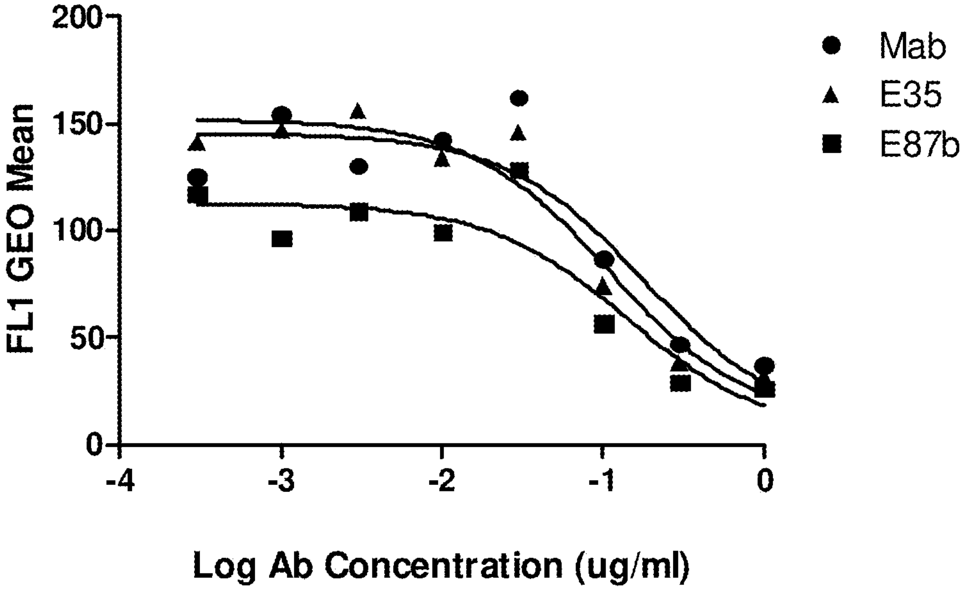
FIG. 11 shows results of the CD11b expression assay for E35 and E87b as compared to Mab.

Inhibitory effect on CD11b expression: Anti-GM-CSFRα antibodies E35 and E87b, as well as Mab were evaluated for their abilities to inhibit the expression of CD11b from cells in the human peripheral blood. Briefly, 50 μL of human peripheral blood was added to each well of a 96-well plate, and incubated with serially diluted antibodies (1:10 dilution; 10 μg/mL to 0.0001 μg/mL). After incubating for 1 hour at 37° C., 10 ng/mL GM-CSF was added, and followed by incubation for an additional hour. FITC conjugated anti-CD11b antibody (BD53310) was used to label CD11b by incubating for 30 minutes at 4° C. Red blood cells were then lysed using 1 mL red blood cell lysis buffer (BD349202), and after two washes with PBS, the expression of CD11b was analyzed using FACS. As shown in FIG. 11 and Table 9, E35 and E87b showed improved abilities to inhibit CD11b expression as compared to Mab. The IC50 of the antibodies are shown in Table 9.

TABLE 9

| Antibody | Mab-IgG4 | E35-IgG4 | E87b-IgG4 |
|---|---|---|---|
| IC50 (μg/mL) | 0.1813 | 0.1111 | 0.1439 |

Figure 12A:
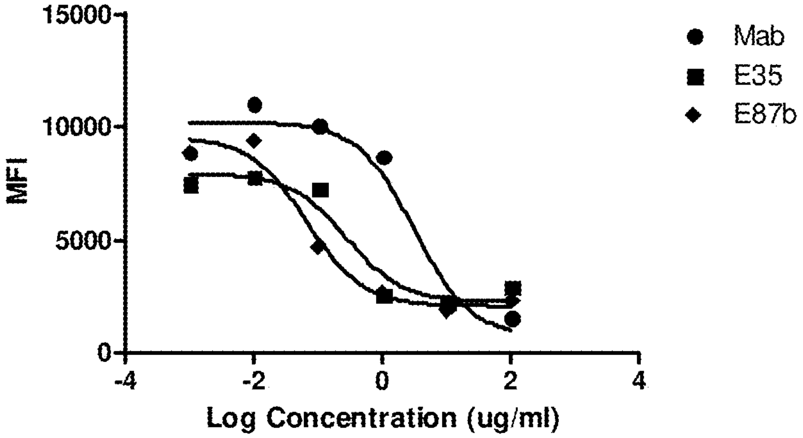
FIGS. 12A and 12B show results of the TNFα release assays for E35 and E87b as compared to Mab.
Figure 13:
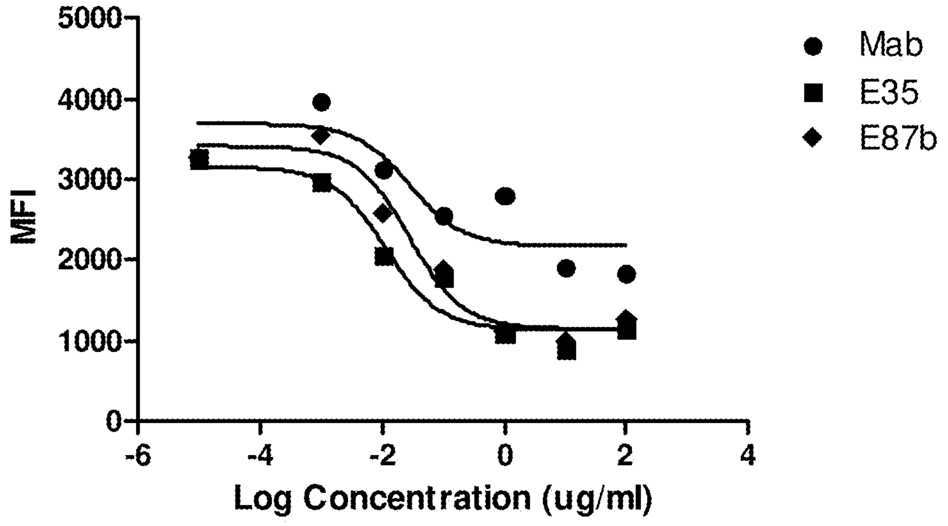
FIG. 13 shows results of the IL-1β production assay for E35 and E87b as compared to Mab.

Inhibitory effects on cytokine production: To evaluate the inhibitory effects of anti-GM-CSFRα antibodies on cytokine production, PBMCs were isolated from 10 mL human peripheral blood using Ficoll gradient, washed with PBS twice, and resuspended in the cell culture media. 1,000,000 cells (100 μL) were added to each well of a 96-well plate, and 50 μL of serially diluted antibodies (100-0.001 μg/mL) were added to the wells and incubated for an hour at 37° C. LPS and GM-CSF were then added to a final concentration of 100 ng/ml and 50 ng/ml, respectively. After incubating at 37° C. for 48 hours, the supernatant was collected and the levels of TNFα and IL-1β were analyzed using the Human Macrophage/Microglia Panel (Biolegend, 740503). As shown in FIG. 12A and Table 10, E35 and E87b (reformatted as human IgG4) showed improved inhibitory effect on TNFα secretion as compared to Mab-IgG4. As shown in FIG. 13 and Table 11, E35 and E87b (reformatted as human IgG4) both exhibited improved inhibitory effect on IL-1β secretion as compared to Mab-IgG4.

TABLE 10

| Antibody | Mab | E35 | E87b |
|---|---|---|---|
| IC50 (μg/mL) | 3.094 | 0.2777 | 0.06664 |

TABLE 11

| Antibody | Mab | E35 | E87b |
|---|---|---|---|
| IC50 (μg/mL) | 0.01263 | 0.003535 | 0.01333 |

Figure 12B:
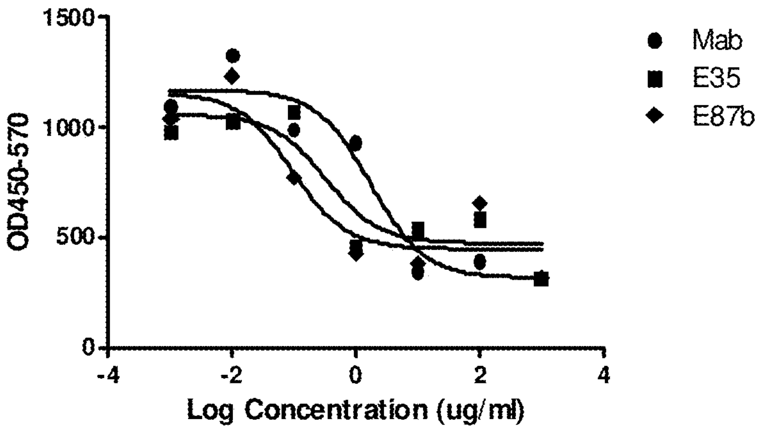

The supernatant was further analyzed for levels of TNFα using ELISA. The ELISA results confirmed that E35 and E87b exhibited improved inhibitory effect on TNFα secretion as compared to Mab (FIG. 12B and Table 12).

TABLE 12

| Antibody | Mab | E35 | E87b |
|---|---|---|---|
| IC50 (μg/mL) | 1.741 | 0.3290 | 0.09349 |

Pharmacokinetics of Anti-GM-CSFRα Antibodies

Figure 14A:
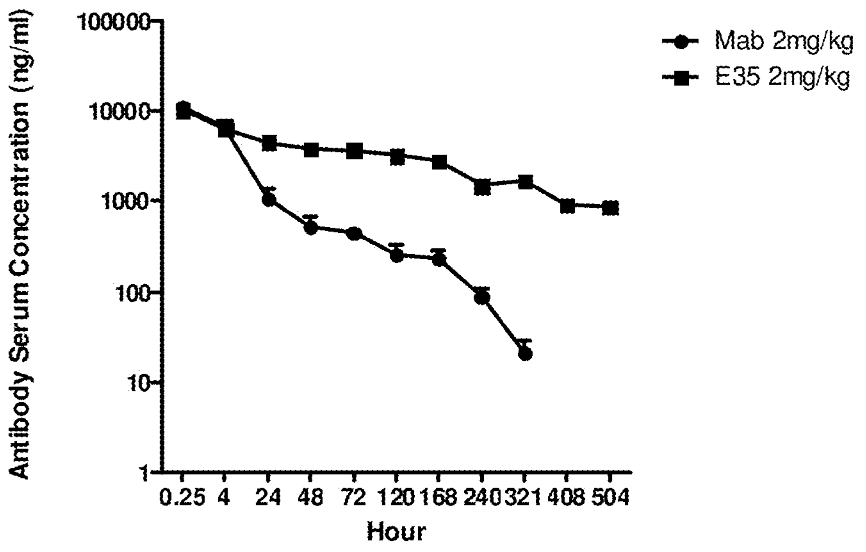
FIGS. 14A and 14B show results of pharmacokinetics analysis of Mab and E35 in rat as measured by ELISA.
Figure 14B:
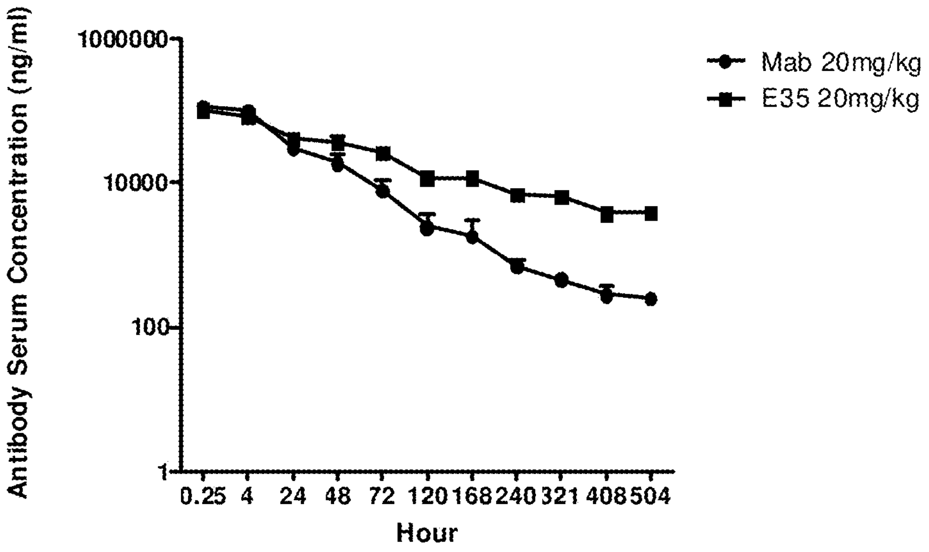

PK values in rat: 10 healthy adult rats (approximately 0.2 kg by weight) were separated into two groups by weight, with 5 in each group. Rat in the first group were injected intravenously with 20 mg/kg of Mab-IgG4 or E35-IgG4, while rat in the second group were injected intravenously with 2 mg/kg of Mab-IgG4 or E35-IgG4. Blood was collected first at one hour after injection, and subsequently at 2 days, 3 days, 5 days, 9 days, and 15 days after injection. After centrifugation, the plasma was used for analyzing antibody concentration using ELISA. Briefly, synthetic GM-CSFRα was used to cover the wells of a 96-well plate. On the following day, after washing with PBST, blocking with 200 μL PBS-milk for an hour, followed by another wash with PBST, the plasma was added and incubated for an hour at 37° C. The plate was washed with 0.1% TBST for 6 times before 100 μL of Goat-anti-human Fc antibody-AP (1:3000 in PBS) was added to each well and incubated for an hour. After washing with 0.1% TBST for 6 times, 50 μL of pNPP was added to each well and color was developed for $10^{-20}$ minutes at 37° C. The results were read by a microplate reader at 410 nm which suggested that the half-life of E35-IgG4 was longer than that of Mab-IgG4 (FIGS. 14A-14B and Table 13).

TABLE 13

| Antibody T1/2 | Mab-IgG4 | E35-IgG4 |
|---|---|---|
| T1/2 (20 mg/kg) | 129 h | 190.9 h |
| T1/2 (2 mg/kg) | 53.09 h | 186.7 h |

Figure 15:
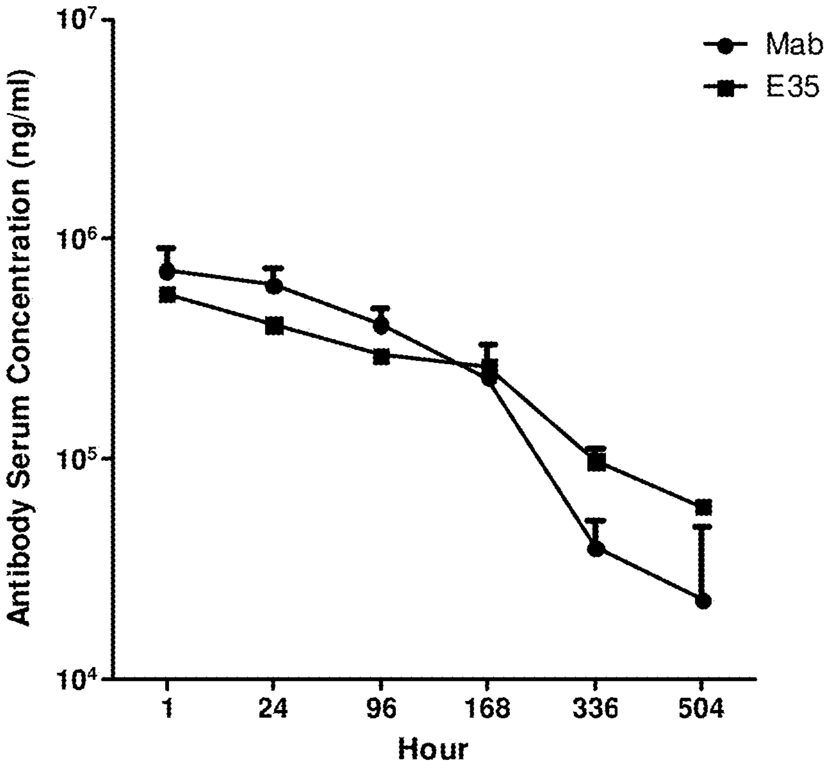
FIG. 15 shows results of pharmacokinetics analysis of Mab and E35 in cynomolgus monkey as measured by ELISA.
Figure 16A:
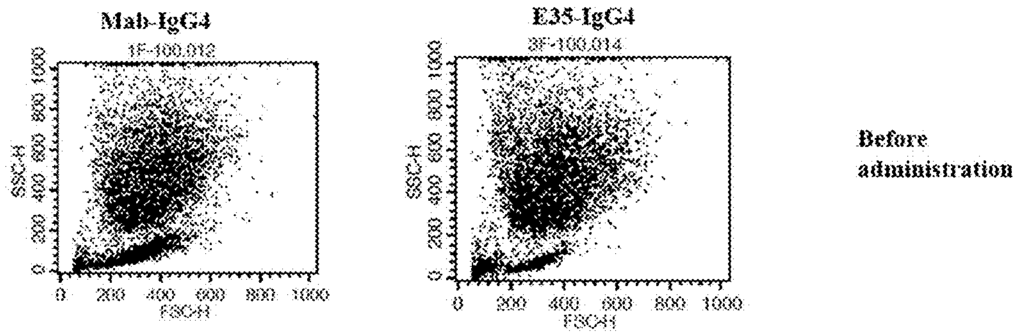
FIGS. 16A-D show FACS plots of in vivo granulocyte shape change analysis upon administration of Mab-IgG4 or E35-IgG4 in cynomolgus monkey.
Figure 16B:
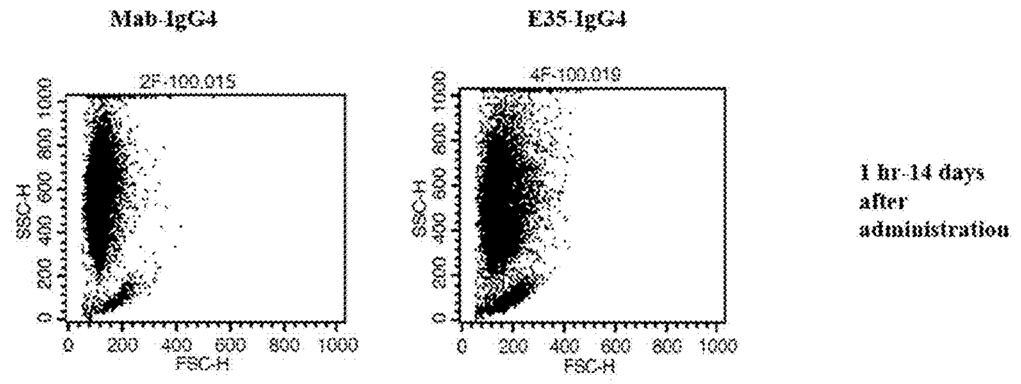
Figure 16C:
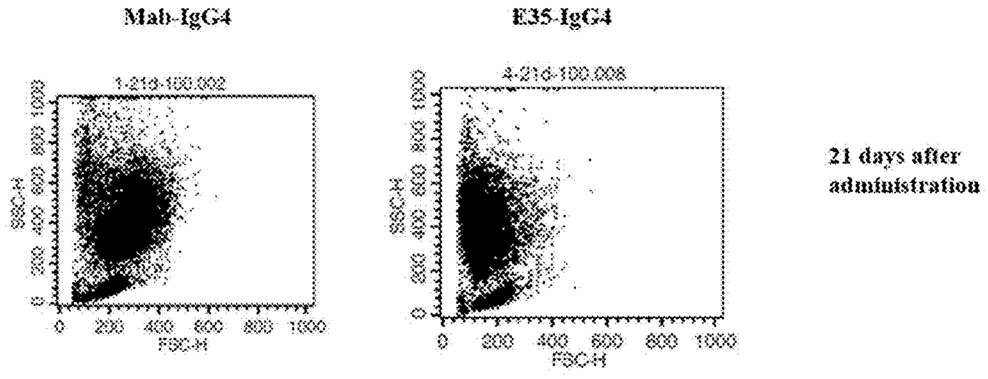
Figure 16D:
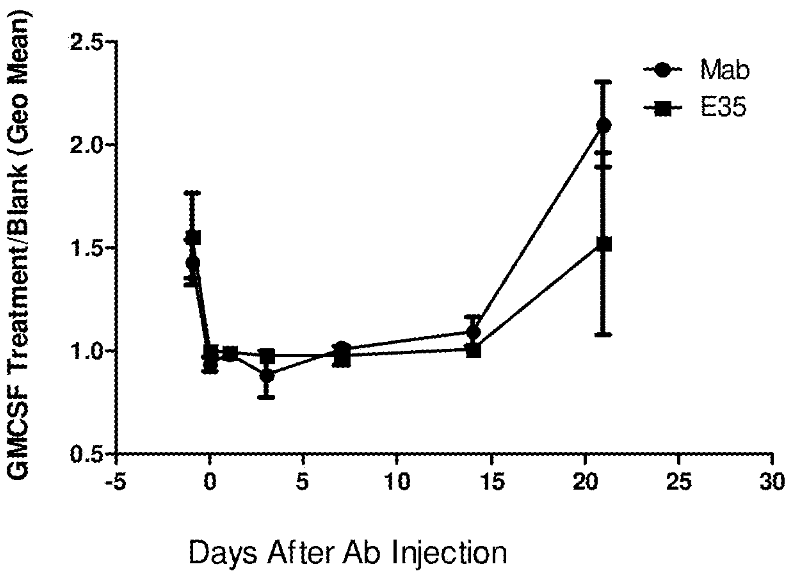
Figure 17A:
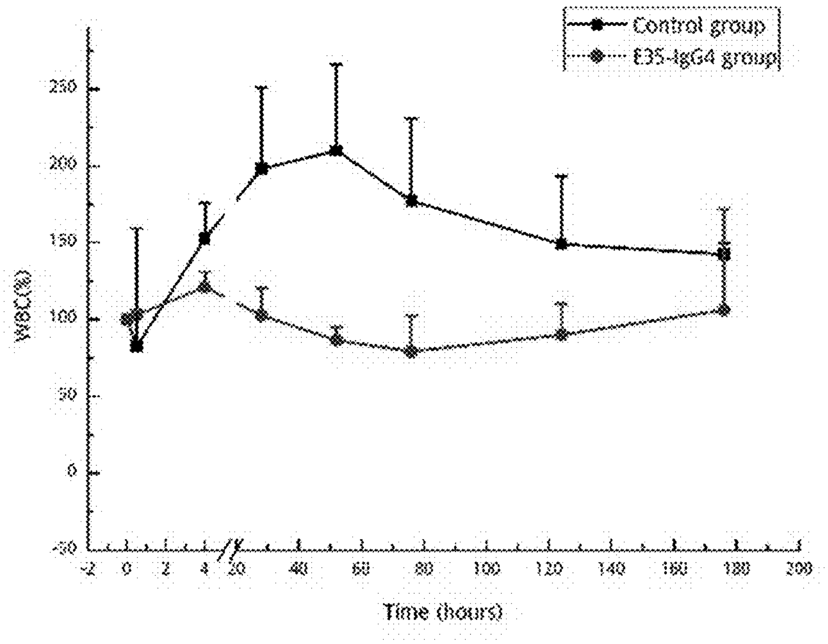
FIGS. 17A-17G show results of the inhibitory effect of E35-IgG4 on GM-CSF-induced increase in inflammatory cells.
Figure 17B:
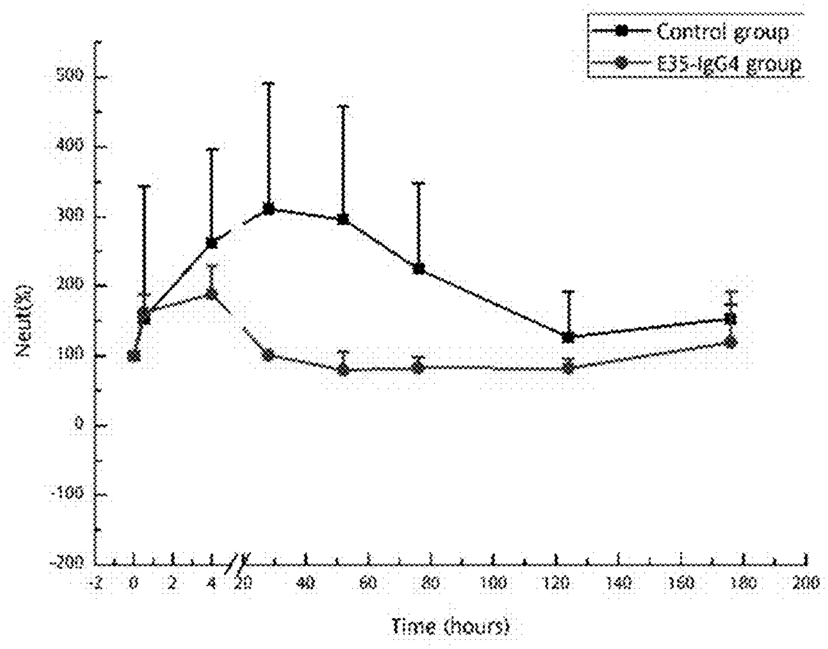
Figure 17C:
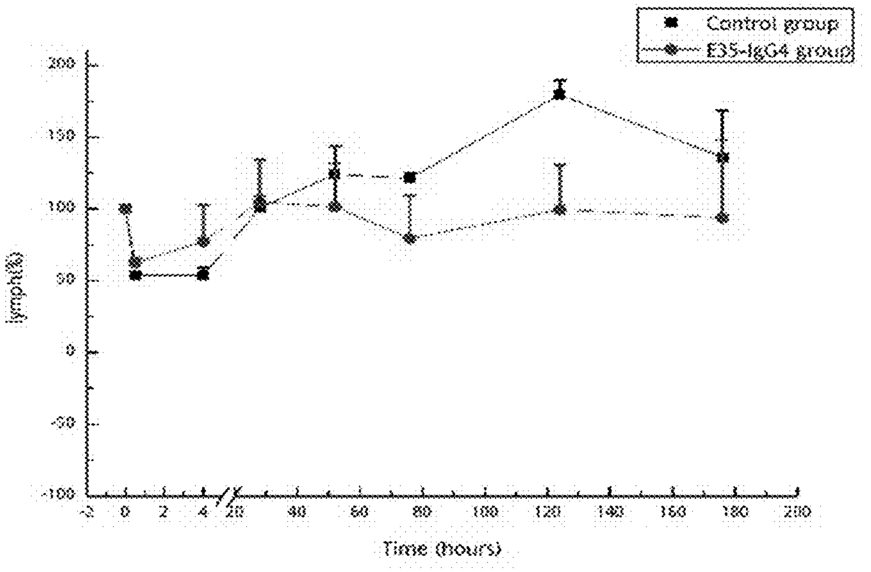
Figure 17D:
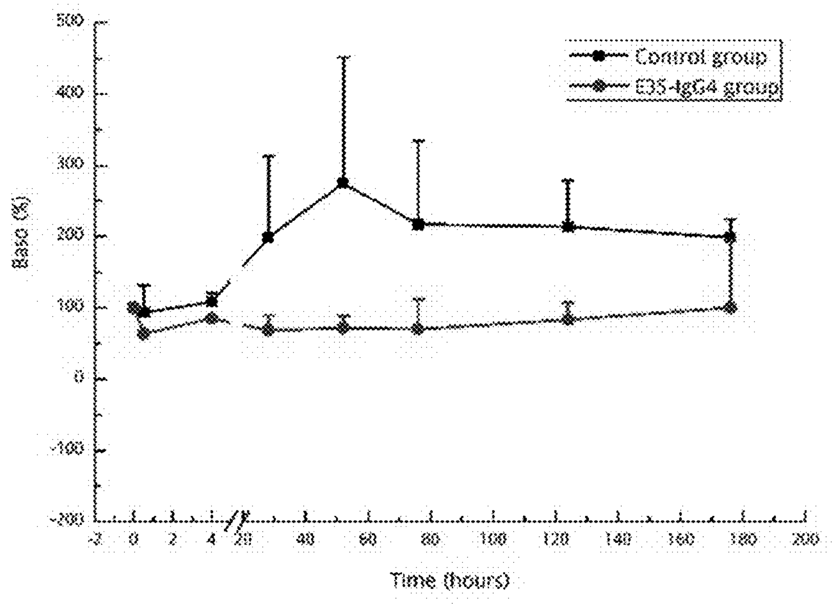
Figure 17E:
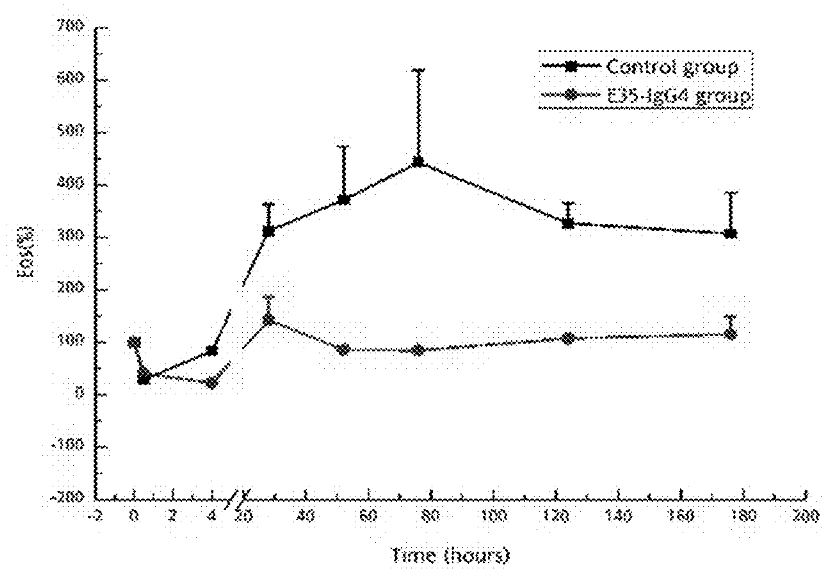
Figure 17F:
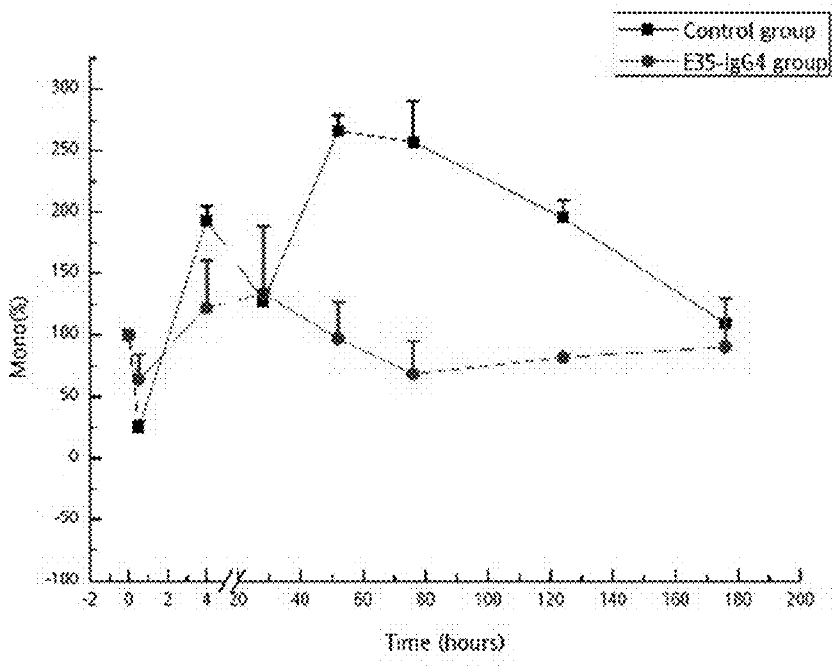
Figure 17G:
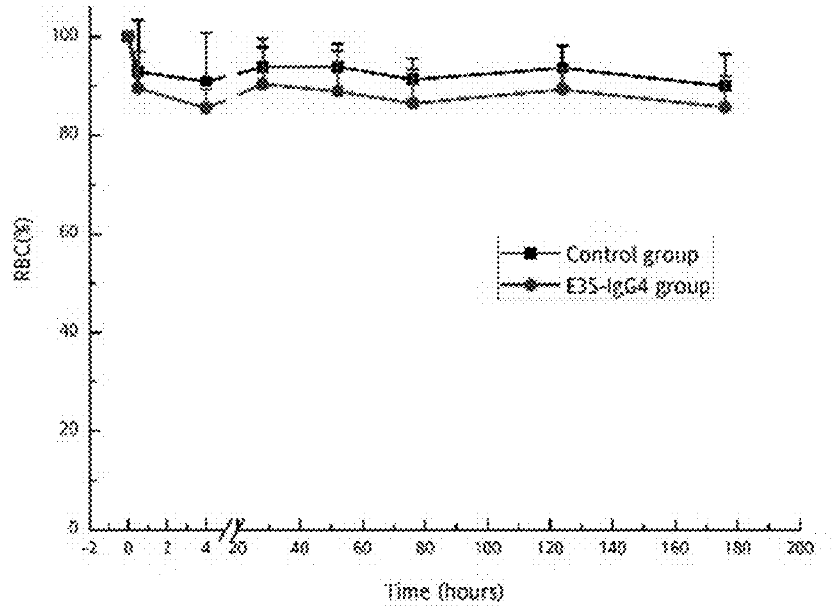

PK and PD studies in cynomolgus monkey: Four cynomolgus monkeys (approximately 3 kg by weight) were injected with either E35-IgG4 or the control antibody Mab-IgG4 at a concentration of 10 mg/kg. Specifically. Animal #1 and #2 were injected with Mab-IgG4, and Animal #3 and #4 were injected with E35-IgG4. 6 mL of blood was collected from each animal the day before injection (D−1), one hour after injection (D1), and subsequently at D2, D4, D8, D15, D22, D29, and D36. To evaluate the pharmacokinetics of the antibodies, plasma was collected from 1 mL of the blood sample collected at each time point by centrifuging for 15 minutes at 5000 g, and stored at −80° C. as 50 μL aliquots. The concentrations of E35-IgG4 and Mab-IgG4 were analyzed using ELISA performed as described above for the pharmacokinetics study in rats. As shown in FIG. 15 and Table 14, the half-life of E35-IgG4 was longer than that of Mab-IgG4. To evaluate the pharmacodynamics of the antibodies, granulocytes were isolated from 5 mL of the blood sample collected at each time point and subjected to granulocyte shape change analysis. Briefly, 100 μL of granulocytes ($2\times10^6$/mL) were added to each well of a 96-well plate, and incubated for 30 minutes at 37° C., followed by incubation with 100 pg/mL GM-CSF for 3 hours. The cells were then subjected to shape change analysis using FACS as described above for the granulocyte shape change assay. The results showed that E35-IgG4 and Mab-IgG4 both prevented granulocyte shape change. Surprisingly, the effect of Mab-IgG4 only lasted for 14 days after the injection, while the effect of E35-IgG4 lasted for at least 21 days (FIGS. 16A-16D).

TABLE 14

| Antibody | Animal No. | T1/2 (h) | Average T1/2 (h) | $T_{max}$ (h) | $C_{max}$ (ng/ml) | AUC |
|---|---|---|---|---|---|---|
| Mab-IgG4 | 1 | 44.86346 | 69.41 | 1 | 95783.719 | 17340604 |
| | 2 | 93.956602 | | 1 | 76499.663 | 14508393 |
| E35-IgG4 | 3 | 104.10626 | 106.4 | 1 | 73486.786 | 14118941 |
| | 4 | 108.76885 | | 1 | 77001.042 | 15830767 |

Inhibitory Effects on GM-CSF-Induced Increase of Inflammatory Cells

To examine the inhibitory effects of anti-GM-CSFRα antibodies on GM-CSF-induced increase of inflammatory cells, GM-CSF was administered to cynomolgus monkeys previously injected with E35-IgG4 or NaCl solution as a control, and the levels of white blood cells, neutrophils, lymphocytes, basophils, eosinophils, monocytes, and red blood cells were evaluated following GM-CSF administration. Briefly, 4 cynomolgus monkeys were assigned to two groups, with 2 in each group. E35-IgG4 was administered to one group via intraperitoneal injections on Day 1 and Day 3. The other group was injected with NaCl solution as control. On Day 3, 4 and 5, both groups were injected with 5.0 μg/kg of GM-CSF (twice a day, approximately 8 hours in between injections). Blood samples were collected prior to the first GM-CSF injection and subsequently at 0.5h, 4.0h, 28.0h, 52.0h, 76.0h, 124.0h, and 176.0h after the first injection, and the levels of various cells types at each time point were analyzed.

The results showed that as compared to the control group, E35-IgG4 completely repressed GM-CSF-induced increase in white blood cells, neutrophils, lymphocytes, basophils, eosinophils, and monocytes. In contrast, the levels of red blood cells remained constant before and after GM-CSF treatment for both groups (FIGS. 17A-17G).

Example 3: Identification of E35 Variants that Retain Biological Activity

The sequence of his-tagged E35-scFv was cloned into a prokaryotic expression vector. Selected residues in the CDR regions were subjected to saturation mutagenesis and screening. The mutated versions were inserted into prokaryotic expression vectors and used to transfect BL21. After plating, 60 clones were randomly selected for sequencing, and 14-19 distinct mutations at each position were obtained. scFvs containing these mutations were generated, purified and subjected to TF-1 proliferation assay to assess their biological activity. The mutations and corresponding IC50 for reducing TF-1 cell proliferation are shown in Table 15 below (numbering is according to the EU index of Kabat):

TABLE 15

The unit for IC50 values indicated is μg/mL

| Mut. | $IC_{50}$ | Mut. | $IC_{50}$ | Mut. | $IC_{50}$ | Mut. | $IC_{50}$ | Mut. | $IC_{50}$ | Mut. | $IC_{50}$ | Mut. | $IC_{50}$ |
|---|---|---|---|---|---|---|---|---|---|---|---|---|---|
| HE31N | 0.11 | E35 | 0.12 | HT28H | 0.06 | LS26L | 0.044 | LQ27Y | 0.065 | LS31T | 0.060 | LS28H | 0.058 |
| HE31G | 0.116 | HT30P | 0.126 | HT28V | 0.08 | LS26N | 0.054 | LQ27P | 0.097 | LS31R | 0.069 | LS28W | 0.060 |
| E35 | 0.12 | HT30D | 0.132 | HT28E | 0.091 | LS26A | 0.062 | LQ27A | 0.104 | LS31A | 0.078 | LS28L | 0.067 |
| HE31D | 0.13 | HT30E | 0.132 | HT28P | 0.093 | LS26K | 0.069 | LQ27I | 0.105 | LS31H | 0.106 | LS28R | 0.077 |
| HE31M | 0.13 | HT30Y | 0.142 | HT28L | 0.100 | LS26R | 0.072 | LQ27F | 0.113 | LS31Q | 0.117 | LS28K | 0.082 |
| HE31S | 0.14 | HT30W | 0.151 | HT28M | 0.11 | LS26I | 0.073 | LQ27T | 0.113 | E35 | 0.12 | LS28T | 0.088 |
| HE31P | 0.17 | HT30V | 0.158 | HT28S | 0.11 | LS26Q | 0.075 | LQ27R | 0.117 | LS31P | 0.139 | LS28P | 0.089 |
| HE31F | 0.18 | HT30M | 0.174 | HT28W | 0.11 | LS26G | 0.078 | E35 | 0.12 | LS31M | 0.156 | LS28I | 0.091 |
| HE31Y | 0.2 | HT30N | 0.178 | HT28C | 0.12 | LS26T | 0.081 | LQ27V | 0.120 | LS31L | 0.235 | LS28F | 0.100 |
| HE31A | 0.21 | HT30L | 0.181 | E35 | 0.12 | LS26H | 0.089 | LQ27L | 0.128 | LS31G | 0.279 | LS28V | 0.104 |
| HE31V | 0.22 | HT30Q | 0.192 | HT28A | 0.13 | LS26M | 0.089 | LQ27E | 0.135 | LS31W | 0.649 | LS28E | 0.111 |
| HE31K | 0.23 | HT30G | 0.199 | HT28G | 0.16 | LS26C | 0.114 | LQ27S | 0.138 | LS31I | 0.681 | LS28A | 0.116 |
| HE31W | 0.26 | HT30S | 0.213 | HT28N | 0.17 | E35 | 0.12 | LQ27C | 0.142 | LS31E | 0.832 | E35 | 0.12 |
| HE31R | 0.31 | HT30A | 0.215 | HT28K | 0.217 | | | | | LS31D | 1.34 | LS28Q | 0.154 |
| HE31C | 0.36 | HT30K | 0.325 | | | | | | | | | | |
| | | HT30R | 0.350 | | | | | | | | | | |
| LS30L | 0.069 | LY32L | 0.07 | LS52A | 0.068 | LA51G | 0.12 | E35 | 0.12 | E35 | 0.12 | LN93D | 0.045 |
| LS30W | 0.071 | E35 | 0.12 | LS52W | 0.073 | LA51R | 0.12 | LG50T | 0.25 | LD92A | 0.282 | LN93E | 0.081 |
| LS30M | 0.073 | LY32F | 0.21 | LS52R | 0.089 | E35 | 0.12 | LG50A | 0.5 | LD92Q | 0.328 | E35 | 0.12 |
| LS30A | 0.078 | LY32M | 0.42 | LS52L | 0.115 | LA51H | 0.162 | LG50D | 0.88 | LD92W | 0.342 | LN93T | 0.14 |
| LS30Y | 0.082 | LY32T | 0.51 | E35 | 0.12 | LA51K | 0.168 | LG50Q | 0.93 | LD92V | 0.387 | LN93Y | 0.156 |
| LS30K | 0.083 | LY32Q | 0.87 | LS52T | 0.136 | LA51S | 0.18 | LG50I | 1.08 | LD92L | 0.420 | LN93G | 0.205 |
| LS30R | 0.088 | LY32W | 1.17 | LS52Q | 0.138 | LA51T | 0.18 | LG50S | 1.3 | LD92T | 0.494 | LN93A | 0.21 |
| LS30G | 0.092 | LY32V | 1.23 | LS52F | 0.167 | LA51M | 0.264 | LG50V | 1.4 | LD92R | 0.495 | LN93M | 0.27 |
| LS30T | 0.092 | LY32A | 1.35 | LS52Y | 0.181 | LA51F | 0.294 | LG50N | 1.59 | LD92M | 0.507 | LN93F | 0.3 |
| LS30E | 0.100 | LY32G | 1.35 | LS52H | 0.192 | LA51N | 0.36 | LG50P | 1.86 | LD92G | 0.522 | LN93S | 0.3 |
| E35 | 0.12 | LY32C | 1.9 | LS52N | 0.253 | LA51V | 0.36 | LG50R | 2.79 | LD92H | 0.530 | LN93I | 0.33 |
| LS30V | 0.124 | LY32N | 2.05 | LS52P | 1.055 | LA51C | 0.37 | LG50L | 3.9 | LD92I | 0.597 | LN93L | 0.33 |
| LS30N | 0.132 | LY32R | 3.12 | LS52D | 1.751 | LA51L | 0.5 | LG50H | 4.29 | LD92S | 0.598 | LN93H | 0.45 |
| LS30F | 0.160 | LY32E | 3.75 | | | LA51E | 0.81 | LG50C | 25.7 | LD92K | 0.640 | LN93R | 0.6 |
| LS30C | 0.221 | LY32P | 5.15 | | | LA51W | 1.59 | LG50E | 29.85 | LD92P | 0.881 | LN93P | 0.66 |
| | | LY32K | 9.6 | | | LA51P | 2.1 | LG50Y | 32 | | | LN93K | 0.78 |
| | | LY32S | NA | | | LA51Q | 18.17 | LG50W | NA | | | | |

Based on these results, it was determined that scFv antibodies having the following amino acid sequences derived from the E35 scFv retained their biological activities as evaluated by the TF-1 proliferation assay:

(i) E, H, N, G, D, M, S, P, F, Y, A, V, K, W, R, or C at position 31 of the $V_H$;
(ii) S, L, N, A, K, R, I, Q, G, T, H, M, or C at position 26 of the $V_L$;
(iii) Q, Y, P, A, I, F, T, R, V, L, E, S, or C at position 27 of the $V_L$;
(iv) S, H, W, L, R, K, T, P, I, F, V, E, A, or Q at position 28 of the $V_L$;
(v) S, L, W, M, A, Y, K, R, G, T, E, V, N, F, or C at position 30 of the $V_L$;
(vi) S, T, R, A, H, Q, P, M, L, or G at position 31 of the $V_L$;
(vii) Y, L or F at position 32 of the $V_L$;
(viii) G, or T at position 50 of the $V_L$;
(ix) A, G, R, H, K, S, T, M, F, N, or V at position 51 of the $V_L$;
(x) S, A, W, R, L, T, Q, F, Y, H, or N at position 52 of the $V_L$;
(xi) D, A, Q, or W at position 92 of the $V_L$;
(xii) N, D, E, T, Y, G, A, M, F, S, I, or L at position 93 of the $V_L$;
(xiii) amino acid residues selected from T, H, V, E, P, L, M, S, W, C, A, G, N, or K at position 28 of the $V_H$;
(xiv) amino acid residues selected from T, P, D, E, Y, W, V, M, N, L, Q, G, S, A, K, or R at position 30 of the $V_H$.

E35 variants containing combinatorial mutations were also generated. The IC50 for reducing TF-1 cell proliferation of full-length IgG4 antibodies containing the E35 variants were analyzed and are shown in Table 16 below. These results suggested that E35 variants containing combinatorial mutations exhibited improved efficacy for reducing TF-1 cell proliferation.

TABLE 16

| Antibody | IC50 (μg/mL) | Normalization |
|---|---|---|
| E35-IG4 | 0.0474 | 1.0000 |
| E35-VL93D-IG4 | 0.03714 | 0.7835 |
| E35-VH28H-IG4 | 0.05693 | 1.2011 |
| E35-VH28E-IG4 | 0.03073 | 0.6483 |
| E35-VH28H-VL93L-IG4 | 0.01628 | 0.3435 |
| E35-VH28H-VL93D-IG4 | 0.02783 | 0.5871 |
| E35-VH28H-VL30L-IG4 | 0.02959 | 0.6243 |
| E35-VH28H-VL30C-IG4 | 0.04306 | 0.9084 |
| E35-VH28E-VL30L-IG4 | 0.02682 | 0.5658 |
| E35-VH28E-VL30C-IG4 | 0.02077 | 0.4382 |
| E35-VH28H-VL30L-93D-IG4 | 0.02414 | 0.5093 |

The exemplary heavy chain variable domain and light chain variable domain sequences of E35 variants are shown in Table 17 below.

TABLE 17

| Antibody | Substitution | $V_H$ SEQ ID NO | $V_L$ SEQ ID NO |
|---|---|---|---|
| AbM-1 | LS26A | 91 | 150 |
| AbM-2 | LS26C | 91 | 151 |
| AbM-3 | LS26G | 91 | 152 |
| AbM-4 | LS26H | 91 | 153 |
| AbM-5 | LS26I | 91 | 154 |
| AbM-6 | LS26K | 91 | 155 |
| AbM-7 | LS26L | 91 | 156 |
| AbM-8 | LS26M | 91 | 157 |
| AbM-9 | LS26N | 91 | 158 |
| AbM-10 | LS26Q | 91 | 159 |
| AbM-11 | LS26R | 91 | 160 |
| AbM-12 | LS26T | 91 | 161 |
| AbM-13 | LQ27A | 91 | 162 |
| AbM-14 | LQ27C | 91 | 163 |
| AbM-15 | LQ27E | 91 | 164 |
| AbM-16 | LQ27F | 91 | 165 |
| AbM-17 | LQ27I | 91 | 166 |
| AbM-18 | LQ27L | 91 | 167 |
| AbM-19 | LQ27P | 91 | 168 |
| AbM-20 | LQ27R | 91 | 169 |
| AbM-21 | LQ27S | 91 | 170 |
| AbM-22 | LQ27T | 91 | 171 |
| AbM-23 | LQ27V | 91 | 172 |
| AbM-24 | LQ27Y | 91 | 173 |
| AbM-25 | LS28A | 91 | 174 |
| AbM-26 | LS28E | 91 | 175 |
| AbM-27 | LS28F | 91 | 176 |
| AbM-28 | LS28H | 91 | 177 |
| AbM-29 | LS28I | 91 | 178 |
| AbM-30 | LS28K | 91 | 179 |
| AbM-31 | LS28L | 91 | 180 |
| AbM-32 | LS28P | 91 | 181 |
| AbM-33 | LS28Q | 91 | 182 |
| AbM-34 | LS28R | 91 | 183 |
| AbM-35 | LS28T | 91 | 184 |
| AbM-36 | LS28V | 91 | 185 |
| AbM-37 | LS28W | 91 | 186 |
| AbM-38 | LS30A | 91 | 187 |
| AbM-39 | LS30C | 91 | 188 |
| AbM-40 | LS30E | 91 | 189 |
| AbM-41 | LS30F | 91 | 190 |
| AbM-42 | LS30G | 91 | 191 |
| AbM-43 | LS30K | 91 | 192 |
| AbM-44 | LS30L | 91 | 193 |
| AbM-45 | LS30M | 91 | 194 |
| AbM-46 | LS30N | 91 | 195 |
| AbM-47 | LS30R | 91 | 196 |
| AbM-48 | LS30T | 91 | 197 |
| AbM-49 | LS30V | 91 | 198 |
| AbM-50 | LS30W | 91 | 199 |
| AbM-51 | LS30Y | 91 | 200 |
| AbM-52 | LS31A | 91 | 201 |
| AbM-53 | LS31G | 91 | 202 |
| AbM-54 | LS31H | 91 | 203 |
| AbM-55 | LS31L | 91 | 204 |
| AbM-56 | LS31M | 91 | 205 |
| AbM-57 | LS31P | 91 | 206 |
| AbM-58 | LS31Q | 91 | 207 |
| AbM-59 | LS31R | 91 | 208 |
| AbM-60 | LS31T | 91 | 209 |
| AbM-61 | LY32F | 91 | 210 |
| AbM-62 | LY32L | 91 | 211 |
| AbM-63 | LG50T | 91 | 212 |
| AbM-64 | LA51F | 91 | 289 |
| AbM-65 | LA51G | 91 | 213 |
| AbM-66 | LA51H | 91 | 214 |
| AbM-67 | LASIK | 91 | 215 |
| AbM-68 | LA51M | 91 | 216 |
| AbM-69 | LA51R | 91 | 217 |
| AbM-70 | LA51S | 91 | 218 |
| AbM-71 | LA51T | 91 | 219 |
| AbM-72 | LS52A | 91 | 220 |
| AbM-73 | LS52F | 91 | 221 |
| AbM-74 | LS52H | 91 | 222 |
| AbM-75 | LS52L | 91 | 223 |
| AbM-76 | LS52N | 91 | 224 |
| AbM-77 | LS52Q | 91 | 225 |
| AbM-78 | LS52R | 91 | 226 |
| AbM-79 | LS52T | 91 | 227 |
| AbM-81 | LS52W | 91 | 229 |
| AbM-83 | LS52Y | 91 | 231 |
| AbM-84 | LD92A | 91 | 232 |

TABLE 17-continued

| Antibody | Substitution | $V_H$ SEQ ID NO | $V_L$ SEQ ID NO |
|---|---|---|---|
| AbM-85 | LD92Q | 91 | 233 |
| AbM-86 | LD92W | 91 | 234 |
| AbM-87 | LN93A | 91 | 235 |
| AbM-88 | LN93D | 91 | 236 |
| AbM-89 | LN93E | 91 | 237 |
| AbM-90 | LN93F | 91 | 238 |
| AbM-91 | LN93G | 91 | 239 |
| AbM-92 | LN93I | 91 | 240 |
| AbM-93 | LN93L | 91 | 241 |
| AbM-94 | LN93M | 91 | 242 |
| AbM-95 | LN93S | 91 | 243 |
| AbM-96 | LN93T | 91 | 244 |
| AbM-97 | LN93Y | 91 | 245 |
| AbM-98 | HT28A | 246 | 126 |
| AbM-99 | HT28C | 247 | 126 |
| AbM-100 | HT28E | 248 | 126 |
| AbM-101 | HT28G | 249 | 126 |
| AbM-102 | HT28H | 250 | 126 |
| AbM-103 | HT28K | 251 | 126 |
| AbM-104 | HT28L | 252 | 126 |
| AbM-105 | HT28M | 253 | 126 |
| AbM-106 | HT28N | 254 | 126 |
| AbM-107 | HT28P | 255 | 126 |
| AbM-108 | HT28S | 256 | 126 |
| AbM-109 | HT28V | 257 | 126 |
| AbM-110 | HT28W | 258 | 126 |
| AbM-111 | HT30A | 259 | 126 |
| AbM-112 | HT30D | 260 | 126 |
| AbM-113 | HT30E | 261 | 126 |
| AbM-114 | HT30G | 262 | 126 |
| AbM-115 | HT30K | 263 | 126 |
| AbM-116 | HT30L | 264 | 126 |
| AbM-117 | HT30M | 265 | 126 |
| AbM-118 | HT30N | 266 | 126 |
| AbM-119 | HT30P | 267 | 126 |
| AbM-120 | HT30Q | 268 | 126 |
| AbM-121 | HT30R | 269 | 126 |
| AbM-122 | HT30S | 270 | 126 |
| AbM-123 | HT30V | 271 | 126 |
| AbM-124 | HT30W | 272 | 126 |
| AbM-125 | HT30Y | 273 | 126 |
| AbM-126 | HE31A | 274 | 126 |
| AbM-127 | HE31C | 275 | 126 |
| AbM-128 | HE31D | 276 | 126 |
| AbM-129 | HE31F | 277 | 126 |
| AbM-130 | HE31G | 278 | 126 |
| AbM-131 | HE31K | 279 | 126 |
| AbM-132 | HE31M | 280 | 126 |
| AbM-133 | HE31N | 281 | 126 |

TABLE 17-continued

| Antibody | Substitution | $V_H$ SEQ ID NO | $V_L$ SEQ ID NO |
|---|---|---|---|
| AbM-134 | HE31P | 282 | 126 |
| AbM-135 | HE31R | 283 | 126 |
| AbM-136 | HE31S | 284 | 126 |
| AbM-137 | HE31V | 285 | 126 |
| AbM-138 | HE31W | 286 | 126 |
| AbM-139 | HE31Y | 287 | 126 |
| AbM-140 | E35-28H-93L-IG4 | 250 | 241 |
| AbM-141 | E35-28H-30L-IG4 | 250 | 193 |
| AbM-142 | E35-28E-30C-IG4 | 248 | 188 |
| AbM-143 | E35-28E-30L-IG4 | 248 | 193 |
| AbM-144 | E35-28H-30L93D-IG4 | 250 | 288 |
| AbM-145 | E35-28H-30C-IG4 | 250 | 188 |
| AbM-146 | E35HT28H-LN93D-IG4 | 250 | 236 |
| AbM-147 | E35-LS30L-LN93D-IG4 | 91 | 288 |

Example 4: Epitope Mapping of Anti-GM-CSFRα Antibodies

Figure 18A:
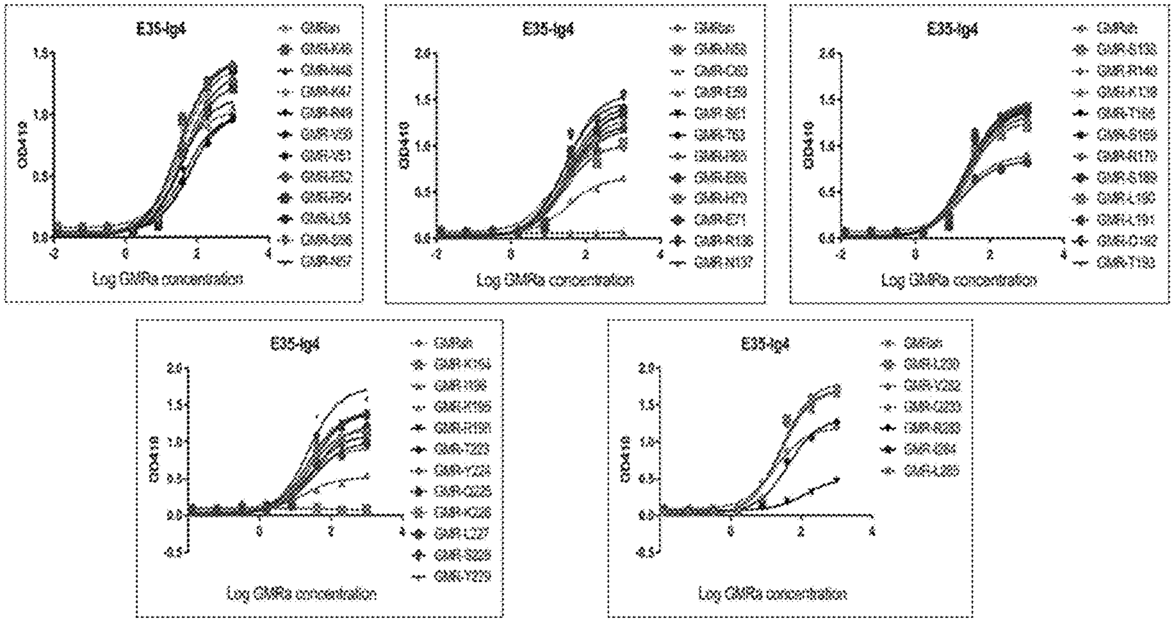
FIGS. 18A-18C show the binding affinity of E35-IgG4, E87b-IgG4 and T119-IgG4 for wild type GMRah and GMRah with mutations at exemplary amino acid residues as measured by ELISA.
Figure 18B:
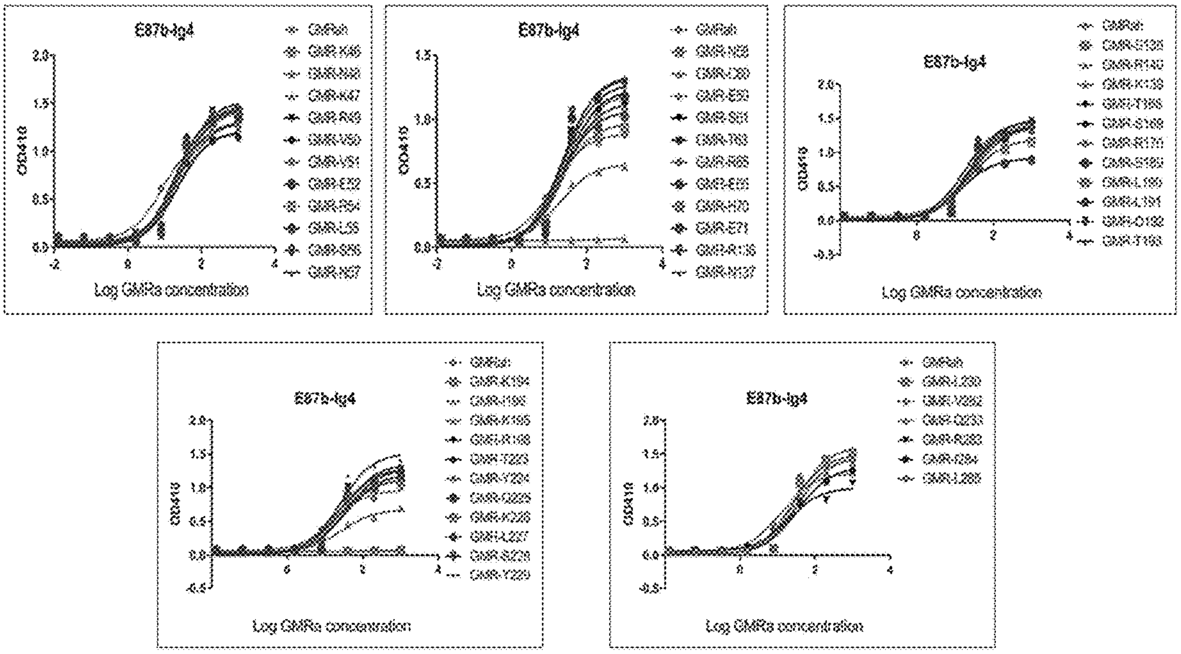
Figure 18C:
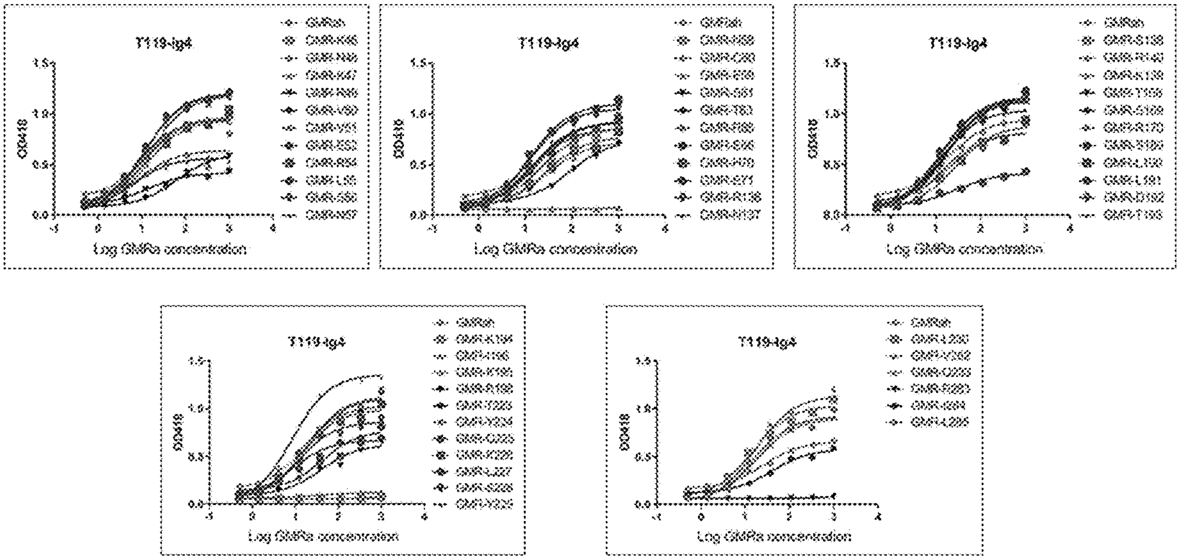

Amino acid residues in proximity to the binding sites of GM-CSF on GM-CSFRα were identified based on their crystal structures, the numbering of GM-CSFRα is according to the crystal structure (PDB id: 4RS1) as shown in FIG. 20. Using the Discovery Studio software, the predicted binding sites for E35 were identified, and the amino acid residues within the binding sites and in proximity to the binding sites were selected and subjected to alanine scanning. GM-CSFRα proteins with these selected mutations were expressed. The binding affinity of E35-IgG4, E87b-IgG4 and T119-IgG4 for each mutated GM-CSFRα protein was analyzed using ELISA. FIGS. 18A-18C show the ELISA binding curves of the antibodies for mutated GM-CSFRα. As used herein, GMRah represents His-tagged wild-type human GM-CSFRα (GM-CSFRα-6His). Mutations at various positions of the amino acid sequence of the wild type GM-CSFRα were generated using alanine scanning as described above. As shown in FIGS. 18A-18C, mutation at position C60 significantly affected the binding affinity E35, E87b, and T119 and was determined to be a mutation that affected the protein structure of GM-CSFRα. Based on these results, exemplary epitopes of antibodies E35, E87b, and T119 were identified as comprising amino acid residues as shown in Table 18. The numbering of the amino acid residues in GM-CSFRα (SEQ ID NO: 292) is shown in FIG. 20.

TABLE 18

| Antibody | R49 | V50 | V51 | N57 | E59 | S61 | T63 | L191 | K194 | K195 | I196 | R283 | I284 |
|---|---|---|---|---|---|---|---|---|---|---|---|---|---|
| E35 | | GMR-V50 | GMR-V51 | | GMR-E59 | | GMR-T63 | | GMR-K194 | GMR-K195 | GMR-I196 | GMR-R283 | GMR-I284 |
| E87b | | GMR-V50 | | | GMR-E59 | | | GMR-L191 | GMR-K194 | GMR-K195 | GMR-I196 | GMR-R283 | GMR-I284 |
| T119 | GMR-R49 | GMR-V50 | GMR-V51 | GMR-N57 | GMR-E59 | GMR-S61 | | | GMR-K194 | GMR-K195 | | GMR-R283 | GMR-I284 |

The invention claimed is:

1. An isolated anti-GM-CSFRα antibody, comprising: a $V_H$ comprising an HC-CDR1 comprising the amino acid sequence of any one of SEQ ID NOs: 1-4; an HC-CDR2 comprising the amino acid sequence of any one of SEQ ID NOs: 6-16; and an HC-CDR3 comprising the amino acid sequence of any one of SEQ ID NOs: 17-50; and a $V_L$ comprising an LC-CDR1 comprising the amino acid sequence of SEQ ID NO: 51; an LC-CDR2 comprising the amino acid sequence of SEQ ID NO: 52; and an LC-CDR3 comprising the amino acid sequence of any one of SEQ ID NOs: 53-61, or 63-75.

2. An isolated anti-GM-CSFRα antibody, comprising a $V_H$ comprising an HC-CDR1, an HC-CDR2, and an HC-CDR3 of a $V_H$ comprising the amino acid sequence of any one of SEQ ID NOs: 81-121; and a $V_L$ comprising an LC-CDR1, an LC-CDR2, and an LC-CDR3 of a $V_L$ comprising the amino acid sequence of any one of SEQ ID NOs: 122-130, or 132-144.

3. The isolated anti-GM-CSFRα antibody of claim 1, comprising:

(i) a $V_H$ comprising an HC-CDR1 comprising the amino acid sequence of SEQ ID NO: 1, an HC-CDR2 comprising the amino acid sequence of SEQ ID NO: 8, and an HC-CDR3 comprising the amino acid sequence of SEQ ID NO: 22; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 56;

(ii) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 23; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57;

(iii) a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57;

(iv) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(v) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 37; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57;

(vi) a $V_H$ comprising an HC-CDR1 comprising the amino acid sequence of SEQ ID NO: 3, an HC-CDR2 comprising the amino acid sequence of SEQ ID NO: 6, and an HC-CDR3 comprising the amino acid sequence of SEQ ID NO: 39; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 54;

(vii) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 35; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57;

(viii) a $V_H$ comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 50; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57;

(ix) a VH comprising an HC-CDR1 comprising the amino acid sequence of SEQ ID NO: 2, an HC-CDR2 comprising the amino acid sequence of SEQ ID NO: 6, and an HC-CDR3 comprising the amino acid sequence of SEQ ID NO: 18; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(x) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 19; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(xi) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 20; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(xii) a VH comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 21; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 55;

(xiii) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 24; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(xiv) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 25; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 58;

(xv) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 17; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 58;

(xvi) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 26; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 59;

(xvii) a VH comprising an HC-CDR1 comprising the amino acid sequence of SEQ ID NO: 2, an HC-CDR2 comprising the amino acid sequence of SEQ ID NO: 6, and an HC-CDR3 comprising the amino acid sequence of SEQ ID NO: 28; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 60;

(xviii) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 29; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 58;

(xix) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 30; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 61;

(xx) a VH comprising an HC-CDR1 comprising the amino acid sequence of SEQ ID NO: 2, an HC-CDR2 comprising the amino acid sequence of SEQ ID NO: 6, and an HC-CDR3 comprising the amino acid sequence of SEQ ID NO: 32; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 63;

(xxi) a VH comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 33; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 60;

(xxii) a VH comprising an HC-CDR1 comprising the amino acid sequence of SEQ ID NO: 1, an HC-CDR2 comprising the amino acid sequence of SEQ ID NO: 7, and an HC-CDR3 comprising the amino acid sequence of SEQ ID NO: 34; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 55;

(xxiii) a VH comprising an HC-CDR1 comprising the amino acid sequence of SEQ ID NO: 2, an HC-CDR2 comprising the amino acid sequence of SEQ ID NO: 6, and an HC-CDR3 comprising the amino acid sequence of SEQ ID NO: 36; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 64;

(xxiv) a VH comprising an HC-CDR1 comprising the amino acid sequence of SEQ ID NO: 2, an HC-CDR2 comprising the amino acid sequence of SEQ ID NO: 6, and an HC-CDR3 comprising the amino acid sequence of SEQ ID NO: 38; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(xxv) a VH comprising an HC-CDR1 comprising the amino acid sequence of SEQ ID NO: 1, an HC-CDR2 comprising the amino acid sequence of SEQ ID NO: 9, and an HC-CDR3 comprising the amino acid sequence of SEQ ID NO: 40; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 65;

(xxvi) a VH comprising an HC-CDR1 comprising the amino acid sequence of SEQ ID NO: 1, an HC-CDR2 comprising the amino acid sequence of SEQ ID NO: 10, and an HC-CDR3 comprising the amino acid sequence of SEQ ID NO: 27; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 66;

(xxvii) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 40; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 67;

(xxviii) a VH comprising an HC-CDR1 comprising the amino acid sequence of SEQ ID NO: 2, an HC-CDR2 comprising the amino acid sequence of SEQ ID NO: 7, and an HC-CDR3 comprising the amino acid sequence of SEQ ID NO: 43; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 55;

(xxix) a VH comprising an HC-CDR1 comprising the amino acid sequence of SEQ ID NO: 2, an HC-CDR2 comprising the amino acid sequence of SEQ ID NO: 6, and an HC-CDR3 comprising the amino acid sequence of SEQ ID NO: 45; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 53;

(xxx) a VH comprising an HC-CDR1 comprising the amino acid sequence of SEQ ID NO: 2, an HC-CDR2 comprising the amino acid sequence of SEQ ID NO: 7, and an HC-CDR3 comprising the amino acid sequence of SEQ ID NO: 48; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 55;

(xxxi) a VH comprising an HC-CDR1 comprising the amino acid sequence of SEQ ID NO: 1, an HC-CDR2 comprising the amino acid sequence of SEQ ID NO: 14, and an HC-CDR3 comprising the amino acid sequence of SEQ ID NO: 49; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 73; or (xxxii) a VH comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27; and a VL comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 61.

4. An isolated anti-GM-CSFRα antibody, comprising a $V_H$ comprising an HC-CDR1 comprising the amino acid sequence of SEQ ID NO: 1, an HC-CDR2 comprising the amino acid sequence of SEQ ID NO: 6, and an HC-CDR3 comprising the amino acid sequence of SEQ ID NO: 27; and a $V_L$ comprising an LC-CDR1 comprising the amino acid sequence of SEQ ID NO: 51, an LC-CDR2 comprising the amino acid sequence of SEQ ID NO: 52, and an LC-CDR3 comprising the amino acid sequence of SEQ ID NO: 57, wherein the antibody comprises one of the following substitutions selected from:

(i) N or G at position 31 of the $V_H$; or (ii) L, N, A, K, R, I, Q, G, T, H, M, or C at position 26 of the $V_L$; or (iii) Y, P, A, I, F, T, R, or V at position 27 of the $V_L$; or (iv) H, W, L, R, K, T, P, I, F, V, E, or A at position 28 of the $V_L$; or (v) L, W, M, A, Y, K, R, G, T, or E at position 30 of the $V_L$;

or (vi) T, R, A, H, or Q at position 31 of the $V_L$; or (vii) L at position 32 of the $V_L$; or (xiii) G or R at position 51 of the $V_L$; or (ix) A, W, R, or L at position 52 of the $V_L$; or (x) D or E at position 93 of the $V_L$; and wherein the numbering is according to the EU index of Kabat.

5. The isolated anti-GM-CSFRα antibody of claim 3, comprising:

(i) a $V_H$ comprising the amino acid sequence of SEQ ID NO: 85, or a variant thereof having at least about 90% sequence identity to the amino acid sequence of SEQ ID NO: 85; and a $V_L$ comprising the amino acid sequence of SEQ ID NO: 125, or a variant thereof having at least about 90% sequence identity to the amino acid sequence of SEQ ID NO: 125;

(ii) a $V_H$ comprising the amino acid sequence of SEQ ID NO: 86, or a variant thereof having at least about 90% sequence identity to the amino acid sequence of SEQ ID NO: 86; and a $V_L$ comprising the amino acid sequence of SEQ ID NO: 126, or a variant thereof having at least about 90% sequence identity to the amino acid sequence of SEQ ID NO: 126;

(iii) a $V_H$ comprising the amino acid sequence of SEQ ID NO: 91, or a variant thereof having at least about 90% sequence identity to the amino acid sequence of SEQ ID NO: 91; and a $V_L$ comprising the amino acid sequence of SEQ ID NO: 126, or a variant thereof having at least about 90% sequence identity to the amino acid sequence of SEQ ID NO: 126;

(iv) a $V_H$ comprising the amino acid sequence of SEQ ID NO: 99, or a variant thereof having at least about 90% sequence identity to the amino acid sequence of SEQ ID NO: 99; and a $V_L$ comprising the amino acid sequence of SEQ ID NO: 122, or a variant thereof having at least about 90% sequence identity to the amino acid sequence of SEQ ID NO: 122;

(v) a $V_H$ comprising the amino acid sequence of SEQ ID NO: 101, or a variant thereof having at least about 90% sequence identity to the amino acid sequence of SEQ ID NO: 101; and a $V_L$ comprising the amino acid sequence of SEQ ID NO: 126, or a variant thereof having at least about 90% sequence identity to the amino acid sequence of SEQ ID NO: 126;

(vi) a $V_H$ comprising the amino acid sequence of SEQ ID NO: 103, or a variant thereof having at least about 90% sequence identity to the amino acid sequence of SEQ ID NO: 103; and a $V_L$ comprising the amino acid sequence of SEQ ID NO: 123, or a variant thereof having at least about 90% sequence identity to the amino acid sequence of SEQ ID NO: 123;

(vii) a $V_H$ comprising the amino acid sequence of SEQ ID NO: 99, or a variant thereof having at least about 90% sequence identity to the amino acid sequence of SEQ ID NO: 99; and a $V_L$ comprising the amino acid sequence of SEQ ID NO: 126, or a variant thereof having at least about 90% sequence identity to the amino acid sequence of SEQ ID NO: 126; or (viii) a $V_H$ comprising the amino acid sequence of SEQ ID NO: 121, or a variant thereof having at least about 90% sequence identity to the amino acid sequence of SEQ ID NO: 121; and a $V_L$ comprising the amino acid sequence of SEQ ID NO: 126, or a variant thereof having at least about 90% sequence identity to the amino acid sequence of SEQ ID NO: 126;

(ix) a $V_H$ comprising the amino acid sequence of SEQ ID NO: 81, or a variant thereof having at least about 90% sequence identity to the amino acid sequence of SEQ ID NO: 81; and a $V_L$ comprising the amino acid sequence of SEQ ID NO: 122, or a variant thereof having at least about 90% sequence identity to the amino acid sequence of SEQ ID NO: 122;

(x) a $V_H$ comprising the amino acid sequence of SEQ ID NO: 82, or a variant thereof having at least about 90% sequence identity to the amino acid sequence of SEQ ID NO: 82; and a $V_L$ comprising the amino acid sequence of SEQ ID NO: 122, or a variant thereof having at least about 90% sequence identity to the amino acid sequence of SEQ ID NO: 122;

(xi) a $V_H$ comprising the amino acid sequence of SEQ ID NO: 83, or a variant thereof having at least about 90% sequence identity to the amino acid sequence of SEQ ID NO: 83; and a $V_L$ comprising the amino acid sequence of SEQ ID NO: 122, or a variant thereof having at least about 90% sequence identity to the amino acid sequence of SEQ ID NO: 122;

(xii) a $V_H$ comprising the amino acid sequence of SEQ ID NO: 84, or a variant thereof having at least about 90% sequence identity to the amino acid sequence of SEQ ID NO: 84; and a $V_L$ comprising the amino acid sequence of SEQ ID NO: 124, or a variant thereof having at least about 90% sequence identity to the amino acid sequence of SEQ ID NO: 124;

(xiii) a $V_H$ comprising the amino acid sequence of SEQ ID NO: 87, or a variant thereof having at least about 90% sequence identity to the amino acid sequence of SEQ ID NO: 87; and a $V_L$ comprising the amino acid sequence of SEQ ID NO: 122, or a variant thereof having at least about 90% sequence identity to the amino acid sequence of SEQ ID NO: 122;

(xiv) a $V_H$ comprising the amino acid sequence of SEQ ID NO: 88, or a variant thereof having at least about 90% sequence identity to the amino acid sequence of SEQ ID NO: 88; and a $V_L$ comprising the amino acid sequence of SEQ ID NO: 127, or a variant thereof having at least about 90% sequence identity to the amino acid sequence of SEQ ID NO: 127;

(XV) a $V_H$ comprising the amino acid sequence of SEQ ID NO: 89, or a variant thereof having at least about 90% sequence identity to the amino acid sequence of SEQ ID NO: 89; and a $V_L$ comprising the amino acid sequence of SEQ ID NO: 127, or a variant thereof having at least about 90% sequence identity to the amino acid sequence of SEQ ID NO: 127;

(xvi) a $V_H$ comprising the amino acid sequence of SEQ ID NO: 90, or a variant thereof having at least about 90% sequence identity to the amino acid sequence of SEQ ID NO: 90; and a $V_L$ comprising the amino acid sequence of SEQ ID NO: 128, or a variant thereof having at least about 90% sequence identity to the amino acid sequence of SEQ ID NO: 128;

(xvii) a $V_H$ comprising the amino acid sequence of SEQ ID NO: 92, or a variant thereof having at least about 90% sequence identity to the amino acid sequence of SEQ ID NO: 92; and a $V_L$ comprising the amino acid sequence of SEQ ID NO: 129, or a variant thereof having at least about 90% sequence identity to the amino acid sequence of SEQ ID NO: 129;

(xviii) a $V_H$ comprising the amino acid sequence of SEQ ID NO: 93, or a variant thereof having at least about 90% sequence identity to the amino acid sequence of SEQ ID NO: 93; and a $V_L$ comprising the amino acid sequence of SEQ ID NO: 127, or a variant thereof having at least about 90% sequence identity to the amino acid sequence of SEQ ID NO: 127;

(xix) a $V_H$ comprising the amino acid sequence of SEQ ID NO: 94, or a variant thereof having at least about 90% sequence identity to the amino acid sequence of SEQ ID NO: 94; and a $V_L$ comprising the amino acid sequence of SEQ ID NO: 130, or a variant thereof having at least about 90% sequence identity to the amino acid sequence of SEQ ID NO: 130;

(xx) a $V_H$ comprising the amino acid sequence of SEQ ID NO: 96, or a variant thereof having at least about 90% sequence identity to the amino acid sequence of SEQ ID NO: 96; and a $V_L$ comprising the amino acid sequence of SEQ ID NO: 132, or a variant thereof having at least about 90% sequence identity to the amino acid sequence of SEQ ID NO: 132;

(xxi) a $V_H$ comprising the amino acid sequence of SEQ ID NO: 97, or a variant thereof having at least about 90% sequence identity to the amino acid sequence of SEQ ID NO: 97; and a $V_L$ comprising the amino acid sequence of SEQ ID NO: 129, or a variant thereof having at least about 90% sequence identity to the amino acid sequence of SEQ ID NO: 129;

(xxii) a $V_H$ comprising the amino acid sequence of SEQ ID NO: 98, or a variant thereof having at least about 90% sequence identity to the amino acid sequence of SEQ ID NO: 98; and a $V_L$ comprising the amino acid sequence of SEQ ID NO: 124, or a variant thereof having at least about 90% sequence identity to the amino acid sequence of SEQ ID NO: 124;

(xxiii) a $V_H$ comprising the amino acid sequence of SEQ ID NO: 100, or a variant thereof having at least about 90% sequence identity to the amino acid sequence of SEQ ID NO: 100; and a $V_L$ comprising the amino acid sequence of SEQ ID NO: 133, or a variant thereof having at least about 90% sequence identity to the amino acid sequence of SEQ ID NO: 133;

(xxiv) a $V_H$ comprising the amino acid sequence of SEQ ID NO: 102, or a variant thereof having at least about 90% sequence identity to the amino acid sequence of SEQ ID NO: 102; and a $V_L$ comprising the amino acid sequence of SEQ ID NO: 122, or a variant thereof having at least about 90% sequence identity to the amino acid sequence of SEQ ID NO: 122;

(xxv) a $V_H$ comprising the amino acid sequence of SEQ ID NO: 104, or a variant thereof having at least about 90% sequence identity to the amino acid sequence of SEQ ID NO: 104; and a $V_L$ comprising the amino acid sequence of SEQ ID NO: 134, or a variant thereof having at least about 90% sequence identity to the amino acid sequence of SEQ ID NO: 134;

(xxvi) a $V_H$ comprising the amino acid sequence of SEQ ID NO: 105, or a variant thereof having at least about 90% sequence identity to the amino acid sequence of SEQ ID NO: 105; and a $V_L$ comprising the amino acid sequence of SEQ ID NO: 135, or a variant thereof having at least about 90% sequence identity to the amino acid sequence of SEQ ID NO: 135;

(xxvii) a $V_H$ comprising the amino acid sequence of SEQ ID NO: 106, or a variant thereof having at least about 90% sequence identity to the amino acid sequence of SEQ ID NO: 106; and a $V_L$ comprising the amino acid sequence of SEQ ID NO: 136, or a variant thereof having at least about 90% sequence identity to the amino acid sequence of SEQ ID NO: 136;

(xxviii) a $V_H$ comprising the amino acid sequence of SEQ ID NO: 109, or a variant thereof having at least about 90% sequence identity to the amino acid sequence of SEQ ID NO: 109; and a $V_L$ comprising the amino acid sequence of SEQ ID NO: 124, or a variant thereof having at least about 90% sequence identity to the amino acid sequence of SEQ ID NO: 124;

(xxix) a $V_H$ comprising the amino acid sequence of SEQ ID NO: 111, or a variant thereof having at least about 90% sequence identity to the amino acid sequence of SEQ ID NO: 111; and a $V_L$ comprising the amino acid sequence of SEQ ID NO: 122, or a variant thereof having at least about 90% sequence identity to the amino acid sequence of SEQ ID NO: 122;

(xxx) a $V_H$ comprising the amino acid sequence of SEQ ID NO: 114, or a variant thereof having at least about 90% sequence identity to the amino acid sequence of SEQ ID NO: 114; and a $V_L$ comprising the amino acid sequence of SEQ ID NO: 124, or a variant thereof having at least about 90% sequence identity to the amino acid sequence of SEQ ID NO: 124; or (xxxi) a $V_H$ comprising the amino acid sequence of SEQ ID NO: 118, or a variant thereof having at least about 90% sequence identity to the amino acid sequence of SEQ ID NO: 118; and a $V_L$ comprising the amino acid sequence of SEQ ID NO: 142, or a variant thereof having at least about 90% sequence identity to the amino acid sequence of SEQ ID NO: 142; or (xxxii) a $V_H$ comprising the amino acid sequence of SEQ ID NO: 91, or a variant thereof having at least about 90% sequence identity to the amino acid sequence of SEQ ID NO: 91; and a $V_L$ comprising the amino acid sequence of SEQ ID NO: 130, or a variant thereof having at least about 90% sequence identity to the amino acid sequence of SEQ ID NO: 130.

6. The isolated anti-GM-CSFRα antibody of claim 3, wherein:

the anti-GM-CSFRα antibody comprises an Fc fragment.

7. The isolated anti-GM-CSFRα antibody of claim 3, wherein the anti-GM-CSFRα antibody is a full-length IgG antibody.

8. The isolated anti-GM-CSFRα antibody according to claim 3, wherein the anti-GM-CSFRα antibody is an antigen binding fragment selected from the group consisting of an Fab, an Fab', an F(ab)'2, an Fab'-SH, a single-chain Fv (scFv), an Fv fragment, and a diabody.

9. An isolated nucleic acid molecule that encodes the anti-GM-CSFRα antibody according to claim 3.

10. A vector comprising the nucleic acid molecule of claim 9.

11. An isolated host cell comprising the anti-GM-CSFRα antibody of claim 3.

12. A method of producing an anti-GM-CSFRα antibody, comprising:

a) culturing the host cell of claim 11 under conditions effective to express the anti-GM-CSFRα antibody; and b) obtaining the expressed anti-GM-CSFRα antibody from the host cell.

13. A pharmaceutical composition comprising the anti-GM-CSFRα antibody according to claim 3, and a pharmaceutically acceptable carrier.

14. The isolated anti-GM-CSFRα antibody of claim 4, comprising:

(i) a $V_H$ comprising the amino acid sequence of SEQ ID NO: 250, or a variant thereof having at least about 90% sequence identity to the amino acid sequence of SEQ ID NO: 250; and a $V_L$ comprising the amino acid sequence of SEQ ID NO: 193, or a variant thereof having at least about 90% sequence identity to the amino acid sequence of SEQ ID NO: 193;

(ii) a $V_H$ comprising the amino acid sequence of SEQ ID NO: 248, or a variant thereof having at least about 90% sequence identity to the amino acid sequence of SEQ ID NO: 248; and a $V_L$ comprising the amino acid sequence of SEQ ID NO: 193, or a variant thereof having at least about 90% sequence identity to the amino acid sequence of SEQ ID NO: 193;

(iii) a $V_H$ comprising the amino acid sequence of SEQ ID NO: 250, or a variant thereof having at least about 90% sequence identity to the amino acid sequence of SEQ ID NO: 250; and a $V_L$ comprising the amino acid sequence of SEQ ID NO: 288, or a variant thereof having at least about 90% sequence identity to the amino acid sequence of SEQ ID NO: 288;

(iv) a $V_H$ comprising the amino acid sequence of SEQ ID NO: 250, or a variant thereof having at least about 90% sequence identity to the amino acid sequence of SEQ ID NO: 250; and a $V_L$ comprising the amino acid sequence of SEQ ID NO: 236, or a variant thereof having at least about 90% sequence identity to the amino acid sequence of SEQ ID NO: 236; or (v) a $V_H$ comprising the amino acid sequence of SEQ ID NO: 91, or a variant thereof having at least about 90% sequence identity to the amino acid sequence of SEQ ID NO: 91; and a $V_L$ comprising the amino acid sequence of SEQ ID NO: 288, or a variant thereof having at least about 90% sequence identity to the amino acid sequence of SEQ ID NO: 288.

15. A pharmaceutical composition comprising the anti-GM-CSFRα antibody according to claim 4, and a pharmaceutically acceptable carrier.

* * * * *